United States Patent
Frank et al.

(10) Patent No.: US 8,334,315 B2
(45) Date of Patent: Dec. 18, 2012

(54) SUBSTITUTED AROMATIC CARBOXAMIDE AND UREA DERIVATIVES AS VANILLOID RECEPTOR LIGANDS

(75) Inventors: Robert Frank, Aachen (DE); Gregor Bahrenberg, Monschau-Konzen (DE); Thomas Christoph, Aachen (DE); Klaus Schiene, Juechen (DE); Jean De Vry, Stolberg (DE); Nils Damann, Cologne (DE); Sven Frormann, Aachen (DE); Bernhard Lesch, Aachen (DE); Jeewoo Lee, Seoul (KR); Yong-Soo Kim, Gyengnam (KR); Myeong-Seop Kim, Gangw-do (KR)

(73) Assignee: Gruenenthal GmbH, Aachen (DE)

( * ) Notice: Subject to any disclaimer, the term of this patent is extended or adjusted under 35 U.S.C. 154(b) by 12 days.

(21) Appl. No.: 12/775,155

(22) Filed: May 6, 2010

(65) Prior Publication Data

US 2011/0003795 A1    Jan. 6, 2011

Related U.S. Application Data

(60) Provisional application No. 61/176,277, filed on May 7, 2009.

(30) Foreign Application Priority Data

May 7, 2009    (EP) .................................... 09006221

(51) Int. Cl.
*A61K 31/415* (2006.01)
*C07D 231/10* (2006.01)

(52) U.S. Cl. ..................................... 514/406; 548/373.1

(58) Field of Classification Search .................. 514/406; 548/373.1
See application file for complete search history.

(56) References Cited

U.S. PATENT DOCUMENTS

| | | |
|---|---|---|
| 6,455,559 B1 | 9/2002 | Pevarello et al. |
| 2008/0207647 A1 | 8/2008 | Hoelzemann et al. |

FOREIGN PATENT DOCUMENTS

| | | |
|---|---|---|
| EP | 0 074 229 A1 | 3/1983 |
| JP | 6-157469 A | 6/1994 |
| WO | WO 2004/043939 A1 | 5/2004 |
| WO | WO 2005/004810 A2 | 1/2005 |
| WO | WO 2005/048948 A2 | 6/2005 |
| WO | WO 2005/110994 A2 | 11/2005 |
| WO | WO 2007/017083 A1 | 2/2007 |
| WO | WO 2007/064872 A2 | 6/2007 |
| WO | WO 2008/059370 A2 | 5/2008 |
| WO | WO 2008/075064 A1 | 6/2008 |
| WO | WO 2008/137102 A2 | 11/2008 |

OTHER PUBLICATIONS

Butlin et al. CAS: 149: 104604, 2008.*
Akiyama et al. CAS:130: 237562, 1999.*
European Search Report with partial translatation date Jul. 31, 2009 (nine (9) pages).
International Search Report dated Aug. 19, 2010 and PCT/ISA/237 (eleven (11) pages).

* cited by examiner

*Primary Examiner* — Rei-tsang Shiao
(74) *Attorney, Agent, or Firm* — Crowell & Moring LLP

(57) ABSTRACT

The invention relates to substituted aromatic carboxamide and urea derivatives, to processes for the preparation thereof, to pharmaceutical compositions containing these compounds and also to the use of these compounds for preparing pharmaceutical compositions.

14 Claims, No Drawings

SUBSTITUTED AROMATIC CARBOXAMIDE AND UREA DERIVATIVES AS VANILLOID RECEPTOR LIGANDS

This application claims priority under 35 U.S.C. §119(e) to U.S. Provisional Patent Application No. 61/176,277, filed on May 7, 2009, and also claims priority under 35 U.S.C. §119 (a) to European Application No. 09 006 221.7, filed May 7, 2009. The contents of both applications are hereby incorporated by reference in their entirety.

The invention relates to substituted aromatic carboxamide and urea derivatives, to processes for the preparation thereof, to pharmaceutical compositions containing these compounds and also to the use of these compounds for preparing pharmaceutical compositions.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain, particularly preferably of neuropathic pain. This receptor is stimulated inter alia by vanilloids such as capsaicin, heat and protons and plays a central role in the formation of pain. In addition, it is important for a large number of further physiological and patho-physiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and in particular urinary incontinence.

There is a demand for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

It was therefore an object of the invention to provide new compounds having advantages over the prior-art compounds. The compounds should be suitable in particular as pharmacological active ingredients in pharmaceutical compositions, preferably in pharmaceutical compositions for the treatment and/or prophylaxis of disorders or diseases which are mediated, at least in some cases, by vanilloid receptors 1 (VR1/TRPV1 receptors).

This object is achieved by the subject matter of the claims.

Now, it has surprisingly been found that the substituted compounds of general formula (I), as indicated below, display outstanding affinity to the subtype 1 vanilloid receptor (VR1/TRPV1 receptor) and are therefore particularly suitable for the prophylaxis and/or treatment of disorders or diseases which are mediated, at least in some cases, by vanilloid receptors 1 (VR1/TRPV1). The substituted compounds of general formula (I), as indicated below, also have anti-inflammatory activity.

The present invention therefore relates to substituted compounds of general formula (I),

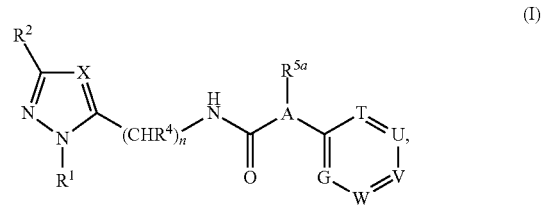

(I)

in which

X represents $CR^3$ or N,
  wherein $R^3$ represents H; $C_{1-10}$ alkyl, saturated or unsaturated, branched or unbranched, unsubstituted or mono- or polysubstituted;

A represents N or $CR^{5b}$, n represents 0, 1, 2, 3 or 4; preferably 1, 2, 3 or 4, $R^0$ represents $C_{1-10}$ alkyl, saturated or unsaturated, branched or unbranched, unsubstituted or mono- or polysubstituted; $C_{3-10}$ cycloalkyl or heterocyclyl, respectively saturated or unsaturated, unsubstituted or mono- or polysubstituted; aryl or heteroaryl, respectively unsubstituted or mono- or polysubstituted; $C_{3-10}$ cycloalkyl or heterocyclyl bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted;

$R^1$ represents H; $C_{1-10}$ alkyl, saturated or unsaturated, branched or unbranched, unsubstituted or mono- or polysubstituted; $C_{3-10}$ cycloalkyl$^1$ or heterocyclyl$^1$, respectively saturated or unsaturated, unsubstituted or mono- or polysubstituted; aryl or heteroaryl, respectively unsubstituted or mono- or polysubstituted; $C_{3-10}$ cycloalkyl$^1$ or heterocyclyl$^1$ bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; $C(=O)—R^0$; $C(=O)—OH$; $C(=O)—OR^0$; $C(=O)—NHR^0$; $C(=O)—N(R^0)_2$; $OH$; $O—R^0$; $SH$; $S—R^0$; $S(=O)_2—R^0$;

S(=O)₂—OR⁰; S(=O)₂—NHR⁰; S(=O)₂—N(R⁰)₂; NH₂; NHR⁰; N(R⁰)₂; NH—S(=O)₂—R⁰; N(R⁰)(S(=O)₂—R⁰; or SCl₃;

R² represents H; R⁰; F; Cl; Br; I; CN; NO₂; OH; SH; CF₃; CF₂H; CFH₂; CF₂Cl; CFCl₂; CH₂CF₃; OCF₃; OCF₂H; OCFH₂; OCF₂Cl; OCFCl₂; SCF₃; SCF₂H; SCFH₂; SCF₂Cl; SCFCl₂; S(=O)₂—CF₃; S(=O)₂—CF₂H; S(=O)₂—CFH₂; or SF₅;

R⁴ represents H; F; Cl; Br; I; OH; C₁₋₁₀ alkyl, saturated or unsaturated, branched or unbranched, unsubstituted or mono- or polysubstituted;

R⁵ᵃ represents H; OH; C₁₋₁₀ alkyl, saturated or unsaturated, branched or unbranched, unsubstituted or mono- or polysubstituted;

R⁵ᵇ represents H or R⁰;

or R⁵ᵃ and R⁵ᵇ form together with the carbon atom connecting them a C₃₋₁₀ cycloalkyl or a heterocyclyl, respectively saturated or unsaturated, unsubstituted or mono- or polysubstituted;

T represents N or CR⁶
U represents N or CR⁷
V represents N or CR⁸
W represents N or CR⁹
G represents N or CR¹⁰
  wherein at most three of the residues T, U, V, W and G may represent N simultaneously, i.e. 0, 1, 2 or 3 of the residues T, U, V, W and G may represent N simultaneously;

R⁶ and R⁷ together and/or R⁸ and R⁹ together; or
R⁷ and R⁸ together and/or R⁹ and R¹⁰ together; or R⁶ and R⁷ together and R⁹ and R¹⁰ together;
R⁶ and R⁷ together and R⁹ and R¹⁰ together;
in pairs, in each case independently of one another, together with the carbon atoms connecting them, form a C₃₋₁₀ cycloalkyl or heterocyclyl, respectively saturated or unsaturated, unsubstituted or mono- or polysubstituted; or an aryl or heteroaryl, respectively unsubstituted or mono- or polysubstituted;

and the respective remaining substituents of R⁶, R⁷, R⁸, R⁹ and R¹⁰ each independently of one another represent H; F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted alkyl", "substituted heterocyclyl" and "substituted cycloalkyl" relate, with respect to the corresponding residues, to the substitution of one or more hydrogen atoms each independently of one another by F; Cl; Br; I; NO₂; CN; =O; =NH; =N(OH); =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted cycloalkyl¹" and "substituted heterocyclyl¹" relate, with respect to the corresponding residues, to the substitution of one or more hydrogen atoms each independently of one another by F; Cl; Br; I; NO₂; CN; =; =C(NH₂)₂; CF₃; CF₂H; CFH₂; CF₂Cl; CFCl₂; R⁰; C(=O)H; C(=O)R⁰; CO₂H; C(=O)OR⁰: CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted aryl" and "substituted heteroaryl" relate, with respect to the corresponding residues, to the substitution of one or more hydrogen atoms each independently of one another by F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in the form of the free compounds; the tautomers; the N-oxides; the racemate; the enantiomers, diastereomers, mixtures of the enantiomers or diastereomers or of an individual enantiomer or diastereomer; or in the form of the salts of physiologically compatible acids or bases; or if appropriate in the form of solvates.

The terms "alkyl" or "C₁₋₁₀ alkyl", "C₁₋₈ alkyl", "C₁₋₆ alkyl", "C₁₋₄ alkyl" comprise in the sense of this invention acyclic saturated or unsaturated aliphatic hydrocarbon residues, i.e. C₁₋₁₀ aliphatic residues, C₁₋₈ aliphatic residues, C₁₋₆ aliphatic residues and C₁₋₄ aliphatic residues, which can be respectively branched or unbranched and also unsubstituted or mono- or polysubstituted, containing 1 to 10 or 1 to 8 or 1 to 6 or 1 to 4 carbon atoms, i.e. C₁₋₁₀ alkanyls, C₂₋₁₀ alkenyls and C₂₋₁₀ alkinyls or C₁₋₈ alkanyls, C₂₋₈ alkenyls and C₂₋₈ alkinyls or C₁₋₆ alkanyls, C₂₋₆ alkenyls and C₂₋₆ alkinyls or C₁₋₄ alkanyls, C₂₋₄ alkenyls and C₂₋₄ alkinyls. In this case, alkenyls comprise at least one C═C double bond and alkinyls comprise at least one C≡C triple bond. Preferably, alkyl is selected from the group comprising methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl, n-decyl, ethenyl (vinyl), ethinyl, propenyl (—CH$_2$CH═CH$_2$, —CH═CH—CH$_3$, —C(═CH$_2$)—CH$_3$), propinyl (—CH—C≡CH, —C≡C—CH$_3$), butenyl, butinyl, pentenyl, pentinyl, hexenyl and hexinyl, heptenyl, heptinyl, octenyl, octinyl, nonenyl, noninyl, decenyl and decinyl.

The terms "cycloalkyl" or "$C_{3-10}$ cycloalkyl" and "cycloalkyl$^1$" or "$C_{3-10}$ cycloalkyl$^1$" mean for the purposes of this invention cyclic aliphatic (cycloaliphatic) hydrocarbons containing 3, 4, 5, 6, 7, 8, 9 or 10 carbon atoms, i.e. $C_{3-10}$-cycloaliphatic residues, wherein the hydrocarbons can be saturated or unsaturated (but not aromatic), unsubstituted or mono- or polysubstituted. The cycloalkyl can be bound to the respective superordinate general structure via any desired and possible ring member of the cycloalkyl residue. The cycloalkyl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. The cycloalkyl residues can furthermore be singly or multiply bridged such as, for example, in the case of adamantyl, bicyclo[2.2.1]heptyl or bicyclo[2.2.2]octyl. Preferably, cycloalkyl is selected from the group comprising cyclopropyl, cyclobutyl, cyclopentyl, cyclohexyl, cycloheptyl, cyclooctyl, cyclononyl, cyclodecyl, adamantyl,

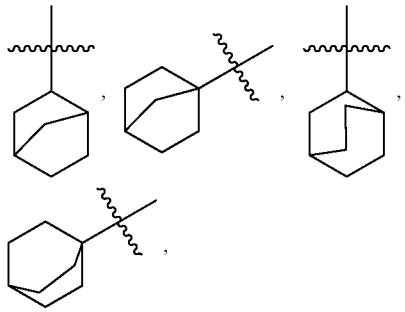

cyclopentenyl, cyclohexenyl, cycloheptenyl and cyclooctenyl.

The terms "heterocyclyl" or "heterocycloalkyl" and "heterocyclyl$^1$" or "heterocycloalkyl$^1$" comprise aliphatic saturated or unsaturated (but not aromatic) cycloalkyls having three to ten, i.e. 3, 4, 5, 6, 7, 8, 9 or 10, ring members, in which at least one, if appropriate also two or three carbon atoms are replaced by a heteroatom or a heteroatom group each selected independently of one another from the group consisting of O, S, N, NH and N(C$_{1-8}$ alkyl), preferably N(CH$_3$), wherein the ring members can be unsubstituted or mono- or polysubstituted. Heterocyclyls are thus heterocycloaliphatic residues. The heterocyclyl can be bound to the superordinate general structure via any desired and possible ring member of the heterocyclyl residue. The heterocyclyl residues can therefore be condensed with further saturated, (partially) unsaturated (hetero)cyclic or aromatic or heteroaromatic ring systems, i.e. with cycloalkyl, heterocyclyl, aryl or heteroaryl which can in turn be unsubstituted or mono- or polysubstituted. Heterocyclyl residues from the group comprising azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl are preferred.

The term "aryl" means in the sense of this invention aromatic hydrocarbons having up to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. Examples of condensed aryl residues are benzodioxolanyl and benzodioxanyl. Preferably, aryl is selected from the group containing phenyl, 1-naphthyl and 2-naphthyl which can be respectively unsubstituted or mono- or polysubstituted. A particularly preferred aryl is phenyl, unsubstituted or mono- or polysubstituted.

The term "heteroaryl" represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cyclic or aromatic or heteroaromatic rings, i.e. with cycloalkyl, heterocyclyl, aryl or heteroaryl which can in turn be unsubstituted or mono- or polysubstituted. It is preferable for the heteroaryl residue to be selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl or triazinyl. Furyl, pyridyl and thienyl are particularly preferred.

The terms "aryl, heteroaryl, heterocyclyl, cycloalkyl, heterocyclyl$^1$ or cycloalkyl$^1$ bridged via $C_{1-4}$ alkyl or $C_{1-8}$ alkyl" mean in the sense of the invention that $C_{1-4}$ alkyl or $C_{1-8}$ alkyl and aryl or heteroaryl or heterocyclyl or cycloalkyl or heterocyclyl$^1$ or cycloalkyl$^1$ have the above-defined meanings and the aryl or heteroaryl or heterocyclyl or cycloalkyl or heterocyclyl$^1$ or cycloalkyl$^1$ residue is bound to the respective superordinate general structure via a $C_{1-4}$ alkyl or a $C_{1-8}$ alkyl group. The alkyl chain of the alkyl group can in all cases be branched or unbranched, unsubstituted or mono- or polysubstituted. The alkyl chain of the alkyl group can furthermore be in all cases saturated or unsaturated, i.e. can be an alkylene group, i.e. a $C_{1-4}$ alkylene group or a $C_{1-8}$ alkylene group, an alkenylene group, i.e. a $C_{2-4}$ alkenylene group or a $C_{2-8}$ alkenylene group, or an alkinylene group, i.e. a $C_{2-4}$ alkinylene group or a $C_{2-8}$ alkinylene group. Preferably, $C_{1-4}$ alkyl is selected from the group comprising —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$C$≡$C$—, —$C$≡$C$—$CH_2$—, —$C$≡$C$—$CH_2$—$CH_2$—, —$C$≡$C$—$CH$($CH_3$)—, —$CH_2$—$C$≡$C$—$CH_2$— and —$C$≡$C$—$C$≡$C$— and $C_{1-8}$ alkyl is selected from the group comprising —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH$($CH_3$)—$CH_2$—, —$CH(CH_3)$—$CH(CH_3)$—, —$CH$($CH_2CH_3$)—$CH_2$—, —$C(CH_3)_2$—$CH_2$—, —$CH$($CH_2CH_2CH_3$)—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$—, —$CH_2$—$(CH_2)_4$—$CH_2$—, —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$CH$=$CH$—$CH_2$—$CH_2$—$CH_2$—, —$CH_2$—$CH$=$CH$—$CH_2$—$CH_2$—, —$CH$=$CH$—$CH$=$CH$—$CH_2$—, —$CH$=$CH$—$CH$=$CH$—, —$C$≡$C$—, —$C$≡$C$—$CH_2$—, —$C$≡$C$—$CH_2$—$CH_2$—, —$C$≡$C$—$CH(CH_3)$—, —$CH_2$—$C$≡$C$—$CH_2$—, —$C$≡$C$—$C$≡$C$—, —$C$≡$C$—$C(CH_3)_2$—, —$C$≡$C$—$CH_2$—$CH_2$—$CH_2$—, —$CH_2$—$C$≡$C$—$CH_2$—$CH_2$—, —$C$≡$C$—$C$≡$C$—$CH_2$— and —$C$≡$C$—$CH_2$—$C$≡$C$—.

In relation to "alkyl", "heterocyclyl" and "cycloalkyl", the term "mono- or polysubstituted" refers in the sense of this invention to the single or multiple, for example double, triple or quadruple, substitution of one or more hydrogen atoms each independently of one another by substituents selected from the group of F; Cl; Br; I; $NO_2$; CN; =O; =NH; =N(OH); =C($NH_2$)$_2$; $CF_3$; $CF_2H$; $CFH_2$; $CF_2Cl$; $CFCl_2$; $R^O$; C(=O)H; C(=O)$R^O$; $CO_2H$; C(=O)$OR^O$; $CONH_2$; C(=O)$NHR^O$; C(=O)N($R^O$)$_2$; OH; $OCF_3$; $OCF_2H$; $OCFH_2$; $OCF_2Cl$; $OCFCl_2$; $OR^O$; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$$OR^O$; O—S(=O)$_2$$NH_2$; O—S(=O)$_2$$NHR^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2$$R^O$; NH—S(=O)$_2$$OR^O$; NH—S(=O)$_2$$NH_2$; NH—S(=O)$_2$$NHR^O$; NH—S(=O)$_2$N($R^O$)$_2$; $NR^O$—S(=O)$_2$OH; $NR^O$—S(=O)$_2$$R^O$; $NR^O$—S(=O)$_2$$OR^O$; $NR^O$—S(=O)$_2$$NH_2$; $NR^O$—S(=O)$_2$$NHR^O$; $NR^O$—S(=O)$_2$N($R^O$)$_2$; SH; $SCF_3$; $SCF_2H$; $SCFH_2$; $SCF_2Cl$; $SCFCl_2$; $SR^O$; S(=O)$R^O$; S(=O)$_2$$R^O$; S(=O)$_2$OH; S(=O)$_2$$OR^O$; S(=O)$_2$$NH_2$; S(=O)$_2$$NHR^O$; or S(=O)$_2$N($R^O$)$_2$; wherein the term "polysubstituted residues" refers to residues of the type that are polysubstituted, for example di-, tri- or tetrasubstituted, either on different or on the same atoms, for example trisubstituted on the same C atom, as in the case of $CF_3$ or $CH_2CF_3$, or at various points, as in the case of CH(OH)—CH=CH—$CHCl_2$. A substituent can if appropriate for its part in turn be mono- or polysubstituted. The multiple substitution can be carried out using the same or using different substituents.

In relation to "cycloalkyl$^1$" and "heterocyclyl$^1$", the term "mono- or polysubstituted" refers in the sense of this invention to the single or multiple, for example double, triple or quadruple, substitution of one or more hydrogen atoms each independently of one another by substituents selected from the group of F; Cl; Br; I; $NO_2$; CN; =O; =C($NH_2$)$_2$; $CF_3$; $CF_2H$; $CFH_2$; $CF_2Cl$; $CFCl_2$; $R^O$; C(=O)H; C(=O)$R^O$; $CO_2H$; C(=O)$OR^O$; $CONH_2$; C(=O)$NHR^O$; C(=O)N($R^O$)$_2$; OH; $OCF_3$; $OCF_2H$; $OCFH_2$; $OCF_2Cl$; $OCFCl_2$; $OR^O$; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$$OR^O$; O—S(=O)$_2$$NH_2$; O—S(=O)$_2$$NHR^O$; O—S(=O)$_2$N($R^O$)$_2$; SH; $SCF_3$; $SCF_2H$; $SCFH_2$; $SCF_2Cl$; $SCFCl_2$; $SR^O$; S(=O)$R^O$; S(=O)$_2$$R^O$; S(=O)$_2$OH; S(=O)$_2$$OR^O$; S(=O)$_2$$NH_2$; S(=O)$_2$$NHR^O$; or S(=O)$_2$N($R^O$)$_2$; wherein the term "polysubstituted residues" refers to residues of the type that are polysubstituted, for example di-, tri- or tetrasubstituted, either on different or on the same atoms, for example trisubstituted on the same C atom, as in the case of 1,1-difluorocyclohexyl, or at various points, as in the case of 1,2-difluorocyclohexyl. A substituent can if appropriate for its part in turn be mono- or polysubstituted. The multiple substitution can be carried out using the same or using different substituents.

Preferred "alkyl", "heterocyclyl" and "cycloalkyl" substituents are selected from the group of F; Cl; Br; I; $NO_2$; $CF_3$; CN; =O; =NH; $R^O$; C(=O)($R^O$ or H); C(=O)O($R^O$ or H); C(=O)N($R^O$ or H)$_2$; OH; $OR^O$; O—C(=O)—$R^O$; O—($C_{1-8}$ alkyl)-OH; O—($C_{1-8}$ alkyl)-O—$C_{1-8}$ alkyl; $OCF_3$; N($R^O$ or H)$_2$; N($R^O$ or H)—C(=O)—$R^O$; N($R^O$ or H)—C(=O)—N($R^O$ or H)$_2$; SH; $SCF_3$; $SR^O$; S(=O)$_2$$R^O$; S(=O)$_2$O($R^O$ or H) and S(=O)$_2$—N($R^O$ or H)$_2$.

Particularly preferred "alkyl", "heterocyclyl" and "cycloalkyl" substituents are selected from the group consisting of F; Cl; Br; I; $NO_2$; $CF_3$; CN; =O; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O) $C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl;

NH—C(=O)-aryl; NH—C(=O)-heteroaryl; SH; S—$C_{1-8}$ alkyl; $SCF_3$; S-benzyl; S-aryl; S-heteroaryl; S(=O)$_2C_{1-8}$ alkyl; S(=O)$_2$ aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; and S(=O)$_2$—NH—$C_{1-8}$ heteroaryl.

Preferred "cycloalkyl$^1$" and "heterocyclyl$^1$" substituents are selected from the group of F; Cl; Br; I; $NO_2$; $CF_3$; CN; =O; $R^O$; C(=O)($R^O$ or H); C(=O)O($R^O$ or H); C(=O)N($R^O$ or H)$_2$; OH; $OR^O$; O—C(=O)—$R^O$; O—($C_{1-8}$ alkyl)-OH; O—($C_{1-8}$ alkyl)-O—$C_{1-8}$ alkyl; $OCF_3$; SH; $SCF_3$; $SR^O$; S(=O)$_2R^O$; S(=O)$_2$O($R^O$ or H) and S(=O)$_2$—N($R^O$ or H)$_2$.

Particularly preferred "cycloalkyl$^1$" and "heterocyclyl$^1$" substituents are selected from the group consisting of F; Cl; Br; I; $NO_2$; $CF_3$; CN; =O; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; SH; S—$C_{1-8}$ alkyl; $SCF_3$; S-benzyl; S-aryl; S-heteroaryl; S(=O)$_2C_{1-8}$ alkyl; S(=O)$_2$aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; and S(=O)$_2$—NH—$C_{1-8}$ heteroaryl.

In relation to "aryl" and "heteroaryl", the term "mono- or polysubstituted" refers in the sense of this invention to the single or multiple, for example double, triple or quadruple, substitution of one or more hydrogen atoms of the ring system each independently of one another by substituents selected from the group of F; Cl; Br; I; $NO_2$; CN; $CF_3$; $CF_2H$; $CFH_2$; $CF_2Cl$; $CFCl_2$; $R^O$; C(=O)H; C(=O)$R^O$; $CO_2H$; C(=O)$OR^O$; $CONH_2$; C(=O)$NHR^O$; C(=O)N($R^O$)$_2$; OH; $OCF_3$; $OCF_2H$; $OCFH_2$; $OCF_2Cl$; $OCFCl_2$; $OR^O$; O—C(=O)—$R^O$; O—C(=O)—O—$R^O$; O—(C=O)—NH—$R^O$; O—C(=O)—N($R^O$)$_2$; O—S(=O)$_2$—$R^O$; O—S(=O)$_2$OH; O—S(=O)$_2$$OR^O$; O—S(=O)$_2NH_2$; O—S(=O)$_2NHR^O$; O—S(=O)$_2$N($R^O$)$_2$; $NH_2$; NH—$R^O$; N($R^O$)$_2$; NH—C(=O)—$R^O$; NH—C(=O)—O—$R^O$; NH—C(=O)—$NH_2$; NH—C(=O)—NH—$R^O$; NH—C(=O)—N($R^O$)$_2$; $NR^O$—C(=O)—$R^O$; $NR^O$—C(=O)—O—$R^O$; $NR^O$—C(=O)—$NH_2$; $NR^O$—C(=O)—NH—$R^O$; $NR^O$—C(=O)—N($R^O$)$_2$; NH—S(=O)$_2$OH; NH—S(=O)$_2R^O$; NH—S(=O)$_2OR^O$; NH—S(=O)$_2NH_2$; NH—S(=O)$_2NHR^O$; NH—S(=O)$_2$N($R^O$)$_2$; $NR^O$—S(=O)$_2$OH; $NR^O$—S(=O)$_2R^O$; $NR^O$—S(=O)$_2OR^O$; $NR^O$—S(=O)$_2NH_2$; $NR^O$—S(=O)$_2NHR^O$; $NR^O$—S(=O)$_2$N($R^O$)$_2$; SH; $SCF_3$; $SCF_2H$; $SCFH_2$; $SCF_2Cl$; $SCFCl_2$; $SR^O$; S(=O)$R^O$; S(=O)$_2R^O$; S(=O)$_2$OH; S(=O)$_2OR^O$; S(=O)$_2NH_2$; S(=O)$_2NHR^O$; or S(=O)$_2$N($R^O$)$_2$, on one or if appropriate different atoms, wherein a substituent can if appropriate for its part in turn be mono- or polysubstituted. The multiple substitution is carried out using the same or using different substituents.

Preferred "aryl" and "heteroaryl" substituents are F; Cl; Br; I; $NO_2$; $CF_3$; CN; $R^O$; C(=O)($R^O$ or H); C(=O)O($R^O$ or H); C(=O)N($R^O$ or H)$_2$; OH; $OR^O$; O—C(=O)—$R^O$; O—($C_{1-8}$ alkyl)-O—$C_{1-8}$ alkyl; $OCF_3$; N($R^O$ or H)$_2$; N($R^O$ or H)—C(=O)—$R^O$; N($R^O$ or H)—C(=O)—N($R^O$ or H)$_2$; SH; $SCF_3$; $SR^O$; S(=O)$_2R^O$; S(=O)$_2$O($R^O$ or H); S(=O)$_2$—N($R^O$ or H)$_2$.

Particularly preferred "aryl" and "heteroaryl" substituents are selected from the group consisting of F; Cl; Br; I; $NO_2$; $CF_3$; CN; $C_{1-8}$ alkyl; aryl; heteroaryl; $C_{3-10}$ cycloalkyl; heterocyclyl; $C_{1-8}$ alkyl-bridged aryl, heteroaryl, $C_{3-10}$ cycloalkyl or heterocyclyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl; NH—C(=O)-aryl; NH—C(=O)-heteroaryl; SH; S—$C_{1-8}$ alkyl; $SCF_3$; S-benzyl; S-aryl; S-heteroaryl; S(=O)$_2C_{1-8}$ alkyl; S(=O)$_2$aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; S(=O)$_2$—NH—$C_{1-8}$ heteroaryl.

The compounds according to the invention are defined by substituents, for example by $R^1$, $R^2$ and $R^3$ ($1^{st}$ generation substituents) which are for their part if appropriate substituted ($2^{nd}$ generation substituents). Depending on the definition, these substituents of the substituents can for their part be resubstituted ($3^{rd}$ generation substituents). If, for example, $R^1$=aryl ($1^{st}$ generation substituent), then aryl can for its part be substituted, for example with $C_{1-8}$ alkyl ($2^{nd}$ generation substituent). This produces the functional group aryl-$C_{1-8}$ alkyl. $C_{1-8}$ alkyl can then for its part be resubstituted, for example with Cl ($3^{rd}$ generation substituent). Overall, this then produces the functional group aryl-$C_{1-8}$ alkyl-Cl.

However, in a preferred embodiment, the $3^{rd}$ generation substituents may not be resubstituted, i.e. there are then no $4^{th}$ generation substituents.

In another preferred embodiment, the $2^{nd}$ generation substituents may not be resubstituted, i.e. there are then not even any $3^{rd}$ generation substituents. In other words, in this embodiment, in the case of general formula (I), for example, the functional groups for $R^1$ to $R^{10}$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, respectively unsubstituted or mono- or polysubstituted. Both these aryl or heteroaryl residues and the aromatic ring systems formed in this way can if appropriate be condensed with $C_{3-10}$ cycloalkyl or heterocyclyl, respectively saturated or unsaturated, or with aryl or heteroaryl, i.e. with a $C_{3-10}$ cycloalkyl such as cyclopentyl or a heterocyclyl such as morpholinyl, or an aryl such as phenyl or a heteroaryl such as pyridyl, wherein the $C_{3-10}$ cycloalkyl or heterocyclyl residues, aryl or heteroaryl residues condensed in this way can for their part be respectively unsubstituted or mono- or polysubstituted.

In some cases, the compounds according to the invention are defined by substituents which are or carry a $C_{3-10}$ cycloalkyl or heterocyclyl residue, respectively unsubstituted or mono- or polysubstituted, or which form together with the carbon atom(s) or heteroatom(s) connecting them, as the ring member or as the ring members, a ring, for example a $C_{3-10}$ cycloalkyl or heterocyclyl, respectively unsubstituted or mono- or polysubstituted. Both these $C_{3-10}$ cycloalkyl or heterocyclyl residues and the aliphatic ring systems formed can if appropriate be condensed with aryl or heteroaryl or with $C_{3-10}$ cycloalkyl or heterocyclyl, i.e. with an aryl such as phenyl or a heteroaryl such as pyridyl or a $C_{3-10}$ cycloalkyl such as cyclohexyl or a heterocyclyl such as morpholinyl, wherein the aryl or heteroaryl residues or $C_{3-10}$ cycloalkyl or heterocyclyl residues condensed in this way can for their part be respectively unsubstituted or mono- or polysubstituted.

Within the scope of the present invention, the symbol

used in the formulae denotes a link of a corresponding residue to the respective superordinate general structure.

The term "($R^0$ or H)" within a residue means that $R^0$ and H can occur within this residue in any possible combination. Thus, for example, the residue "$N(R^0$ or $H)_2$" can represent "$NH_2$", "$NHR^0$" and "$N(R^0)_2$". If, as in the case of "$N(R^0)_2$", $R^0$ occurs multiply within a residue, then $R^0$ can respectively have the same or different meanings: in the present example of "$N(R^0)_2$", $R^0$ can for example represent aryl twice, thus producing the functional group "$N(aryl)2$", or $R^0$ can represent once aryl and once $C_{1-10}$ alkyl, thus producing the functional group "$N(aryl)(C_{1-10}$ alkyl)".

If a residue occurs multiply within a molecule, such as for example the residue $R^0$, then this residue can have respectively different meanings for various substituents: if, for example, both $R^1=R^0$ and $R^2=R^0$, then $R^0$ can represent $R^1$=aryl and $R^0$ can represent $R^2=C_{1-10}$ alkyl.

The term "salt formed with a physiologically compatible acid" refers in the sense of this invention to salts of the respective active ingredient with inorganic or organic acids which are physiologically compatible—in particular when used in human beings and/or other mammals. Hydrochloride is particularly preferred. Examples of physiologically compatible acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

Physiologically compatible salts with cations or bases are salts of the respective compound—as an anion with at least one, preferably inorganic, cation—which are physiologically compatible—in particular when used in human beings and/or other mammals. Particularly preferred are the salts of the alkali and alkaline earth metals but also ammonium salts $[NH_xR_{4-x}]^+$, in which x=0, 1, 2, 3 or 4 and R represents a branched or unbranched $C_{1-4}$ alkyl residue, in particular (mono-) or (di)sodium, (mono-) or (di)potassium, magnesium or calcium salts.

In preferred embodiments of the compounds according to the invention of general formula (I), n represents 1, 2, 3 or 4, preferably 1, 2 or 3, particularly preferably 1 or 2, most particularly preferably 1.

Further preferred embodiments of the compounds according to the invention of general formula (I) have general formula (Ia), (Ib), (Ic) or (Id):

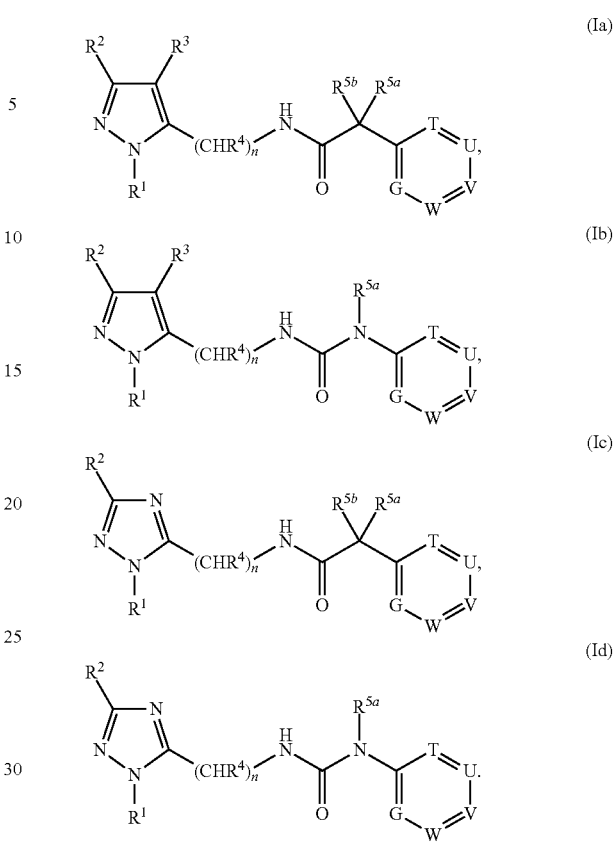

Compounds of general formulae (Ia) and (Ib) are most particularly preferred.

In a further preferred embodiment of the compounds according to the invention of general formula (I), the residue $R^1$ represents H; $C_{1-10}$ alkyl, $C(=O)-C_{1-10}$ alkyl, $C(=O)-$NH$-C_{1-10}$ alkyl, $C(=O)-N(C_{1-10}$ alkyl$)_2$, $O-C_{1-10}$ alkyl, $S-C_{1-10}$ alkyl, NH($C_{1-10}$ alkyl), $N(C_{1-10}$ alkyl$)_2$, NH$-S(=O)_2-C_{1-10}$ alkyl, $N(C_{1-10}$ alkyl)$-S(=O)_2$$-C_{1-10}$ alkyl, $S(=O)_2-C_{1-10}$ alkyl, $S(=O)_2-$NH$-C_{1-10}$ alkyl, $S(=O)_2-N(C_{1-10}$ alkyl$)_2$, in which $C_{1-10}$ alkyl can be respectively saturated or unsaturated, branched or unbranched, unsubstituted or mono- or polysubstituted with one or more substituents each selected independently of one another from the group consisting of F, Cl, Br, I, $NO_2$, CN, OH, =O, $O-C_{1-4}$ alkyl, $OCF_3$, $CF_3$, $NH_2$, NH($C_{1-4}$ alkyl), $N(C_{1-4}$ alkyl$)_2$, SH, S$-C_{1-4}$ alkyl, $SCF_3$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, $O-C_{1-4}$ alkyl, $OCF_3$, $C_{1-4}$ alkyl, $C(=O)-$OH, $CF_3$, $NH_2$, NH($C_{1-4}$ alkyl), $N(C_{1-4}$ alkyl$)_2$, SH, S$-C_{1-4}$ alkyl, $SCF_3$ and $S(=O)_2$OH;

or $C_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, $NO_2$, CN, OH, =O, $O-C_{1-4}$ alkyl, $OCF_3$, $CF_3$, SH, S$-C_{1-4}$ alkyl, $SCF_3$, phenyl and pyridyl, wherein phenyl or pyridyl are respectively unsubstituted or mono- or polysubstituted with one or more substituents each selected independently of one another from the group consisting of F, Cl, Br, I, $NO_2$, CN, OH, $O-C_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH;

or C$_{3-10}$ cycloalkyl$^1$ or heterocyclyl$^1$ bridged via C$_{1-8}$ alkyl, respectively saturated or unsaturated, unsubstituted or mono- or polysubstituted with one or more substituents each selected independently of one another from the group consisting of F, Cl, Br, I, NO$_2$, CN, OH, =O, O—C$_{1-4}$ alkyl, OCF$_3$, CF$_3$, SH, S—C$_{1-4}$ alkyl, SCF$_3$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH; wherein the alkyl chain can be respectively branched or unbranched, saturated or unsaturated, unsubstituted, mono- or polysubstituted with one or more substituents each selected independently of one another from the group consisting of F, Cl, Br; I, OH and O—C$_{1-4}$ alkyl;

or C(=O)—C$_{3-10}$ cycloalkyl, O—C$_{3-10}$ cycloalkyl, S—C$_{3-10}$ cycloalkyl, NH—C(=O)-cycloalkyl, NH—C(=O)-heterocyclyl, respectively saturated or unsaturated, unsubstituted or mono- or polysubstituted with one or more substituents each selected independently of one another from the group consisting of F, Cl, Br, I, NO$_2$, CN, OH, =O, O—C$_{1-4}$ alkyl, OCF$_3$, CF$_3$, NH$_2$, NH(C$_{1-4}$ alkyl), N(C$_{1-4}$ alkyl)$_2$, SH, S—C$_{14}$ alkyl, SCF$_3$, phenyl and pyridyl, wherein phenyl or pyridyl are respectively unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH;

or aryl, heteroaryl, C(=O)-aryl, C(=O)-heteroaryl, O-aryl, O-heteroaryl, NH(aryl), N(aryl)$_2$, NH(heteroaryl), N(heteroaryl)$_2$, NH—C(=O)-aryl, NH—C(=O)-heteroaryl, NH—S(=O)$_2$-aryl, NH—S(=O)$_2$-heteroaryl, S(=O)$_2$-aryl, S(=O)$_2$-heteroaryl or aryl or heteroaryl bridged via C$_{1-8}$ alkyl, can be respectively unsubstituted or mono- or polysubstituted with one or more substituents each selected independently of one another from the group consisting of F, Cl, Br, I, NO$_2$, CN, OH, =, O—C$_{1-4}$ alkyl, OCF$_3$, CF$_3$, NH$_2$, NH(C$_{1-4}$ alkyl), N(C$_{1-4}$ alkyl)$_2$, SH, S—C$_{1-4}$ alkyl, SCF$_3$, S(=O)$_2$OH and NH—S(=O)$_2$—C$_{1-4}$ alkyl, and wherein if appropriate the alkyl chain can be respectively branched or unbranched, saturated or unsaturated, unsubstituted, mono- or polysubstituted with one or more substituents each selected independently of one another from the group consisting of F, Cl, Br, I, OH and O—C$_{1-4}$ alkyl.

In another preferred embodiment of the compounds according to the invention of general formula (I), the residue R$^1$ represents substructure (T1)

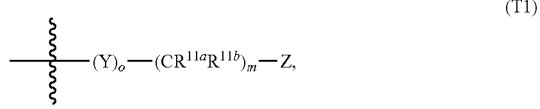

(T1)

in which

Y represents C(=O), O, S, S(=O)$_2$, NH—C(=O) or NR$^{12}$, wherein R$^{12}$ represents H; C$_{1-8}$ alkyl or S(=O)$_2$—C$_{1-8}$ alkyl, in which C$_{1-8}$ alkyl can be respectively saturated or unsaturated, branched or unbranched, unsubstituted or mono- or polysubstituted with one or more substituents each selected independently of one another from the group consisting of F, Cl, Br, I, OH, O—C$_{1-4}$ alkyl, OCF$_3$, NH$_2$, NH—C$_{1-4}$ alkyl and N(C$_{1-4}$ alkyl)$_2$;

o represents 0 or 1,

R$^{11a}$ and R$^{11b}$ each independently of one another represent H; F; Cl; Br; I; NO$_2$; CF$_3$; CN; OH; OCF$_3$; NH$_2$; C$_{1-4}$ alkyl, O—C$_{1-4}$ alkyl, NH—C$_{1-4}$ alkyl, N(C$_{1-4}$ alkyl)$_2$, in which C$_{1-4}$ alkyl can be respectively saturated or unsaturated, branched or unbranched, unsubstituted or mono- or polysubstituted with one or more substituents each selected independently of one another from the group consisting of F, Cl, Br, I, O—C$_{1-4}$ alkyl, OH and OCF$_3$;

on the condition that if R$^{11a}$ and R$^{11b}$ are bound to the same carbon atom, only one of the substituents R$^{11a}$ and R$^{11b}$ can represent OH, OCF$_3$, NH$_2$, O—C$_{1-4}$ alkyl, NH—C$_{1-4}$ alkyl or N(C$_{1-4}$ alkyl)$_2$;

m represents 0, 1, 2, 3 or 4;

Z represents C$_{1-4}$ alkyl, saturated or unsaturated, branched or unbranched, unsubstituted or mono- or polysubstituted with one or more substituents each selected independently of one another from the group consisting of F, Cl, Br, I, NO$_2$, CN, OH, =O, O—C$_{1-4}$ alkyl, OCF$_3$, C(=O)—OH, CF$_3$, NH$_2$, NH(C$_{1-4}$ alkyl), N(C$_{1-4}$ alkyl)$_2$, SH, S—C$_{14}$ alkyl, SCF$_3$ and S(=O)$_2$OH; C$_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, SH, S—C$_{1-4}$ alkyl, SCF$_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH; aryl or heteroaryl, respectively unsubstituted or mono- or polysubstituted with one or more substituents each selected independently of one another from the group consisting of F, Cl, Br, I, NO$_2$, CN, OH, O—C$_{1-4}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, NO$_2$, CN, OH, O—C$_{1-8}$ alkyl, OCF$_3$, C$_{1-4}$ alkyl, C(=O)—OH, CF$_3$, NH$_2$, NH(C$_{1-4}$ alkyl), N(C$_{1-4}$ alkyl)$_2$, SH, S—C$_{1-4}$ alkyl, SCF$_3$ and S(=O)$_2$OH.

If m≠0, then the residues R$^{11a}$ and R$^{11b}$ can, taking account of the foregoing condition, both on the same carbon atom and on different carbon atoms, each independently of one another represent H; F; Cl; Br; I; NO$_2$; CF$_3$; CN; OH; OCF$_3$; NH$_2$; C$_{1-4}$ alkyl, O—C$_{1-4}$ alkyl, NH—C$_{1-4}$ alkyl, N(C$_{1-4}$ alkyl)$_2$, in which C$_{1-4}$ alkyl can be respectively saturated or unsaturated, branched or unbranched, unsubstituted or mono- or polysubstituted with one or more substituents each selected independently of one another from the group consisting of F, Cl, Br, I, O—C$_{1-4}$ alkyl, OH and OCF$_3$.

Preferably, the residue $R^1$ represents substructure (T1) in which

Y represents C(=O), O, S, S(=O)$_2$, NH—C(=O) or $NR^{12}$, wherein $R^{12}$ represents H; methyl; ethyl; n-propyl; isopropyl; n-butyl; sec.-butyl; tert.-butyl; S(=O)$_2$-methyl; S(=O)$_2$-ethyl;

o represents 0 or 1;

$R^{11a}$ and $R^{11b}$ each independently of one another represent H; F; Cl; Br; I; NO$_2$; CF$_3$; CN; methyl; ethyl; n-propyl; isopropyl; n-butyl; sec.-butyl; tert.-butyl; CH$_2$CF$_3$; OH; O-methyl; O-ethyl; O—(CH$_2$)$_2$—O—CH$_3$; O—(CH$_2$)$_2$—OH; OCF$_3$; NH$_2$; NH-methyl; N(methyl)$_2$; NH-ethyl; N(ethyl)$_2$; or N(methyl)(ethyl);

on the condition that if $R^{11a}$ and $R^{11b}$ are bound to the same carbon atom, only one of the substituents $R^{11a}$ and $R^{11b}$ can represent OH; OCF$_3$; O-methyl; O-ethyl; O—(CH$_2$)$_2$—O—CH$_3$; O—(CH$_2$)$_2$—OH; NH$_2$; NH-methyl; N(methyl)$_2$; NH-ethyl; N(ethyl)$_2$; or N(methyl)(ethyl);

m represents 0, 1 or 2;

Z represents C$_{1-4}$ alkyl, saturated or unsaturated, branched or unbranched, unsubstituted or mono- or polysubstituted with one or more substituents each selected independently of one another from the group consisting of F, Cl, Br, I, OH, =O, O—C$_{1-4}$ alkyl, OCF$_3$, C(=O)—OH and CF$_3$; phenyl, naphthyl, furyl, pyridyl or thienyl, respectively unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, NH$_2$, NH(C$_{1-4}$ alkyl), N(C$_{1-4}$ alkyl)$_2$, SH, S—C$_{1-8}$ alkyl, SCF$_3$, benzyl and phenyl, wherein benzyl and phenyl can be respectively unsubstituted or mono- or polysubstituted with one or more substituents selected independently of one another from the group consisting of F, Cl, Br, I, CN, OH, O—C$_{1-4}$ alkyl, OCF$_3$, C$_{1-4}$ alkyl, CF$_3$, NH$_2$, NH(C$_{1-4}$ alkyl), N(C$_{1-4}$ alkyl)$_2$, SH, S—C$_{1-4}$ alkyl and SCF$_3$; C$_{3-10}$ cycloalkyl$^1$ or heterocyclyl$^1$, respectively saturated or unsaturated, unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, benzyl, phenyl and pyridyl, wherein benzyl, phenyl and pyridyl can be respectively unsubstituted or mono- or polysubstituted with one or more substituents selected independently of one another from the group consisting of F, Cl, Br, I, ON, OH, O—C$_{1-4}$ alkyl, OCF$_3$, C$_{1-4}$ alkyl, CF$_3$, NH$_2$, NH(C$_{1-4}$ alkyl), N(C$_{1-4}$ alkyl)$_2$, SH, S—C$_{1-4}$ alkyl and SCF$_3$.

If m≠0, then the residues $R^{11a}$ and $R^{11b}$ can, taking account of the foregoing condition, both on the same carbon atom and on different carbon atoms, each independently of one another represent H; F; Cl; Br; I; NO$_2$; CF$_3$; CN; methyl; ethyl; n-propyl; isopropyl; n-butyl; sec.-butyl; tert.-butyl; CH$_2$CF$_3$; OH; O-methyl; O-ethyl; O—(CH$_2$)$_2$—O—CH$_3$; O—(CH$_2$)$_2$—OH; OCF$_3$; NH$_2$; NH-methyl; N(methyl)$_2$; NH-ethyl; N(ethyl)$_2$; or N(methyl)(ethyl).

Particularly preferably, the residue $R^1$ represents substructure (T1) in which Y represents C(=O), O, S, S(=O)$_2$, NH—C(=O) or $NR^{12}$, wherein $R^{12}$ represents H; methyl; ethyl; n-propyl; isopropyl; n-butyl; sec.-butyl; tert.-butyl; S(=O)$_2$-methyl; S(=O)$_2$-ethyl;

o represents 0 or 1;

$R^{11a}$ and $R^{11b}$ each independently of one another represent H; F; Cl; Br; I; methyl; ethyl; n-propyl; isopropyl; n-butyl; sec.-butyl; tert.-butyl; OH; O-methyl; O-ethyl;

on the condition that if $R^{11a}$ and $R^{11b}$ are bound to the same carbon atom, only one of the substituents $R^{11a}$ and $R^{11b}$ can represent OH; O-methyl; O-ethyl;

m represents 0, 1 or 2;

Z represents C$_{1-4}$ alkyl, saturated or unsaturated, branched or unbranched, unsubstituted or mono- or polysubstituted with one or more substituents each selected independently of one another from the group consisting of F, Cl, Br, I, OH, O—C$_{1-4}$ alkyl, OCF$_3$, and CF$_3$; C$_{3-10}$ cycloalkyl$^1$, saturated or unsaturated, unsubstituted or mono- or polysubstituted with one or more substituents each selected independently of one another from the group consisting of F, Cl, Br, I, OH, O—C$_{1-4}$ alkyl, OCF$_3$, C$_{1-4}$ alkyl, CF$_3$, benzyl and phenyl, wherein benzyl and phenyl can be respectively unsubstituted or mono- or polysubstituted with one or more substituents selected independently of one another from the group consisting of F, Cl, Br, I, OH, O—C$_{1-4}$ alkyl, OCF$_3$, C$_{1-4}$ alkyl, CF$_3$, and SCF$_3$; morpholinyl, thiomorpholinyl, piperidinyl, pyrrolidinyl, 4-methylpiperazinyl, piperazinyl, respectively unsubstituted or mono- or polysubstituted with one or more substituents each selected independently of one another from the group consisting of F, Cl, Br, I, OH, O—C$_{1-4}$ alkyl, OCF$_3$, C$_{1-4}$ alkyl, CF$_3$, benzyl and phenyl, wherein benzyl and phenyl can be respectively unsubstituted or mono- or polysubstituted with one or more substituents selected independently of one another from the group consisting of F, Cl, Br, I, OH, O—C$_{1-4}$ alkyl, OCF$_3$, C$_{1-4}$ alkyl, CF$_3$ and SCF$_3$; phenyl, naphthyl, pyridyl or thienyl, respectively unsubstituted or mono- or polysubstituted with one or more substituents each selected independently of one another from the group consisting of F, Cl, Br, I, CN, OH, O—C$_{1-4}$ alkyl, OCF$_3$, C$_{1-4}$ alkyl, CF$_3$, SH, S—C$_{1-4}$ alkyl, SCF$_3$, benzyl and phenyl, wherein benzyl and phenyl can be respectively unsubstituted or mono- or polysubstituted with one or more substituents selected independently of one another from the group consisting of F, Cl, Br, I, OH, O—C$_{1-4}$ alkyl, OCF$_3$, C$_{1-4}$ alkyl, CF$_3$ and SCF$_3$.

If m≠0, then the residues $R^{11a}$ and $R^{11b}$ can, taking account of the foregoing condition, both on the same carbon atom and on different carbon atoms, each independently of one another represent H; F; Cl; Br; I; methyl; ethyl; n-propyl; isopropyl; n-butyl; sec.-butyl; tert.-butyl; OH; O-methyl; O-ethyl.

Most particularly preferably, the residue $R^1$ represents substructure (T1) in which Y represents C(=O), O, S, S(=O)$_2$, NH—C(=O) or $NR^{12}$, wherein $R^{12}$ represents H; methyl; ethyl; n-propyl; isopropyl; n-butyl; sec.-butyl; tert.-butyl; S(=O)$_2$-methyl;

o represents 0 or 1;

$R^{11a}$ and $R^{11b}$ each independently of one another represent H; methyl; ethyl; n-propyl; isopropyl; n-butyl; sec.-butyl; tert.-butyl;

m represents 0, 1 or 2;

Z represents C$_{1-4}$ alkyl, saturated or unsaturated, branched or unbranched, unsubstituted or mono- or polysubstituted with one or more substituents each selected independently of one another from the group consisting of F, Cl, Br, I, OH, O—C$_{1-4}$ alkyl; C$_{3-10}$ cycloalkyl$^1$, saturated or unsaturated, morpholinyl, piperidinyl, 4-methylpiperazinyl, piperazinyl, respectively unsubstituted or mono- or polysubstituted with one or more substituents each selected independently of one another from the group consisting of F, Cl, Br, I, OH, O—C$_{1-4}$ alkyl and C$_{1-4}$ alkyl; phenyl or pyridyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$.

If m≠0, then the residues $R^{11a}$ and $R^{11b}$ can, both on the same carbon atom and on different carbon atoms, each independently of one another represent H; methyl; ethyl; n-propyl; isopropyl; n-butyl; sec.-butyl; tert.-butyl.

In a further preferred embodiment of the compounds according to the invention of general formula (I), the residue $R^2$ represents H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =, O—$C_{1-4}$ alkyl, $OCF_3$, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$; $C_{3-10}$ cycloalkyl or heterocyclyl, respectively saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$, C(=O)—OH and $CF_3$; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br, I, OH, =O, $C_{1-4}$ alkyl, O—$C_{1-4}$ alkyl, $OCF_3$, C(=O)—OH and $CF_3$, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-8}$ alkyl, $SCF_3$, $S(=O)_2OH$, benzyl, phenyl, pyridyl and thienyl, wherein benzyl, phenyl, pyridyl, thienyl can be respectively unsubstituted or mono- or polysubstituted with one or more substituents each selected independently of one another from the group consisting of F, Cl, Br, I, OH, =O and O—$C_{1-4}$ alkyl.

Preferably, the residue $R^2$ represents H; F; Cl; Br; I; CN; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently of one another from the group consisting of F, Cl, Br, I, CN, OH, =O, O—$C_{1-4}$ alkyl, $OCF_3$, $CF_3$, $NH_2$, $NH(C_{1-4}$ alkyl), $N(C_{1-4}$ alkyl$)_2$, SH, S—$C_{1-4}$ alkyl, $SCF_3$; $C_{3-10}$ cycloalkyl, saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$ and $CF_3$; or $C_{3-10}$ cycloalkyl bridged via $C_{1-8}$ alkyl, saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$ and $CF_3$, wherein the alkyl chain can be respectively branched or unbranched, saturated or unsaturated, unsubstituted; aryl or heteroaryl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-8}$ alkyl, $SCF_3$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$ and $S(=O)_2OH$, wherein the alkyl chain can be respectively branched or unbranched, saturated or unsaturated, unsubstituted.

Particularly preferably, $R^2$ represents H; F; Cl; Br; I; CN; $C_{1-10}$ alkyl, saturated or unsaturated, branched or unbranched, unsubstituted or mono- or polysubstituted with one or more substituents selected independently of one another from the group consisting of F, Cl, Br, I and OH; $C_{3-10}$ cycloalkyl, saturated or unsaturated, unsubstituted; or $C_{3-10}$ cycloalkyl bridged via $C_{1-4}$ alkyl, saturated or unsaturated, unsubstituted, wherein the alkyl chain can be branched or unbranched, saturated or unsaturated, unsubstituted; or phenyl, pyridyl, thienyl, respectively unsubstituted or mono- or polysubstituted with one or more substituents selected independently of one another from the group consisting of $C_{1-4}$ alkyl, O—$C_{1-4}$ alkyl, F, Cl, Br, I, $CF_3$, $OCF_3$, OH, SH and $SCF_3$; or phenyl, pyridyl or thienyl bridged via $C_{1-4}$ alkyl, respectively unsubstituted or mono- or polysubstituted with one or more substituents selected independently of one another from the group consisting of $C_{1-4}$ alkyl, O—$C_{1-4}$ alkyl, F, Cl, Br, I, $CF_3$, $OCF_3$, OH, SH and $SCF_3$, wherein the alkyl chain can be branched or unbranched, saturated or unsaturated, unsubstituted.

Most particularly preferably, the substituent $R^2$ is selected from the group consisting of H; F; Cl; Br; I; CN; cyclopropyl; cyclobutyl; $C_{1-10}$ alkyl, saturated or unsaturated, branched or unbranched, unsubstituted, or mono- or polysubstituted with one or more substituents selected independently of one another from the group consisting of F, Cl, Br; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$.

Particularly preferably, the substituent $R^2$ represents H; F; Cl; Br; I; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$;

Especially particularly preferably, $R^2$ represents tert.-butyl or $CF_3$.

In another preferred embodiment of the compounds according to the invention of general formula (I), X represents $CR^3$ or N, preferably $CR^3$,
wherein $R^3$ represents H; $C_{1-10}$ alkyl, saturated or unsaturated, branched or unbranched, unsubstituted, mono- or polysubstituted with one or more substituents each selected independently of one another from the group consisting of F, Cl, Br, I and OH;

Preferably,

X represents $CR^3$ or N, preferably $CR^3$,
wherein $R^3$ represents H; $C_{1-10}$ alkyl, saturated or unsaturated, branched or unbranched, unsubstituted; or $CF_3$.

Particularly preferably,

X represents $CR^3$ or N, preferably $CR^3$,
wherein $R^3$ represents H; methyl; ethyl; n-propyl; isopropyl; n-butyl; sec.-butyl; tert.-butyl; or $CF_3$.

Most particularly preferably,

X represents $CR^3$ or N, preferably $CR^3$,
wherein $R^3$ represents H or $CH_3$, most preferred represents H.

In a further preferred embodiment of the compounds according to the invention of general formula (I), the residue $R^4$ represents H; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

A represents N or $CR^{5b}$;

$R^{5a}$ represents H; OH; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl; $C_{3-10}$ cycloalkyl or heterocyclyl, respectively saturated or unsaturated, unsubstituted or mono- or polysubstituted with one or more substituents each selected independently of one another from the group consisting of F, Cl, Br; I, OH, =O and O—$C_{1-4}$ alkyl; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br; I, OH, =O and O—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br; I, OH, =O and O—$C_{1-4}$ alkyl; or aryl, heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, $S(=O)_2OH$ and NH—$S(=O)_2$—$C_{1-4}$ alkyl; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, $S(=O)_2OH$ and NH—$S(=O)_2$—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br; I, OH, =O and O—$C_{1-4}$ alkyl;

or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently of one another from the group consisting of F, Cl, Br; I, OH, =O and O—$C_{1-4}$ alkyl.

Preferably, the residue $R^4$ represents H; or $C_{1-10}$ alkyl, saturated or unsaturated, branched or unbranched, unsubstituted;

A represents N or $CR^{5b}$;

$R^{5a}$ represents H; or $C_{1-10}$ alkyl, saturated or unsaturated, branched or unbranched, unsubstituted;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br, I, OH and $C_{1-4}$ alkyl; $C_{3-10}$ cycloalkyl, saturated or unsaturated, unsubstituted or mono- or polysubstituted with one or more substituents each selected independently of one another from the group consisting of F, Cl, Br, I and $C_{1-4}$ alkyl; or $C_{3-10}$ cycloalkyl bridged via $C_{1-4}$ alkyl, saturated or unsaturated, unsubstituted or mono- or polysubstituted with one or more substituents each selected independently of one another from the group consisting of F, Cl, Br, I and $C_{1-4}$ alkyl, wherein the alkyl chain can be respectively branched or unbranched, saturated or unsaturated, unsubstituted; or phenyl or pyridyl, respectively unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-4}$ alkyl, $SCF_3$ and NH—$S(=O)_2$—$C_{1-4}$ alkyl; or phenyl or pyridyl bridged via $C_{1-4}$ alkyl, respectively unsubstituted or mono- or polysubstituted with one or more substituents each selected independently of one another from the group consisting of F, Cl, Br, I, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl$)_2$, SH, S—$C_{1-4}$ alkyl, $SCF_3$ and NH—$S(=O)_2$—$C_{1-4}$ alkyl, wherein the alkyl chain can be respectively branched or unbranched, saturated or unsaturated, unsubstituted, or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently of one another from the group consisting of F, Cl, Br, I, OH, =O and O—$C_{1-4}$ alkyl.

Particularly preferably, the residue $R^4$ represents H; methyl; ethyl; n-propyl; or isopropyl;

A represents N or $CR^{5b}$;

$R^{5a}$ represents H if A or $CH_3$, preferably H, represents N;

or $R^{5a}$ represents H or $CH_3$, preferably H, if A represents $CR^{5b}$, wherein $R^{5b}$ represents H; or $C_{1-4}$ alkyl, saturated or unsaturated, branched or unbranched, unsubstituted; $C_{3-10}$ cycloalkyl, saturated or unsaturated, unsubstituted; or phenyl or benzyl, in each case unsubstituted or mono- or polysubstituted with one or more substituents each selected independently of one another from the group consisting of F, Cl, Br, I, $CF_3$, O—$C_{1-4}$ alkyl, $OCF_3$ and $C_{1-4}$ alkyl, or $R^{5a}$ and $R^{5b}$ form together with the carbon atom connecting them a $C_{3-10}$ cycloalkyl, saturated or unsaturated, unsubstituted or mono- or polysubstituted with one or more substituents each selected independently of one another from the group consisting of F, Cl, Br, I, OH, =O and O—$C_{1-4}$ alkyl.

Most particularly preferably, the residue

A represents N or $CR^{5b}$;

$R^4$ represents H;

$R^{5a}$ represents H;

$R^{5b}$ represents H; or $C_{1-4}$ alkyl, saturated or unsaturated, branched or unbranched, unsubstituted; cyclohexyl, unsubstituted; or phenyl or benzyl, in each case unsubstituted or mono- or polysubstituted with one or more substituents each selected independently of one another from the group consisting of F, Cl, Br, I, O—$C_{1-4}$ alkyl, $CF_3$, $OCF_3$ and $C_{1-4}$ alkyl, or $R^{5a}$ and $R^{5b}$ form together with the carbon atom connecting them a $C_{3-10}$ cycloalkyl, saturated or unsaturated, unsubstituted.

In a further preferred embodiment of the compounds according to the invention of general formula (I), T represents $CR^6$;
U represents $CR^7$;
V represents $CR^8$;
W represents N or $CR^9$;
G represents N or $CR^{10}$.

In another preferred embodiment of the compounds according to the invention of general formula (I),

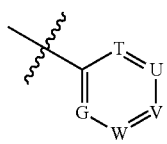

substructure (T2)

represents one of the substructures (T2a), (T2b), (T2c) or (T2d)

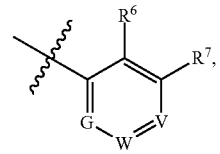
(T2a)

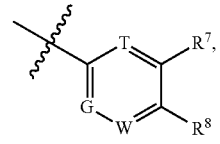
(T2b)

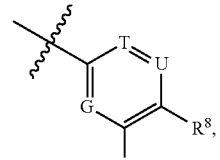
(T2c)

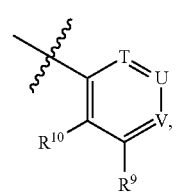
(T2d)

in which
in the substructure (T2a) $R^6$ and $R^7$ together;
in the substructure (T2b) $R^7$ and $R^8$ together;
in the substructure (T2c) $R^8$ and $R^9$ together;
in the substructure (T2d) $R^9$ and $R^{10}$ together;
in pairs, in each case independently of one another, together with the carbon atoms connecting them,
form a $C_{3-10}$ cycloalkyl or heterocyclyl, respectively saturated or unsaturated, unsubstituted or mono- or polysubstituted with one or more substituents each selected independently of one another from the group consisting of =O, =N(OH), =NH, —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$,
wherein it is possible for $C_{3-10}$ cycloalkyl or heterocyclyl if appropriate to be condensed in each case with aryl or heteroaryl, respectively unsubstituted or mono- or polysubstituted with one or more substituents each selected independently of one another from the group consisting of —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;
or form an aryl or heteroaryl, respectively unsubstituted or mono- or polysubstituted with one or more substituents each selected independently of one another from the group consisting of $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein it is possible for aryl or heteroaryl if appropriate to be condensed in each case with $C_{3-10}$ cycloalkyl or heterocyclyl, respectively saturated or unsaturated, unsubstituted or mono- or polysubstituted with one or more substituents each selected independently of one another from the group consisting of =O, =N(OH), =NH, —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;

wherein at most three, preferably at most two of the remaining residues T, U, V, W or G are able to represent N simultaneously, more preferably at most one of the residues T, U, V, W or G, most preferably none of the residues T, U, V, W or G are able to represent N;

the respective remaining substituents of $R^6$, $R^7$, $R^8$, $R^9$ and $R^{10}$ are each selected independently of one another from the group consisting of H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$.

The substructure (T2) preferably represents one of the substructures (T2a), (T2b), (T2c) or (T2d),
in which
in the substructure (T2a) $R^6$ and $R^7$ together;
in the substructure (T2b) $R^7$ and $R^8$ together;
in the substructure (T2c) $R^8$ and $R^9$ together;
in the substructure (T2d) $R^9$ and $R^{10}$ together;
in pairs, in each case independently of one another, together with the carbon atoms connecting them,
form a $C_{3-10}$ cycloalkyl or heterocyclyl, respectively saturated or unsaturated, unsubstituted or mono- or polysubstituted with one or more substituents each selected independently of one another from the group consisting of =O, =N(OH), =NH, —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein it is possible for $C_{3-10}$ cycloalkyl or heterocyclyl if appropriate to be condensed in each case with aryl or heteroaryl, respectively unsubstituted or mono- or polysubstituted with one or more substituents each selected independently of one another from the group consisting of —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;

or form an aryl or heteroaryl, respectively unsubstituted or mono- or polysubstituted with one or more substituents each selected independently of one another from the group consisting of $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-14}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$, wherein it is possible for aryl or heteroaryl if appropriate to be condensed in each case with $C_{3-10}$ cycloalkyl or heterocyclyl, respectively saturated or unsaturated, unsubstituted or mono- or polysubstituted with one or more substituents each selected independently of one another from the group consisting of =O, =N(OH), =NH, —O—$C_{1-4}$ alkyl-O—, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;

wherein at most three, preferably at most two of the remaining residues T, U, V, W or G are able to represent N simultaneously, more preferably at most one of the residues T, U, V, W or G, most preferably none of the residues T, U, V, W or G are able to represent N;

the respective remaining substituents of $R^6$, $R^7$, $R^8$, $R^9$ and $R^{10}$ are each selected independently of one another from the group consisting of H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl and $SCF_3$, preferably are each selected independently of one another from the group consisting of H, OH, $C_{1-4}$ alkyl, O—$C_{1-4}$ alkyl, F, Cl, Br, I, $CF_3$, and NH—$SO_2$—$C_{1-4}$ alkyl, more preferably are each selected independently of one another from the group consisting of H, OH, $C_{1-4}$ alkyl, O—$C_{1-4}$ alkyl and NH—$SO_2$—$C_{1-4}$ alkyl, most preferably respectively represent H.

In a further preferred embodiment of the compounds according to the invention of general formula (I), substructure (T2)

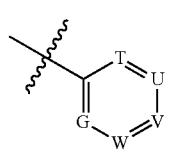

(a1) represents one of the substructures (T3a) or (T3b)

(T3a)

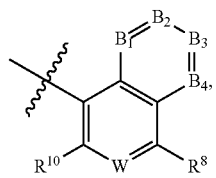

(T3b)

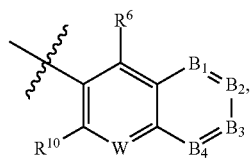

in which
W represents N or $CR^9$;
$B_1$ in each case represents N or $CR^{100a}$;
$B_2$ in each case represents N or $CR^{100b}$;

$B_3$ in each case represents N or $CR^{100c}$;
$B_4$ in each case represents N or $CR^{100d}$;
wherein in each case at most two of the residues $B_1$, $B_2$, $B_3$ and $B_4$ are able to represent N simultaneously;
$R^{100a}$, $R^{100b}$, $R^{100c}$ and $R^{100d}$ are each selected independently of one another from the group consisting of H, $C_{1-4}$ alkyl, O—$C_{1-4}$ alkyl, —O—$C_{1-4}$ alkyl-O—, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;
and the remaining substituents $R^6$, $R^8$, $R^9$ and $R^{10}$ each independently of one another represent H, $C_{1-4}$ alkyl, O—$C_{1-4}$ alkyl, F, Cl, Br, I, $CF_3$, $OCF_3$, OH, SH, $NH_2$ or $SCF_3$, preferably each independently of one another represent H, OH, $C_{1-4}$ alkyl, O—$C_{1-4}$ alkyl, F, Cl, Br, I or $CF_3$, more preferably each independently of one another represent H, OH, $C_{1-4}$ alkyl or O—$C_{1-4}$ alkyl, most preferably each represent H;

or (a2) represents one of the substructures (T3c) or (T3d)

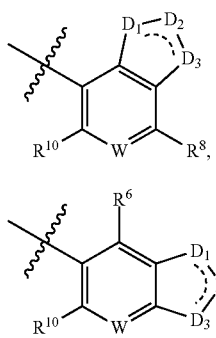

in which
W represents N or $CR^9$;
$D_1$ in each case represents N, N—$R^{101d}$, O, S or $CR^{101a}$ or CH—$R^{101a}$;
$D_2$ in each case represents N, N—$R^{101e}$, O, S or $CR^{101b}$ or CH—$R^{101b}$;
$D_3$ in each case represents N, N—$R^{101f}$, O, S or $CR^{101c}$ or CH—$R^{101c}$;
in each case represents the presence of precisely one double bond between $D_1$ and $D_2$ or between $D_2$ and $D_3$,
wherein it is possible in each case for at most one of the residues $D_1$, $D_2$ and $D_3$ to represent O, S, or N—$R^{101d-f}$ and in each case for at most two of the residues $D_1$, $D_2$ and $D_3$ simultaneously to represent N, and at least one of the residues $D_1$, $D_2$ and $D_3$ has to represent $CR^{101a}$, $CR^{101b}$ or $CR^{101c}$ if one of the remaining residues $D_1$, $D_2$ or $D_3$ represents O or S;
$R^{101a}$, $R^{101b}$ and $R^{101c}$ are each selected independently of one another from H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$, phenyl, unsubstituted or mono- or polysubstituted with one or more from the group consisting of F, Cl, Br, I, $C_{1-4}$ alkyl, O—$C_{1-4}$ alkyl, $CF_3$ and $OCF_3$; and may also represent =O, =NH or =N(OH) in the groups $CR^{101a}$, $CR^{101b}$ and $CR^{101c}$;

$R^{101d}$, $R^{101e}$, $R^{101f}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;
the remaining substituents $R^6$, $R^8$, $R^9$ and $R^{10}$ each independently of one another represent H, $C_{1-4}$ alkyl, O—$C_{1-4}$ alkyl, F, Cl, Br, I, $CF_3$, $OCF_3$, OH, SH, $NH_2$ or $SCF_3$, preferably each independently of one another represent H, OH, $C_{1-4}$ alkyl, O—$C_{1-4}$ alkyl, F, Cl, Br, I or $CF_3$, more preferably each independently of one another represent H, OH, $C_{1-4}$ alkyl or O—$C_{1-4}$ alkyl, most preferably each represent H;

or (a3) represents one of the substructures (T3e) or (T3f)

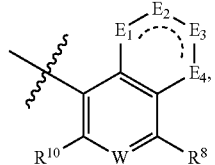

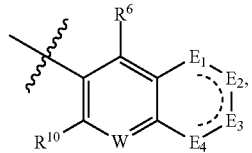

in which
W represents N or $CR^9$;
$E_1$ in each case represents N, N—$R^{102e}$, O, S, $CR^{102a}$, or CH—$R^{102a}$;
$E_2$ in each case represents N, N—$R^{102f}$, O, S, $CR^{102b}$, or CH—$R^{102b}$;
$E_3$ in each case represents N, N—$R^{102g}$, O, S, $CR^{102c}$, or CH—$R^{102c}$;
$E_4$ in each case represents N, N—$R^{102f}$, O, S, $CR^{102d}$, or CH—$R^{102d}$;
in each case represents the presence of precisely one double bond between $E_1$ and $E_2$ or between $E_2$ and $E_3$ or between $E_3$ and $E_4$; or represents the absence of a double bond, i.e. represents a single bond between $E_1$ and $E_2$ and between $E_2$ and $E_3$ and between $E_3$ and $E_4$;
wherein it is only possible in each case for two of the residues $E_1$, $E_2$, $E_3$ and $E_4$ simultaneously each independently of one another to represent N, N—$R^{102e-h}$, O or S, on the condition that if two of the residues $E_1$, $E_2$, $E_3$ and $E_4$ represent O or S, these are not mutually adjacent;
$R^{102a}$, $R^{102b}$, $R^{102c}$ and $R^{102d}$ are each selected independently of one another from H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and may also represent =O, =NH or =N(OH) in the groups $CR^{102a}$, $CR^{102b}$, $CR^{102c}$ and $CR^{101d}$;
$R^{102e}$, $R^{102f}$, $R^{102g}$, $R^{102h}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, $O-C_{1-4}$ alkyl, $CF_3$ and $OCF_3$;

the remaining substituents $R^6$, $R^8$, $R^9$ and $R^{10}$ each independently of one another represent H, $C_{1-4}$ alkyl, $O-C_{1-4}$ alkyl, F, Cl, Br, I, $CF_3$, $OCF_3$, OH, SH, $NH_2$ or $SCF_3$, preferably each independently of one another represent H, OH $C_{1-4}$ alkyl, $O-C_{1-4}$ alkyl, F, Cl, Br, I or $CF_3$, most preferably each independently of one another represent H, OH, $C_{1-4}$ alkyl or $O-C_{1-4}$ alkyl, most preferably each represent H;

or (a4) represents one of the substructures (T3g) or (T3h)

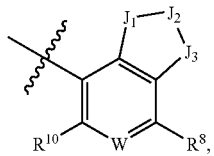
(T3g)

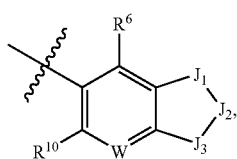
(T3h)

in which

W represents N or $CR^9$;

$J_1$ in each case represents $N-R^{103d}$, O, S, or $C(R^{103a})_2$;

$J_2$ in each case represents $N-R^{103e}$, O, S, or $C(R^{103b})_2$;

$J_3$ in each case represents $N-R^{103f}$, O, S, or $C(R^{103c})_2$;

wherein it is only possible in each case for two of the residues $J_1$, $J_2$ and $J_3$ simultaneously each independently of one another to represent $N-R^{103d-f}$, O or S, on the condition that if two of the residues $J_1$, $J_2$ and $J_3$ represent O or S, these are not mutually adjacent;

$R^{103a}$, $R^{103b}$ and $R^{103c}$ are each selected independently of one another from H, $C_{1-4}$ alkyl, =O; =NH; =N(OH); $O-C_{1-4}$ alkyl, F, Cl, Br, I, $CF_3$, $OCF_3$, OH, SH, $NH_2$, $NH-C_{1-4}$ alkyl, $N(C_{1-4}$ alkyl$)_2$, $NH-SO_2-C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, $O-C_{1-4}$ alkyl, $CF_3$ and $OCF_3$;

$R^{103d}$, $R^{103e}$ and $R^{103f}$ each independently of one another represent H, $C_{1-4}$ alkyl, $SO_2-C_{1-4}$ alkyl or phenyl, unsubstituted or mono- or polysubstituted with one or more substituents each selected independently of one another from the group consisting of F, Cl, Br, I, $C_{1-4}$ alkyl, $O-C_{1-4}$ alkyl, $CF_3$ and $OCF_3$;

the remaining substituents $R^6$, $R^8$, $R^9$ and $R^{10}$ each independently of one another represent H, OH, $C_{1-4}$ alkyl, $O-C_{1-4}$ alkyl, F, Cl, Br, I, $CF_3$, $OCF_3$, OH, SH, $NH_2$ or $SCF_3$;

or (a5) represents one of the substructures (T3i) or (T3j)

(T3i)

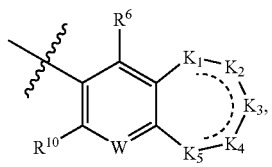
(T3j)

in which $K_1$ in each case represents N, $N-R^{104f}$, O, S, $CR^{104a}$, or $CH-R^{104a}$;

$K_2$ in each case represents N, $N-R^{104g}$, O, S, $CR^{104b}$, or $CH-R^{104b}$;

$K_3$ in each case represents N, $N-R^{104h}$, O, S, $CR^{104c}$, or $CH-R^{104c}$;

$K_4$ in each case represents N, $N-R^{104i}$, O, S, $CR^{104d}$, or $CH-R^{104d}$;

$K_5$ in each case represents N, $N-R^{104j}$, O, S, $CR^{104e}$, or $CH-R^{104e}$;

in each case represents the presence of precisely one double bond between $K_1$ and $K_2$ or between $K_2$ and $K_3$ or between $K_3$ and $K_4$ or between $K_4$ and $K_5$; or represents the absence of a double bond, i.e. represents a single bond between $K_1$ and $K_2$ and between $K_2$ and $K_3$ and between $K_3$ and $K_4$ and between $K_4$ and $K_5$;

wherein it is only possible in each case for two of the residues $K_1$, $K_2$, $K_3$, $K_4$ and $K_5$ simultaneously each independently of one another to represent N, $N-R^{104f}$, O or S; on the condition that if two of the residues $K_1$, $K_2$, $K_3$, $K_4$ and $K_5$ represent O or S, these are not mutually adjacent;

$R^{104a}$, $R^{104b}$, $R^{104c}$, $R^{104d}$ and $R^{104e}$ are each selected independently of one another from H, $C_{1-4}$ alkyl, $O-C_{1-4}$ alkyl, F, Cl, Br, I, $CF_3$, $OCF_3$, OH, SH, $NH_2$, $NH-C_{1-4}$ alkyl, $N(C_{1-4}$ alkyl$)_2$, $NH-SO_2-C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, $O-C_{1-4}$ alkyl, $CF_3$ and $OCF_3$; and may also represent =O, =NH or =N(OH) in the groups $CR^{104a}$, $CR^{104b}$, $CR^{104c}$, $CR^{104d}$ and $CR^{101e}$;

$R^{104f}$, $R^{104g}$, $R^{104h}$, $R^{104i}$ and $R^{104j}$ each independently of one another represent H, $C_{1-4}$ alkyl, $SO_2-C_{1-4}$ alkyl or phenyl, unsubstituted or mono- or polysubstituted with one or more substituents each selected independently of one another from the group consisting of F, Cl, Br, I, $C_{1-4}$ alkyl, $O-C_{1-4}$ alkyl, $CF_3$ and $OCF_3$;

the remaining substituents $R^6$, $R^8$, $R^9$ and $R^{10}$ each independently of one another represent H, $C_{1-4}$ alkyl, $O-C_{1-4}$ alkyl, F, Cl, Br, I, $CF_3$, $OCF_3$, OH, SH, $NH_2$ or $SCF_3$, preferably each independently of one another represent H, OH, $C_{1-4}$ alkyl, $O-C_{1-4}$ alkyl, F, Cl, Br, I or $CF_3$, more preferably each independently of one another represent H, OH, $C_{1-4}$ alkyl or $O-C_{1-4}$ alkyl, most preferably each represent H.

In a further preferred embodiment of the compounds according to the invention of general formula (I), (a1) the substructures (T3a) and (T3b) are selected from the following substructures

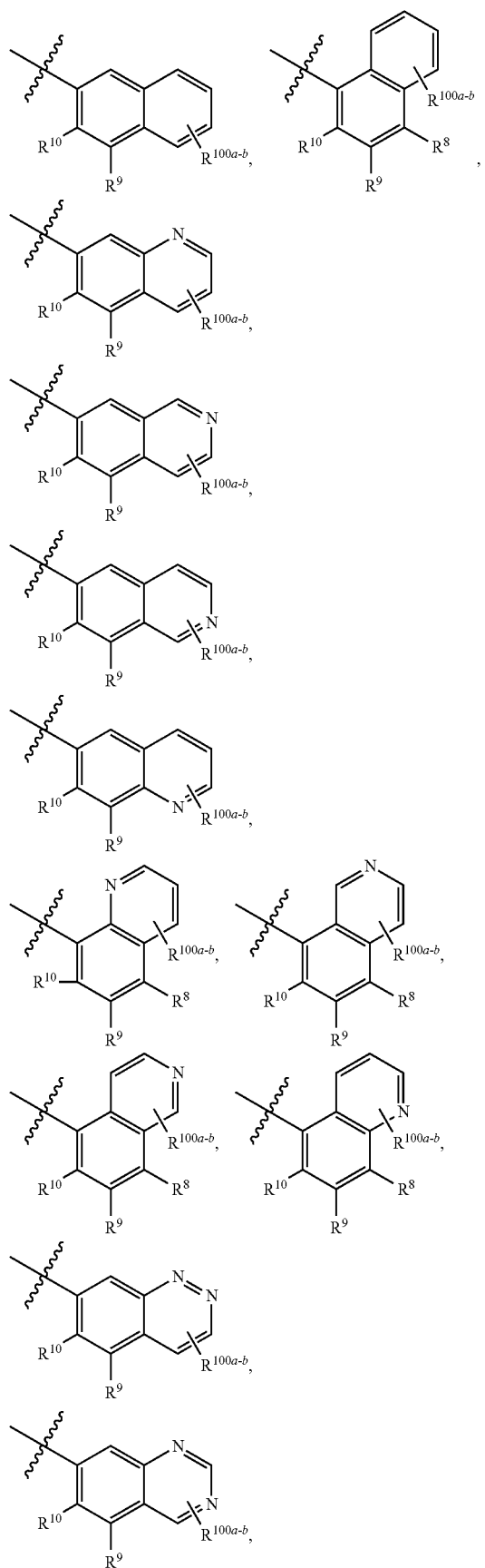
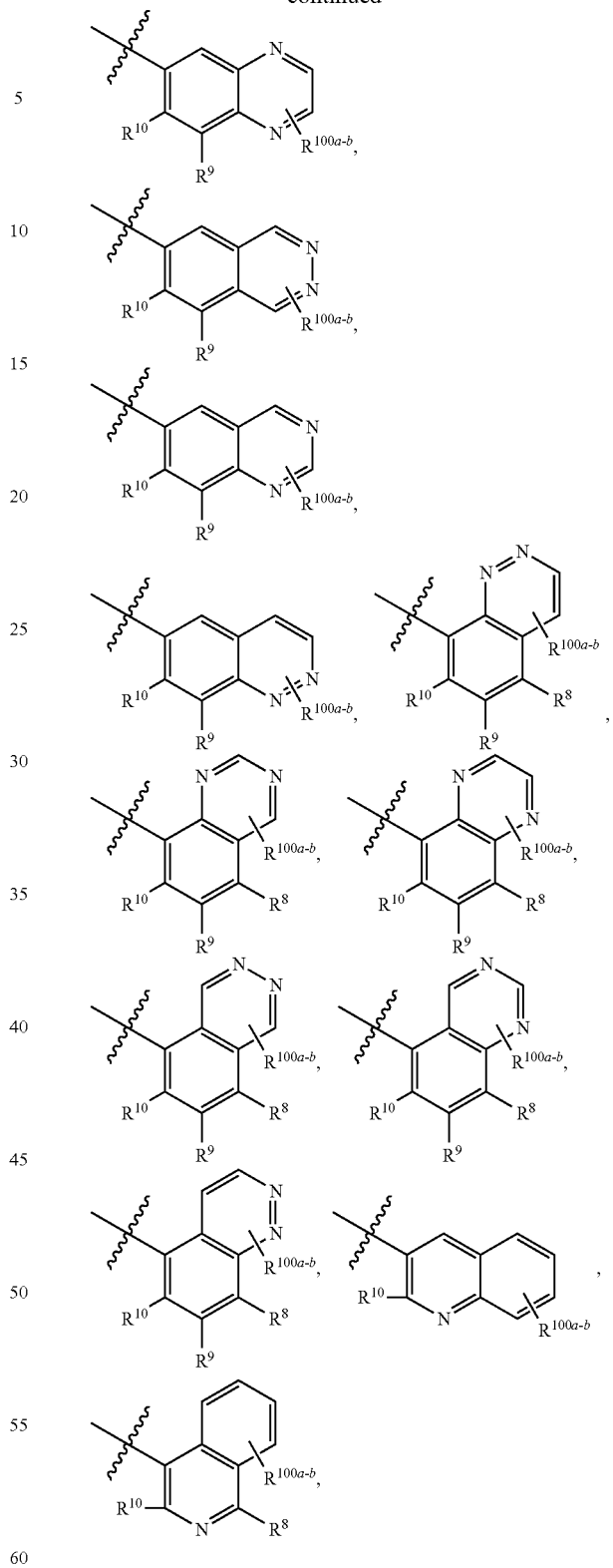

wherein $R^{100a\text{-}b}$ represents the substituents $R^{100a}$ and $R^{100b}$ and these are each independently of one another selected from H, $C_{1\text{-}4}$ alkyl, O—$C_{1\text{-}4}$ alkyl, F, Cl, Br, I, $CF_3$, $OCF_3$, OH, SH, $NH_2$, NH—$C_{1\text{-}4}$ alkyl, N($C_{1\text{-}4}$ alkyl)$_2$, NH—$SO_2$—$C_{1\text{-}4}$ alkyl, $SCF_3$ and phenyl, unsubstituted; $R^8$, $R^9$ and $R^{10}$ each independently of one another represent H; $C_{1\text{-}4}$ alkyl, OH or O—$C_{1\text{-}4}$ alkyl;

(a2) the substructures (T3c) and (T3d) are selected from the following substructures
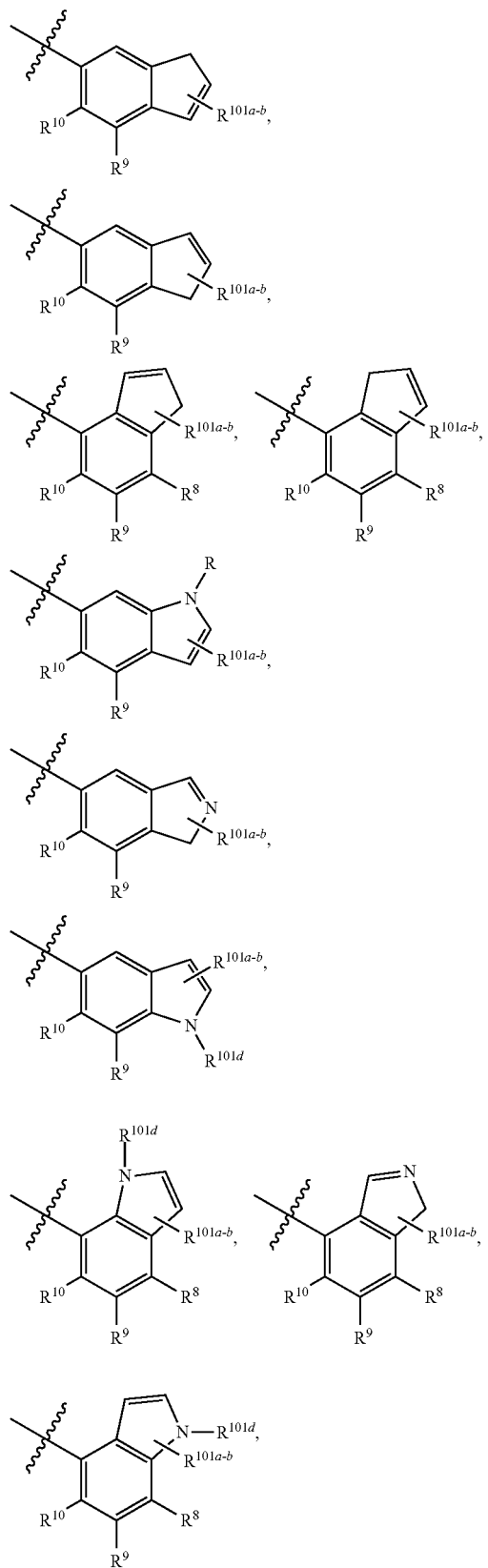
-continued
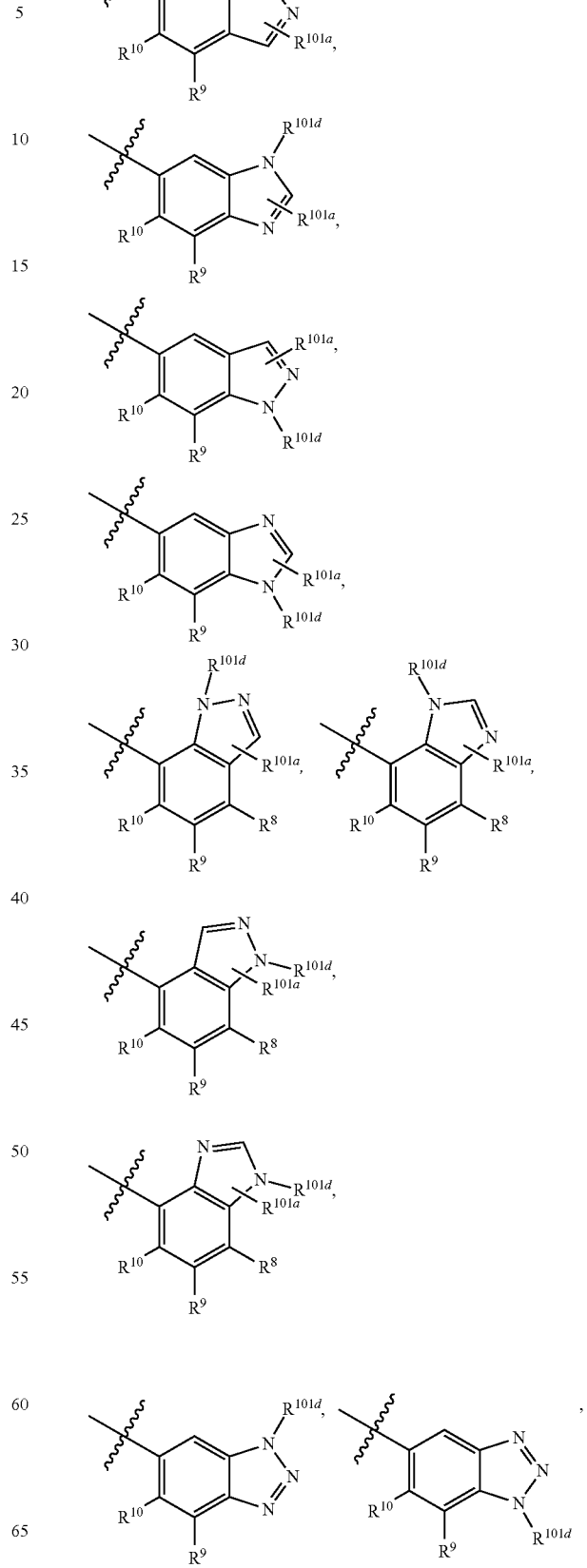

-continued

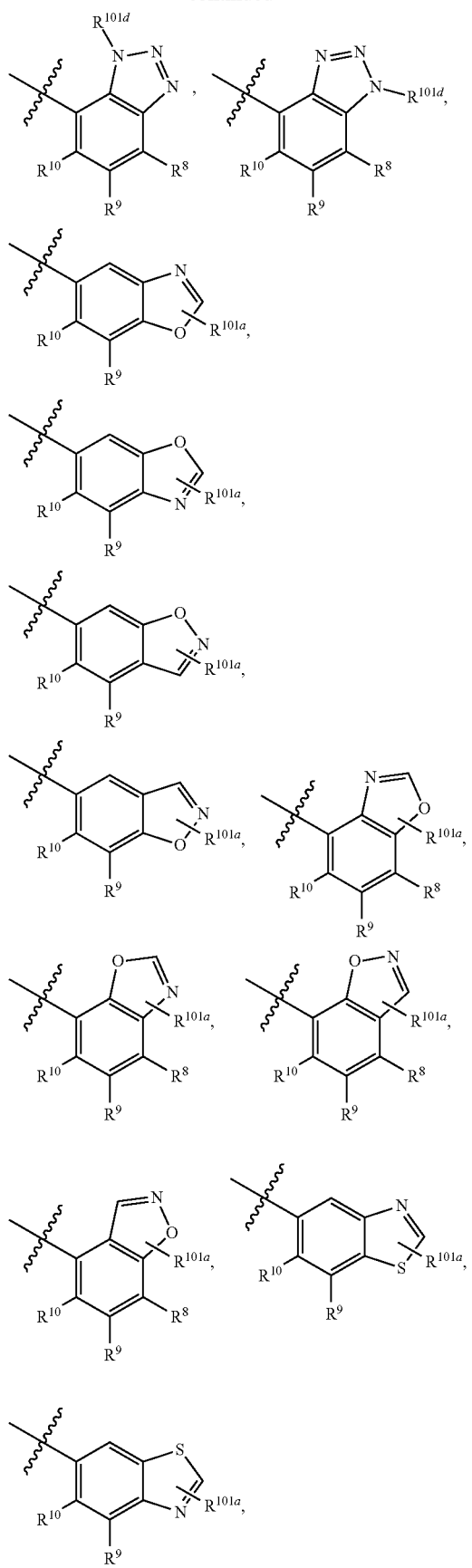

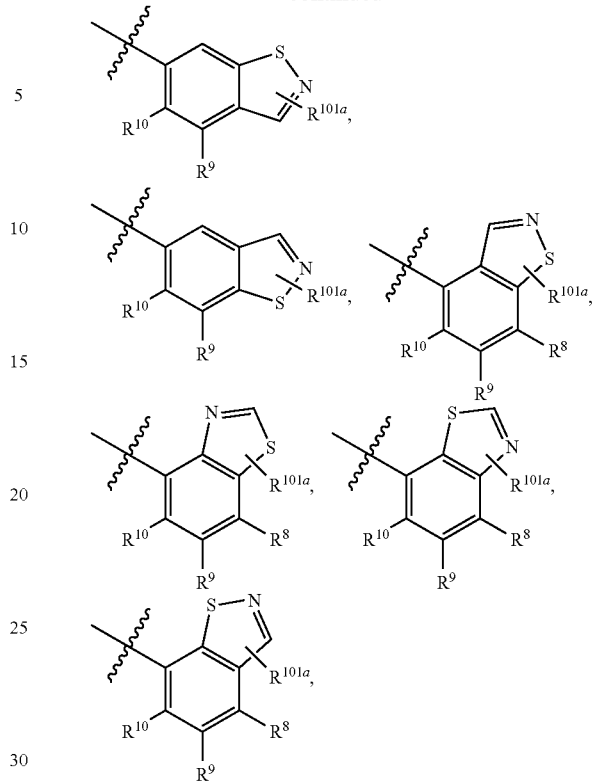

wherein $R^{101a-b}$ represents the substituents $R^{101a}$ and $R^{101b}$ and these are each selected independently of one another from H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, $N(C_{1-4}$ alkyl$)_2$, NH—$SO_2$—$C_{1-4}$ alkyl, $SCF_3$ and phenyl and also if appropriate from the group consisting of =O, =NH and =N(OH);

$R^{101d}$ is in each case independently selected from H, $SO_2$—$C_{1-4}$ alkyl, $C_{1-4}$ alkyl and phenyl, unsubstituted;

$R^8$, $R^9$ and $R^{10}$ each independently of one another represent H; $C_{1-4}$ alkyl, OH or O—$C_{1-4}$ alkyl;

(a3) the substructures (T3e) and (T3f) are selected from the following substructures

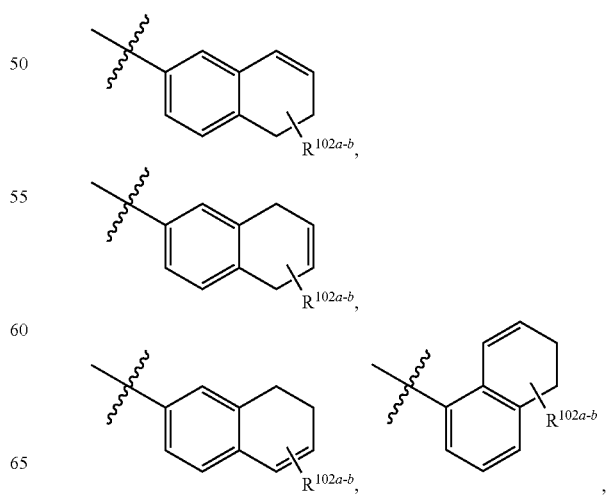

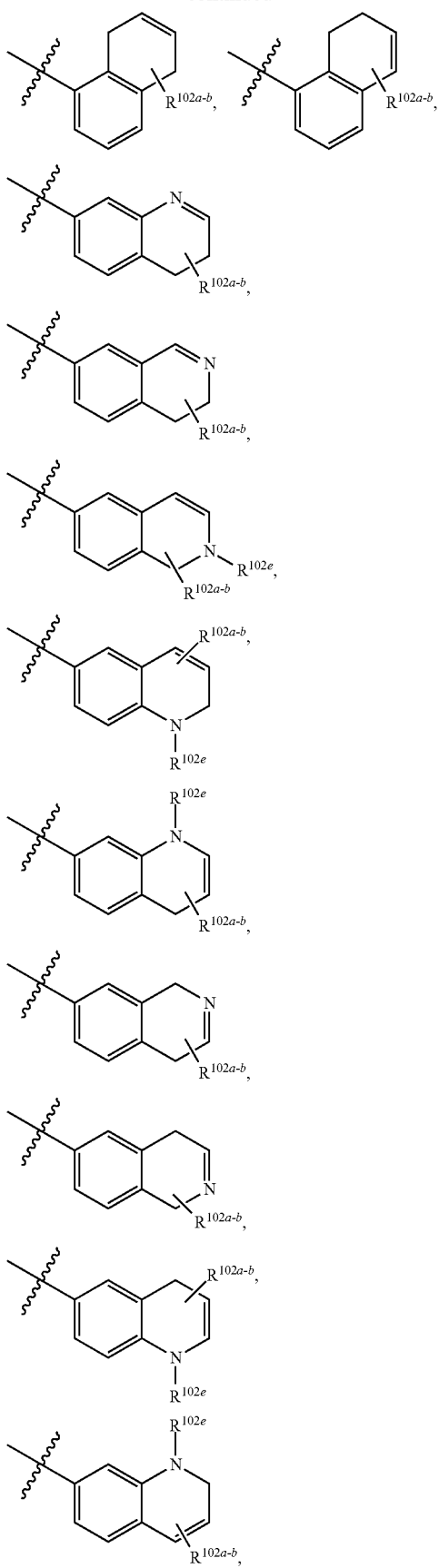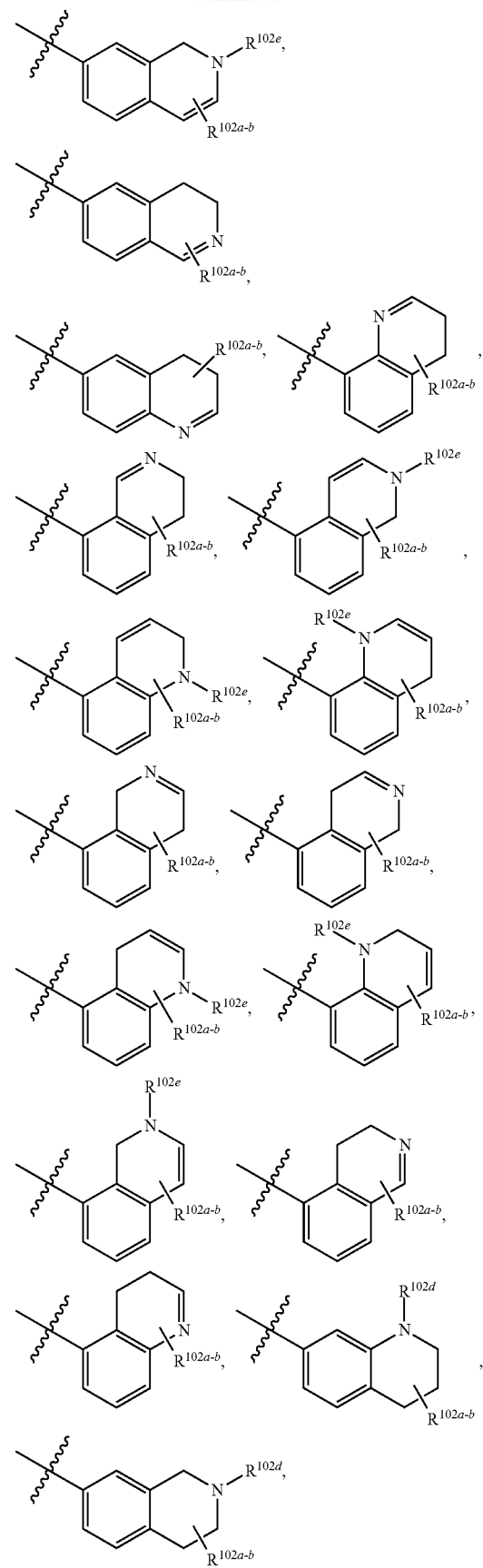

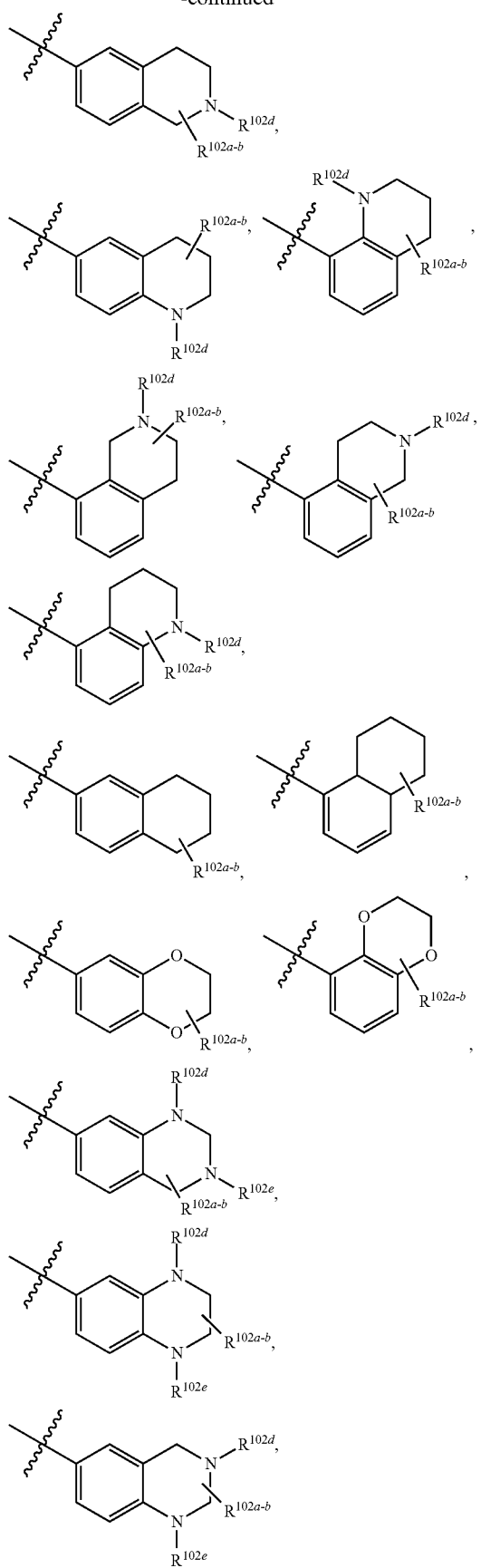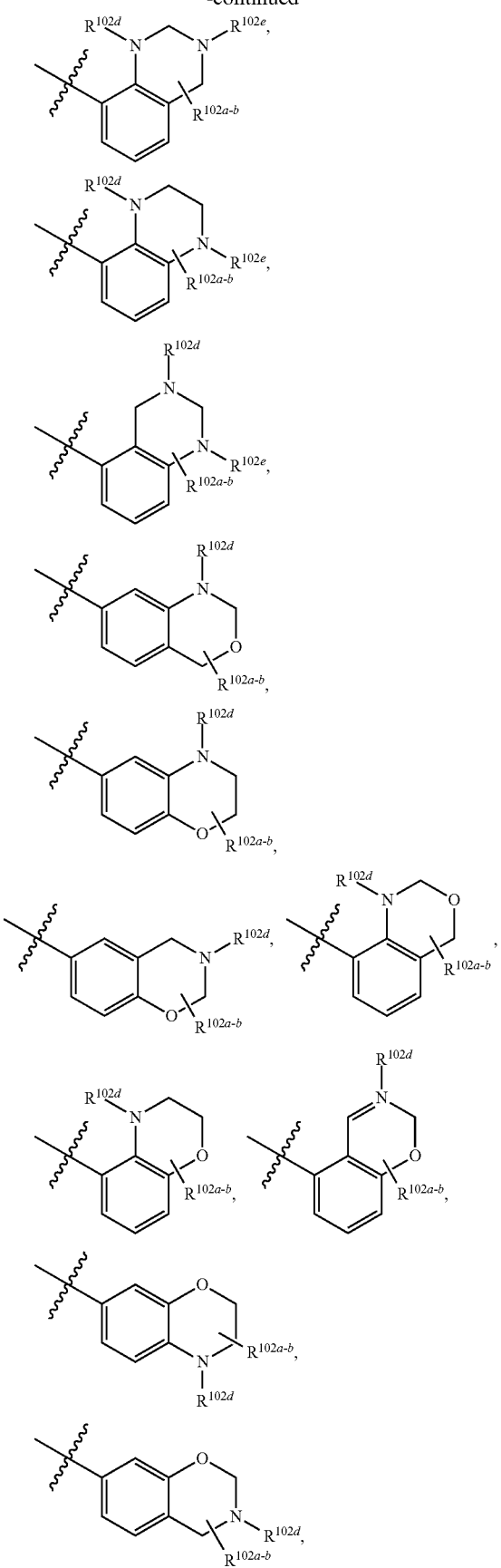

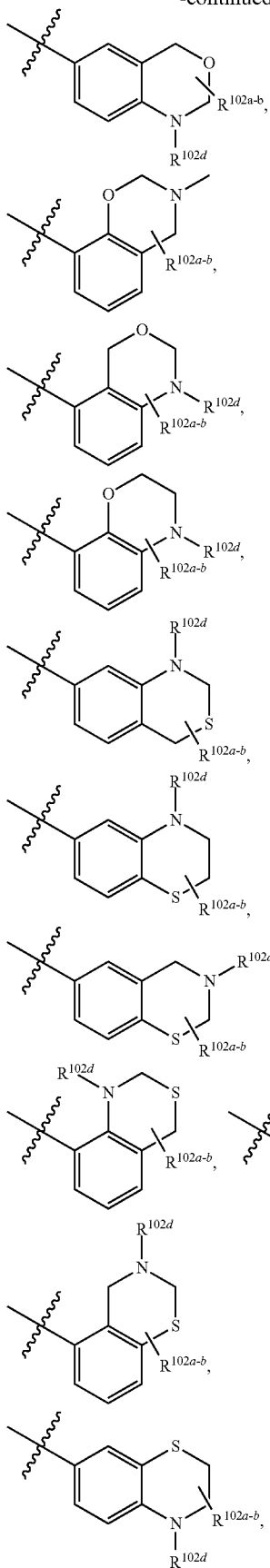

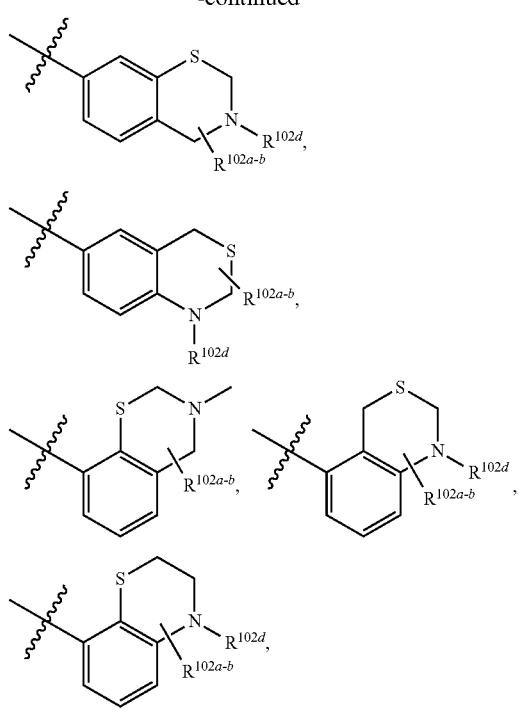

wherein $R^{102a\text{-}b}$ represents the substituents $R^{102a}$ and $R^{102b}$ and these are each selected independently of one another from H, $C_{1\text{-}4}$ alkyl, O—$C_{1\text{-}4}$ alkyl, F, Cl, Br, I, $CF_3$, $OCF_3$, OH, SH, $NH_2$, NH—$C_{1\text{-}4}$ alkyl, N($C_{1\text{-}4}$ alkyl)$_2$, NH—$SO_2$—$C_{1\text{-}4}$ alkyl, $SCF_3$ and phenyl, unsubstituted; and also if appropriate from the group consisting of =O, =NH and =N(OH);

$R^{102d}$ is in each case independently selected from H, $C_{1\text{-}4}$ alkyl, $SO_2$—$C_{1\text{-}4}$ alkyl and phenyl, unsubstituted;

(a4) the substructures (T3g) and (T3h) are selected from the following substructures

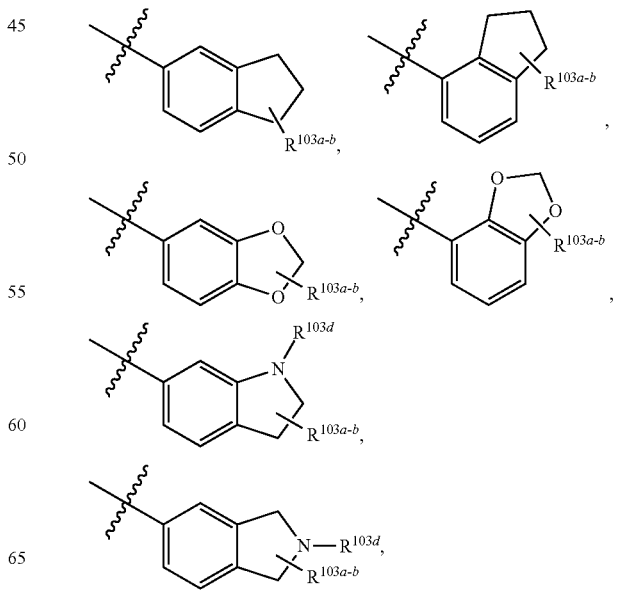

-continued

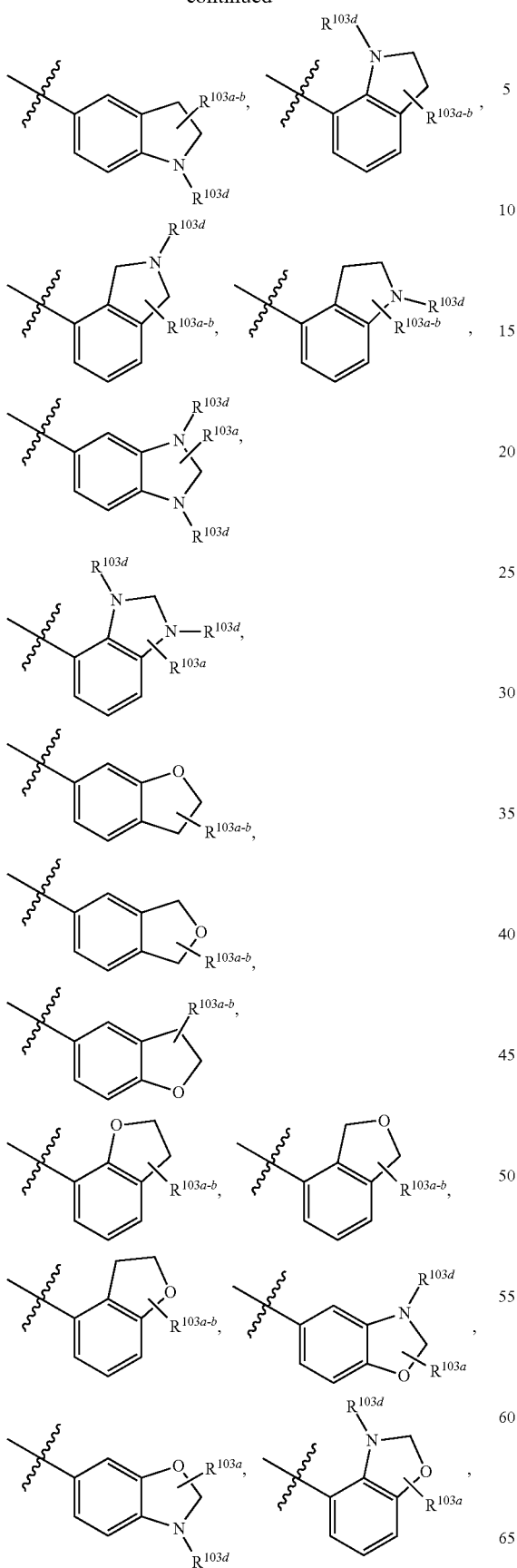

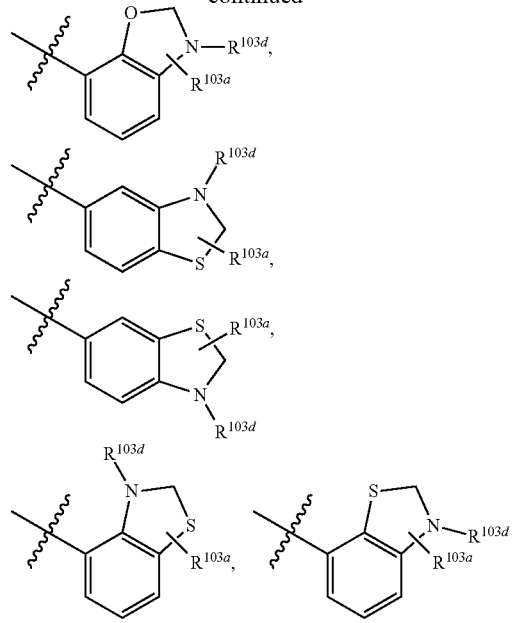

wherein $R^{103a\text{-}b}$ represents the substituents $R^{103a}$ and $R^{103b}$ and these are each selected independently of one another from H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted; and also if appropriate from the group consisting of =O, =NH or =N(OH);

$R^{103d}$ is in each case selected independently from H, $C_{1-4}$ alkyl, $SO_2$—$C_{1-4}$ alkyl and phenyl, unsubstituted;

(a5) the substructures (T3i) and (T3j) are selected from the following substructures

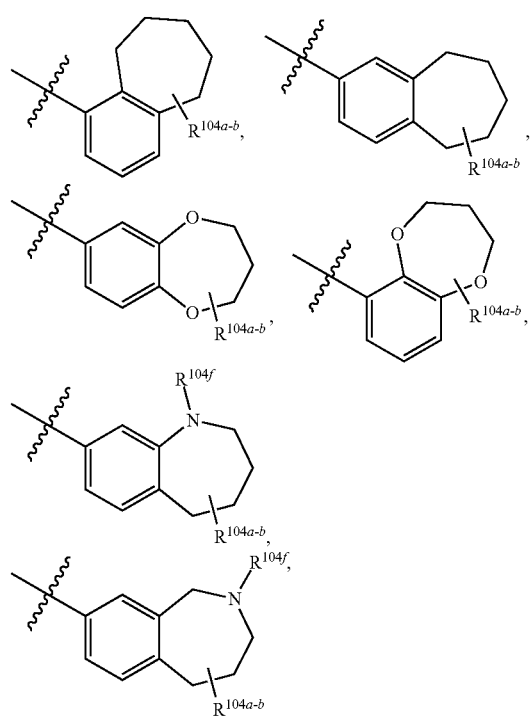

-continued

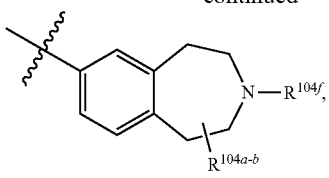

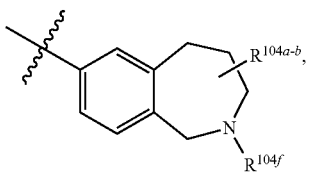

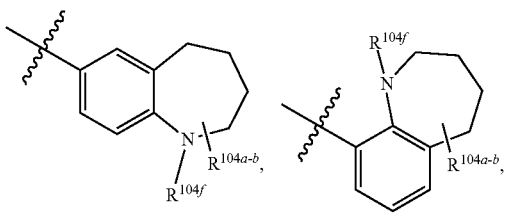

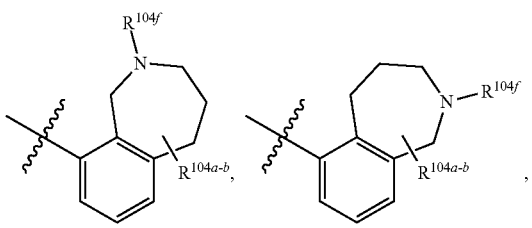

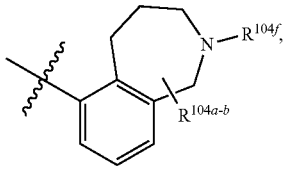

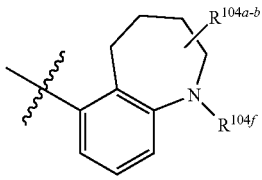

wherein $R^{104a-b}$ represents the substituents $R^{104a}$ and $R^{104b}$ and these are each selected independently from one another from H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, N($C_{1-4}$ alkyl)$_2$, NH—$SO_2$—$C_{1-4}$ alkyl, $SCF_3$ and phenyl, unsubstituted; and also if appropriate from the group consisting of =, =NH or =N(OH);

$R^{104f}$ is in each case selected independently from H, $C_{1-4}$ alkyl, $SO_2$—$C_{1-4}$ alkyl and phenyl, unsubstituted.

In a further, particularly preferred embodiment, the compounds according to the invention of general formula (I) have general formula (If)

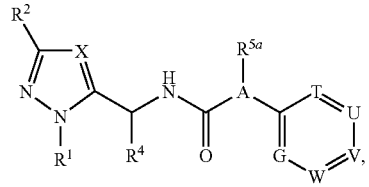

in which
X represents $CR^3$ or N,
  wherein $R^3$ represents H; methyl; ethyl; n-propyl; isopropyl; n-butyl; sec.-butyl; tert.-butyl; or $CF_3$;
A represents N or $CR^{5b}$;
  wherein $R^{5b}$ represents H; methyl; ethyl; n-propyl; isopropyl; cyclopentyl; cyclohexyl; or phenyl or benzyl, in each case unsubstituted or mono-, di- or trisubstituted with one, two or three substituents each selected independently of one another from the group consisting of $C_{1-4}$ alkyl, O—$C_{1-4}$ alkyl, F, Cl, Br, I, $CF_3$ and $OCF_3$;
$R^1$ represents substructure (T1)

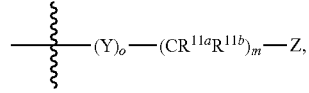

in which
Y represents C(=O), O, S, S(=O)$_2$, NH—C(=O) or $NR^{12}$,
  wherein $R^{12}$ represents H; methyl; ethyl; n-propyl; isopropyl; n-butyl; sec.-butyl; tert.-butyl; S(=O)$_2$-methyl;
o represents 0 or 1;
$R^{11a}$ and $R^{11b}$ each independently of one another represent H; methyl; ethyl; n-propyl; isopropyl; n-butyl; sec.-butyl; tert.-butyl;
m represents 0, 1 or 2;
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, O—$C_{1-4}$ alkyl; $C_{3-10}$ cycloalkyl$^1$, saturated or unsaturated, morpholinyl, piperidinyl, 4-methylpiperazinyl, piperazinyl, respectively unsubstituted or mono- or polysubstituted with one or more substituents each selected independently of one another from the group consisting of F, Cl, Br, I, OH, O—$C_{1-4}$ alkyl and $C_{1-4}$ alkyl; phenyl or pyridyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$;
$R^2$ represents H; F; Cl; Br; I; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$;
$R^4$ represents H; methyl; ethyl; n-propyl; or isopropyl;
$R^{5a}$ represents H if A represents N; or represents H; methyl; ethyl; n-propyl; isopropyl if A represents $CR^{5b}$;
or $R^{5a}$ and $R^{5b}$ form together with the carbon atom connecting them a $C_{3-10}$ cycloalkyl, saturated or unsaturated, unsubstituted, T represents $CR^6$;
U represents $CR^7$;
V represents $CR^8$;
W represents N or $CR^9$;
G represents $CR^{10}$;
$R^6$ and $R^7$ together with the carbon atoms connecting them form a $C_{3-10}$ cycloalkyl, saturated or unsaturated, unsubstituted or mono- or disubstituted with OH, =O, =N(OH); or a phenyl, pyrrolidinyl, piperidinyl, morpholinyl, oxazolyl, oxazolidinyl, pyrrolyl, pyrazolyl, pyridyl, pyrimidinyl, pyrazinyl, imidazolyl, thiazolyl, triazolyl, dioxolanyl, dioxanyl, dioxepanyl, respectively unsubstituted or mono- or disubstituted with F, Cl, Br, I, $CF_3$, $C_{1-4}$ alkyl, O—$C_{1-4}$ alkyl, $SO_2$—$C_{1-4}$ alkyl, phenyl, $NH_2$, =O, NH—$SO_2$—$C_{1-4}$ alkyl; and
$R^8$, $R^9$ and $R^{10}$ each independently of one another represent H, F, Cl, Br or OH;
or $R^7$ and $R^8$ together with the carbon atoms connecting them form a $C_{3-10}$ cycloalkyl, saturated or unsaturated, unsubstituted or mono- or disubstituted with OH, =O, =N(OH); or a phenyl, pyrrolidinyl, piperidinyl, morpholinyl, oxazolyl, oxazolidinyl, pyrrolyl, pyrazolyl, pyridyl, pyrimidinyl, pyrazinyl, imidazolyl, thiazolyl, triazolyl, dioxolanyl, dioxanyl, dioxepanyl, respectively unsubstituted or mono- or disubstituted with F, Cl, Br, I, $CF_3$, $C_{1-4}$ alkyl, O—$C_{1-4}$ alkyl, $SO_2$—$C_{1-4}$ alkyl, phenyl, $NH_2$, =O, NH—$SO_2$—$C_{1-4}$ alkyl; and
$R^6$, $R^9$ and $R^{10}$ each independently of one another represent H, F, Cl, Br or OH.

Particularly preferred are compounds from the group
1 N-((1-(3-chlorophenyl)-3-(trifluoromethyl)-1H-pyrazol-5-yl)methyl)-2-(2,3-dihydro-1H-inden-4-yl)propanamide;
2 N-((1-(3-chlorophenyl)-3-(trifluoromethyl)-1H-pyrazol-5-yl)methyl)-2-(5,6,7,8-tetrahydronaphthalen-1-yl)propanamide;
3 N-((1-(3-chlorophenyl)-3-(trifluoromethyl)-1H-pyrazol-5-yl)methyl)-2-(3-hydroxy-2,3-dihydro-1H-inden-5-yl)propanamide;
4 N-((1-(3-chlorophenyl)-3-(trifluoromethyl)-1H-pyrazol-5-yl)methyl)-2-(2-hydroxy-2,3-dihydro-1H-inden-5-yl)propanamide;
5 N-((1-(3-chlorophenyl)-3-(trifluoromethyl)-1H-pyrazol-5-yl)methyl)-2-(7-hydroxy-5,6,7,8-tetrahydronaphthalen-1-yl)propanamide;
6 N-((1-(3-chlorophenyl)-3-(trifluoromethyl)-1H-pyrazol-5-yl)methyl)-2-(3-oxo-2,3-dihydro-1H-inden-5-yl)propanamide;
7 (E)-N-((1-(3-chlorophenyl)-3-(trifluoromethyl)-1H-pyrazol-5-yl)methyl)-2-(3-(hydroxyimino)-2,3-dihydro-1H-inden-5-yl)propanamide;
8 N-((1-(3-chlorophenyl)-3-(trifluoromethyl)-1H-pyrazol-5-yl)methyl)-2-(indolin-5-yl)propanamide hydrochloride;
9 N-((1-(3-chlorophenyl)-3-(trifluoromethyl)-1H-pyrazol-5-yl)methyl)-2-(1-methylindolin-5-yl)propanamide;
10 N-((3-tert-butyl-1-(3-chlorophenyl)-1H-pyrazol-5-yl)methyl)-2-(1-(methylsulphonyl)indolin-5-yl)propanamide;
11 2-(benzo[d][1,3]dioxol-5-yl)-N-((3-tert-butyl-1-(3-chlorophenyl)-1H-pyrazol-5-yl)methyl)propanamide;
12 N-((3-tert-butyl-1-(4-chlorophenyl)-1H-pyrazol-5-yl)methyl)-2-(2,3-dihydrobenzo[b][1,4]dioxin-6-yl)acetamide;
13 N-((3-tert-butyl-1-(3-chlorophenyl)-1H-pyrazol-5-yl)methyl)-2-(2,3-dihydrobenzo[b][1,4]dioxin-6-yl)propanamide;
14 N-((3-tert-butyl-1-(3-chlorophenyl)-1H-pyrazol-5-yl)methyl)-2-(2,3-dihydrobenzo[b][1,4]dioxin-5-yl)propanamide;
15 N-((3-tert-butyl-1-(3-chlorophenyl)-1H-pyrazol-5-yl)methyl)-2-(3,4-dihydro-2H-benzo[b][1,4]dioxepin-7-yl)propanamide;
16 N-((1-(3-chlorophenyl)-3-(trifluoromethyl)-1H-pyrazol-5-yl)methyl)-2-(1,2,3,4-tetrahydroquinolin-6-yl)propanamide hydrochloride;
17 N-((1-(3-chlorophenyl)-3-(trifluoromethyl)-1H-pyrazol-5-yl)methyl)-2-(1-methyl-1,2,3,4-tetrahydroquinolin-6-yl)propanamide;
18 N-((1-(3-chlorophenyl)-3-(trifluoromethyl)-1H-pyrazol-5-yl)methyl)-2-(1-(methylsulphonyl)-1,2,3,4-tetrahydroquinolin-6-yl)propanamide;
19 N-((1-(3-chlorophenyl)-3-(trifluoromethyl)-1H-pyrazol-5-yl)methyl)-2-(3,4-dihydro-2H-benzo[b][1,4]oxazin-7-yl)propanamide;
20 N-((1-(3-chlorophenyl)-3-(trifluoromethyl)-1H-pyrazol-5-yl)methyl)-2-(3,4-dihydro-2H-benzo[b][1,4]oxazin-6-yl)propanamide;
21 N-((1-(3-chlorophenyl)-3-(trifluoromethyl)-1H-pyrazol-5-yl)methyl)-2-(2-oxo-2,3-dihydrobenzo[d]oxazol-6-yl)propanamide;
22 N-((1-(3-chlorophenyl)-3-(trifluoromethyl)-1H-pyrazol-5-yl)methyl)-2-(2-oxo-1,2,3,4-tetrahydroquinolin-6-yl)propanamide;
23 N-((1-(3-chlorophenyl)-3-(trifluoromethyl)-1H-pyrazol-5-yl)methyl)-2-(3-oxo-3,4-dihydro-2H-benzo[b][1,4]oxazin-7-yl)propanamide;
24 N-((1-(3-chlorophenyl)-3-(trifluoromethyl)-1H-pyrazol-5-yl)methyl)-2-(1H-inden-7-yl)propanamide;
25 N-((3-tert-butyl-1-(3-chlorophenyl)-1H-pyrazol-5-yl)methyl)-2-(1H-indol-4-yl)propanamide;
26 N-((1-(3-chlorophenyl)-3-(trifluoromethyl)-1H-pyrazol-5-yl)methyl)-2-(1-methyl-1H-indol-4-yl)propanamide;
27 N-((1-(3-chlorophenyl)-3-(trifluoromethyl)-1H-pyrazol-5-yl)methyl)-2-(1H-indazol-4-yl)propanamide;
28 N-((1-(3-chlorophenyl)-3-(trifluoromethyl)-1H-pyrazol-5-yl)methyl)-2-(1-methyl-1H-indazol-4-yl)propanamide;
29 N-((1-(3-chlorophenyl)-3-(trifluoromethyl)-1H-pyrazol-5-yl)methyl)-2-(1-phenyl-1H-indazol-4-yl)propanamide;
30 2-(1H-benzo[d][1,2,3]triazol-4-yl)-N-((1-(3-chlorophenyl)-3-(trifluoromethyl)-1H-pyrazol-5-yl)methyl)propanamide;
31 N-((1-(3-chlorophenyl)-3-(trifluoromethyl)-1H-pyrazol-5-yl)methyl)-2-(1H-indol-5-yl)propanamide;
32 N-((1-(3-chlorophenyl)-3-(trifluromethyl)-1H-pyrazol-5-yl)methyl)-2-(1-methyl-1H-indol-5-yl)propanamide;
33 2-(1H-benzo[d]imidazol-5-yl)-N-((1-(3-chlorophenyl)-3-(trifluoromethyl)-1H-pyrazol-5-yl)methyl)propanamide;
34 2-(2-amino-1H-benzo[d]imidazol-5-yl)-N-((1-(3-chlorophenyl)-3-(trifluromethyl)-1H-pyrazol-5-yl)methyl)propanamide;
35 N-((1-(3-chlorophenyl)-3-(trifluoromethyl)-1H-pyrazol-5-yl)methyl)-2-(1H-indazol-5-yl)propanamide;
36 2-(benzo[d]oxazol-4-yl)-N-((1-(3-chlorophenyl)-3-(trifluoromethyl)-1H-pyrazol-5-yl)methyl)propanamide;
37 2-(benzo[d]oxazol-7-yl)-N-((1-(3-chlorophenyl)-3-(trifluoromethyl)-1H-pyrazol-5-yl)methyl)propanamide;
38 2-(benzo[d]thiazol-4-yl)-N-((1-(3-chlorophenyl)-3-(trifluoromethyl)-1H-pyrazol-5-yl)methyl)propanamide;

39 2-(benzo[d]thiazol-7-yl)-N-((1-(3-chlorophenyl)-3-(trifluoromethyl)-1H-pyrazol-5-yl)methyl)propanamide;
40 2-(benzo[d]oxazol-5-yl)-N-((3-tert-butyl-1-(3-chlorophenyl)-1H-pyrazol-5-yl)methyl)propanamide;
41 2-(benzo[d]oxazol-6-yl)-N-((3-tert-butyl-1-(3-chlorophenyl)-1H-pyrazol-5-yl)methyl)propanamide;
42 2-(benzo[d]thiazol-6-yl)-N-((1-(3-chlorophenyl)-3-(trifluoromethyl)-1H-pyrazol-5-yl)methyl)propanamide;
43 2-(2-aminobenzo[d]thiazol-6-yl)-N-((1-(3-chlorophenyl)-3-(trifluoromethyl)-1H-pyrazol-5-yl)methyl)propanamide;
44 N-((1-(3-chlorophenyl)-3-(trifluoromethyl)-1H-pyrazol-5-yl)methyl)-2-(2-(methylsulphonamido)benzo[d]thiazol-6-yl)propanamide;
45 N-((1-(3-chlorophenyl)-3-(trifluoromethyl)-1H-pyrazol-5-yl)methyl)-2-(2-methylbenzo[d]thiazol-6-yl)propanamide;
46 2-(benzo[d]thiazol-5-yl)-N-((1-(3-chlorophenyl)-3-(trifluoromethyl)-1H-pyrazol-5-yl)methyl)propanamide;
47 N-((3-tert-butyl-1-(3-chlorophenyl)-1H-pyrazol-5-yl)methyl)-2-(naphthalen-1-yl)propanamide;
48 N-((3-tert-butyl-1-(3-chlorophenyl)-1H-pyrazol-5-yl)methyl)-2-(naphthalen-2-yl)propanamide;
49 N-((3-tert-butyl-1-(3-chlorophenyl)-1H-pyrazol-5-yl)methyl)-2-(6-hydroxynaphthalen-2-yl)propanamide;
50 N-((1-(3-chlorophenyl)-3-(trifluoromethyl)-1H-pyrazol-5-yl)methyl)-2-(6-hydroxynaphthalen-2-yl)propanamide;
51 N-((1-(3-chlorophenyl)-3-(trifluoromethyl)-1H-pyrazol-5-yl)methyl)-2-(6-methoxynaphthalen-2-yl)propanamide;
52 N-((3-tert-butyl-1-methyl-1H-pyrazol-5-yl)methyl)-2-(7-hydroxynaphthalen-1-yl)propanamide;
53 N-((3-tert-butyl-1-hexyl-1H-pyrazol-5-yl)methyl)-2-(7-hydroxynaphthalen-1-yl)propanamide;
54 N-((3-tert-butyl-1-p-tolyl-1H-pyrazol-5-yl)methyl)-2-(7-hydroxynaphthalen-1-yl)propanamide;
55 N-((3-tert-butyl-1-(4-tert-butylphenyl)-1H-pyrazol-5-yl)methyl)-2-(7-hydroxynaphthalen-1-yl)propanamide;
56 N-((3-tert-butyl-1-(4-chlorophenyl)-1H-pyrazol-5-yl)methyl)-2-(7-hydroxynaphthalen-1-yl)propanamide;
57 N-((3-tert-butyl-1-(3-chlorophenyl)-1H-pyrazol-5-yl)methyl)-2-(7-hydroxynaphthalen-1-yl)propanamide;
58 N-((1-(3-chlorophenyl)-3-(trifluoromethyl)-1H-pyrazol-5-yl)methyl)-2-(7-hydroxynaphthalen-1-yl)propanamide;
59 N-((3-tert-butyl-1-(3-chloro-4-fluorophenyl)-1H-pyrazol-5-yl)methyl)-2-(7-hydroxynaphthalen-1-yl)propanamide;
60 N-((3-tert-butyl-1-cyclohexenyl-1H-pyrazol-5-yl)methyl)-2-(7-hydroxynaphthalen-1-yl)propanamide;
61 N-((3-tert-butyl-1-(3-chlorophenyl)-1H-pyrazol-5-yl)methyl)-2-(quinolin-8-yl)propanamide;
62 N-((3-tert-butyl-1-(3-chlorophenyl)-1H-pyrazol-5-yl)methyl)-2-(isoquinolin-8-yl)propanamide;
63 N-((3-tert-butyl-1-(3-chlorophenyl)-1H-pyrazol-5-yl)methyl)-2-(isoquinolin-5-yl)propanamide;
64 N-((1-(3-chlorophenyl)-3-(trifluoromethyl)-1H-pyrazol-5-yl)methyl)-2-(isoquinolin-5-yl)propanamide;
65 N-((1-(3-chlorophenyl)-3-(trifluoromethyl)-1H-pyrazol-5-yl)methyl)-2-(3-methylisoquinolin-5-yl)propanamide;
66 N-((1-(3-chlorophenyl)-3-(trifluoromethyl)-1H-pyrazol-5-yl)methyl)-2-(1-methylisoquinolin-5-yl)propanamide;
67 N-((1-(3-chlorophenyl)-3-(trifluoromethyl)-1H-pyrazol-5-yl)methyl)-2-(1,3-dimethylisoquinolin-5-yl)propanamide;
68 N-((1-(4-chlorophenyl)-3-(trifluoromethyl)-1H-pyrazol-5-yl)methyl)-2-(isoquinolin-5-yl)propanamide;
69 N-((3-tert-butyl-1-(3-chloro-4-fluorophenyl)-1H-pyrazol-5-yl)methyl)-2-(isoquinolin-5-yl)propanamide;
70 N-((3-tert-butyl-1-(3-chlorophenyl)-1H-pyrazol-5-yl)methyl)-2-(quinolin-5-yl)propanamide;
71 N-((3-tert-butyl-1-(3-chlorophenyl)-1H-pyrazol-5-yl)methyl)-2-(quinolin-7-yl)propanamide;
72 N-((1-(3-chlorophenyl)-3-(trifluoromethyl)-1H-pyrazol-5-yl)methyl)-2-(quinolin-7-yl)propanamide;
73 N-((3-tert-butyl-1-(3-chlorophenyl)-1H-pyrazol-5-yl)methyl)-2-(isoquinolin-7-yl)propanamide;
74 N-((3-tert-butyl-1-(3-chlorophenyl)-1H-pyrazol-5-yl)methyl)-2-(isoquinolin-6-yl)propanamide;
75 N-((3-tert-butyl-1-(3-chlorophenyl)-1H-pyrazol-5-yl)methyl)-2-(quinolin-6-yl)propanamide;
76 N-((3-tert-butyl-1-(3-chlorophenyl)-1H-pyrazol-5-yl)methyl)-2-(quinazolin-6-yl)propanamide;
77 N-((3-tert-butyl-1-(3-chlorophenyl)-1H-pyrazol-5-yl)methyl)-2-(quinoxalin-6-yl)propanamide;
78 1-((3-tert-butyl-1-(3-chlorophenyl)-1H-pyrazol-5-yl)methyl)-3-(2,3-dihydro-1H-inden-4-yl)urea;
79 1-((3-tert-butyl-1-(3-chlorophenyl)-1H-pyrazol-5-yl)methyl)-3-(2,3-dihydro-1H-inden-5-yl)urea;
80 1-((3-tert-butyl-1-(3-chlorophenyl)-1H-pyrazol-5-yl)methyl)-3-(5,6,7,8-tetrahydronaphthalen-1-yl)urea;
81 1-((1-(3-chlorophenyl)-3-(trifluoromethyl)-1H-pyrazol-5-yl)methyl)-3-(2-hydroxy-2,3-dihydro-1H-inden-4-yl)urea;
82 1-((1-(3-chlorophenyl)-3-(trifluoromethyl)-1H-pyrazol-5-yl)methyl)-3-(7-hydroxy-5,6,7,8-tetrahydronaphthalen-1-yl)urea;
83 1-(Benzo[d][1,3]dioxol-5-yl)-3-((1-(3-chlorophenyl)-3-(trifluoromethyl)-1H-pyrazol-5-yl)methyl)urea;
84 1-((1-(3-chlorophenyl)-3-(trifluoromethyl)-1H-pyrazol-5-yl)methyl)-3-(2,3-dihydrobenzo[b][1,4]dioxin-6-yl)urea;
85 1-((3-tert-butyl-1-(3-chlorophenyl)-1H-pyrazol-5-yl)methyl)-3-(2,3-dihydrobenzo[b][1,4]dioxin-5-yl)urea;
86 1-((1-(3-chlorophenyl)-3-(trifluoromethyl)-1H-pyrazol-5-yl)methyl)-3-(1H-indol-4-yl)urea;
87 1-((1-(3-chlorophenyl)-3-(trifluoromethyl)-1H-pyrazol-5-yl)methyl)-3-(1-methyl-1H-indol-4-yl)urea;
88 1-((1-(3-chlorophenyl)-3-(trifluoromethyl)-1H-pyrazol-5-yl)methyl)-3-(1H-indazol-4-yl)urea;
89 1-((1-(3-chlorophenyl)-3-(trifluoromethyl)-1H-pyrazol-5-yl)methyl)-3-(1-methyl-1H-indazol-4-yl)urea;
90 1-((1-(3-chlorophenyl)-3-(trifluoromethyl)-1H-pyrazol-5-yl)methyl)-3-(1H-indol-5-yl)urea;
91 1-((1-(3-chlorophenyl)-3-(trifluoromethyl)-1H-pyrazol-5-yl)methyl)-3-(2-methyl-1H-indol-5-yl)urea;
92 1-(1H-benzo[d]imidazol-5-yl)-3-((1-(3-chlorophenyl)-3-(trifluoromethyl)-1H-pyrazol-5-yl)methyl)urea;
93 1-((1-(3-chlorophenyl)-3-(trifluoromethyl)-1H-pyrazol-5-yl)methyl)-3-(1H-indazol-5-yl)urea;
94 1-(benzo[d]oxazol-6-yl)-3-((1-(3-chlorophenyl)-3-(trifluoromethyl)-1H-pyrazol-5-yl)methyl)urea;
95 1-(benzo[d]oxazol-5-yl)-3-((1-(3-chlorophenyl)-3-(trifluoromethyl)-1H-pyrazol-5-yl)methyl)urea;
96 1-(benzo[d]thiazol-6-yl)-3-((1-(3-chlorophenyl)-3-(trifluoromethyl)-1H-pyrazol-5-yl)methyl)urea;
97 1-(benzo[d]thiazol-5-yl)-3-((1-(3-chlorophenyl)-3-(trifluoromethyl)-1H-pyrazol-5-yl)methyl)urea;
98 1-((3-tert-butyl-1-(3-chlorophenyl)-1H-pyrazol-5-yl)methyl)-3-(naphthalen-1-yl)urea;
99 1-((3-tert-butyl-1-(3-chlorophenyl)-1H-pyrazol-5-yl)methyl)-3-(6-hydroxynaphthalen-2-yl)urea;
100 1-((3-tert-butyl-1-(3-chlorophenyl)-1H-pyrazol-5-yl)methyl)-3-(5-hydroxynaphthalen-2-yl)urea;

101  1-((3-tert-butyl-1-(3-chlorophenyl)-1H-pyrazol-5-yl)methyl)-3-(7-hydroxynaphthalen-1-yl)urea;
102  1-((1-(3-chlorophenyl)-3-(trifluoromethyl)-1H-pyrazol-5-yl)methyl)-3-(7-hydroxynaphthalen-1-yl)urea;
103  1-((3-tert-butyl-1-(3-chlorophenyl)-1H-pyrazol-5-yl)methyl)-3-(7-ethoxynaphthalen-1-yl)urea;
104  1-((3-tert-butyl-1-(3-chlorophenyl)-1H-pyrazol-5-yl)methyl)-3-(6-hydroxynaphthalen-1-yl)urea;
105  1-((3-tert-butyl-1-(3-chlorophenyl)-1H-pyrazol-5-yl)methyl)-3-(5-hydroxynaphthalen-1-yl)urea;
106  1-((3-tert-butyl-1-(3-chlorophenyl)-1H-pyrazol-5-yl)methyl)-3-(4-hydroxynaphthalen-1-yl)urea;
107  1-((3-tert-butyl-1-(3-chlorophenyl)-1H-pyrazol-5-yl)methyl)-3-(quinolin-8-yl)urea;
108  1-((3-tert-butyl-1-(3-chlorophenyl)-1H-pyrazol-5-yl)methyl)-3-(isoquinolin-8-yl)urea;
109  1-((3-tert-butyl-1-(3-chlorophenyl)-1H-pyrazol-5-yl)methyl)-3-(isoquinolin-5-yl)urea;
110  1-((1-(3-chlorophenyl)-3-(trifluoromethyl)-1H-pyrazol-5-yl)methyl)-3-(isoquinolin-5-yl)urea;
111  1-((3-tert-butyl-1-(3-chlorophenyl)-1H-pyrazol-5-yl)methyl)-3-(quinolin-5-yl)urea;
112  1-((3-tert-butyl-1-(3-chlorophenyl)-1H-pyrazol-5-yl)methyl)-3-(isoquinolin-4-yl)urea;
113  1-((3-tert-butyl-1-(3-chlorophenyl)-1H-pyrazol-5-yl)methyl)-3-(quinolin-3-yl)urea;
114  N-[[2-(6-chloro-pyridin-2-yl)-5-(trifluoromethyl)-2H-pyrazol-3-yl]-methyl]-2-(6-hydroxy-naphthalen-2-yl)-propionamide;
115  1-[[2-(6-chloro-pyridin-2-yl)-5-(trifluoromethyl)-2H-pyrazol-3-yl]-methyl]-3-(7-hydroxy-naphthalen-1-yl)-urea;
116  N-[[2-(6-chloro-pyridin-2-yl)-5-(trifluoromethyl)-2H-pyrazol-3-yl]-methyl]-2-(1H-indol-5-yl)-propionamide;
117  N-[[5-tert-butyl-2-(6-chloro-pyridin-2-yl)-2H-pyrazol-3-yl]-methyl]-2-isoquinolin-5-yl-propionamide;
118  1-[[5-tert-butyl-2-(6-chloro-pyridin-2-yl)-2H-pyrazol-3-yl]-methyl]-3-(1-methyl-isoquinolin-5-yl)-urea;
119  2-(1,3-benzodioxol-5-yl)-N-[[5-tert-butyl-2-(6-chloro-pyridin-2-yl)-2H-pyrazol-3-yl]-methyl]-propionamide;
120  2-(1H-indol-5-yl)-N-[[2-pyridin-2-yl-5-(trifluoromethyl)-2H-pyrazol-3-yl]-methyl]-propionamide;
121  N-[[5-tert-butyl-2-(3,3-difluoro-cyclobutanecarbonyl)-2H-pyrazol-3-yl]-methyl]-2-(1H-indazol-4-yl)-propionamide;
122  1-[[2-(3-chlorophenyl)-4-methyl-5-(trifluoromethyl)-2H-pyrazol-3-yl]-methyl]-3-(1H-indazol-4-yl)-urea;
123  N-[[2-(dipropyl-amino)-5-(trifluoromethyl)-2H-pyrazol-3-yl]-methyl]-2-(6-hydroxy-naphthalen-2-yl)-propionamide;
124  1-[[2-(dipropyl-amino)-5-(trifluoromethyl)-2H-pyrazol-3-yl]-methyl]-3-(7-hydroxy-naphthalen-1-yl)-urea;
125  N-[[2-(dipropyl-amino)-5-(trifluoromethyl)-2H-pyrazol-3-yl]-methyl]-2-isoquinolin-5-yl-propionamide;
126  N-[[2-(dipropyl-amino)-5-(trifluoromethyl)-2H-pyrazol-3-yl]-methyl]-2-(1H-indol-5-yl)-propionamide;
127  2-(1H-benzotriazol-4-yl)-N-[[2-(dipropyl-amino)-5-(trifluoromethyl)-2H-pyrazol-3-yl]-methyl]-propionamide;
128  1-(benzothiazol-6-yl)-3-[[2-(dipropyl-amino)-5-(trifluoromethyl)-2H-pyrazol-3-yl]-methyl]-urea;
129  1-(2,3-dihydro-1H-inden-5-yl)-3-[[2-(dipropyl-amino)-5-(trifluoromethyl)-2H-pyrazol-3-yl]-methyl]-urea;
130  1-[[2-(dipropyl-amino)-5-(trifluoromethyl)-2H-pyrazol-3-yl]-methyl]-3-(1H-indazol-4-yl)-urea;
131  2-(1,3-benzodioxol-5-yl)-N-[[5-tert-butyl-2-(dipropyl-amino)-2H-pyrazol-3-yl]-methyl]-propionamide;
132  1-(7-hydroxy-naphthalen-1-yl)-3-[[2-piperidin-1-yl-5-(trifluoromethyl)-2H-pyrazol-3-yl]-methyl]-urea;
133  2-(2-methyl-quinolin-5-yl)-N-[[2-piperidin-1-yl-5-(trifluoromethyl)-2H-pyrazol-3-yl]-methyl]-propionamide;
134  2-isoquinolin-5-yl-N-[[2-piperidin-1-yl-5-(trifluoromethyl)-2H-pyrazol-3-yl]-methyl]-propionamide;
135  1-(3-chloro-isoquinolin-5-yl)-3-[[2-piperidin-1-yl-5-(trifluoromethyl)-2H-pyrazol-3-yl]-methyl]-urea;
136  1-(1-chloro-isoquinolin-5-yl)-3-[[2-piperidin-1-yl-5-(trifluoromethyl)-2H-pyrazol-3-yl]-methyl]-urea;
137  1-(1-methyl-isoquinolin-5-yl)-3-[[2-piperidin-1-yl-5-(trifluoromethyl)-2H-pyrazol-3-yl]-methyl]-urea;
138  N-[(5-tert-butyl-2-piperidin-1-yl-2H-pyrazol-3-yl)-methyl]-2-(2-methyl-quinolin-5-yl)-propionamide;
139  2-(1H-indol-5-yl)-N-[[2-piperidin-1-yl-5-(trifluoromethyl)-2H-pyrazol-3-yl]-methyl]-propionamide;
140  2-(1,3-benzodioxol-5-yl)-N-[[2-piperidin-1-yl-5-(trifluoromethyl)-2H-pyrazol-3-yl]-methyl]-propionamide;
141  N-[[2-[(4-fluorophenyl)-methyl-methyl-amino]-5-(trifluoromethyl)-2H-pyrazol-3-yl]-methyl]-2-(6-hydroxy-naphthalen-2-yl)-propionamide;
142  N-[[2-[(4-fluorophenyl)-methyl-methyl-amino]-5-(trifluoromethyl)-2H-pyrazol-3-yl]-methyl]-2-(1-methyl-1H-indazol-4-yl)-propionamide;
143  N-[[2-[(4-fluorophenyl)-methyl-methyl-amino]-5-(trifluoromethyl)-2H-pyrazol-3-yl]-methyl]-2-(2-methyl-quinolin-5-yl)-propionamide;
144  2-(1,3-benzodioxol-5-yl)-N-[[2-[(4-fluorophenyl)-methyl-methylsulphonyl-amino]-5-(trifluoromethyl)-2H-pyrazol-3-yl]-methyl]-propionamide;
145  N-[[2-[(4-fluorophenyl)-methyl-methylsulphonyl-amino]-5-(trifluoromethyl)-2H-pyrazol-3-yl]-methyl]-2-(1-methyl-1H-indazol-4-yl)-propionamide;
146  N-[[2-[(4-fluorophenyl)-methyl-methylsulphonyl-amino]-5-(trifluoromethyl)-2H-pyrazol-3-yl]-methyl]-2-(1H-indol-5-yl)-propionamide;
147  1-[[2-butoxy-5-(trifluoromethyl)-2H-pyrazol-3-yl]-methyl]-3-(1H-indazol-4-yl)-urea;
148  1-[[2-butoxy-5-(trifluoromethyl)-2H-pyrazol-3-yl]-methyl]-3-(1-methyl-1H-indazol-4-yl)-urea;
149  N-[[2-butoxy-5-(trifluoromethyl)-2H-pyrazol-3-yl]-methyl]-2-(1H-indazol-4-yl)-propionamide;
150  1-[[2-(cyclopropyl-methoxy)-5-(trifluoromethyl)-2H-pyrazol-3-yl]-methyl]-3-(1H-indazol-4-yl)-urea;
151  1-[[2-cyclopentyloxy-5-(trifluoromethyl)-2H-pyrazol-3-yl]-methyl]-3-(1H-indazol-4-yl)-urea;
152  1-(1H-indazol-4-yl)-3-[[2-(thiophen-2-yl-methoxy)-5-(trifluoromethyl)-2H-pyrazol-3-yl]-methyl]-urea;
153  1-[[2-butoxy-5-(trifluoromethyl)-2H-pyrazol-3-yl]-methyl]-3-(2,3-dihydro-1H-inden-5-yl)-urea;
154  N-[[2-butoxy-5-(trifluoromethyl)-2H-pyrazol-3-yl]-methyl]-2-isoquinolin-5-yl-propionamide;
155  1-(1H-indazol-4-yl)-3-[[2-[(4-methoxyphenyl)-methyl]-5-(trifluoromethyl)-2H-pyrazol-3-yl]-methyl]-urea;
156  1-[[2-[(4-methoxyphenyl)-methyl]-5-(trifluoromethyl)-2H-pyrazol-3-yl]-methyl]-3-(1-methyl-1H-indazol-4-yl)-urea;
157  2-(1H-indol-5-yl)-N-[[2-pyridin-4-yloxy-5-(trifluoromethyl)-2H-pyrazol-3-yl]-methyl]-propionamide;
158  2-(1H-indol-5-yl)-N-[[2-pyridin-2-yloxy-5-(trifluoromethyl)-2H-pyrazol-3-yl]-methyl]-propionamide;
159  1-[[2-(3-cyano-5-fluoro-phenoxy)-5-(trifluoromethyl)-2H-pyrazol-3-yl]-methyl]-3-(1-methyl-1H-indazol-4-yl)-urea;
160  N-[[2-(3-cyano-5-fluoro-phenoxy)-5-(trifluoromethyl)-2H-pyrazol-3-yl]-methyl]-2-(1H-indol-5-yl)-propionamide;

161 2-(1,3-benzodioxol-5-yl)-N-[[2-(3-cyano-5-fluoro-phenoxy)-5-(trifluoromethyl)-2H-pyrazol-3-yl]-methyl]-propionamide;

162 2-(6-hydroxy-naphthalen-2-yl)-N-[[2-phenylmethoxy-5-(trifluoromethyl)-2H-pyrazol-3-yl]-methyl]-propionamide;

163 N-[[2-(benzenesulphonyl)-5-tert-butyl-2H-pyrazol-3-yl]-methyl]-2-(1,3-benzodioxol-5-yl)-propionamide;

164 N-[[2-(benzenesulphonyl)-5-tert-butyl-2H-pyrazol-3-yl]-methyl]-2-(1H-indol-5-yl)-propionamide;

165 2-(1,3-benzodioxol-5-yl)-N-[(5-tert-butyl-2-phenylsulphanyl-2H-pyrazol-3-yl)-methyl]-propionamide;

166 1-[[2-(cyclohexylsulphanyl)-5-(trifluoromethyl)-2H-pyrazol-3-yl]-methyl]-3-(7-hydroxy-naphthalen-1-yl)-urea;

167 1-[[2-(cyclohexylsulphanyl)-5-(trifluoromethyl)-2H-pyrazol-3-yl]-methyl]-3-(1H-indazol-4-yl)-urea;

168 1-[[5-tert-butyl-2-(cyclohexylsulphanyl)-2H-pyrazol-3-yl]-methyl]-3-(2-methyl-quinolin-5-yl)-urea;

169 N-[[2-(3-chlorophenyl)-5-(trifluoromethyl)-2H-[1,2,4]triazol-3-yl]-methyl]-2-(6-hydroxy-naphthalen-2-yl)-propionamide;

170 2-(1,3-benzodioxol-5-yl)-N-[[5-tert-butyl-2-(3-chlorophenyl)-2H-[1,2,4]triazol-3-yl]-methyl]-propionamide;

171 2-(1,3-benzodioxol-5-yl)-N-[[2-(3-chlorophenyl)-5-cyclopropyl-2H-[1,2,4]triazol-3-yl]-methyl]-propionamide;

172 N-[[2-cyclohexyl-5-(trifluoromethyl)-2H-[1,2,4]triazol-3-yl]-methyl]-2-(2-methyl-quinolin-5-yl)-propionamide;

173 2-(1,3-benzodioxol-5-yl)-N-[[2-cyclohexyl-5-(trifluoromethyl)-2H-[1,2,4]triazol-3-yl]-methyl]-propionamide;

174 1-((1-(4-chlorophenyl)-3-(trifluoromethyl)-1H-pyrazol-5-yl)methyl)-3-(2,3-dihydro-1H-inden-5-yl)urea;

175 1-(2,3-dihydro-1H-inden-5-yl)-3-((1-(4-fluorophenyl)-3-(trifluoromethyl)-1H-pyrazol-5-yl)methyl)urea;

176 1-(3-tert-butyl-1-(3-fluorophenyl)-1H-pyrazol-5-yl)methyl)-3-(2,3-dihydro-1H-inden-5-yl)urea;

177 1-((3-tert-butyl-1-(3-chloro-4-fluorophenyl)-1H-pyrazol-5-yl)methyl)-3-(2,3-dihydro-1H-inden-5-yl)urea;

178 1-(2,3-dihydro-1H-inden-5-yl)-3-((1-(4-methoxyphenyl)-3-(trifluoromethyl)-1H-pyrazol-5-yl)methyl)urea;

179 1-(2,3-dihydro-1H-inden-5-yl)-3-((3-(trifluoromethyl)-1-(4-(trifluoromethyl)phenyl)-1H-pyrazol-5-yl)methyl)urea;

180 1-(2,3-dihydro-1H-inden-5-yl)-3-((1-(4-(trifluoromethoxy)phenyl)-3-(trifluoromethyl)-1H-pyrazol-5-yl)methyl)urea;

181 1-(2,3-dihydro-1H-inden-5-yl)-3-((1-(3,4-dimethylphenyl)-3-(trifluoromethyl)-1H-pyrazol-5-yl)methyl)urea;

182 1-((3-tert-butyl-1-(3,5-dichlorophenyl)-1H-pyrazol-5-yl)methyl)-3-(2,3-dihydro-1H-inden-5-yl)urea;

183 2-(benzo[d][1,3]dioxol-5-yl)-N-((1-(3-chlorophenyl)-3-cyclopropyl-1H-pyrazol-5-yl)methyl)propanamide;

184 N-((1-cyclohexyl-3-(trifluoromethyl)-1H-pyrazol-5-yl)methyl)-2-(2,3-dihydrobenzo[b][1,4]dioxin-6-yl)propanamide;

185 1-((3-tert-butyl-1-(3-chlorophenyl)-1H-pyrazol-5-yl)methyl)-3-(2,3-dihydrobenzofuran-7-yl)urea;

186 N-((3-tert-butyl-1-(3-chlorophenyl)-1H-pyrazol-5-yl)methyl)-2-(2,3-dihydro-1H-inden-5-yl)acetamide;

187 1-((3-tert-butyl-1-(3-chlorophenyl)-1H-pyrazol-5-yl)methyl)-3-(2,2-difluorobenzo[d][1,3]dioxol-5-yl)urea;

188 N-((3-tert-butyl-1-(3-chlorophenyl)-1H-pyrazol-5-yl)methyl)-2-(2,3-dihydrobenzo[b][1,4]dioxin-6-yl)acetamide;

189 N-((1-(3-chlorophenyl)-3-(trifluoromethyl)-1H-pyrazol-5-yl)methyl)-2-(2,2-dimethylchroman-6-yl)propanamide;

190 N-((1-(3-chlorophenyl)-3-(trifluoromethyl)-1H-pyrazol-5-yl)methyl)-2-(2,2-dimethyl-2H-chromen-6-yl)propanamide;

191 N-((1-(3-chlorophenyl)-3-(trifluoromethyl)-1H-pyrazol-5-yl)methyl)-2-(1-(methylsulfonyl)-1H-indazol-5-yl)propanamide;

192 1-((1-(3-chlorophenyl)-3-(trifluoromethyl)-1H-pyrazol-5-yl)methyl)-3-(2-methyl-1H-indol-4-yl)urea;

193 N-((3-tert-butyl-1-(3-chlorophenyl)-1H-pyrazol-5-yl)methyl)-2-(6-fluoro-1H-indazol-4-yl)propanamide;

194 1-((1-(3-chlorophenyl)-3-(trifluoromethyl)-1H-pyrazol-5-yl)methyl)-3-(6-fluoro-1H-indazol-4-yl)urea;

195 N-((1-(3-chlorophenyl)-3-(trifluoromethyl)-1H-pyrazol-5-yl)methyl)-2-(7-fluoro-1H-indazol-4-yl)propanamide;

196 1-((1-(3-chlorophenyl)-3-(trifluoromethyl)-1H-pyrazol-5-yl)methyl)-3-(1-oxo-1,2-dihydroisoquinolin-5-yl)urea;

197 N-((1-(3-chlorophenyl)-3-(trifluoromethyl)-1H-pyrazol-5-yl)methyl)-2-(5-fluoronaphthalen-1-yl)propanamide;

198 5-(1-((1-(3-chlorophenyl)-3-(trifluoromethyl)-1H-pyrazol-5-yl)methylamino)-1-oxopropan-2-yl)quinolin 1-oxide;

199 2-(1H-indazol-4-yl)-N-((1-pentyl-3-(trifluoromethyl)-1H-pyrazol-5-yl)methyl)propanamide;

200 N-((1-(3-chlorophenyl)-4-methyl-3-(trifluoromethyl)-1H-pyrazol-5-yl)methyl)-2-(2,3-dihydrobenzo[b][1,4]dioxin-6-yl)propanamide;

201 N-((3-tert-butyl-1-(2,2,2-trifluoroethylamino)-1H-pyrazol-5-yl)methyl)-2-(2,3-dihydrobenzo[b][1,4]dioxin-6-yl)propanamide;

202 2-(2,3-dihydrobenzo[b][1,4]dioxin-6-yl)-N-((1-(4-methoxybenzyl)-3-(trifluoromethyl)-1H-pyrazol-5-yl)methyl)propanamide;

203 2-(1H-indazol-4-yl)-N-((1-(2-methoxyethylamino)-3-(trifluoromethyl)-1H-pyrazol-5-yl)methyl)propanamide;

204 2-(1H-indazol-4-yl)-N-((1-(pyridin-2-ylmethylamino)-3-(trifluoromethyl)-1H-pyrazol-5-yl)methyl)propanamide;

205 1-(5-chloro-1H-indazol-4-yl)-3-((1-(3-chlorophenyl)-3-(trifluoromethyl)-1H-pyrazol-5-yl)methyl)urea;

206 N-((1-(3-chlorophenyl)-3-(trifluoromethyl)-1H-pyrazol-5-yl)methyl)-2-(1-oxo-2,3-dihydro-1H-inden-4-yl)propanamide;

207 N-((1-(3-chlorophenyl)-3-(trifluoromethyl)-1H-pyrazol-5-yl)methyl)-2-(1-hydroxy-2,3-dihydro-1H-inden-4-yl)propanamide;

208 N-((1-(3-chlorophenyl)-3-(trifluoromethyl)-1H-pyrazol-5-yl)methyl)-2-(2-hydroxy-2,3-dihydro-1H-inden-4-yl)propanamide;

209 N-((1-(3-chlorophenyl)-3-(trifluoromethyl)-1H-pyrazol-5-yl)methyl)-2-(1H-indazol-6-yl)propanamide;

210 N-((1-(3-chlorophenyl)-3-(trifluoromethyl)-1H-pyrazol-5-yl)methyl)-2-(1H-indazol-7-yl)propanamide;

211 N-((1-(3-chlorophenyl)-3-(trifluoromethyl)-1H-pyrazol-5-yl)methyl)-2-(6-fluornaphthalen-1-yl)propanamide;

212 N-((1-(3-chlorophenyl)-3-(trifluoromethyl)-1H-pyrazol-5-yl)methyl)-2-(7-methoxynaphthalen-1-yl)propanamide;

213 2-(3-chloroisoquinolin-5-yl)-N-((1-(3-chlorophenyl)-3-(trifluoromethyl)-1H-pyrazol-5-yl)methyl)propanamide;

214 (S)-1-((1-(3-chlorophenyl)-3-(trifluoromethyl)-1H-pyrazol-5-yl)methyl)-3-(7-hydroxy-5,6,7,8-tetrahydronaphthalen-1-yl)urea;

215 (R)-1-((1-(3-chlorophenyl)-3-(trifluoromethyl)-1H-pyrazol-5-yl)methyl)-3-(7-hydroxy-5,6,7,8-tetrahydronaphthalen-1-yl)urea;

216  1-((3-tert-butyl-1-(pyridin-2-yl)-1H-pyrazol-5-yl)methyl)-3-(6-fluoro-1H-indazol-4-yl)urea;

217  N-(5-((3-(6-fluoro-1H-indazol-4-yl)ureido)methyl)-3-(trifluormethyl)-1H-pyrazol-1-yl)benzamide;

respectively in the form of the free compounds; the racemate; the enantiomers, diastereomers, mixtures of the enantiomers or diastereomers or of an individual enantiomer or diastereomer; or in the form of the salts of physiologically compatible acids or bases; or if appropriate in the form of solvates.

Furthermore, preference may be given to compounds according to the invention of general formula (I) that cause a 50 per cent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The present invention further relates to a process for preparing compounds of the above-indicated general formula (I), according to which at least one compound of general formula (II),

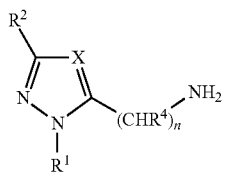
(II)

in which X, $R^1$, $R^2$, $R^4$ and n have one of the foregoing meanings, is reacted in a reaction medium, if appropriate in the presence of at least one suitable coupling reagent, if appropriate in the presence of at least one base, with a compound of general formula (III) or (IV),

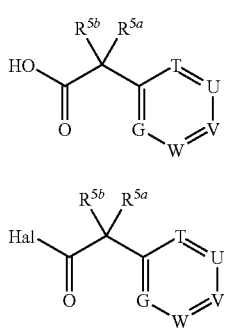
(III)
(IV)

in which Hal represents a halogen, preferably Br or Cl, and $R^{5a}$, $R^{5b}$, T, U, V, W and G each have one of the foregoing meanings, in a reaction medium, if appropriate in the presence of at least one suitable coupling reagent, if appropriate in the presence of at least one base, to form a compound of general formula (I),

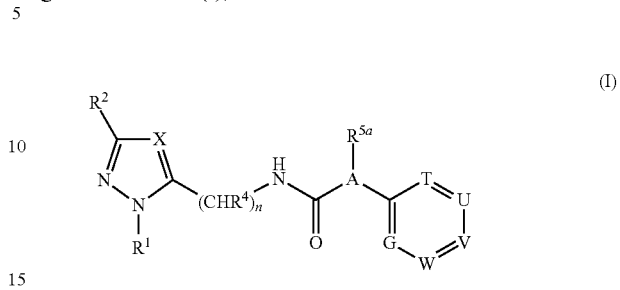
(I)

in which A represents $CR^{5b}$ and X, $R^1$, $R^2$, $R^4$, $R^{5a}$, $R^{5b}$, T, U, V, W and G and n have one of the foregoing meanings;

or in that at least one compound of general formula (II),

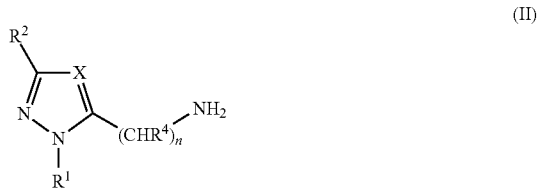
(II)

in which X, $R^1$, $R^2$, $R^4$ and n have one of the foregoing meanings, is reacted to form a compound of general formula (V)

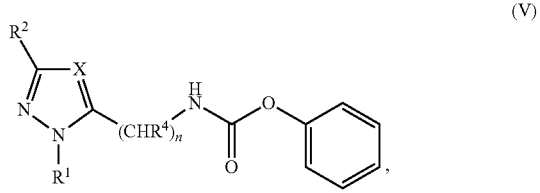
(V)

in which X, $R^1$, $R^2$, $R^4$ and n have one of the foregoing meanings, in a reaction medium, in the presence of phenyl chloroformate, if appropriate in the presence of at least one base and/or at least one coupling reagent, and said compound is if appropriate purified and/or isolated, and a compound of general formula (V) is reacted with a compound of general formula (VI),

(VI)

in which T, U, V, W and G have one of the foregoing meanings, in a reaction medium, if appropriate in the presence of at least one suitable coupling reagent, if appropriate in the presence of at least one base, to form a compound of general formula (I),

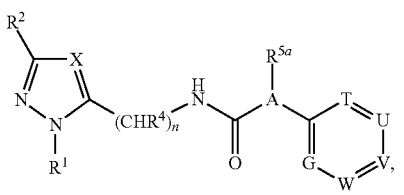

(I)

in which A represents N and X, $R^1$, $R^2$, $R^4$, $R^{5a}$, T, U, V, W and G and n have one of the foregoing meanings.

The reaction of compounds of the above-indicated general formulae (II) and (VI) with carboxylic acids of the above-indicated general formula (III) to form compounds of the above-indicated general formula (I) is carried out preferably in a reaction medium selected from the group consisting of diethyl ether, tetrahydrofuran, acetonitrile, methanol, ethanol, (1,2)-dichloroethane, dimethylformamide, dichloromethane and corresponding mixtures, if appropriate in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), if appropriate in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the above-indicated general formulae (II) and (VI) with carboxylic acid halides of the above-indicated general formula (IV), in which Hal represents a halogen as the leaving group, preferably a chlorine or bromine atom, to form compounds of the above-indicated general formula (I) is carried out in a reaction medium preferably selected from the group consisting of diethyl ether, tetrahydrofuran, acetonitrile, methanol, ethanol, dimethylformamide, dichloromethane and corresponding mixtures, if appropriate in the presence of an organic or inorganic base, preferably selected from the group consisting of triethylamine, dimethylaminopyridine, pyridine and diisopropylamine, at temperatures of from −70° C. to 100° C.

The compounds of the above-indicated formulae (II), (III), (IV), (V) and (VI) are each commercially available and/or can be prepared using conventional processes known to the person skilled in the art.

The reactions described hereinbefore can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described hereinbefore, as well as the respective purification and/or isolation of intermediate or end products, can be carried out partly or completely under an inert gas atmosphere, preferably under a nitrogen atmosphere.

The substituted compounds according to the invention of the aforementioned general formula (I) and also corresponding stereoisomers can be isolated both in the form of their free bases, their free acids and also in the form of corresponding salts, in particular physiologically compatible salts.

The free bases of the respective substituted compounds according to the invention of the aforementioned general formula (I) and also of corresponding stereoisomers can be converted into the corresponding salts, preferably physiologically compatible salts, for example by reaction with an inorganic or organic acid, preferably with hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulphame.

Accordingly, the free acids of the substituted compounds of the aforementioned general formula (I) and of corresponding stereoisomers can be converted into the corresponding physiologically compatible salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds according to the invention of the aforementioned general formula (I) and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the prophylaxis and/or treatment of disorders or diseases which are mediated, at least in some cases, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of the above-indicated formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations.

Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or prophylaxis of one or more disorders selected from the group consisting of pain selected from the group consisting of acute pain, chronic pain, neuropathic pain and visceral pain; joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or prophylaxis of pain, preferably of pain selected from the group consisting of acute pain, chronic pain, neuropathic pain and visceral pain, and/or urinary incontinence.

The present invention further relates to the use of at least one compound according to the invention and also if appropriate of one or more pharmaceutically compatible auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to the use of at least one substituted compound according to the invention and also if appropriate of one or more pharmaceutically compatible auxiliaries for the preparation of a pharmaceutical composition for the prophylaxis and/or treatment of disorders or diseases which are mediated, at least in some cases, by vanilloid receptors 1.

Particular preference is given to the use of at least one compound according to the invention and also if appropriate of one or more pharmaceutically compatible auxiliaries for the preparation of a pharmaceutical composition for the treatment and/or prophylaxis of one or more disorders selected from the group consisting of pain, preferably of pain selected from the group consisting of acute pain, chronic pain, neuropathic pain and visceral pain and joint pain.

Particular preference is given to the use of at least one compound according to the invention and also if appropriate of one or more pharmaceutically compatible auxiliaries for the preparation of a pharmaceutical composition for the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to the use of at least one substituted compound according to the invention and also if appropriate of one or more pharmaceutically compatible auxiliaries for the preparation of a pharmaceutical composition for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to the use of at least one substituted compound according to the invention and also if appropriate of one or more pharmaceutically compatible auxiliaries for the preparation of a pharmaceutical composition for the treatment and/or prophylaxis of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for the prophylaxis and/or treatment of disorders or diseases which are mediated, at least in some cases, by vanilloid receptors 1.

Particular preference is given to at least one compound according to the invention and also if appropriate to one or more pharmaceutically compatible auxiliaries for the treatment and/or prophylaxis of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for the treatment and/or prophylaxis of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for use in vanilloid receptor 1-(VR1/TRPV1) regulation, preferably for use in vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for use in the prophylaxis and/or treatment of disorders or diseases which are mediated, at least in some cases, by vanilloid receptors 1.

Particular preference is given to at least one compound according to the invention and also if appropriate to one or more pharmaceutically compatible auxiliaries for use in the treatment and/or prophylaxis of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for use in the treatment and/or prophylaxis of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for use in the treatment and/or prophylaxis of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for use in the treatment and/or prophylaxis of pain, preferably selected from the group consisting of acute pain, chronic pain, neuropathic pain and visceral pain, and/or urinary incontinence.

Pharmacological Methods

I. Functional Testing Carried Out on the Vanilloid Receptor 1 (VRI/TRPV1 Receptor)

The agonistic or antagonistic effect of the substances to be tested on the rat-species vanilloid receptor 1 (VR1/TRPV1) can be determined using the following assay. In this assay, the influx of $Ca^{2+}$ through the receptor channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:
Complete medium: 50 ml HAMS F12 nutrient mixture (Gibco Invitrogen GmbH, Karlsruhe, Germany) with
10% by volume of FCS (foetal calf serum, Gibco Invitrogen GmbH, Karlsruhe, Germany, heat-inactivated);
2 mM L-glutamine (Sigma, Munich, Germany);
1% by weight of AA solution (antibiotic/antimyotic solution, PAA, Pasching, Austria) and 25 ng/ml NGF medium (2.5 S, Gibco Invitrogen GmbH, Karlsruhe, Germany)

Cell culture plate: Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 µg/ml. Aliquots having a laminin concentration of 100 µg/ml are removed and stored at −20° C. The aliquots are diluted with PBS in a ratio of 1:10 to 10 µg/ml of laminin and respectively 50 µL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:
The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (per cent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 µL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 µL of complete medium are added to each of the remaining DRG. The DRG are respectively suspended several times, drawn through cannulae No. 1, No. 12 and No. 16 using a syringe and transferred to a 50 ml Falcon tube which is filled up to 15 ml with complete medium. The contents of each Falcon tube are respectively filtered through a 70 µm Falcon filter element and centrifuged for 10 minutes at 1,200 rpm and RT. The resulting pellet is respectively taken up in 250 µL of complete medium and the cell count is determined.

The number of cells in the suspension is set to $3\times10^5$ per ml and 150 µL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 µM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at RT used for $Ca^{2+}$ measurement in a FLIPR assay. The $Ca^{2+}$-dependent fluorescence is in this case measured before and after the addition of substances ($\lambda ex=488$ nm, $\lambda em=540$ nm). Quantification is carried out by measuring the highest fluorescence intensity (FC, fluorescence counts) over time.

FLIPR Assay:
The FLIPR protocol consists of 2 substance additions. First the compounds to be tested (10 µM) are pipetted onto the cells and the $Ca^{2+}$ influx is compared with the control (capsaicin 10 µM). This provides the result in % activation based on the $Ca^{2+}$ signal after the addition of 10 µM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 µM of capsaicin.

Triple analyses (n=3) are carried out and repeated in at least 3 independent experiments (N=4).

Starting from the percentage displacement caused by different concentrations of the compounds to be tested of general formula I, $IC_{50}$ inhibitory concentrations which cause a 50-per cent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

II. Functional Tests Carried Out on the Vanilloid Receptor (VR1)

The agonistic or antagonistic effect of the substances to be tested on the vanilloid receptor 1 (VR1) can also be determined using the following assay. In this assay, the influx of $Ca^{2+}$ through the channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:
Chinese hamster ovary cells (CHO K1 cells, European Collection of Cell Cultures (ECACC) United Kingdom) are stably transfected with the VR1 gene. For functional testing, these cells are plated out on poly-D-lysine-coated black 96-well plates having a clear base (BD Biosciences, Heidelberg, Germany) at a density of 25,000 cells/well. The cells are incubated overnight at 37° C. and 5% $CO_2$ in a culture medium (Ham's F12 nutrient mixture, 10% by volume of FCS (foetal calf serum), 18 µg/ml of L-proline). The next day the cells are incubated with Fluo-4 (Fluo-4 2 µM, 0.01% by volume of Pluronic F127, Molecular Probes in HBSS (Hank's buffered saline solution), Gibco Invitrogen GmbH, Karlsruhe, Germany) for 30 minutes at 37° C. Subsequently, the plates are washed three times with HBSS buffer and after further incubation for 15 minutes at RT used for $Ca^{2+}$ measurement in a FLIPR assay. The $Ca^{2+}$-dependent fluorescence is measured before and after the addition of the substances to be tested (λex wavelength=488 nm, λem=540 nm). Quantification is carried out by measuring the highest fluorescence intensity (FC, fluorescence counts) over time.

FLIPR Assay:

The FLIPR protocol consists of 2 substance additions. First the compounds to be tested (10 μM) are pipetted onto the cells and the $Ca^{2+}$ influx is compared with the control (capsaicin 10 μM) (% activation based on the $Ca^{2+}$ signal after the addition of 10 μM of capsaicin). After 5 minutes' incubation, 100 nM of capsaicin are applied and the $Ca^{2+}$ influx is also determined.

Desensitising agonists and antagonists led to suppression of the $Ca^{2+}$ influx. The % inhibition is calculated compared to the maximum achievable inhibition with 10 μM of capsaicin.

Starting from the percentage displacement caused by different concentrations of the compounds to be tested of general formula I, $IC_{50}$ inhibitory concentrations which cause a 50-per cent displacement of capsaicin were calculated. $K_i$ values for the test substances were obtained by conversion by means of the Cheng-Prusoff equation (Cheng, Prusoff; Biochem. Pharmacol. 22, 3099-3108, 1973).

III. Formalin Test Carried Out on Mice

In the formalin test, the testing to determine the antinociceptive effect of the compounds according to the invention is carried out on male mice (NMRI, 20 to 30 g body weight, Iffa, Credo, Belgium).

In the formalin test as described by D. Dubuisson et al., Pain 1977, 4, 161-174, a distinction is drawn between the first (early) phase (0 to 15 minutes after the injection of formalin) and the second (late) phase (15 to 60 minutes after the injection of formalin). The early phase, as an immediate reaction to the injection of formalin, is a model of acute pain, whereas the late phase is regarded as a model of persistent (chronic) pain (T. J. Coderre et al., Pain 1993, 52, 259-285). The corresponding descriptions in the literature are introduced herewith by way of reference and form part of the disclosure.

The compounds according to the invention are tested in the second phase of the formalin test to obtain information about the effects of substances on chronic/inflammatory pain.

The moment at which the compounds according to the invention are applied before the injection of formalin is selected as a function of the type of application of the compounds according to the invention. 10 mg of the test substances/kg of body weight are applied intravenously 5 minutes before the injection of formalin which is carried out by a single subcutaneous injection of formalin (20 μL, 1% aqueous solution) into the dorsal side of the right hind paw, thus inducing in free moving test animals a nociceptive reaction which manifests itself in marked licking and biting of the paw in question.

Subsequently, the nociceptive behaviour is continuously detected by observing the animals over a test period of three minutes in the second (late) phase of the formalin test (21 to 24 minutes after the injection of formalin). The pain behaviour is quantified by adding up the seconds over which the animals display licking and biting of the paw in question during the test period.

The comparison is carried out respectively with control animals which are given vehicles (0.9% aqueous sodium chloride solution) instead of the compounds according to the invention before the administration of formalin. Based on the quantification of the pain behaviour, the effect of the substance is determined in the formalin test as a percentage change relative to the corresponding control.

After the injection of substances having an antinociceptive effect in the formalin test, the described behaviour of the animals, i.e. licking and biting, is reduced or eliminated.

IV. Testing of Analgesic Efficacy in the Writhing Test

The testing of analgesic efficacy in the compounds according to the invention of general formula I was carried out by phenylquinone-induced writhing in mice (modified in accordance with I. C. Hendershot and J. Forsaith (1959), J. Pharmacol. Exp. Ther. 125, 237-240). The corresponding description in the literature is introduced herewith by way of reference and forms part of the disclosure.

Male NMRI mice weighing from 25 to 30 g were used for this purpose. 10 minutes after intravenous administration of the compounds to be tested, groups of 10 animals per compound dose received 0.3 ml/mouse of a 0.02% aqueous solution of phenylquinone (phenylbenzoquinone, Sigma, Deisenhofen, Germany; solution prepared by adding 5% by weight of ethanol and storage in a water bath at 45° C.) applied intraperitoneally. The animals were placed individually into observation cages. A pushbutton counter was used to record the number of pain-induced stretching movements (what are known as writhing reactions=straightening of the torso with stretching of the rear extremities) for 5 to 20 minutes after the administration of phenylquinone. The control was provided by animals which had received only physiological saline solution. All the compounds were tested at the standard dosage of 10 mg/kg.

V. Hypothermia Assay Carried Out on Mice

Description of the Method:

The hypothermia assay is carried out on male NMRI mice (weight 25-35 grams, breeder IFFA CREDO, Brussels, Belgium). The animals were kept under standardised conditions: light/dark rhythm (from 6:00 to 18:00 light phase; from 18:00 to 6:00 dark phase), RT 19-22° C., relative humidity 35-70%, 15 room air changes per hour, air movement<0.2 m/sec. The animals received standard feed (ssniff R/M-Haltung, ssniff Spezialdiäten GmbH, Soest, Germany) and tap water. Water and feed were withdrawn during the experiment. All the animals were used only once during the experiment. The animals had an acclimatisation period of at least 5 days.

Acute application of capsaicin (VR-1 agonist) leads to a drop in the core temperature of the body in rats and mice due to stimulation of heat sensors. Only specifically effective VR-1 receptor antagonists can antagonise the capsaicin-induced hypothermia. By contrast, hypothermia induced by morphine is not antagonised by VR-1 antagonists. This model is therefore suitable for identifying substances with VR-1 antagonistic properties via their effect on body temperature.

Measurement of the core temperature was carried out using a digital thermometer (Thermalert TH-5, physitemp, Clifton N.J., USA). The sensing element is in this case inserted into the rectum of the animals.

To give an individual basic value for each animal, the body temperature is measured twice at an interval of approx. half an hour. One group of animals (n=6 to 10) then receives an intraperitoneal (i.p.) application of capsaicin 3 mg/kg and vehicle (control group). Another group of animals receives the substance to be tested (i.v. or p.o.) and additionally capsaicin (3 mg/kg) i.p. The test substance is applied i.v. 10 min, or p.o 15 minutes, prior to capsaicin. The body temperature is then measured 7.5/15 and 30 min following capsaicin (i.v.+i.p.) or 15/30/60/90/120 min (p.o.+i.p.) following capsaicin. In addition, one group of animals is treated with the test substance only and one group with vehicle only. The evaluation or representation of the measured values as the mean+/− SEM of the absolute values is carried out as a graphical representation. The antagonistic effect is calculated as the percentage reduction of the capsaicin-induced hypothermia.

VI. Neuropathic Pain in Mice

Efficacy in neurotic pain was tested using the Bennett model (chronic constriction injury; Bennett and Xie, 1988, Pain 33: 87-107).

Three loose ligatures are tied around the right ischiadic nerve of Ketavet/Rompun-anaesthetised NMRI mice weighing 16-18 g. The animals develop hypersensitivity of the innervated paw caused by the damaged nerve, which hypersensitivity is quantified, following a recovery phase of one week, over a period of approximately three weeks by means of a cold metal plate (temperature 4° C.) (cold allodynia). The animals are observed on this plate over a period of 2 min and the withdrawal reactions of the damaged paw are counted. Based on the pre-value prior to the application of the substance, the substance's effect over a certain period of time is determined at various points in time (for example 15, 30, 45, or 60 min following application) and the resultant area under the curve (AUC) and/or the inhibition of cold allodynia at the individual measuring points is/are expressed as a percentage effect relative to the vehicle control (AUC) or to the starting value (individual measuring points). The group size is n=10, the significance of an antiallodynic effect (*=p<0.05) is determined with the aid of an analysis of variance with repeated measures and Bonferroni post hoc analysis.

The invention will be described hereinafter with the aid of a few examples. This description is intended merely by way of example and does not limit the general idea of the invention.

EXAMPLES

The indication "equivalents" ("eq.") means molar equivalents, "RT" means room temperature, "M" and "N" are indications of concentration in mol/l, "aq." means aqueous, "sat." means saturated, "sol." means solution, "conc." means concentrated.

Further Abbreviations:
AcOH acetic acid
d days
bipy 2,2'-bipyridine/2,2'-bipyridyl
BOC/Boc tert.-butyloxycarbonyl
BOP 1-benzotriazolyloxy-tris-(dimethylamino)phosphonium hexafluorophosphate
brine saturated sodium chloride solution (NaCl sol.)
DCC N,N'-dicyclohexylcarbodiimide
DCM dichloromethane
DIPEA N,N-diisopropylethylamine
DMF N,N-dimethylformamide
DMAP 4-dimethylaminopyridine
EDC N-(3-dimethylaminopropyl)-N'-ethylcarbodiimide
EDCl N-ethyl-N'-(3-dimethylaminopropyl)carbodiimide hydrochloride
EE ethyl acetate
ether diethyl ether
EtOH ethanol
sat. saturated
h hour(s)
$H_2O$ water
HOBt N-hydroxybenzotriazole
LAH lithium aluminium hydride
LG leaving group
m/z mass-to-charge ratio
MeCN acetonitrile
MeOH methanol
min minutes
MS mass spectrometry
NA not available
$NEt_3$ triethylamine
RT/r.t./rt room temperature
$R_f$ retention factor
SC silica gel column chromatography
THF tetrahydrofuran
TFA trifluoroacetic acid
TLC thin layer chromatography
vv volume ratio The yields of the compounds prepared were not optimised.

All temperatures are uncorrected.

All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US, for example) or the synthesis thereof has already been described precisely in the specialist literature (experimental guidelines can be looked up in the Reaxys® Database of Elsevier, Amsterdam, NL, for example) or can be prepared using the conventional methods known to the person skilled in the art.

The stationary phase used for the column chromatography was silica gel 60 (0.0-0-0.063 mm) from E. Merck, Darmstadt. The thin-layer chromatographic tests were carried out using HPTLC precoated plates, silica gel 60 F 254, from E. Merck, Darmstadt.

The mixing ratios of solvents, mobile solvents or for chromatographic tests are respectively specified in volume/volume.

All the intermediate products and exemplary compounds were analytically characterised by means of $^1$H-NMR spectroscopy. In addition, mass spectrometry tests (MS, m/z indication for [M+H]$^+$) were carried out for all the exemplary compounds and selected intermediate products.

General reaction scheme (scheme 1a):

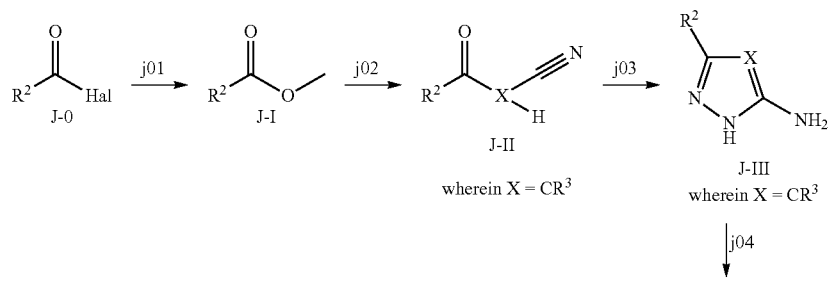

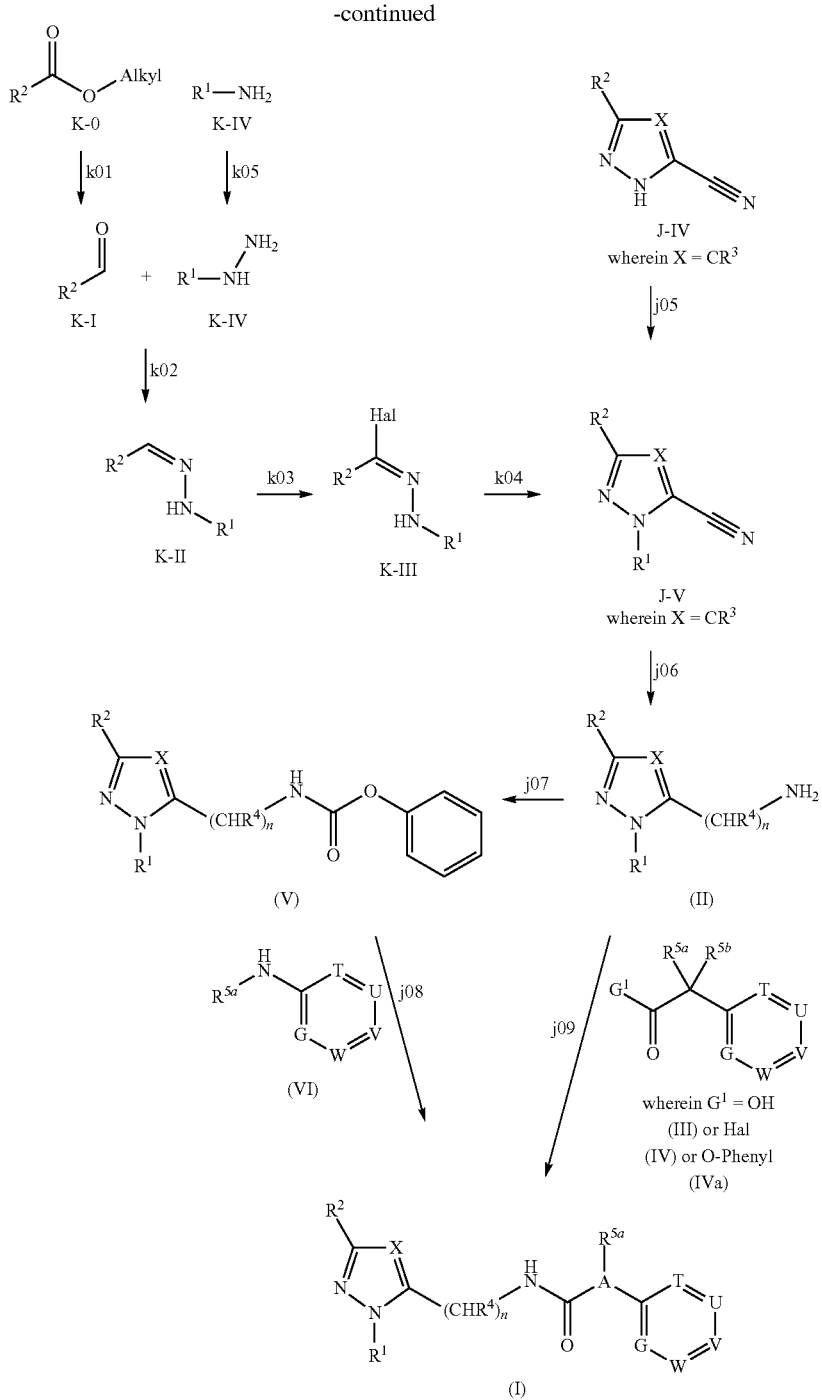

In step j01 an acid halide J-0, in which Hal preferably represents Cl or Br, can be esterified using methanol to form the compound J-I by means of methods with which the person skilled in the art is familiar.

In step j02 the methyl pivalate J-I can be converted into an oxoalkylnitrile J-II, wherein $X=CR^3$, by means of methods known to the person skilled in the art, such as for example using an alkyl nitrile $R^3CH_2$—CN, if appropriate in the presence of a base.

In step j03 the compound J-II can be converted into an amino-substituted pyrazolyl derivative J-III, wherein $X=CR^3$, by means of methods known to the person skilled in the art, such as for example using hydrazine hydrate, with cyclisation.

In step j04 the amino compound J-III can first be converted into a diazonium salt by means of methods known to the person skilled in the art, such as for example using nitrite, and the diazonium salt can be converted into a cyano-substituted pyrazolyl derivative J-IV, wherein $X=CR^3$, with elimination of nitrogen using a cyanide, if appropriate in the presence of a coupling reagent.

In step j05 the compound J-IV can be substituted in the N position by means of methods known to the person skilled in the art, for example using a halide $R^1$-Hal, if appropriate in the presence of a base and/or a coupling reagent, wherein Hal is preferably Cl, Br or I, or using a boronic acid $B(OH)_2R^1$ or a corresponding boronic acid ester, if appropriate in the presence of a coupling reagent and/or a base and the compound J-V, wherein $X=CR^3$, can in this way be obtained. If $R^1$ is linked to general formula (I) via a heteroatom (if $R^1$ represents substructure (T-1), for example, in which o represents 1 and Y can represent inter alia O, S, S(=O)$_2$ or $NR^{12}$), then the substitution can be carried out using methods known to the person skilled in the art, for example with the aid of hydroxylamine-O-sulphonic acid and subsequent conversion into secondary or tertiary amines, wherein $Y=NR^{13}$. In the case of Y=O, the substitution can be carried out using methods known to the person skilled in the art, for example with the aid of peroxy reagents and subsequent conversion into ether. In the case of $Y=S(=O)_2$, the substitution can be carried out by sulphonylation with sulphonyl chlorides, for example. In the case of Y=S, the preparation can for example be carried out by reaction with disulphides or else with sulphenyl chlorides or sulphene amides, or else by transformation into the mercaptan by means of methods known to the person skilled in the art and subsequent conversion into the thioether.

Alternatively, a second synthesis pathway, in which in step k01 an ester K-0 is first reduced to form the aldehyde K-I by means of methods known to the person skilled in the art, for example using suitable hydrogenation reagents such as metal hydrides, is suitable for preparing the compound J-V, wherein $X=CR^3$.

In step k02 the aldehyde K-I can then be reacted with a hydrazine K-V, which can be obtained in step k05, starting from the primary amine K-IV, by means of methods known to the person skilled in the art, to form the hydrazine K-II by means of methods known to the person skilled in the art with elimination of water.

In step k03 the hydrazine K-II can be halogenated, preferably chlorinated, by means of methods known to the person skilled in the art with the double bond intact, such as for example using a chlorination reagent such as NCS, and the compound K-III can in this way be obtained.

In step k04 the hydrazonoyl halide K-III can be converted into a cyano-substituted compound J-V, wherein $X=CR^3$, by means of methods known to the person skilled in the art, such as for example using a halogen-substituted nitrile, with cyclisation.

In step j06 the compound J-V can be hydrogenated by means of methods known to the person skilled in the art, for example using a suitable catalyst such as palladium/activated carbon or using suitable hydrogenation reagents, and the compound (II) can in this way be obtained.

In step j07 the compound (II) can be converted into the compound (V) by means of methods known to the person skilled in the art, such as for example using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j08 the amine (VI) can be converted into the urea compound (I) (wherein A=N). This can be achieved by reaction with (V) by means of methods with which the person skilled in the art is familiar, if appropriate in the presence of a base.

In step j09 the amine (II) can be converted into the amide (I) (wherein $A=C-R^{5b}$). This can for example be achieved by reaction with an acid halide, preferably a chloride of formula (IV) by means of methods with which the person skilled in the art is familiar, if appropriate in the presence of a base or by reaction with an acid of formula (III), if appropriate in the presence of a suitable coupling reagent, for example HATU or CDI, if appropriate with the addition of a base. Further, the amine (II) may be converted into the amide (I) (wherein $A=C-R^{5b}$) by reaction of a compound (IVa) by means of methods with which the person skilled in the art is familiar, if appropriate in the presence of a base.

For preparing compounds (II), wherein X=N, it is necessary to take a third synthesis route according to the general reaction scheme 1b. The compounds (II) which are then obtained, wherein X=N, can subsequently be further reacted in accordance with the above-described steps j07-j09.

General reaction scheme (scheme 1b):

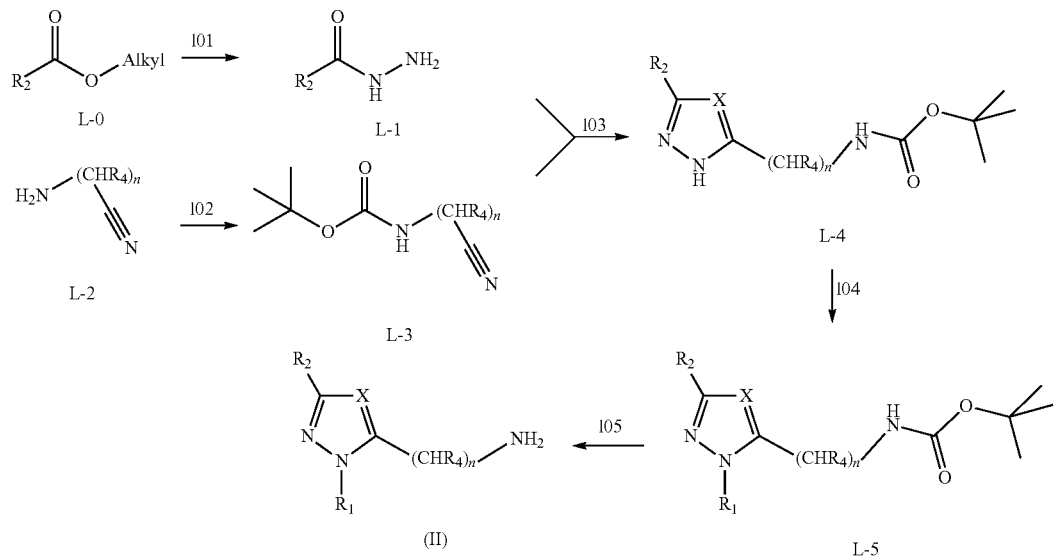

In step 101 a carboxylic acid alkyl ester L-0, preferably a methyl or ethyl ester, can be reacted with hydrazine hydrate to form the hydrazide L-1 by means of methods with which the person skilled in the art is familiar.

In step 102 the amino-substituted nitrile L-2 or the salts thereof can be reacted with boc anhydride to form the urethane L-3 by means of methods with which the person skilled in the art is familiar.

In step 103 L-1 and L-3 can be condensed in the presence of a base, preferably an alkali alcoholate, particularly preferably sodium methanolate, to form the triazole L-4, wherein X=N, by means of methods with which the person skilled in the art is familiar.

In step 104 the compound L-4, wherein X=N, can be substituted in the N position by means of methods known to the person skilled in the art, in a manner similar to the step j05 according to general reaction scheme 1a by means of the methods described hereinbefore, and compound L-5, wherein X=N, can in this way be obtained.

In step 105 the ester group in L-4 can be eliminated in the presence of an acid, preferably trifluoroacetic acid or hydrochloric acid, by means of methods known to the person skilled in the art, and the amine (II) can in this way be obtained.

The compounds according to general formula (I), wherein A=N, may be further prepared by a reaction sequence according to general reaction scheme 1c.

k01 to k05 and l01 to l05 as well as j10 and j11 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

Synthesis of Intermediate Products

1. Synthesis of 3-tert-butyl-1-methyl-1H-pyrazol-5-yl-methanamine (Steps j01-j06)

Step j01: Pivaloyl chloride (J-0) (1 eq., 60 g) was added dropwise to a solution of MeOH (120 ml) within 30 min at 0° C. and the mixture was stirred for 1 h at room temperature. After the addition of water (120 ml), the separated organic phase was washed with water (120 ml), dried over sodium sulphate and codistilled with dichloromethane (150 ml). The liquid product J-I was able to be obtained at 98.6% purity (57 g).

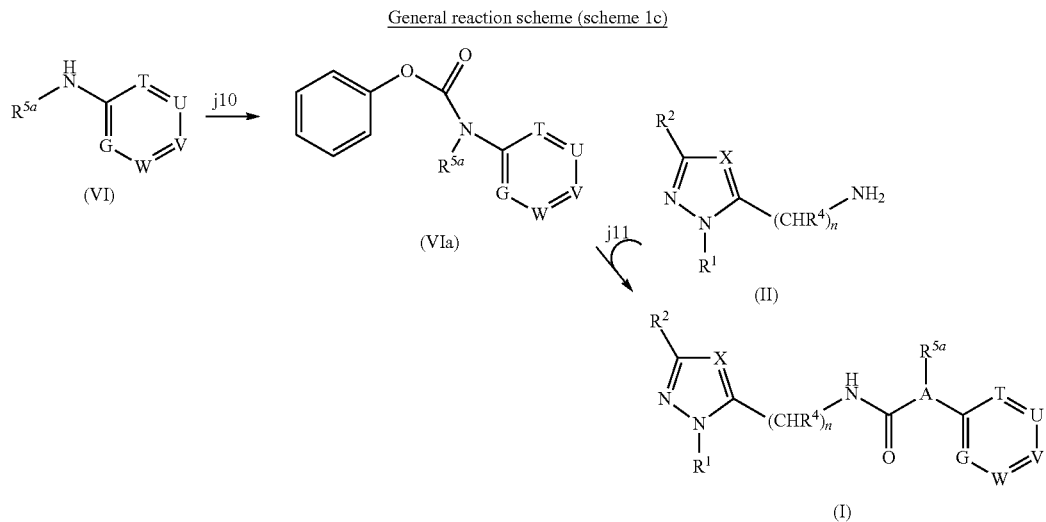

In step j10 the compound (VI) can be converted into the compound (VIa) by means of methods known to the person skilled in the art, such as for example using phenyl chloroformate, if appropriate in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j11 the amine (II) can be converted into the urea compound (I) (wherein A=N). This can be achieved by reaction with (VIa) by means of methods with which the person skilled in the art is familiar, if appropriate in the presence of a base.

The methods with which the person skilled in the art is familiar for carrying out the reaction steps j01 to j09 and also Step j02: NaH (50% in paraffin oil) (1.2 eq., 4.6 g) was dissolved in 1,4-dioxane (120 ml) and the mixture was stirred for a few minutes. Acetonitrile (1.2 eq., 4.2 g) was added dropwise within 15 min and the mixture was stirred for a further 30 min. The methyl pivalate (J-I) (1 eq., 10 g) was added dropwise within 15 min and the reaction mixture was refluxed for 3 h. After complete reaction, the reaction mixture was placed in iced water (200 g), acidified to pH 4.5 and extracted with dichloromethane (12×250 ml). The combined organic phases were dried over sodium sulphate, distilled and after recrystallisation from hexane (100 ml) 5 g of the product (J-II) (51% yield) was able to be obtained as a solid brown substance.

Step j03: At room temperature 4,4-dimethyl-3-oxopentanenitrile (J-II) (1 eq., 5 g) was taken up in EtOH (100 ml), mixed with hydrazine hydrate (2 eq., 4.42 g) and refluxed for 3 h. The residue obtained after removal of the EtOH by distillation was taken up in water (100 ml) and extracted with EE (300 ml). The combined organic phases were dried over sodium sulphate, the solvent was removed under vacuum and the product (J-III) (5 g, 89% yield) was obtained as a light red solid after recrystallisation from hexane (200 ml).

Step j04: 3-Tert-butyl-1H-pyrazol-5-amine (J-III) (1 eq., 40 g) was dissolved in dilute HCl (120 ml of HCl in 120 ml of water) and mixed dropwise with $NaNO_2$ (1.03 eq., 25 g in 100 ml) at 0-5° C. over a period of 30 min. After stirring for 30 minutes, the reaction mixture was neutralised with $Na_2CO_3$. A diazonium salt obtained by reaction of KCN (2.4 eq., 48 g), water (120 ml) and CuCN (1.12 eq., 31 g) was added dropwise to the reaction mixture within 30 min and the mixture was stirred for a further 30 min at 75° C. After complete reaction, the reaction mixture was extracted with EE (3×500 ml), the combined organic phases were dried over sodium sulphate and the solvent was removed under vacuum. The purification ($SiO_2$, 20% EE/hexane) of the residue by column chromatography produced a white solid (J-IV) (6.5 g, 15.1% yield).

Step j05 (Method 1):
3-tert.-butyl-1H-pyrazol-5-carbonitrile (J-IV) (10 mmol) was added to a suspension of NaH (60%) (12.5 mmol) in DMF (20 ml) at room temperature while stirring. After stirring for 15 minutes, methyl iodide (37.5 mmol) was added dropwise to this reaction mixture at room temperature. After stirring for 30 min at 100° C., the reaction mixture was mixed with water (150 ml) and extracted with dichloromethane (3×75 ml). The combined organic extracts were washed with water (100 ml) and sat. NaCl solution (100 ml) and dried over magnesium sulphate. After removal of the solvent under vacuum, the residue was purified by column chromatography ($SiO_2$, various mixtures of EE and cyclohexane as the mobile solvent) and the product J-V was obtained.

Step j06:
Method 1:
J-V was dissolved together with palladium on carbon (10%, 500 mg) and concentrated HCl (3 ml) in MeOH (30 ml) and exposed to a hydrogen atmosphere for 6 hours at room temperature. The reaction mixture was filtered over celite and the filtrate was concentrated under vacuum. The residue was purified by means of flash chromatography ($SiO_2$, EE) and the product (II) was in this way obtained.

Method 2:
J-V was dissolved in THF (10 ml) and $BH_3 \cdot S(CH_3)_2$ (2.0 M in THF, 3 ml, 3 equivalent) was added thereto. The reaction mixture was heated to reflux for 8 hours, aq. 2 N HCl (2 N) was added thereto and the reaction mixture was refluxed for a further 30 minutes. The reaction mixture was mixed with aq. NaOH solution (2N) and washed with EE. The combined organic phases were washed with sat. aq. NaCl solution and dried over magnesium sulphate. The solvent is removed under vacuum and the residue is purified by column chromatography ($SiO_2$, various mixtures of dichloromethane and methanol as the mobile solvent) and the product (II) (3-tert-butyl-1-methyl-1H-pyrazol-5-yl)methanamine) is in this way obtained.

2. The Following Further Intermediate Products were Synthesised in a Similar Manner Using the Process Described Hereinbefore Under 1

3-tert-butyl-1-hexyl-1H-pyrazol-5-yl-methanamine

3. Alternatively, Step j05 can also be Carried Out as follows (Method 2)

Step j05 (Method 2):
A mixture of 3-tert-butyl-1H-pyrazol-5-carbonitrile (J-IV) (10 mmol), a boronic acid $B(OH)_2R^1$ or a corresponding boronic acid ester (20 mmol) and copper (II) acetate (15 mmol) is placed in dichloromethane (200 ml), mixed with pyridine (20 mmol) while stirring at room temperature and the mixture is stirred for 16 h. After removal of the solvent under vacuum, the residue obtained is purified by column chromatography ($SiO_2$, various mixtures of EE and cyclohexane as the mobile solvent) and the product J-V is in this way obtained.

The following further intermediate products were prepared in this way (steps j01-j06):
(3-tert-butyl-1-cyclohexenyl-1H-pyrazol-5-yl)methanamine
(3-tert-butyl-1-(3,5-dichlorophenyl)-1H-pyrazol-5-yl) methanamine
(3-tert-butyl-1-phenyl-1H-pyrazol-5-yl)methanamine
(3-tert-butyl-1-p-tolyl-1H-pyrazol-5-yl)methanamine
(3-tert-butyl-1-(4-tert-butylphenyl)-1H-pyrazol-5-yl)methanamine
(3-tert-butyl-1-(4-chlorophenyl)-1H-pyrazol-5-yl)methanamine
(3-tert-butyl-1-(3-chlorophenyl)-1H-pyrazol-5-yl)methanamine
(3-tert-butyl-1-(3-chloro-4-fluorophenyl)-1H-pyrazol-5-yl) methanamine
(3-tert-butyl-1-(4-methoxyphenyl)-1H-pyrazol-5-yl)methanamine
(E)-(3-tert-butyl-1-(4-methylstyryl)-1H-pyrazol-5-yl) methanamine 4. Synthesis of 1-(3-chlorophenyl)-3-(trifluoromethyl)-1H-pyrazol-5-yl-methanamine (Steps k01-k05 and 106)

Step k01: LAlH (lithium aluminium hydride) (0.25 eq., 0.7 g) was dissolved in dry diethyl ether (30 ml) under a protective gas atmosphere and stirred for 2 h at room temperature. The suspension obtained was taken up in diethyl ether (20 ml). Ethyl-2,2,2-trifluoroacetate (K-0) (1 eq., 10 g) was taken up in dry diethyl ether (20 ml) and added dropwise to the suspension at −78° C. over a period of 1 h. The mixture was then the stirred for a further 2 h at −78° C. EtOH (95%) (2.5 ml) was then added dropwise, the reaction mixture was heated to room temperature and placed on iced water (30 ml) with concentrated $H_2SO_4$ (7.5 ml). The organic phase was separated and concentrated under vacuum and the reaction product K-I was immediately introduced into the next reaction step k02.

Step k05: 3-chloroaniline (K-IV) (1 eq., 50 g) was dissolved at −5 to 0° C. in concentrated HCl (300 ml) and stirred for 10 min. A mixture of $NaNO_2$ (1.2 eq., 32.4 g), water (30 ml), $SnCl_2 \cdot 2H_2O$ (2.2 eq., 70.6 g) and concentrated HCl (100 ml) was added dropwise over a period of 3 h while maintaining the temperature. After stirring for a further 2 h at −5 to 0° C., the reaction mixture was set to pH 9 using NaOH solution and extracted with EE (250 ml). The combined organic phases were dried over magnesium sulphate and the solvent was removed under vacuum. The purification by column chromatography ($SiO_2$, 8% EE/hexane) produced 40 g (72% yield) of (3-chlorophenyl)hydrazine (K-IV) as a brown oil.

Step k02: The aldehyde (K-I) (2 eq., 300 ml) obtained from k01 and (3-chlorophenyl)hydrazine (K-IV) (1 eq., 20 g) were placed in EtOH (200 ml) and refluxed for 5 h. The solvent was removed under vacuum, the residue was purified by column chromatography ($SiO_2$, hexane) and the product (25 g, 72% yield) K-II was obtained as a brown oil.

Step k03: The hydrazine K-II (1 eq., 25 g) was dissolved in DMF (125 ml). N-chlorosuccinimide (1.3 eq., 19.5 g) was added portionwise at room temperature within 15 min and the mixture was stirred for 3 h. The DMF was removed by distillation and the residue was taken up in EE. The EE was removed under vacuum, the residue obtained was purified by column chromatography (SiO$_2$, hexane) and the product K-III (26.5 g, 92% yield) was obtained as a pink-coloured oil.

Step k04: At room temperature the hydrazonoyl chloride K-III (1 eq., 10 g) was taken up in toluene (150 ml) and mixed with 2-chloroacrylonitrile (2 eq., 6.1 ml) and TEA (2 eq., 10.7 ml). This reaction mixture was stirred for 20 h at 80° C. The mixture was then diluted with water (200 ml) and the phases were separated. The organic phase was dried over magnesium sulphate and the solvent was removed under vacuum. The residue was purified by means of column chromatography (SiO$_2$, 5% EE/hexane) and the product (5.5 g, 52% yield) was obtained as a white solid J-V.

Step j06 (Method 3):

The carbonitrile J-V (1 eq., 1 g) was dissolved in methanolic ammonia solution (150 ml, 1:1) and hydrogenated in an H-cube (10 bar, 80° C., 1 ml/min, 0.25 mol/L). After removal of the solvent under vacuum, (1-(3-chlorophenyl)-3-(trifluoromethyl)-1H-pyrazol-5-yl)methanamine (II) was able to be obtained as a white solid (0.92 g, 91% yield).

5. The Following Further Intermediate Products were Synthesised in a Similar Manner Using the Process Described Hereinbefore Under 4

(1-(4-fluorophenyl)-3-(trifluoromethyl)-1H-pyrazol-5-yl)methanamine (1-(3-chloro-4-fluorophenyl)-3-(trifluoromethyl)-1H-pyrazol-5-yl)methanamine (1-(4-methoxyphenyl)-3-(trifluoromethyl)-1H-pyrazol-5-yl)methanamine (1-(4-(trifluoromethoxy)phenyl)-3-(trifluoromethyl)-1H-pyrazol-5-yl)methanamine (1-(3,4-dimethylphenyl)-3-(trifluoromethyl)-1H-pyrazol-5-yl)methanamine

6. Preparation of Selected Acids of General Formula (III)

6.1 Synthesis of 2-(7-hydroxynaphthalen-1-yl)propanoic acid

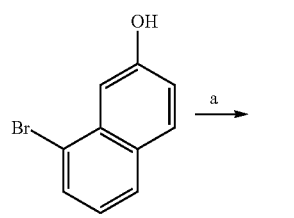

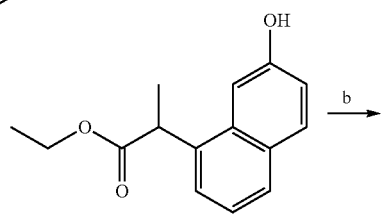

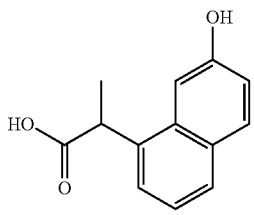

Step a: 8-bromo-naphtol (4.48 mmol, 1 g) and ethyl-2-chloropropionate (5.83 mmol, 0.796 g) were dissolved in DMF (7 ml) in a protective gas atmosphere at room temperature. Subsequently, manganese (8.96 mmol, 0.493 g), (2,2'-bipyridine) nickel(II)-dibromide (0.314 mmol, 0.117 g) and TFA (0.117 mmol, 9 µl) were added and stirring was carried out at 50° C. for 12 h. After cooling the reaction mixture to room temperature, hydrolysis was carried out with 1 N HCl (25 ml) and the mixture was extracted with diethyl ether (3×25 ml). The combined organic phases were washed with water (25 ml) and aq. sat. NaCl solution (25 ml) and dried over magnesium sulphate. After removing the solvent in a vacuum and purifying the residue by column chromatography (SiO$_2$, hexane/diethyl ether=3:1), 0.359 g (33% yield) of the ethyl 2-(7-hydroxynaphthalol)propanoate were obtained.

Step b: The propanoate (1.43 mmol, 0.35 g) obtained in step a was dissolved in a THF-water mixture (5 ml, 2:1), the LiOH (4.3 mmol, 0.104 g) was added and refluxing was carried out for 14 h. The reaction mixture was extracted with diethyl ether (25 ml), the aqueous phase was acidified to pH 2 with 1 N HCl, and extraction was carried out with EE (3×25 ml). The combined organic phases were dried over magnesium sulphate and the solvent was concentrated in a vacuum until dry. It was possible to obtain 2-(7-hydroxynaphthalen-1-yl)propanoic acid in a 97% yield (0.301 g).

6.2 Synthesis of 2-(1-(methylsulphonyl)indolin-5-yl)propanoic acid

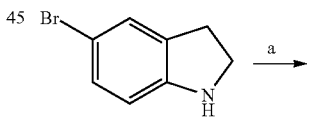

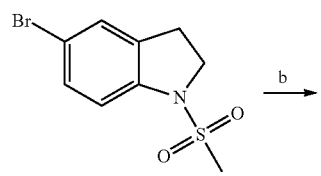

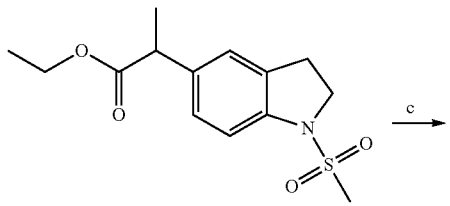

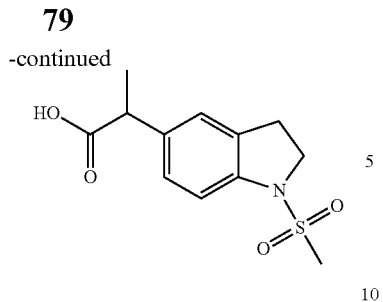

Step a: 5-bromo-indoline (13.88 mmol, 2.75 g) was dissolved in pyridine (12 ml) and cooled to 0° C. in a protective gas atmosphere and methanesulphonylchloride (20.82 mmol, 1.61 ml) was added dropwise. After stirring for one hour at 0° C., the reaction mixture was cooled with ice and water (25 ml) was added, the pH was set to 1 with 16% HCl and extraction was carried out with dichloromethane (2×50 ml). The combined organic phases were dried over magnesium sulphate, the solvent was removed in a vacuum and 3.7 g of the product (96% yield) were obtained.

Step b: 5-bromo-1-(methylsulphonyl)indoline (13.4 mmol, 3.7 g) and ethyl-2-chloropropionate (17.4 mmol, 2.38 g) were dissolved in DMF (7 ml) in a protective gas atmosphere at room temperature. Subsequently, manganese (26.8 mmol, 1.47 g), (2,2'-bipyridine) nickel(II)-dibromide (0.938 mmol, 0.351 g) and TFA (0.348 mmol, 27 μl) were added and stirring was carried out at 50° C. for 1.5 h. After cooling the reaction mixture to room temperature, hydrolysis was carried out at room temperature with 1 N HCl (25 ml) and the mixture was extracted with diethyl ether (3×25 ml). The combined organic phases were washed with water (25 ml) and aq. sat. NaCl solution (25 ml) and dried over magnesium sulphate. After removing the solvent in a vacuum and purifying the residue by column chromatography (SiO$_2$, diethyl ether/hexane=3:1), 0.558 g (14% yield) of ethyl 2-(1-(methylsulphonyl)indolin-5-yl)propanoate were obtained.

Step c: the propanoate (1.78 mmol, 0.53 g) obtained in step b was dissolved in a THF-water mixture (5 ml, 2:1), LiOH (5.34 mmol, 0.128 g) was added and refluxing was carried out for 12 h. The reaction mixture was extracted with diethyl ether (25 ml), the aqueous phase was acidified to pH 2 with 1 N HCl and extraction was carried out with EE (3×25 ml). The combined organic phases were dried over magnesium sulphate and the solvent was removed in a vacuum. It was possible to obtain 2-(1-(methylsulphonyl)indolin-5-yl)propanoic acid in an 80% yield (0.382 g).

6.3 Synthesis of 2-(benzo[d]oxazol-5-yl)propanoic acid

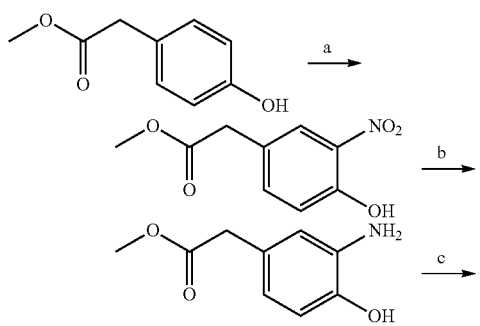

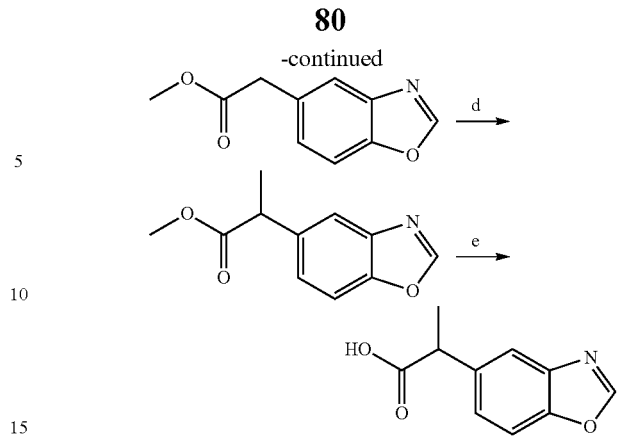

Step a: methyl-2-(4-hydroxyphenyl)acetate (12.0 mmol, 2.0 g) were dissolved in acetic acid (15 ml) and nitric acid (60%) (12.1 mmol, 1.27 g) was added at room temperature. The reaction mixture was stirred for 30 minutes at room temperature, poured into iced water (100 ml) and extracted with EE. The organic phase was dried over magnesium sulphate, the solvent was removed in a vacuum and the residue was purified by column chromatography (SiO$_2$, hexane/EE=4:1).

Step b: methyl-2-(4-hydroxy-3-nitrophenyl)acetate (10.9 mmol, 2.31 g) was dissolved in THF (20 ml) and MeOH (20 ml), and 10% palladium on charcoal (210 mg) was added slowly at room temperature. The reaction mixture was hydrogenated at 39 psi hydrogen pressure for 2 h, filtered over celite and washed with MeOH. The solvent was removed in a vacuum and the residue was purified by column chromatography (SiO$_2$, hexane/EE=2:1).

Step c: triethylorthoformate (10 ml) was added to methyl-2-(3-amino-4-hydroxyphenyl)acetate (7.67 mmol, 1.39 g) at room temperature. The reaction mixture was heated to reflux for 12 h and subsequently cooled to room temperature. Water (70 ml) was added to the reaction mixture and extraction was carried out with EE. The combined organic phases were dried over magnesium sulphate and filtered. The solvent was removed under vacuum and the residue was purified by column chromatography (SiO$_2$, hexane/EE=2:1).

Step d: methyl-2-(benzo[d]oxazol-5-yl)acetate (4.71 mmol, 0.90 g) was dissolved in DMF (5 ml) and sodium hydride (4.95 mmol, 198 mg) and methyl iodide (4.65 mmol, 661 mg) were added at 0° C. The reaction mixture was stirred for 30 min at 0° C. and subsequently for 1 h at room temperature. Water (70 ml) was added to the reaction mixture, which was extracted with EE. The combined organic phases were dried and filtered over magnesium sulphate. The solvent was removed under vacuum and the residue was purified by column chromatography (SiO$_2$, hexane/EE=4/1). $^1$H-NMR (CDCl$_3$) δ [ppm]: 8.10 (s, 1H, Ar), 7.74 (d, 1H, J=1.7 Hz, Ar), 7.54 (d, 1H, 8.4 Hz, Ar), 7.35 (dd, 1H, J=8.6, 1.8 Hz, Ar), 3.87 (q, 1H, J=7.3 Hz, CHCH$_3$), 3.67 (s, 3H, OCH$_3$), 1.57 (d, 3H, J=7.1 Hz, CHCH$_3$). IR [cm$^{-1}$] 2982, 1735, 1517, 1437, 1248, 1201, 1170, 1067.

Step e: methyl-2-(benzo[d]oxazol-5-yl)propanoate (2.07 mmol, 425 mg) was dissolved in THF (8 ml) and water (8 m). LiOH*H$_2$O (2.21 mmol, 93 mg) was added at room temperature. The reaction mixture was stirred at room temperature for 40 h, water (25 ml) was added and the pH was set to 3 with acetic acid. The reaction mixture was extracted with dichloromethane and the combined organic phases were dried and filtered over magnesium sulphate. The solvent was removed in a vacuum and the residue was purified by column chromatography (SiO$_2$, dichloromethane/MeOH=15:1). $^1$H-NMR (CD$_3$OD) δ [ppm]: 8.46 (s, 1H, Ar), 7.70 (d, 1H, J=1.7 Hz, Ar), 7.61 (d, 1H, 8.0 Hz, Ar), 7.42 (dd, 1H, J=8.6, 1.8 Hz, Ar), 3.87 (q, 1H, J=7.1 Hz, CHCH$_3$), 1.51 (d, 3H, J=7.1 Hz, CHCH$_3$).

6.4 Synthesis of 2-(benzo[d]oxazol-6-yl)propanoic acid

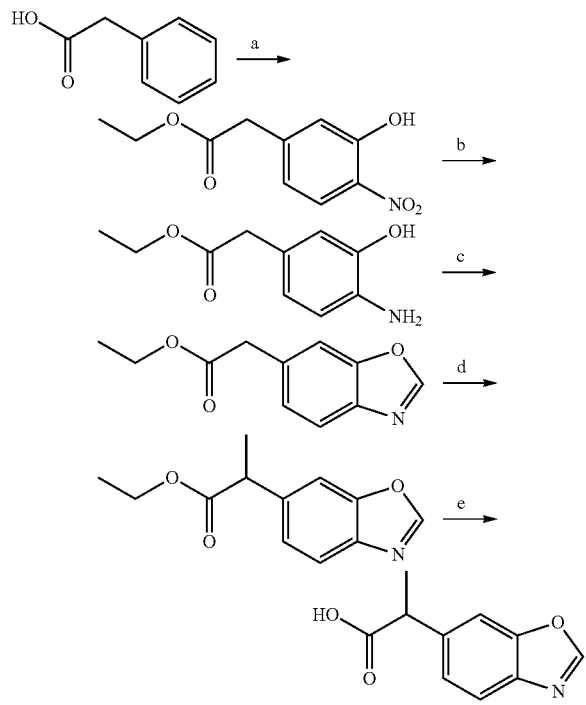

Steps a to e were carried out as in 6.3. However, after step a, the acid function of the resulting product was esterified with ethanol under reflux.

6.5 Synthesis of 2-(5,6,7,8-tetrahydronaphthalen-1-yl)propanoic acid (Employed for the Synthesis of Example Compound No. 2)

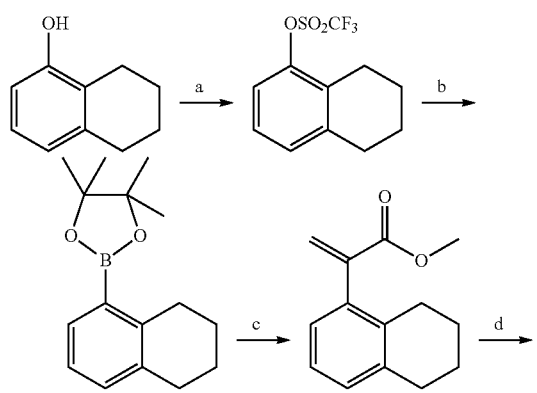

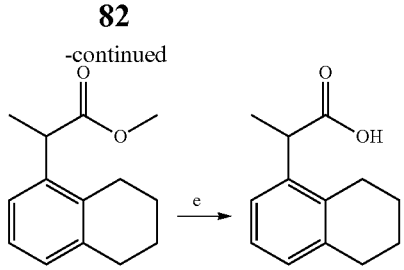

Step a: To a stirred solution of 5,6,7,8-tetrahydronaphthalen-1-ol (5 g, 0.03 mol) in dichloromethane (50 mL) DMAP (7.0 g, 0.057 mol) was added under nitrogen atmosphere. Triflic anhydride (14.25 g, 0.05 mol) was added drop wise in 10 minutes. It was allowed to stir at ambient temperature for 10 hours. TLC showed complete conversion was taken place. Water (100 mL) was added to the reaction mixture and extracted with dichloromethane (2×50 mL). The combined organic layer was dried over magnesium sulfate and concentrated to afford crude compound, which was purified through column chromatography (silica: 100-200 mesh; eluent: 5% ethyl acetate in hexane) to afford the desired compound (9.0 g, 61% yield).

Step b: To a stirred solution of step-a product (6 g, 0.02 mol) in 1,4-dioxane (150 mL), bis-pinacolatodiboron (5.2 g, 0.021 mol) was added and deoxygenated twice. Potassium acetate (6.3 g, 0.06 mol), Pd(dppf)Cl$_2$ (0.78 g, 0.001 mol) and dppf (0.59 g, 0.001 mol) were added simaltaneously to it and finally deoxygenated. The reaction mixture was heated at 100° C. for 12 hours. It was then filtered through celite bed and the organic solvent was concentrated. The residue was diluted with ethyl acetate (200 mL) and was washed with water (2×100 mL). The final organic layer was dried over anhydrous magnesium sulfate and evaporated to dryness to afford crude compound, which was purified through column chromatography (silica: 100-200 mesh, eluent: 3% ethyl acetate in hexane) to afford 2.0 g (36.7% yield).

Step c: To a stirred solution of step-b product (2.5 g, 0.009 mol) in toluene (35 mL) methyl 2-halo acrylate (3.1 g, 0.011 mol) was added and deoxygenated twice. Pd(PPh$_3$)$_4$ (0.5 g, 0.0005 mol) was then added to it and deoxygenated again. Finally aq. sodium carbonate solution (2M, 12 mL) was added to the reaction mixture and heated at 60° C. for 10 hours. The reaction mixture was diluted with water (100 mL) and was extracted with ethyl acetate (2×100 mL). The combined organic layer was dried over anhydrous magnesium sulfate and evaporated to dryness to afford crude compound, which was purified through column chromatography (silica: 100-200 mesh, eluent: 2% ethyl acetate in hexane) to obtain pure compound. (1.8 g, 86% yield).

Step d: Step-c product (1.8 g, 0.008 mol) was dissolved in ethyl acetate (20 mL) and was charged in Parr hydrogenation bottle followed by palladium on charcoal (180 mg, 10% Pd) under nitrogen atmosphere and was hydrogenated at 50 psi for 16 hours. The reaction mixture was filtered through celite bed and was concentrated to afford the crude compound (1.7 g, 94% yield).

Step e: To a stirred solution of step-d product (1.7 g, 0.008 mol) in tetrahydrofuran (15 mL), 1M LiOH (15 mL) was added. The reaction mixture was stirred at ambient temperature for 10 hours. TLC showed complete conversion of starting material. The organic solvent was concentrated and water (50 mL) was added to the residue. This aqueous part was washed with ethyl acetate (30 mL). The aqueous layer was acidified with 1N hydrochloric acid up to pH 2 and extracted with ethyl acetate (3×25 mL). The combined organic layer

6.6 Synthesis of 2-(1-oxo-indan-4-yl)-propionic acid (Employed for the Synthesis of Example Compound No. 206)

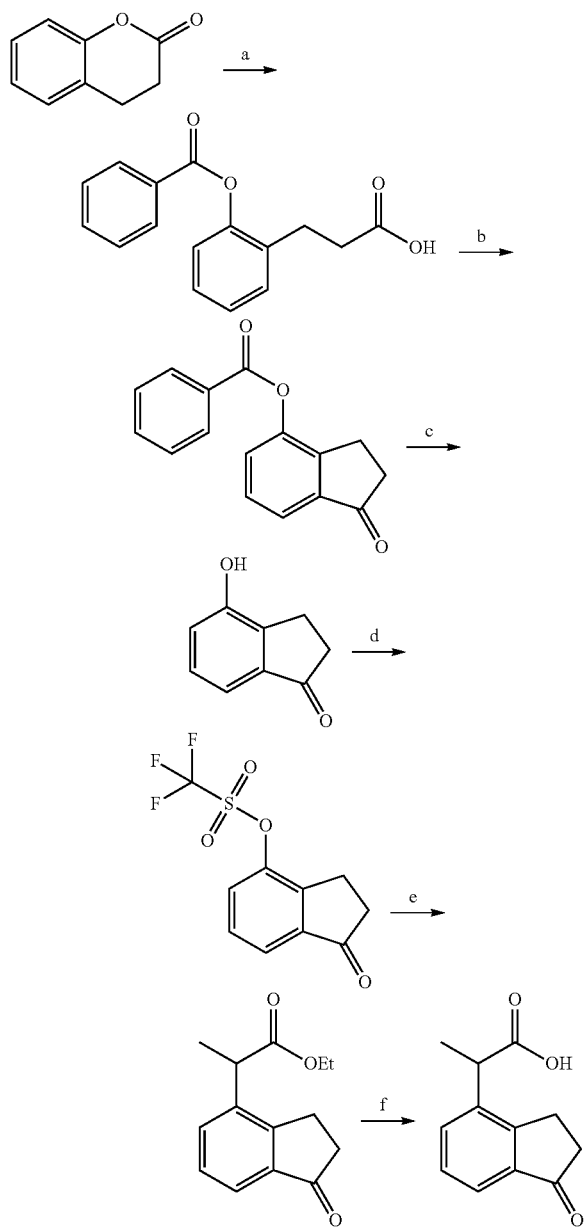

Step a: Dihydrocoumarin (100 g, 0.67 mol) was dissolved in 30% sodium hydroxide solution (180 mL) and was cooled to 20-25° C. Benzoyl chloride (95 g, 0.67 mol) was added to it slowly over the period of 40 minutes. Reaction mixture was stirred at ambient temperature for 20 minutes. TLC showed that no starting was left. The reaction mixture was cooled to 10-12° C. and acidified with concentrated hydrochloric acid (57 mL). White solid precipitated out and it was filtered through sintered funnel. The residue was washed with water (2×500 mL) and dried under reduced pressure at 80° C. The crude material was crystallized by toluene to afford 140 g (76%).

was dried over anhydrous magnesium sulfate and evaporated to dryness to obtained compound (1.5 g, 94% yield).

Step b: Step-a product (37 g, 0.137 mol) was dissolved in dichloromethane (260 mL) and thionyl chloride (24.8 mL, 0.342 mol) was added to it. The reaction mixture was refluxed for 4 hours. The organic solvent was then concentrated under reduced pressure and the residue was azeotroped by benzene (2×200 mL). The solution of acid chloride in dichloromethane (60 mL) was added drop wise at −50° C. to a suspension of aluminum chloride (93 g, 0.688 mol) in dichloromethane (100 mL) in a separate round-bottomed flask (500 mL). The resultant mixture was allowed to come to ambient temperature and finally refluxed for overnight. TLC showed complete consumption of starting material. The reaction mixture was poured in to crushed ice (500 g). A solid separated out which was filtered and the filtrate was extracted with dichloromethane (3×350 mL). The organic layer was washed with water (500 mL), brine (500 mL) and finally dried over anhydrous magnesium sulfate. It was then concentrated under reduced pressure to get the crude compound, which was purified through column chromatography (silica gel: 100-200; eluent: 10% ethyl acetate in hexane) to afford the pure compound (20 g, 58% yield).

Step c: In a 3 L round-bottomed flask step-b product (50 g, 0.198 mol); benzyltriethylammonium chloride (55 g, 0.198 mol) was dissolved in dichloromethane (900 mL). Sodium hydroxide solution (2N, 800 mL) was added to it and the resulting mixture was refluxed for 20 hours. TLC (in 20% ethyl acetate in hexane; $R_f$: 0.3) showed complete consumption of starting material. Reaction mixture was cooled to ambient temperature and the aqueous part was separated out. The aqueous layer was washed with ethyl acetate (300 mL). The aqueous part was acidified with 6N HCl (300 mL) and extracted with ethyl acetate (3×600 mL). The combined organic layer was washed with brine (500 mL) and dried over anhydrous magnesium sulfate. It was then concentrated under reduced pressure to get the crude compound. The crude solid compound was washed with dichloromethane (3×100 mL) to afford 25 g product (85% yield).

Step d: Step-c product (10 g, 0.068 mol), was dissolved in pyridine (150 mL cooled to 0° C. Trifluoromethane sulphonic anhydride (28.56 g, 0.101 mol) was slowly added to it. The reaction mixture was allowed to come to ambient temperature and stirred for 4 hours. TLC (in 20% ethyl acetate in hexane; $R_f$: 0.6) showed complete consumption of starting material. Reaction mixture was diluted with water (500 mL) and extracted with 40% ethyl acetate in hexane (3×250 mL). The combined organic layer was washed with hydrochloric acid (4N, 500 mL) and brine (500 mL). The combined organic layer was dried over anhydrous magnesium sulfate and concentrated under reduced pressure to get the crude compound. The crude compound was purified by column chromatography (silica gel: 100-200; eluent: 5% ethyl acetate in hexane) to afford the pure compound (16 g, 85% yield).

Step e: A 50 mL two necked round bottom flask were charged with srep-d product (500 mg, 0.002 mol), 2-chloroethylpropionate (0.3 mL, 0.002 mol) and dry dimethyformamide (4 mL). It was stirred for a homogenious mixing. Manganese (196 mg, 0.0036 mol), Nickel bromide bipyridyl (54 mg, 0.0001 mol) and Trifluoro acetic acid (4 μL) were added to it. The reaction mixture was degasified and finally stirred under nitrogen atmosphere. It was then heated to 65° C. and maintained the temperature for 15 hours. TLC (in 20% ethyl acetate in hexane; $R_f$: 0.5) showed complete consumption of starting material. Reaction mixture was diluted with water (50 mL) and extracted with 40% ethyl acetate in hexane (3×50 mL). The combined organic layer was dried over anhydrous magnesium sulfate and concentrated under reduced pressure to get the crude compound. The crude compound was purified by column chromatography (silica gel: 100-200; eluent: 10% ethyl acetate in hexane) to afford the pure compound (130 mg, 31% yield).

Step f: Step-e product (1.1 g, 0.005 mol), was dissolved in tetrahydrofuran (8 mL). Lithium hydroxide solution (1M, 7.1 mL, 0.007 mol) was added to it and was stirred for 15 hours at ambient temperature. TLC (in ethyl acetate; $R_f$: 0.1) showed complete consumption of starting material. Reaction mixture was diluted with water (50 mL) and extracted with ethyl acetate (2×50 mL). The aqueous part was then acidified with hydrochloric acid (1M, 10 mL) and extracted with ethyl acetate (3×50 mL). The combined organic layer was dried over anhydrous magnesium sulfate and concentrated under reduced pressure to get the crude compound. The crude compound was purified by column chromatography (silica gel: 100-200; eluent: 25% ethyl acetate in hexane) to afford the desired compound (260 mg, 27% yield).

6.7 Synthesis of 2-(1-hydroxy-2,3-dihydro-1H-inden-4-yl)propanoic acid (Employed for the Synthesis of Example Compound No. 207)

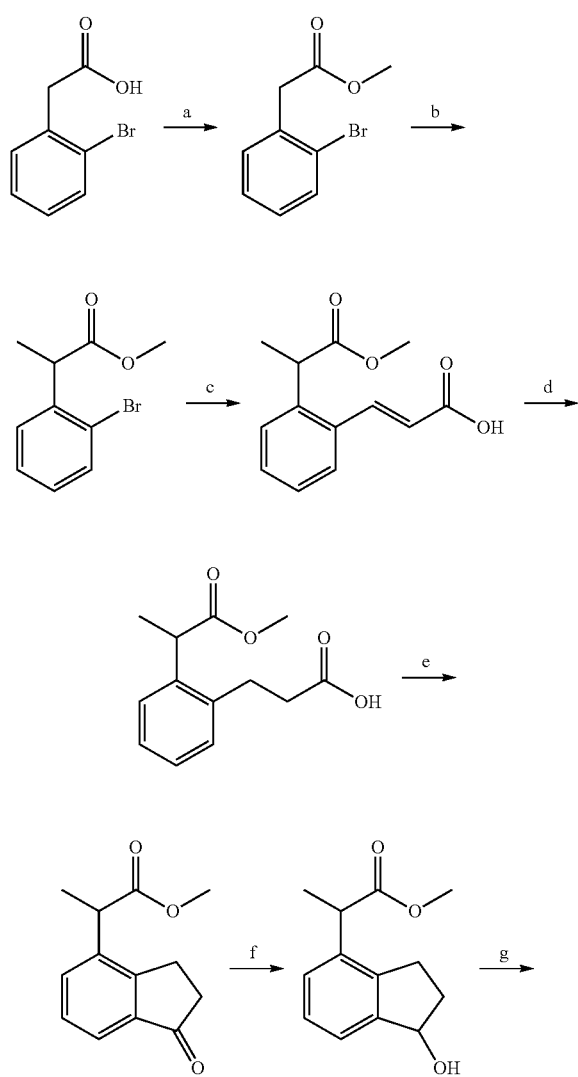

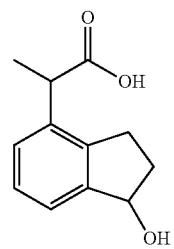

Step a: In a single necked round-bottomed flask (500 mL) 2-(2-bromophenyl)acetic acid (23 g, 0.107 mol) was dissolved in methanol (230 mL) followed by addition of concentrated sulfuric acid (1 mL) under stirring. The reaction mixture was refluxed for 1 hour. TLC (in 20% ethyl acetate-hexane, $R_f$=0.7) showed complete consumption of starting material. The reaction mixture was cooled to ambient temperature and the solvent was removed under reduced pressure. The reaction mixture was diluted with water (200 mL) and extracted with 30% ethyl acetate in hexane (3×150 mL). The combined organic part was dried over anhydrous magnesium sulfate and concentrated under reduced pressure to afford pure compound (24 g, 97% yield).

Step b: In a double-necked round-bottomed flask (1 L) step-a product (22 g, 0.096 mol) was dissolved in tetrahydrofuran (300 mL) in an inert atmosphere. The solution was cooled to −78° C. A solution of lithiumhexamethyldisilazide in tetrahydrofuran (104 mL, 0.1248 mol, 1.2 M) was added drop wise under stirring in an inert atmosphere over a period of 40 minutes at −78° C. The reaction mixture was stirred at the same temperature for 1 h. Iodomethane (20.5 g, 9 mL, 0.144 mol) was added drop wise at −78° C. under stirring. Then the reaction mixture was allowed to warm at −20° C. and stirred at same temperature for 50 minutes. TLC (in 20% ethyl acetate-hexane, $R_f$=0.6) showed complete consumption of starting material. Excess LiHMDS was quenched with a saturated solution of ammonium chloride (100 mL). Organic solvent was removed under reduced pressure and the residue was diluted with water (250 mL). The aqueous solution was extracted with 10% ethyl acetate in hexane (3×250 mL). The organic part was dried over anhydrous magnesium sulfate and concentrated under reduced pressure. The crude product was purified by column chromatography (silica gel: 100-200, eluent: 5% ethyl acetate in hexane) to afford the pure compound (21.7 g, 93% yield).

Step c: In a 500 mL two necked round bottomed flask step-b product (27 g, 0.111 mol), Pd-L[#] (2.08 g, 0.002 mol) and N,N-dimethy acetamide (130 mL) were charged under inert atmosphere. Tributyl amine (26.4 mL, 0.11 mol) was added to it followed by addition of acrylic acid (12 g, 0.167 mol). The resulting mixture was heated to 130° C. for 24 hours. TLC (in 50% E.A-Hexane, $R_f$=0.2) showed complete consumption of starting material. The reaction mixture was cooled to ambient temperature and diluted with water (1.3 L). The compound was extracted with ethyl acetate (3×300 mL). The combined organic part was washed with water (2×400 mL) and brine (500 mL). The organic layer was dried over anhydrous magnesium sulfate and concentrated under reduced pressure to afford crude (26 g), which was purified by column chromatography (silica gel: 100-200, eluent: 10% ethyl acetate in hexane) to afford the pure compound (21 g, 81% yield).

N.B: Pd-L[#] was synthesized from palladium acetate (1 eq) and tri-o-tolylphosphene (1.3 eq.) in dry toluene.

Step d: In a Parr hydrogenation vessel (500 mL) step-c product (20 g, 0.085 mol) in acetic acid (200 mL), palladium on carbon (10% on Pd, 2 g) was charged under inert atmosphere. The resulting mixture was hydrogenated at 45 psi for 15 hours at ambient temperature. TLC (in 50% ethyl acetate in hexane; $R_f$=0.2) showed complete consumption of starting material. The catalyst was filtered through celite bed and the filtrate was concentrated under reduced pressure to afford crude material, which was purified by column chromatography (silica gel: 100-200, eluent: 10% ethyl acetate in hexane) to afford the pure compound (18 g. 89% yield).

Step e: A two-necked round bottom flask (500 mL) was charged with step-d product (25 g, 0.106 mol), benzene (250 mL), thionyl chloride (11.52 mL, 0.159 mol), and dimethyl formamide (5 drops). The resulting mixture was refluxed for 1.5 hours. Benzene was removed under reduced pressure and the excess of thionyl chloride was removed by azeotroping with benzene (2×200 mL), the acid chloride was formed. This acid chloride was dissolved in dichloromethane (125 mL) and was slowly added to the stirred suspension of aluminium chloride (28.75 g, 0.212 mol) in dichloromethane (125 mL) at −50° C. The reaction mixture was then stirred at ambient temperature for 20 minutes then it was refluxed for 2 hours. TLC (in 30% ethyl acetate in hexane, $R_f$=0.4) showed complete consumption of starting material. The reaction mixture was cooled to ambient temperature and poured into crushed ice (1.5 kg). The compound was extracted with 50% ethyl acetate in hexane (3×300 mL). The combined organic part was washed with water (2×400 mL) and brine (500 mL). The organic layer was dried over anhydrous magnesium sulfate and concentrated under reduced pressure to afford crude (22 g), which was purified by column chromatography (silica gel: 100-200; eluent: 10% ethyl acetate in hexane) to afford the pure compound (18 g, 78% yield).

Step f: Step-e product (15 g, 0.069 mol) was dissolved in tetrahydrofuran (150 mL). Sodium borohydride (1.04 g, 0.027 mol) was added to it. Methanol (10 mL) was added portion wise to the reaction mixture and stirred at ambient temperature for half an hour. TLC (in 30% E.A-Hexane, $R_f$=0.3) showed complete consumption of starting material. Tetrahydrofuran was removed under reduced pressure and the residue was diluted with water (200 mL). It was extracted with ethyl acetate (3×150 mL). The combined organic part was washed with water (2×150 mL) and brine (200 mL). The organic layer was dried over anhydrous magnesium sulfate and concentrated under reduced pressure to afford crude materials which was purified by column chromatography (silica gel: 100-200, eluent: 10% ethyl acetate in hexane) to afford the pure compound (13 g, 86% yield).

Step g: Methyl 2-(1-hydroxy-2,3-dihydro-1H-inden-4-yl) propanoate (2 g, 0.0091 mol) was dissolved in tetrahydrofuran (18 mL). Lithium hydroxide solution (18 mL, 0.018 mol, 1M) was added to it and the reaction mixture was stirred at ambient temperature for 5 hours. TLC (in 60% ethyl acetate in hexane, $R_f$=0.1) showed complete consumption of starting material. Tetrahydrofuran was removed under reduced pressure and the residue was diluted with water (100 mL). The aqueous part was washed with ethyl acetate (2×100 mL) and acidified with hydrochloric acid (1N, 25 mL). The compound was extracted with ethyl acetate (3×50 mL). The combined organic part was washed with water (2×50 mL) and brine (100 mL). The organic layer was dried over anhydrous magnesium sulfate and concentrated under reduced pressure to afford desired compound (1.6 g, 85% yield).

6.8 Synthesis of 2-(3H-inden-4-yl)-propionic acid (Employed for the Synthesis of Example Compound No. 24)

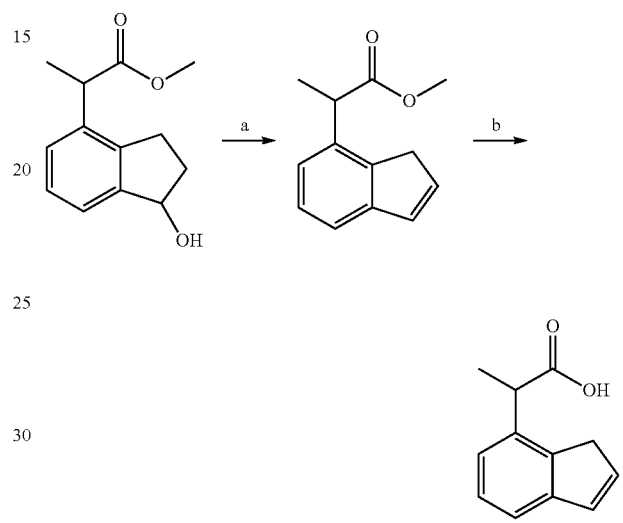

Step a: Methyl 2-(1-hydroxy-2,3-dihydro-1H-inden-4-yl) propanoate (10 g, 0.045 mol) was dissolved in benzene (100 mL). p-toluenesulphonic acid (862 mg, 0.0045 mol) was added to it. The resulting reaction mass was refluxed for 1 hour. TLC (in 60% ethyl acetate in hexane, $R_f$=0.7) showed complete consumption of starting material. The reaction was cooled to ambient temperature and washed with water (200 mL). The organic layer was washed with sodium bicarbonate (200 mL), and brine (200 mL). The organic layer was dried over anhydrous magnesium sulfate and concentrated under reduced pressure to afford crude materials which was purified by column chromatography (100-200 silica gel, eluent: 5% ethyl acetate in hexane) to afford the pure compound (7 g, 77% yield).

Step b: Step-a product (2 g, 0.01 mol) was dissolved in tetrahydrofuran (20 mL). Lithium hydroxide solution (20 mL, 0.02 mol, 1M) was added to it and the reaction mixture was stirred at ambient temperature for 5 hours. TLC (in 60% E.A-Hexane, $R_f$=0.3) showed complete consumption of starting material. Tetrahydrofuran was removed under reduced pressure and the residue was diluted with water (100 mL). The aqueous part was washed with ethylacetate (2×100 mL) and acidified with hydrochloric acid (1N, 25 mL). The compound was extracted with ethylacetate (3×50 mL). The combined organic part was washed with water (2×50 mL) and brine (100 mL). The organic layer was dried over anhydrous magnesium sulfate and concentrated under reduced pressure to afford desired compound (1.5 g, 81% yield).

6.9 Synthesis of 2-(2-hydroxy-Indan-4-yl)-propionic acid (Employed for the Synthesis of Example Compound No. 208)

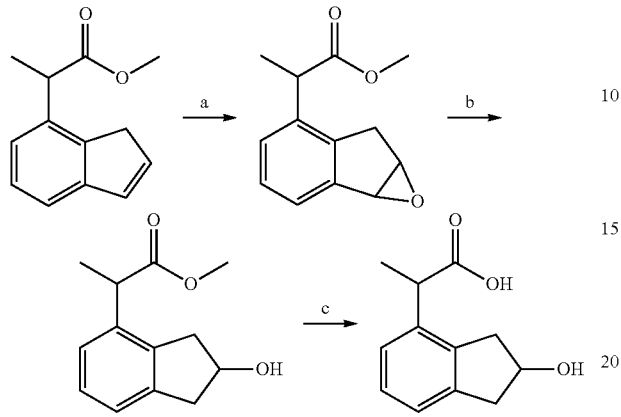

Step a: Methyl 2-(1H-inden-7-yl)propanoate (2 g, 0.01 mol) was dissolved in dichloromethane (100 mL). m-chloroperbenzoic acid (6.82 g, 0.039 mol) was added portion wise to it at 0° C. and it was stirred at 0° C. for 4 hours. TLC (in 20% ethyl acetate in hexane, $R_f$=0.4) showed complete consumption of starting material. Excess m-CPBA was quenched with saturated solution of sodium carbonate (400 mL). The aqueous phase was extracted with dichloromethane (3×50 mL). The combined organic layer was washed with water (200 mL) and brine (200 mL). The organic layer was dried over anhydrous magnesium sulfate and contracted under reduced pressure to afford crude material, which was purified by column chromatography (100-200 silica gel, eluent: 10% ethyl acetate in hexane) to afford the pure compound (1.2 g, 55% yield).

Step b: Step-a product (1.5 g, 0.007 mol) was dissolved in dichloroethane (30 mL). Zinc iodide (3.3 g, 0.01 mol) was added at ambient temperature. Sodium cyanoborohydride (3.25 g, 0.05 mol) was added portion wise to it at ambient temperature and the reaction mixture was refluxed at 70° C. for 1 hour. TLC (in 30% E.A-Hexane, $R_f$=0.3) showed complete consumption of starting material. The reaction mixture was quenched with 2 n hydrochloric acid (100 mL). The aqueous phase was extracted with dichloromethane (3×100 mL). The combine organic layer was washed with water (200 mL) and brine (200 mL). The organic layer was dried over anhydrous magnesium sulfate and contracted under reduced pressure to afford crude material, which was purified by column chromatography (100-200 silica gel, eluent: 10% ethyl acetate in hexane) to afford the pure compound (1.3 g, 87% yield).

Step c: Step-b product (1.3 g, 0.006 mol) was dissolved in tetrahydrofuran (15 mL). Lithium hydroxide solution (15 mL, 0.015 mol, 1M) was added to it and the reaction mixture was stirred at ambient temperature for 4 hours. TLC (in 70% E.A-Hexane, $R_f$=0.2) showed complete consumption of starting material. Tetrahydrofuran was removed under reduced pressure and the residue was diluted with water (100 mL). The aqueous part was washed with ethylacetate (2×100 mL) and acidified with hydrochloric acid (1N, 25 mL). The compound was extracted with ethylacetate (3×50 mL). The combined organic part was washed with water (2×50 mL) and brine (100 mL). The organic layer was dried over anhydrous magnesium sulfate and concentrated under reduced pressure to afford desired compound (1.0 g, 81% yield).

6.10 Synthesis of 2-(benzo[d][1,3]dioxol-5-yl)acetic acid and 2-(benzo[d][1,3]dioxol-5-yl)propanoic acid (Employed for the Synthesis of Example Compounds No. 11, 119, 131, 140, 144, 161, 163, 165, 170, 171, 173 and 183)

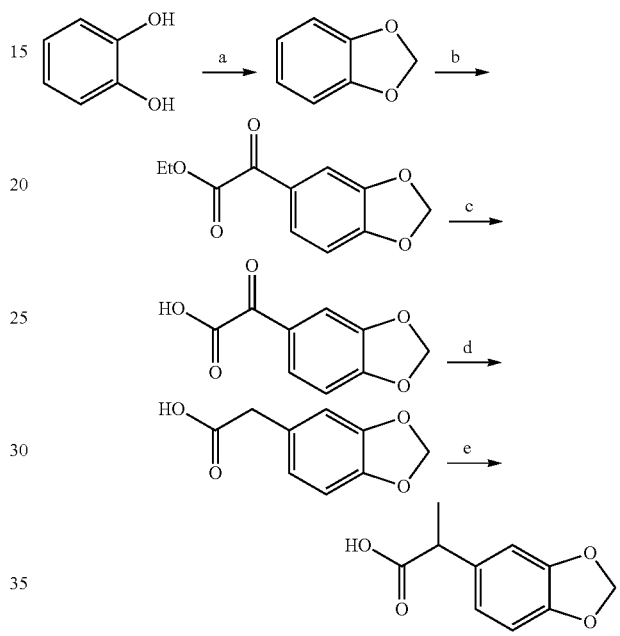

Step a: To a solution of pyrocatechol (100 g, 0.9 mol) in DMSO (300 ml), sodium hydroxide (145 g, 4 eq) was added and heated the contents to 80° C. A mixture of DCM (150 ml) and DMSO (200 ml) was heated to reflux and the above reaction contents were added drop wise. Overall reaction mixture was heated to reflux for 4-5 hrs. Progress of the reaction was monitored by TLC (10% ethyl acetate/hexane, $R_f$~0.8). On completion of the reaction, reaction contents were steam distilled to yield the required product as a yellow colored oily liquid (60 g, 54% yield).

Step b: A solution of ethyloxalyl chloride (34 g, 1.5 eq) in DCM (50 ml) was added to aluminium chloride (49.2 g, 1.8 eq) taken in DCM (100 ml) at −10 to 0° C. A solution of step-a product (25 g, 0.02 mol) in DCM (100 ml) was added at −10° C. and the overall reaction mixture was allowed to stir for 1 hr at 0° C. Progress of the reaction was monitored by TLC (10% ethyl acetate/hexane, $R_f$~0.5). On completion of the reaction, reaction contents were poured into ice water (500 ml) and the product extracted with ethyl acetate (2×300 ml). Combined organic layer was dried over sodium sulfate, concentrated under reduced pressure and the crude obtained was purified by column chromatography (silica gel, 10% ethyl acetate/hexane) to yield the required product as an yellow colored oily liquid (56 g, 45% yield).

Step c: To a solution of step-b product (50 g, 0.22 mol) in methanol (350 ml, 7 times), 3M NaOH solution (13.5 g, 1.5 eq) was added at 0° C. Overall reaction mixture was allowed to stir for 2 hrs. Progress of the reaction was monitored by TLC (50% ethyl acetate/hexane, $R_f$~0.3). On completion of the reaction, excess methanol was distilled off. Residue obtained was taken in water (200 ml), acidified to a pH~3-4 and extracted with ethyl acetate (2×100 ml). Combined extract was dried over sodium sulfate, concentrated under reduced pressure and the crude obtained was purified by column chromatography (silica gel, 30% ethyl acetate/hexane) to yield the required product as an yellow colored solid (30 g, 70% yield).

Step d: Step-c product (30 g, 0.077 mol) was added portion wise to hydrazine hydrate (37 ml, 5 eq) at 0° C. Heated the contents to 80° C. and potassium hydroxide (19 g, 2.3 eq) was added portion wise. Overall reaction mixture was heated to 110° C. and maintained for overnight at the same temperature. Progress of the reaction was monitored by TLC (50% ethyl acetate/hexane, $R_f$~0.6). On completion of the reaction, reaction contents were acidified to a pH~3-4 with dilute HCl at 0° C. and the product extracted with ethyl acetate (2×250 ml). Combined extract was dried over sodium sulfate, concentrated under reduced pressure and the crude obtained was purified by column chromatography (silica gel, 20% ethyl acetate/hexane) to yield the required product as a white solid (12 g, 45% yield).

Step e: n-BuLi (21.3 g (208 ml), 0.33 mol, 4 eq) was added drop wise to Diisopropyl amine (46.7 ml, 4 eq) taken in THF (200 ml) at 0° C. and stirred the contents for 1.5 hrs. A solution of 2-(benzo[d][1,3]dioxol-5-yl)acetic acid (15 g, 0.08 mol) in THF (100 ml) was added drop wise at 0° C. and stirred the contents for 1 hr at RT. Methyl iodide (10.3 ml, 2 eq) was added drop wise and the reaction mixture was allowed to stir for 3-4 hrs at RT. Progress of the reaction was monitored by TLC (30% ethyl acetate/hexane, $R_f$~0.5). On completion of the reaction, reaction contents were acidified to a pH~3 with dilute HCl and the product extracted with ethyl acetate (2×150 ml). Combined extract was dried over sodium sulfate, concentrated under reduced pressure and the crude obtained was subjected to column chromatography (silica gel, 10% ethyl acetate/hexane) to yield the required product as a brown colored solid (4.2 g, 46% yield).

6.11 Synthesis of 2-(2,3-dihydrobenzo[b][1,4]dioxin-6-yl)acetic acid and 2-(2,3-dihydrobenzo[b][1,4]dioxin-6-yl)propanoic acid (Employed for the Synthesis of Example Compounds No. 12, 13, 184, 188, 200, 201 and 202)

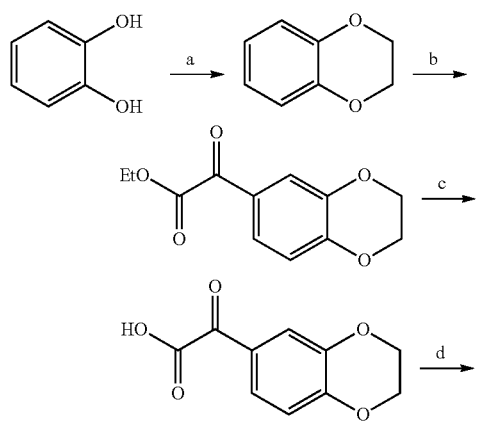

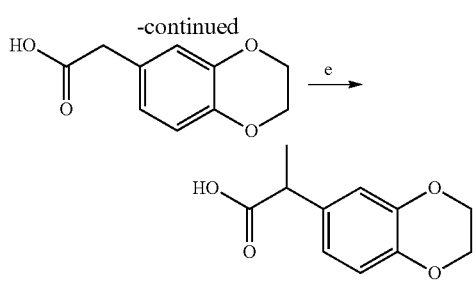

Step a: To pyrocatechol (50 g, 0.45 mol) taken in ethylene glycol (500 ml, 10 times), potassium carbonate (124 g, 2 eq) was added portion wise at RT. 1,2-dibromo ethane (78 ml, 2 eq) was added drop wise at RT and the reaction mixture was heated to reflux for 7-8 hrs. Progress of the reaction was monitored by TLC (10% ethyl acetate/hexane, $R_f$~0.8). On completion of the reaction, filtered the reaction contents and the filtrate was diluted with water (200 ml) and ethyl acetate (200 ml). Layers formed were separated out and the aqueous layer was extracted with ethyl acetate (2×200 ml). Combined organic layer was dried over sodium sulfate and concentrated under reduced pressure to yield the required product as a brown colored liquid (50 g, 81% yield).

Step b: A solution of ethyloxalyl chloride (103 g (86.6 ml), 0.76 mol, 2 eq) in chloroform (100 ml) was added to aluminium chloride (102 g, 0.76 mol, 2 eq) taken in chloroform (100 ml) at −10 to 0° C. A solution of step-a product (52 g, 0.38 mol) in chloroform (160 ml) was added at −10° C. and the overall reaction mixture was allowed to stir for 2-3 hrs at RT. Progress of the reaction was monitored by TLC (10% ethyl acetate/hexane, Rf~0.3). On completion of the reaction, reaction contents were poured into ice water (500 ml) and the layers formed were separated out. Aqueous layer was extracted with DCM (2×200 ml). Combined organic layer was dried over sodium sulfate and concentrated under reduced pressure to yield the required product as a brown colored oily liquid (67 g, 74% yield).

Step c: To a solution of step-b product (67.6 g, 0.28 mol) in toluene (540 ml, 8 times), 3M NaOH solution (114 ml) was added at 0° C. Overall reaction mixture was allowed to stir for 2 hrs. Progress of the reaction was monitored by TLC (75% ethyl acetate/hexane, $R_f$~0.1). On completion of the reaction, cooled the contents to RT, water (300 ml) was added the layers formed were separated out. Aqueous layer was acidified to a pH~3 with dilute HCl, solid thrown out was filtered and dried to yield the required product as a pale yellow colored solid (50 g, 88% yield).

Step d: Step-c product (50 g, 0.24 mol) was added portion wise to hydrazine hydrate (69.7 g (67.6 ml), 5 eq) at 0° C. Contents were heated to 80° C. and potassium hydroxide (30 g, 2.3 eq) was added portion wise. Overall reaction mixture was heated to 110° C. and maintained for overnight at the same temperature. Progress of the reaction was monitored by TLC (50% ethyl acetate/hexane, $R_f$~0.7). On completion of the reaction, reaction contents were diluted with water (100 ml). Then the contents were acidified to a pH~3-4 with diluted HCl at 0° C., solid thrown out was filtered and dried to yield the required product as a white solid (40 g, 85% yield, mp 79-82° C.).

Step e: n-BuLi (11.08 g (115.4 ml), 4.2 eq) was added drop wise to diisopropyl amine (24.2 ml, 4.2 eq) taken in THF (30 ml) at 0° C. and stirred the contents for 1.5 hrs. Cooled the contents to −78° C., TMEDA (12.3 ml) was added followed by a solution of 2-(2,3-dihydrobenzo[b][1,4]dioxin-6-yl)acetic acid (8 g, 0.09 mol) in THF (50 ml) was added drop wise at 0° C. and stirred the contents for 3 hrs at −78° C. Methyl iodide (6.42 ml, 2.5 eq) was added drop wise and the reaction mixture was allowed to stir for overnight at RT. Progress of the reaction was monitored by TLC (30% ethyl acetate/hexane, $R_f$~0.5). On completion of the reaction, reaction contents were acidified to a pH~3 with dilute HCl and the product extracted with ethyl acetate (2×100 ml). Aqueous layer was extracted with ethyl acetate (2×50 ml). Combined extract was dried over sodium sulfate and concentrated under reduced pressure and the crude obtained was subjected to column chromatography (silica gel, 10% ethyl acetate/hexane) to yield the required product as a brown colored solid (5.2 g, 60% yield, mp 81-83° C.).

6.12 Synthesis of 2-(1H-indazol-5-yl)propanoic acid (Employed for the Synthesis of Example Compound No. 35)

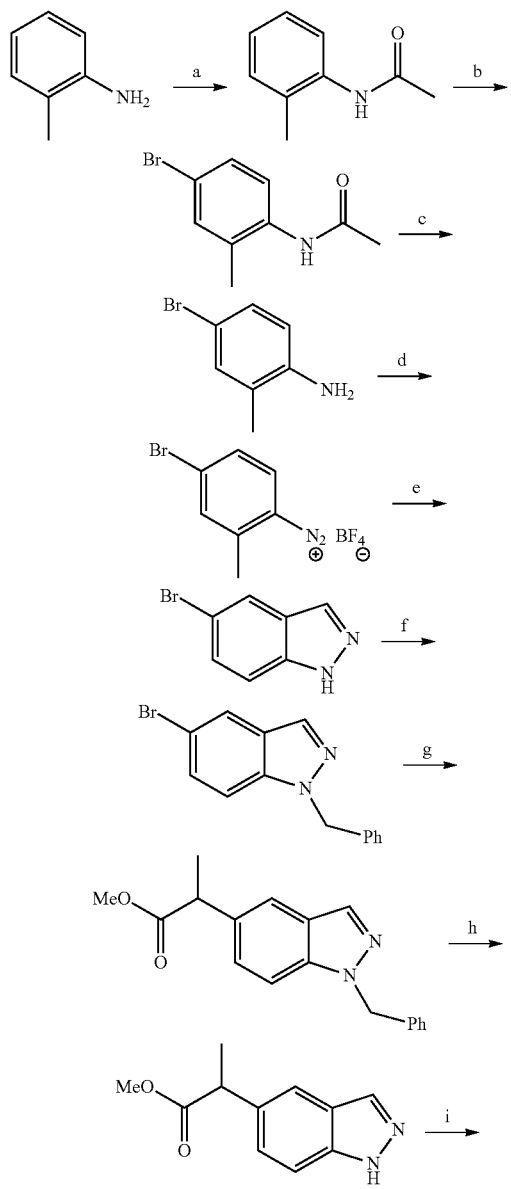

-continued

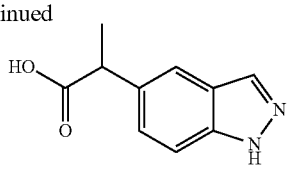

Step a: Acetic acid (74 ml, ~4 times) was added to o-toluidine (20 g, 0.18 mol) at r.t., heated the contents to 110-115° C. and refluxed for 2 hrs at the same temperature. Progress of the reaction was monitored by TLC (30% ethyl acetate/hexane, $R_f$~0.2). On completion of the reaction, reaction contents were poured into ice cold water and solid thrown out was filtered. The solid obtained was washed with water and dried. Then the solid was dissolved in DCM (25 ml), dried over sodium sulfate and the DCM was distilled off completely to yield the required product as a pale pink solid (22 g, 87% yield).

Step b: To a stirred solution of step-a product (24 g, 0.16 mol) in acetic acid (88 ml, 3.7 times), bromine (25.6 g (8.3 ml), 0.16 mol) was added drop wise at rt. Heated the reaction mass to 50-55° C. and allowed stirred for 1.5 hrs at the same temperature. Progress of the reaction was monitored by TLC (50% ethyl acetate/hexane, $R_f$~0.6). On completion of the reaction, poured the reaction contents into ice cold water. The solid thrown out was filtered and dried to obtain the crude product as a pale pink solid (55 g, crude). The crude obtained was directly used for the next step without any further purification.

Step c: Step-b product (55 g, 0.28 mol) was dissolved in ethanol (65 ml, 1 time) and heated to a reflux temperature. While boiling the contents, conc.HCl (65 ml) was added and the reaction mass was refluxed for 3 hrs. Progress of the reaction was monitored by TLC (50% ethyl acetate/hexane, $R_1$~0.8). On completion of the reaction, cooled the contents to rt and the solid thrown out was filtered. The solid obtained was dried (35 g) and dissolved in water (93 ml). A solution of sodium hydroxide (16.3 g, 0.4 mol, 2.7 eq) in water (81.5 ml) was added and the reaction mass was stirred for 30 min at rt. Progress of the reaction was monitored by TLC (50% ethyl acetate/hexane, $R_f$~0.8). On completion of the reaction, solid thrown out was filtered. The solid obtained was dissolved in ethyl acetate (250 ml), dried over sodium sulfate and concentrated under reduced pressure. The crude obtained was washed with hexane and dried to yield the required product as a brown colored solid (22 g, 63% yield).

Step d: To step-c product (5 g, 0.026 mol), 50% $HBF_4$ (8.8 ml) was added and stirred for 15 min at rt. Aqueous solution of sodium nitrite (2.04 g, 1.1 eq) was added drop wise at 0-5° C. and stirred at it for 2 hrs. Progress of the reaction was monitored by TLC (30% ethyl acetate/hexane, $R_f$~0.2). On completion of the reaction, reaction contents were filtered. The solid obtained was washed with diethyl ether and dried under vacuum to yield the required product as an off white solid (7 g, 91% yield).

Step e: To a well stirred mixture of potassium acetate (0.688 g, 0.007 mol, 2 eq) in 18-crown-6 (0.045 g, 0.04 eq), chloroform (40 ml) was added with stirring. Step-d product (1 g, 0.0035 mol) was added to the above contents at it and the reaction mass was stirred for 2 hrs at rt. Progress of the reaction was monitored by TLC (50% ethyl acetate/hexane, $R_f$~0.7). On completion of the reaction, chloroform was distilled off, residue obtained was dissolved in water and the compound extracted with ethyl acetate. Combined extract was dried over sodium sulfate, concentrated under reduced pressure and the crude obtained was washed with petroleum ether to yield the required product as an yellow colored solid (0.45 g, 65% yield).

Step f: To a solution of step-e compound (20 g, 0.1 mol) in DMF (120 ml), potassium carbonate (21 g, 0.15 mol, 1.5 eq) was added and stirred for 30 min at rt. Benzyl bromide (22.5 g, 1.3 eq) was added, overall reaction mass was heated to 60° C. and stirred for 6 hrs at the same temperature. Progress of the reaction was monitored by TLC (20% ethyl acetate/hexane, $R_f$~0.4). On completion of the reaction, contents were poured into ice cold water and the compound extracted with ethyl acetate (2×150 ml). Combined extract was dried over sodium sulfate, concentrated under reduced pressure and the crude obtained was purified by column chromatography (silica gel, 5% ethyl acetate/hexane) to yield the required product as an off white solid (12 g, 43% yield).

Step g: To a solution of step-f compound (1 g, 0.003 mol) in DMF (8 ml), methyl 2-chloropropanoate (0.55 g (0.48 ml), 1.3 eq) was added and bubbled with nitrogen for 10 min. Manganese (0.38 g, 2 eq) was added and bubbled with nitrogen gas for 10 min. Nickel bipyridine (0.12 g) was added followed by catalytic amount of TFA was added and bubbled with nitrogen for 10 min. The overall reaction mass was heated to 55-60° C. and allowed to stir for 8 hrs at the same temperature. Progress of the reaction was monitored by TLC (20% ethyl acetate/hexane, $R_f$~0.3). On completion of the reaction, filtered the reaction contents, filtrate was added with water and extracted with ethyl acetate (3×300 ml). Combined extract was dried over sodium sulfate, concentrated under reduced pressure and the crude obtained was purified by column chromatography (silica gel, 12-15% ethyl acetate/hexane) to yield the required product as an yellow colored liquid (0.3 g, 23% yield).

Step h: To a solution of step-g product (0.2 g) in ethanol (20 ml), 10% Pd/C (0.1 g) was added and heated to a reflux temperature. Ammonium formate (10 eq) was added portion wise at 85-90° C. and the reaction mass was refluxed for 8 hrs at the same temperature. Progress of the reaction was monitored by TLC. On completion of the reaction, filtered the contents over celite bed, washed with methanol and the filtrate was concentrated under reduced pressure. Residue obtained was taken in water and washed with ethyl acetate. Combined organic layer was dried over sodium sulfate, concentrated under reduced pressure and the crude obtained was purified by column chromatography (silica gel, 15% ethyl acetate/hexane) to yield the required product as a pale yellow thick liquid (0.1 g, 93% yield).

Step i: To a solution of step-h product (1.5 g, 0.007 mol) in methanol (5 ml, ~3 times), a solution of sodium hydroxide (0.88 g, 0.02, 3 eq) in water (5 ml) was added at rt and the overall reaction mass was allowed to stir for 6 hrs at rt. Progress of the reaction was monitored by TLC (50% ethyl acetate/hexane, $R_f$~0.1). On completion of the reaction, methanol was distilled off completely, residue obtained was taken in water and the compound extracted with 20% ethyl acetate/hexane (2×50 ml). Aqueous layer was acidified to a pH~4 with drop wise addition of 6N HCl at 0-5° C. and stirred the contents for 30 min at rt. Solid thrown out was filtered and dried to yield the required product as a white solid (1.1 g, 80% yield, mp 188-191° C.).

6.13 Synthesis of 2-(1H-indazol-5-yl)propanoic acid (Employed for the Synthesis of Example Compound No. 209)

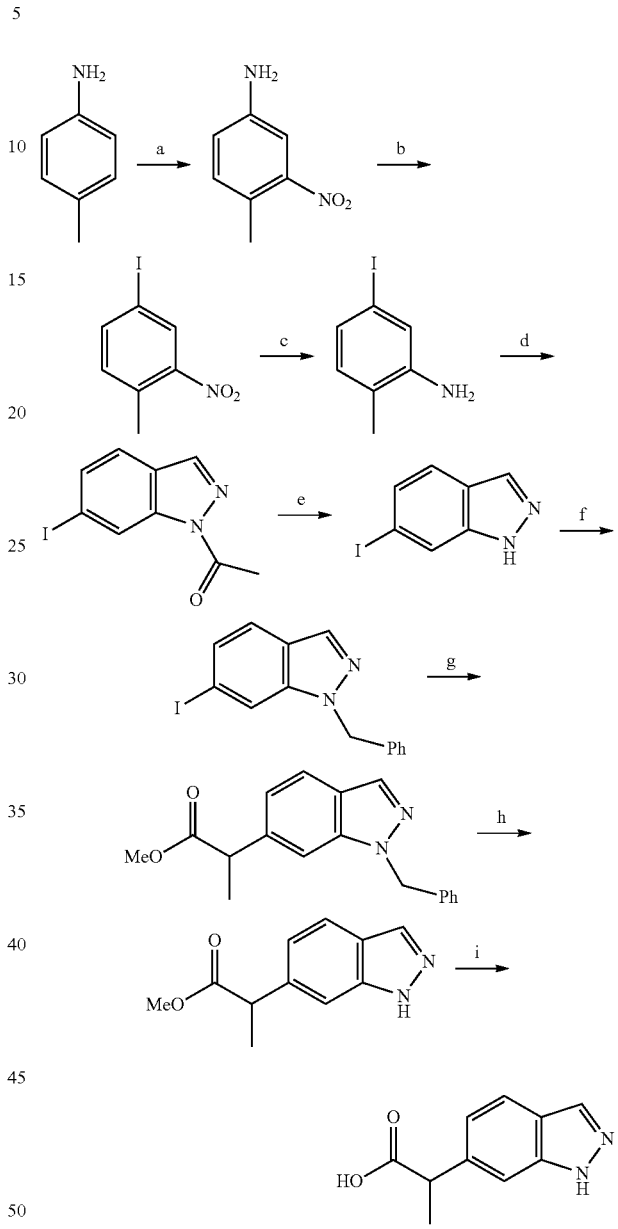

Step a: Sulfuric acid (365.8 g, 3.73 mol, 10 eq) was added drop wise to p-toluidine (40 g, 0.37 mol) at it and stirred the contents to obtain a clear solution. Then Urea nitrate (45.5 g, 0.37 mol, 1 eq) was added at 0-10° C. and stirred the reaction mass for 30 min at the same temperature. Progress of the reaction was monitored by TLC (30% ethyl acetate/hexane, $R_f$~0.5). On completion of the reaction, reaction mixture was quenched with ice water and the solid formed was filtered. Solid obtained was taken in 20% NaOH solution (up to pH~12) and filtered. Washed the solid and dried to yield the required product as an yellow colored solid (50 g, 88% yield).

Step b: To a step-a product (35 g, 0.23 mol), 6N HCl (194 ml) was added drop wise at rt. Cooled the contents to 0-5° C. and HCl gas was bubbled. A solution of sodium nitrite (29.2 g, 0.42 mol, 1.84 eq) in water (110 ml) was added drop wise at 0-5° C. and stirred for 10 min. Then a solution of potassium iodide (65.9 g, 0.39 mol, 1.78 eq) in water (100 ml) was added drop wise at 0-5° C. Heated the reaction contents to a reflux temperature and allowed to reflux for 12 hrs. Progress of the reaction was monitored by TLC (15% ethyl acetate/hexane, $R_f$~0.6). On completion of the reaction, cooled the reaction contents to it and the compound extracted with DCM (2×100 ml). Combined extract was washed with hypo solution, dried over sodium sulfate and concentrated under reduced pressure. The crude obtained was purified by column chromatography (silica gel, pure hexane) to yield the required product as pale yellow colored solid (38 g, 58% yield).

Step c: To a solution of step-b product (17 g, 0.06 mol) in ethanol (238 ml, 14 times), conc. HCl (85 ml, 5 times) was added drop wise at 0-5° C. Then Tin chloride (51.05 g, 0.226 mol, 3.5 eq) was added portion wise at it and the overall reaction mass was stirred for 3 hrs. Progress of the reaction was monitored by TLC (30% ethyl acetate/hexane, $R_f$~0.4). On completion of the reaction, ethanol was distilled off completely under reduced pressure. Residue obtained was basified to a pH~12-14 with NaOH solution and the compound extracted with ethyl acetate (2×50 ml). Combined extract was dried over sodium sulfate and concentrated under reduced pressure to yield the required product as a black colored solid (14 g, 94% yield).

Step d: To a solution of step-c product (5 g, 0.02 mol) in chloroform (30 ml, 6 times), acetic anhydride (4.96 g, 0.04 mol, 2.27 eq) was added at 0° C. and the contents were stirred for 1 hr at rt. Progress of the reaction was monitored by TLC (30% ethyl acetate/hexane, $R_f$~0.7). On completion, potassium acetate (061 g, 0.006 mol, 0.29 eq) followed by isoamyl nitrate (5.3 g, 0.046 mol, 2.1 eq) were added. The overall reaction mixture was heated to a reflux temperature and allowed to reflux for 12 hrs. Progress of the reaction was monitored by TLC (30% ethyl acetate/hexane, $R_f$~0.7). On completion of the reaction, cooled the reaction contents to it and the layers formed were separated out. Organic layer was washed with water, dried over sodium sulfate and concentrated under reduced pressure. The crude obtained was purified by column chromatography (silica gel, 15% ethyl acetate/hexane) to yield the required product as an yellow colored solid (2 g, 32.7% yield).

Step e: To a solution of step-d product (12 g, 0.04 mol) in 1,4-dioxane (60 ml, 5 times), 6N HCl (60 ml, 5 times) was added at rt. Reaction mixture was heated to 70° C. and allowed to stir for 2 hrs at the same temperature. Progress of the reaction was monitored by TLC (30% ethyl acetate/hexane, $R_f$~0.5). On completion of the reaction, 1,4-dioxane was distilled off completely, residue obtained was basified to a pH~12-13 with sodium hydroxide solution and the compound extracted with ethyl acetate (2×75 ml). Combined extract was dried over sodium sulfate and concentrated under reduced pressure to yield the required product (10 g, 78% yield).

Step f: To a solution of step-e product (2.5 g, 0.01 mol) in DMF (10 ml, 4 times), potassium carbonate (2.827 g, 0.02 mol, 1.5 eq), benzyl bromide (3.48 g, 0.02 mol, 1.5 eq) were added at rt Reaction mixture was heated to 70° C. and allowed it to stir for 4 hrs at the same temperature Progress of the reaction was monitored by TLC (30% ethyl acetate/hexane, $R_f$~0.8). On completion of the reaction, reaction contents were poured into ice cold water and the compound extracted with ethyl acetate (2×25 ml). Combined extract was dried over sodium sulfate and concentrated under reduced pressure. The crude obtained was purified by column chromatography (silica gel, 10% ethyl acetate/hexane) to yield the required product as a yellow colored solid (2.2 g, 78% yield).

Step g: To a solution of step-f product (6 g, 0.017 mol) in DMF (48 ml, 8 times), methyl 2-chloropropanoate (2.87 g, 0.023 mol, 1.3 eq) was added and the contents were bubbled with nitrogen gas. Then manganese powder (1.97 g, 0.035 mol, 2 eq), Ni(bipyr)dibromide (0.667 g, 0.0012 mol, 0.07 eq), finally TFA (1 ml) were added one after other each time by passing nitrogen gas. The overall reaction mixture was allowed to stir for 12 hrs at rt. Progress of the reaction was monitored by TLC (30% ethyl acetate/hexane, $R_f$~0.3). On completion of the reaction, water (50 ml) was added, filtered the contents and the filtrate was extracted with ethyl acetate (2×50 ml). Combined extract was dried over sodium sulfate and concentrated under reduced pressure. The crude obtained was purified by column chromatography (silica gel, 15% ethyl acetate/hexane) to yield the required product as a brown colored solid (2 g, 37% yield).

Step h: To a solution of step-g product (2.4 g, 0.008 mol) in methanol (24 ml, 10 times), 10% Pd/C (0.5 g, catalytic) was added at rt. Heated the contents to a reflux temperature, ammonium formate 5 eq was added and the overall reaction mixture was allowed to reflux for 24 hrs. Progress of the reaction was monitored by TLC (40% ethyl acetate/hexane, $R_f$~0.2). On completion of the reaction, methanol was distilled off completely and the residue obtained was taken in water. Then the contents were acidified to a pH~5 with dilute HCl and the solid thrown out was filtered. The solid obtained was washed with water and dried to yield the required product (0.76 g, 45% yield).

Step i: To a solution of step-h product (1 g, 0.005 mol) in methanol (20 ml, 20 times), sodium hydroxide (0.98 g, 0.024 mol, 5 eq) was added at it and the overall reaction mixture was allowed to stir for 3 hrs. Progress of the reaction was monitored by TLC (30% ethyl acetate/hexane, $R_f$~0.1). On completion of the reaction, methanol was distilled off completely and the residue obtained was taken in water (50 ml). Then the contents were acidified to a pH~4 with dilute HCl and the solid thrown out was filtered. The solid obtained was washed with water and dried to yield the titled product as a brown colored solid (0.63 g, 67% yield, mp 91-96° C.).

6.14 Synthesis of 2-(1H-indazol-7-yl)propanoic acid (Employed for the Synthesis of Example Compound No. 210)

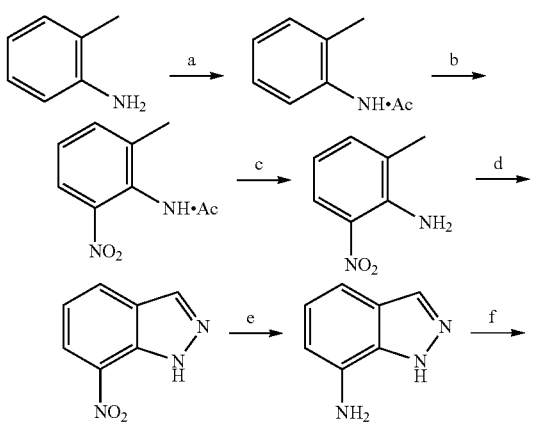

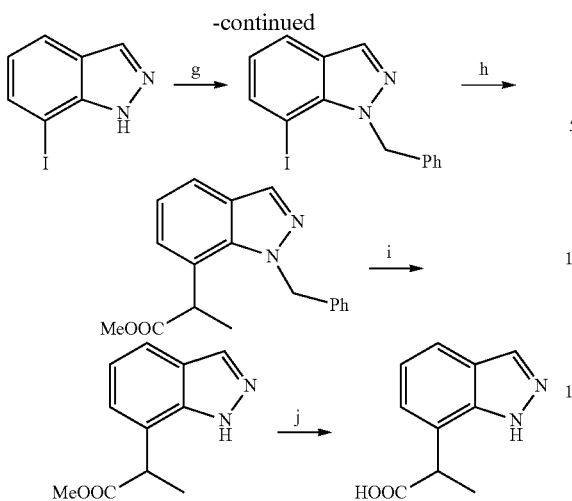

Step a-c: Ortho-toluidine (70 g, 0.65 mol) was added to acetic anhydride (425.2 ml, 6 times) drop wise for 30-45 min at rt. Checked TLC (20% ethyl acetate/hexane, compound-1 Rf~0.1). Cooled the contents to 10-12° C. and 70% nitric acid (82.4 ml, 2 eq) was added drop wise for 2-3 hrs. Checked TLC (50% ethyl acetate/hexane, compound-2 $R_f$~0.4). After addition, poured the contents to ice cold water (2.5 ltrs) and stirred for 10 min. Solid formed was filtered, washed with cold water and dried. The solid obtained was taken in conc.HCl (250 ml, 3 eq) and refluxed for 4-5 hrs. Checked TLC (40% ethyl acetate/hexane, compound-3 $R_f$~0.7). On completion of the reaction, cooled the reaction contents and filtered. The solid obtained was washed with 50% ethyl acetate/hexane (only ortho isomer is soluble in 50% ethyl acetate/hexane) and concentrated to yield the required ortho isomer product as an orange coloured solid (50 g, 51% yield).

Step d: To a stirred solution of step-a-c product (10 g, 0.065 mol) in acetic acid (470 ml, 47 times), a solution of sodium nitrite (1.54 g, 0.06 mol, 1.1 eq) in water (9 ml) was added and the reaction mass was stirred for 30-45 min. Progress of the reaction was monitored by TLC (30% ethyl acetate/hexane, $R_f$~0.7). On completion of the reaction, acetic acid was distilled off and the residue obtained was taken in ice water (200 ml). Solid formed was filtered, washed with cold water and dried to yield the required product as an yellow colored solid (10 g, 98% yield).

Step e: To mixture of 10% Pd/C (0.5 g, 0.1 times) in ethanol (100 ml), step-d product (5 g, 0.03 mol), ammonium formate (11.59 g, 0.18 mol, 6 eq) were added and the reaction contents were heated to 75-80° C. and refluxed for 30-45 min. Progress of the reaction was monitored by TLC (30% ethyl acetate/hexane, $R_f$~0.2). On completion of the reaction, filtered the reaction contents over celite bed and the bed was washed with methanol. Filtrate was concentrated under reduced pressure to obtain the crude product as a brown colored solid (3 g, crude).

Step f: To a solution of sulfuric acid (30 ml, 1.5 times) in water (80 ml), step-e product (20 g, 0.15 mol) was added portion wise for 30 min and stirred the contents for 1 hr. Cooled the contents to 0-5° C., a solution of sodium nitrite (10.35 g, 0.15 mol, 1 eq) in water (20 ml) was added drop wise for 20-30 min and the overall reaction mass was stirred for another 30 min. The above contents were added to a solution of potassium iodide (39.9 g, 0.24 mol, 1.6 eq) in water (120 ml) was added slowly and stirred the contents for 30 min. Progress of the reaction was monitored by TLC (30% ethyl acetate/hexane, $R_f$~0.5). On completion of the reaction, reaction contents were diluted with water (200 ml) and the product extracted with ethyl acetate (2×100 ml). Combined extract was dried over sodium sulfate, concentrated under reduced pressure and the crude obtained was purified by column chromatography (silica gel, 5% ethyl acetate/hexane) to yield the required product as a pale brown colored solid (20 g, 54% yield).

Step g: To a solution of step-f compound (20 g, 0.08 mol) in DMF (100 ml, 5 times), potassium carbonate (16.9 g, 0.12 mol, 1.5 eq) was added and stirred for 30 min at rt. Benzyl bromide (16.32 g, 1.2 eq) was added and the overall reaction contents were stirred for 12 hrs at rt. Progress of the reaction was monitored by TLC (30% ethyl acetate/hexane, $R_f$~0.4). On completion of the reaction, ice cold water was added to the reaction contents and stirred for 30 min. Solid thrown out was filtered, washed with hexane (200 ml) and dried to yield the required product as a pale yellow colored solid (11 g, 40% yield).

Step h: To a solution of step-g compound (11 g, 0.03 mol) in DMF (88 ml), methyl 2-chloropropanoate (5.26 g, 1.3 eq) was added and bubbled with nitrogen for 10 min. Manganese (3.29 g, 2 eq) was added and bubbled with nitrogen gas for 10 min. Nickel bipyridile dibromide (1.11 g) followed by TFA (1 ml) were added and bubbled with nitrogen for 10 min. The overall reaction mass was stirred for 12 hrs at rt. Progress of the reaction was monitored by TLC (20% ethyl acetate/hexane, $R_f$~0.5). On completion of the reaction, ice cold water was added to the reaction contents and the compound extracted with ethyl acetate (2×100 ml). Combined extract was filtered over celite bed and washed the bed with ethyl acetate. Dried the contents over sodium sulfate, concentrated under reduced pressure and the crude obtained was purified by column chromatography (silica gel, 10% ethyl acetate/hexane) to yield the required product as a pale brown colored liquid (4 g, 50% yield).

Step i: To a solution of step-h product (4 g, 0.013 mol) in methanol (80 ml, 20 times), 10% Pd/C (2 g), formic acid (4.8 g, 8 eq) were added. Heated the overall reaction contents to 70-75° C. and refluxed for 18 hrs at the same temperature. Progress of the reaction was monitored by TLC (40% ethyl acetate/hexane, $R_f$~0.2). On completion of the reaction, filtered the contents over celite bed and the bed was washed with methanol. Filtrate was concentrated under reduced pressure and the residue obtained was taken in water (50 ml). Basified the contents to a pH~9 with potassium carbonate and the compound extracted with DCM (2×50 ml). Combined organic layer was dried over sodium sulfate and concentrated under reduced pressure to yield the product as brown liquid (1.9 g, 73% yield).

Step j: To a solution of step-i product (1 g, 0.004 mol) in methanol (10 ml, 10 times), a solution of sodium hydroxide (0.78 g, 0.019, 9 eq) in water (5 ml) was added at rt and the overall reaction mass was allowed to stir for 3 hrs at rt. Progress of the reaction was monitored by TLC (30% ethyl acetate/hexane, $R_f$~0.1). On completion of the reaction, methanol was distilled off completely, residue obtained was taken in water (50 ml). Acidified the contents with 6N HCl solution at 0-5° C. and the solid thrown out was filtered. The crude obtained was washed with hexane and dried to yield the titled product as a white colored solid (0.7 g 75% yield, mp 171-176° C.).

6.15 Synthesis of 2-(5-fluoronaphthalen-1-yl)propanoic acid (Employed for the Synthesis of Example Compound No. 197)

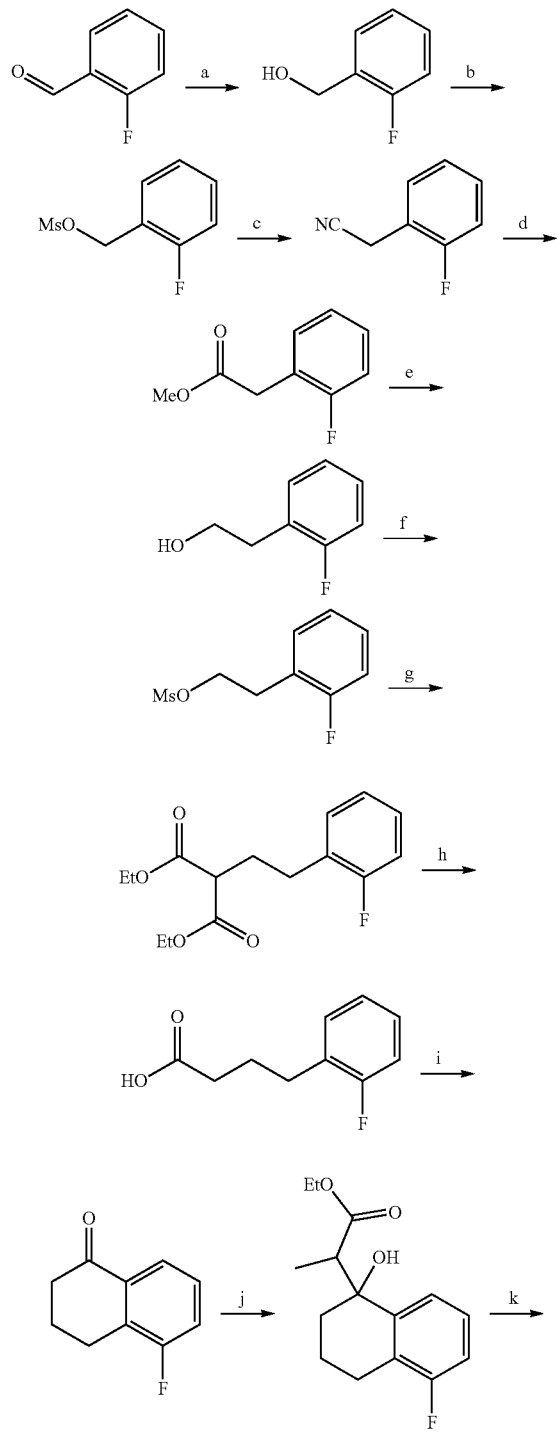

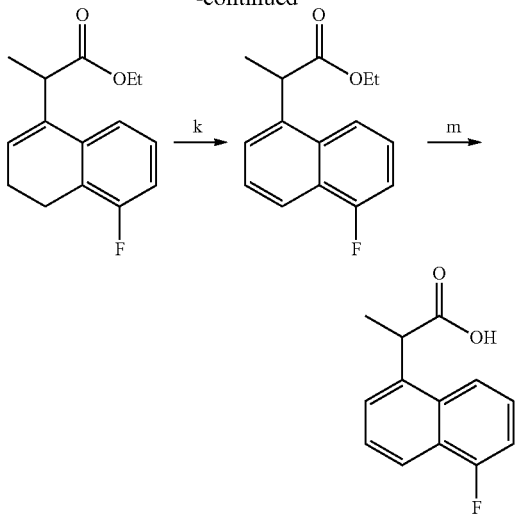

Step a: 2-fluorobenzaldehyde (25 g, 0.201 mol) was dissolved in THF (200 mL) and sodium borohydride (3.8 g, 0.1 mol) was added to the reaction mixture. After that methanol (10 mL) was added to it drop wise. The reaction mixture was stirred for 2 hours at ambient temperature. After total consumption of starting material the reaction mixture was washed with water (2×100 mL) and brine (100 mL). The organic layer was dried over magnesium sulphate and concentrated under reduced pressure to afford the product (27 g).

Step b: Step-a product (10 g, 0.079 mol) was dissolved in dichloromethane (75 mL) and triethylamine (16.6 mL, 0.119 mol) was added to it. The reaction mixture was then cooled to −15° C. and a solution of mesyl chloride (7.42 mL, 0.095 mol) in dichloromethane (25 mL) was added to it. The reaction mixture stirred for 30 minutes at same temperature. After total consumption of starting material the reaction mixture was diluted with dichloromethane (100 mL) and washed with water (3×50 mL). The organic layer was dried over magnesium sulfate and concentrated under reduced pressure to afford 12 g compound.

Step c: Step-b product (12 g, 0.064 mol) was dissolved in DMF (63.82 mL) and sodium cyanide (6.25 g, 0.128 mol) was added to it. The reaction mixture was stirred for 30 minutes at ambient temperature. After total consumption of starting material the reaction mixture was diluted with water (600 mL) and extracted with 30% ethyl acetate in hexane (3×100 mL). The combined organic layer was dried over magnesium sulfate and concentrated under reduced pressure. The crude compound was purified by column chromatography using 5% ethyl acetate in hexane as eluent to afford pure compound (7 g).

Step d: The step-c product (7 g) was dissolved in methanol (70 mL) and hydrogen chloride gas was passed over a period of two hours. After that the reaction mixture was stirred for one hour. After total consumption of starting material solvent was removed under reduced pressure and the residue was diluted with water and extracted with 30% ethyl acetate in hexane (3×100 mL). The combined organic layer was dried over magnesium sulfate and concentrated under reduced pressure to afford 7 g pure compound.

Step e: To the suspension of LAH (9.95 g, 0.262 mol) in tetrahydrofuran (150 mL), a solution of compound 5 (22 g, 0.131 mol) in tetrahydrofuran (70 mL) was added under nitrogen atmosphere at −5° C. The reaction mixture was stirred for one hour at ambient temperature. After total consumption of starting material LAH was quenched by Fischer process. The precipitate was filtered and filtrate was concentrated under reduced pressure. The crude compound was purified by column chromatography using 10% ethyl acetate in hexane as eluent to afford 18 g pure compound.

Step f: Step-e product (18 g, 0.128 mol) was dissolved in dichloromethane (150 mL) and triethylamine (26.8 mL, 0.193 mol) was added to it. The reaction mixture was cooled to −15-° C. and solution of mesyl chloride (12.02 mL, 0.154 mol) in dichloromethane (30 mL) was added to it. The reaction mixture stirred for 30 minutes at same temperature. After total consumption of starting material, the reaction mixture was diluted with dichloromethane (200 mL) and washed with water (3×100 mL). The combined organic layer was dried over magnesium sulfate and concentrated under reduced pressure to afford 18 g product.

Step g: To the suspension of sodium hydride (1.82 g, 0.046 mol) in tetrahydrofuran (30 mL), diethyl malonate (4.5 mL, 0.03 mol) was added at −10° C. and it was stirred for 30 minutes at ambient temperature. After that solution of step-f product (5 g, 0.023 mol) in THF (20 mL) was added at −10° C. and it was refluxed for 12 hours. After total consumption of starting material the reaction mixture was diluted with water (100 mL) and extracted with 30% ethyl acetate in hexane (3×50 mL). The combined organic layer was dried over magnesium sulfate and concentrated under reduced pressure. The crude compound was purified by column chromatography using 10% ethyl acetate in hexane as eluent to afford pure compound (yield 3.3 g).

Step h: Step-g product (5 g, 0.017 mol) was taken in a 250 mL round bottomed flask and 6N hydrochloric acid (80 mL) was added to it. The reaction mixture was refluxed for 12 hours. After total consumption of starting material the reaction mixture was diluted with water (50 mL) and extracted with ethyl acetate (3×50 mL). The combined organic layer was dried over magnesium sulfate and concentrated under reduced pressure. The crude compound was purified by column chromatography using 5% ethyl acetate in hexane as eluent to afford 2 g pure compound.

Step i: Step-h product (5 g, 0.027 mol) was dissolved in benzene (50 mL) and thionyl chloride (6.01 mL, 0.082 mol) was added to it followed by two drops of DMF. The reaction mixture was refluxed for two hours. After that solvent was removed under reduced pressure and water was removed by forming azeotrope with benzene. The residue was dissolved in dichloromethane (25 mL) and added to the suspension of aluminium chloride (14.65 g, 0.109 mol) in dichloromethane (25 mL) under nitrogen atmosphere at −10° C. Total consumption of starting material occurred in 30 min. The reaction mixture was poured into the ice and was extracted with 30% ethyl acetate in hexane (3×100 mL). The combined organic layer was dried over magnesium sulfate and concentrated under reduced pressure. The crude compound was purified by column chromatography using 5% ethyl acetate in hexane as eluent to afford 4 g pure compound.

Step j: Step-i product (2 g, 0.012 mol) was dissolved in distilled benzene (26 mL) and activated zinc (0.95 g, 0.0146 mol) was added followed by ethyl-2-bromopropionate (2.42 g, 0.0134 mol) and one pinch of iodine. The reaction mixture was refluxed for 2.5 hours. After total consumption of starting material the reaction mixture was diluted with 10% sulfuric acid (20 mL) and extracted with 20% ethyl acetate in hexane (3×20 mL). The combined organic layer was dried over magnesium sulfate and concentrated under reduced pressure. The crude compound was purified by column chromatography using 5% ethyl acetate in hexane as eluent to afford pure compound (3.3 g).

Step k: Step-j product (1 g, 0.0037 mol) was dissolved in THF (4.5 mL) and 6N hydrochloric acid (4.5 mL) was added to it. The reaction mixture was stirred for 2 hours at ambient temperature. After total consumption of starting material the reaction mixture was diluted with water (10 mL) and extracted with 10% ethyl acetate in hexane (3×10 mL). The combined organic layer was dried over magnesium sulphate and concentrated under reduced pressure. The crude compound was purified by column chromatography using 5% ethyl acetate in hexane as eluent to afford pure compound (800 mg).

Step l: Step-k product (1.9 g, 0.0076 mol) was dissolved in dioxane (22.5 mL) and DDQ (3.82 g, 0.0168 mol) was added to it. The reaction mixture was refluxed for 2 hours. It was then diluted with methanol (100 mL) and silica gel (15 g) was added to it to make the slurry. It was purified by column chromatography using 5% ethyl acetate in hexane as eluent to afford pure compound (1.5 g).

Step m: Step-l product (1.5 g, 0.006 mol) was dissolved in THF (12.2 mL) and 1N LiOH (12.2 mL) was added to it. The reaction mixture was stirred for 24 hours at ambient temperature. After total consumption of starting material the reaction mixture was diluted with water (20 mL) and washed with ethyl acetate (2×20 mL). The aqueous layer was acidified with 6N hydrochloric acid and extracted with ethyl acetate (3×20 mL). The combined organic layer was dried over magnesium sulfate and concentrated under reduced pressure to afford desired compound (1.2 g).

6.16 Synthesis of
2-(6-fluoronaphthalen-1-yl)propanoic acid
(Employed for the Synthesis of Example Compound
No. 211)

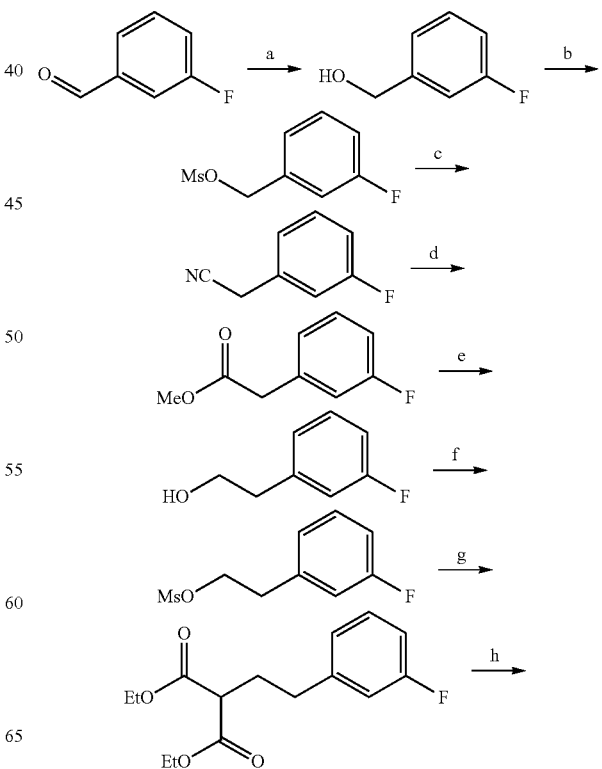

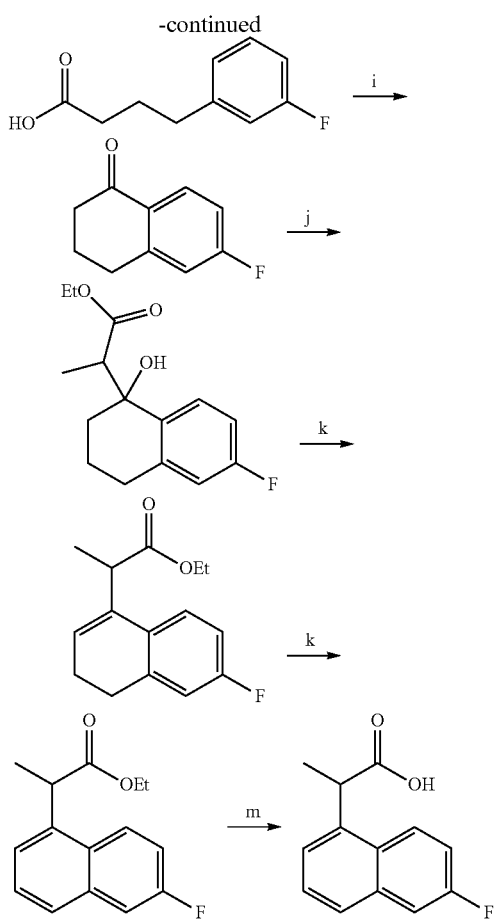

Step a: 3-Fluorobenzaldehyde (20 g, 0.161 mol) was dissolved in THF (200 mL) and sodium borohydride (2.03 g, 0.054 mol) was added to the reaction mixture. After that methanol (15 mL) was added to it dropwise. The reaction mixture was stirred for 2 hours at ambient temperature. After total consumption of starting material the reaction mixture was washed with water (3×100 mL) and brine (100 mL). The organic layer was dried over magnesium sulphate and concentrated under reduced pressure to afford compound (20.8 g).

Step b: Step-a product (10 g, 0.079 mol) was dissolved in dichloromethane (75 mL) and triethylamine (16.6 mL, 0.119 mol) was added to it. The reaction mixture was cooled to −15° C. and solution of mesyl chloride (7.42 mL, 0.095 mol) in dichloromethane (25 mL) was added to it. The reaction mixture stirred for 30 minutes at same temperature. After total consumption of starting material the reaction mixture was diluted with dichloromethane (100 mL) and washed with water (3×50 mL). The organic layer was dried over magnesium sulphate and concentrated under reduced pressure to afford 14 g compound.

Step c: Step-b product (14 g, 0.074 mol) was dissolved in DMF (74.5 mL) and sodium cyanide (7.3 g, 0.149 mol) was added to it. The reaction mixture was stirred for 30 minutes at ambient temperature. After total consumption of starting material the reaction mixture was diluted with water (800 mL) and extracted with 30% ethyl acetate in hexane (3×200 mL).). The combined organic layer was dried over magnesium sulphate and concentrated under reduced pressure. The crude compound was purified by column chromatography using 5% ethyl acetate in hexane as eluent to afford 8 g pure compound.

Step d: 8 g Step-c product was dissolved in methanol (80 mL) and hydrogen chloride gas was passed over a period of two hours. After that the reaction mixture was stirred for one hour. After total consumption of starting material solvent was removed under reduced pressure and the residue was diluted with water and extracted with 30% ethyl acetate in hexane (3×50 mL). The combined organic layer was dried over magnesium sulfate and concentrated under reduced pressure to afford 6 g pure compound.

Step e: To the solution of LAH (13.68 g, 0.36 mol) in tetrahydrofuran (200 mL) solution of step-d product (30 g, 0.18 mol) in tetrahydrofuran (100 mL) was added under nitrogen atmosphere at −10° C. The reaction mixture was stirred for one hour at ambient temperature. After total consumption of starting material LAH was quenched by Fischer process. The precipitate was filtered and filtrate was concentrated under reduced pressure. The crude compound was purified by column chromatography using 10% ethyl acetate in hexane as eluent to afford 26 g pure compound.

Step f: Step-e product (26 g, 0.18 mol) was dissolved in dichloromethane (200 mL) and triethylamine (38.8 mL, 0.28 mol) was added to it. The reaction mixture was cooled to −15° C. and solution of mesyl chloride (17.3 mL, 0.22 mol) in dichloromethane (60 mL) was added to it. The reaction mixture stirred for 30 minutes at ambient temperature. After total consumption of starting material the reaction mixture was diluted with dichloromethane (200 mL) and washed with water (3×100 mL). The combined organic layer was dried over magnesium sulphate and concentrated under reduced pressure to afford 36 g compound.

Step g: To the suspension of sodium hydride (13.16 g, 0.33 mol) in THF (300 mL), diethyl malonate (32.6 mL, 0.214 mol) was added at −10° C. and it was stirred for 30 minutes at ambient temperature. After that solution of step-f product (36 g, 0.16 mol) in THF (60 mL) was added at −10° C. and it was refluxed for 12 hours. After total consumption of starting material the reaction mixture was diluted with water (200 mL) and extracted with 30% ethyl acetate in hexane (3×200 mL). The combined organic layer was dried over magnesium sulphate and concentrated under reduced pressure. The crude compound was purified by column chromatography using 10% ethyl acetate in hexane as eluent to afford 38 g pure compound.

Step h: Step-g product (38 g, 0.135 mol) was taken in a 1000 mL round bottomed flask and 6N hydrochloric acid (500 mL) was added to it. The reaction mixture was refluxed for 12 hours. After total consumption of starting material the reaction mixture was diluted with water (250 mL) and extracted with ethyl acetate (3×200 mL). The combined organic layer was dried over magnesium sulfate and concentrated under reduced pressure. The crude compound was purified by column chromatography using 5% ethyl acetate in hexane as eluent to afford 9 g pure compound.

Step i: Step-h product (9 g, 0.049 mol) was dissolved in benzene (90 mL) and thionyl chloride (10.8 mL, 0.148 mol) was added to it followed by two drops of DMF. The reaction mixture was refluxed for two hours. After that solvent was removed under reduced pressure and water was removed by forming azeotrope with benzene. The residue was dissolved in dichloromethane (50 mL) and added to the suspension of aluminium chloride (26.37 g, 0.198 mol) in dichloromethane (100 mL) under nitrogen atmosphere at −10° C. After 30 minutes total consumption of starting material occurred and the reaction mixture was poured into the ice and it was extracted with 30% ethyl acetate in hexane (3×100 mL). The combined organic layer was dried over magnesium sulphate and concentrated under reduced pressure. The crude compound was purified by column chromatography using 5% ethyl acetate in hexane as eluent to afford 7 g pure compound.

Step j: Step-1 product (3 g, 0.018 mol) was dissolved in distilled benzene (39 mL) and activated zinc (1.43 g, 0.022 mol) was added followed by ethyl-2-bromopropionate (3.63 g, 0.020 mol) and one pinch of iodine. The reaction mixture was refluxed for 2.5 hours. After total consumption of starting material the reaction mixture was diluted with 10% sulfuric acid and extracted with 20% ethyl acetate in hexane (3×20 mL). The combined organic layer was dried over magnesium sulphate and concentrated under reduced pressure. The crude compound was purified by column chromatography using 5% ethyl acetate in hexane as eluent to afford 5 g pure compound.

Step k: Step-j product (5 g, 0.018 mol) was dissolved in THF (22.5 mL) and 6N hydrochloric acid (22.5 mL) was added to it. The reaction mixture was stirred for 2 hours at ambient temperature. After total consumption of starting material the reaction mixture was diluted with water (50 mL) and extracted with 10% ethyl acetate in hexane (3×50 mL). The combined organic layer was dried over magnesium sulfate and concentrated under reduced pressure. The crude compound was purified by column chromatography using 5% ethyl acetate in hexane as eluent to afford 3.2 g pure compound.

Step l: Step-k product (3.2 g, 0.013 mol) was dissolved in dioxane (38 mL) and DDQ (6.4 g, 0.028 mol) was added to it. The reaction mixture was refluxed for 2 hours. The reaction mixture was diluted with methanol (200 mL) and silica gel (35 g) was added to it to make the slurry. It was purified by column chromatography using 5% ethyl acetate in hexane as eluent to afford 3 g pure compound.

Step m: Step-1 product (3 g, 0.013 mol) was dissolved in THF (26.8 mL) and 1N LiOH (26.8 mL) was added to it. The reaction mixture was stirred for 24 hours at ambient temperature. After total consumption of starting material the reaction mixture was diluted with water (50 mL) and washed with ethyl acetate (2×50 mL). The aqueous layer was acidified with 6N hydrochloric acid and extracted with ethyl acetate (3×50 mL). The combined organic layer was dried over magnesium sulphate and concentrated under reduced pressure to afford desired product (2.4 g).

6.17 Synthesis of 2-(7-methoxynaphthalen-1-yl)propanoic acid (Employed for the Synthesis of Example Compound No. 212)

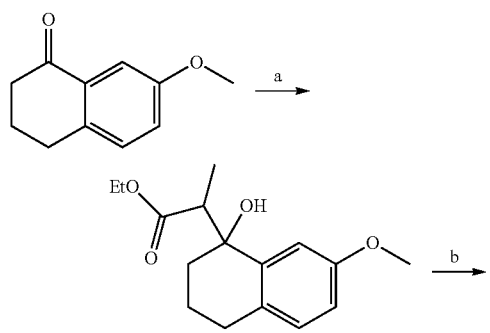

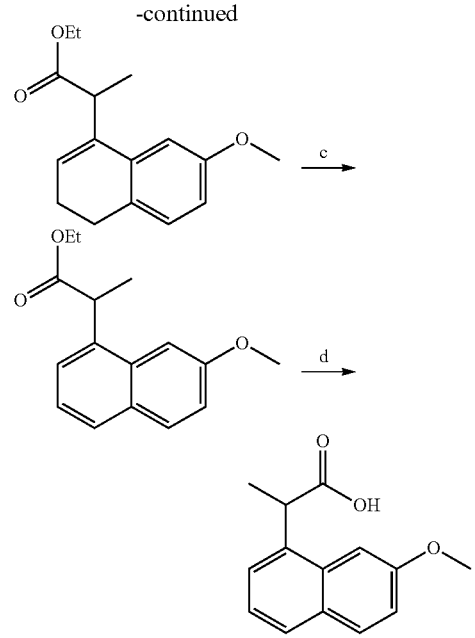

Step a: 7-Methoxy-3,4-dihydronaphthalen-1(2H)-one (5 g, 0.028 mol) was taken in dry tetrahydrofuran (25 mL) under argon atmosphere. Zinc dust (3.7 g, 0.057 mol) and 2-bromo ethyl propionate (5.53 mL, 0.043 mol) was added to the mixture. This mixture was stirred at 50° C. for 10 hours. TLC showed complete consumption of the starting material (20% ethyl acetate in hexane; $R_f$=0.5). The reaction mixture was then quenched with 10% $H_2SO_4$ (10 mL) and ice cold water (20 mL) at 0° C. The aqueous was extracted with ethyl acetate (2×150 mL). The combined organic part was washed with ice-cold water (200 mL) and brine (100 mL). The organic layer was dried over anhydrous magnesium sulfate and concentrated under reduced pressure to afford the crude product, which was purified by column chromatography (silica gel: 100-200 mesh, eluent: 15% ethyl acetate in hexane) to afford title compound (4.8 g, 62% yield)

Step b: Step-a product (3 g, 0.011 mol) was dissolved in tetrahydrofuran (12.5 mL) and hydrochloric acid (6N, 12.5 mL) was added to the solution. The reaction mixture was stirred for 3 hours at 25° C. The completion of the reaction was confirmed by TLC (10% ethyl acetate in hexane, $R_f$=0.5). The reaction mixture was extracted with ethyl acetate (3×50 mL). The combined organic layer was washed with cold water (2×30 mL) and brine (100 mL) and dried over anhydrous magnesium sulfate. The organic part was concentrated and purified through column chromatography (silica gel: 100-200 mesh, eluent: 5% ethyl acetate in hexane) to afford the compound (2 g, 71%).

Step c: Step-b product (3 g, 0.012 mol) was taken in dry 1,4-dioxane (34 mL) under argon atmosphere and DDQ (5.75 g, 0.025 mol) was added to the solution. This reaction mixture was refluxed for 2 hours under argon atmosphere. The completion of the reaction was confirmed by LCMS monitoring. The reaction mixture was cooled to 25° C. and methanol (600 mL) was added to the mixture to make it homogeneous. Silica gel (mesh size: 100-200, 30 g) was added to this mixture and the solvent was evaporated to get slurry. It was then purified through column chromatography (silica gel: 100-200 mesh, eluent: 10% ethyl acetate in hexane) to afford the pure compound as reddish brown liquid (2.45 g, 82.5%).

Step d: Step-c product (2.45 g, 0.009 mol) was dissolved in tetrahydrofuran (7 mL) and 1(M) aqueous lithium hydroxide solution (28.48 mL, 0.028 mol) was added to this mixture. The reaction mixture was stirred for 36 hours at 25° C. The completion of the reaction was confirmed by TLC monitoring (50% ethyl acetate in hexane, $R_f$=0.5). The pH of the reaction mixture was brought to 5 using 1(M) HCl. The aqueous part was extracted with ethyl acetate (3×50 mL). The combined organic part was washed with ice-cold water (3×20 mL) and brine (100 mL) and dried over anhydrous magnesium sulfate. The organic part was concentrated and triturated from 10% ethyl acetate in hexane to afford the pure product (2.1 g, 96% yield).

6.18 Synthesis of 2-(3-chloroisoquinolin-5-yl)propanoic acid (Employed for the Synthesis of Example Compound No. 213)

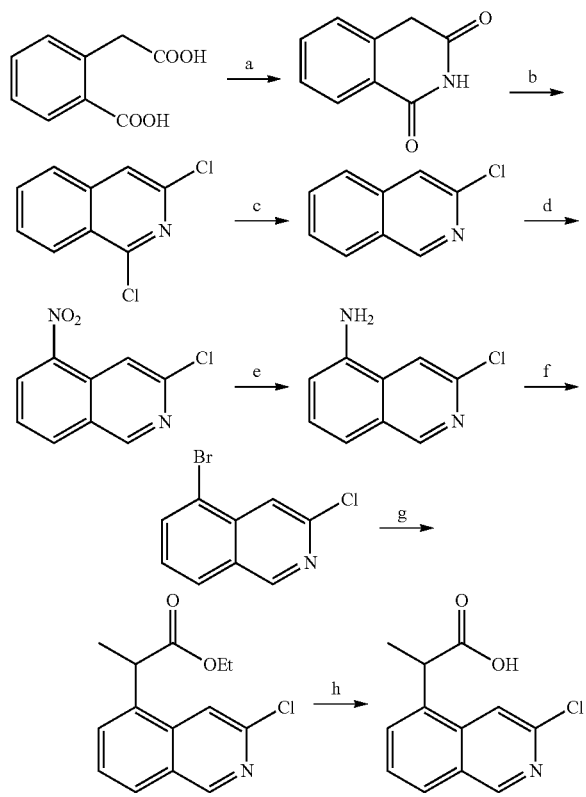

Step a: 2-(Carboxymethyl)benzoic acid (20 g, 0.111 mol) was dissolved in 1,2-dichlorobenzene (200 mL) and ammonium hydroxide (25.6 mL, 0.166 mol) was added to it. The reaction mixture was heated to 200° C. and stirred at that temperature for four hours. TLC showed that no starting left. It was then cooled to room temperature and diluted with methanol (40 mL). The resulting solution was allowed to stand overnight. A solid residue formed, which was filtered through sintered funnel and washed with methanol (20 mL) to afford the pure compound (17 g).

Step b: A mixture of step-a product (5 g, 0.031 mol) and phenylphosphoryl dichloride (8.7 mL, 0.06 mol) were heated at 160° C. for 4 hours. TLC showed complete consumption of starting material. It was cooled to ambient temperature and diluted with water (200 mL). The resulting mixture was extracted with 10% ethyl acetate in hexane (3×200 mL). The whole organic layer was dried over anhydrous magnesium sulfate and concentrated under reduced pressure to afford the crude compound. It was purified by column chromatography (silica gel: 100-200; eluent: 2% ethyl acetate in hexane) to get the pure compound (1.5 g).

Step c: Step-b product (5 g, 0.025 mol) was suspended in a mixture of glacial acetic acid (27.5 mL) and concentrated hydrochloric acid (9.7 mL). Tin powder was added to it and the mixture was heated at 55° C. for 3 hours. TLC showed complete consumption of starting material. The reaction mixture was filtered through sintered funnel and the filtrate was diluted with water. The overall filtrate was basified with ammonium hydroxide solution up to pH=9 and extracted with ethyl acetate (3×100 mL). The organic layer was washed with sodium bi carbonate solution and brine. It was dried over anhydrous magnesium sulfate and concentrated under reduced pressure to afford the crude compound 4, which was directly taken to next step (yield: 2 g).

Step d: To a stirred solution of crude step-c product (17 g, 0.104 mol) in concentrated sulfuric acid (10 mL) was added potassium nitrate (11 g, 0.109 mol) in concentrated sulfuric acid solution slowly at −15° C. in 30 minutes. It was allowed to stir for 12 hours. After complete conversion the reaction mixture was poured into crushed ice. A yellow precipitate came out which was filtered and washed with water (3×50 mL). The solid was dried under vacuum at 80° C. to afford 20 crude compound.

Step e: Step-d product (17 g, 0.081 mol) was taken in glacial acetic acid and water (1:1), Iron powder (17 gm, 0.323 mol) was added portion wise at 60° C. for 10 minutes. It was stirred at the same temperature for 3 hours. After checking the TLC (starting was consumed totally) it was filtered through celite bed and the filtrate was basified with sodium hydroxide solution. The basified filtrate was extracted with ethyl acetate (3×100 mL). The combined ethyl acetate layer was dried over anhydrous magnesium sulfate and concentrated under reduced pressure to afford 13 g crude compound.

Step f: Step-e product (13 g, 0.073 mol) was taken in hydrobromic acid (35 mL) and water (35 mL) and heated to 50° C. for 30 minutes. It was then allowed to cool to 0 to −5° C. Sodium nitrite (6.8 g) dissolved in water (35 mL) was added drop wise for 10 minutes maintaining temperature between 0 to −5° C. It was allowed to stir at 0° C. for 10 minutes. It was added to copper bromide (13.8 g) in hydrobromic acid (115 mL) slowly at 75° C. for 10 minutes and allowed to come at room temperature and stirred for 2 hours. After starting was consumed it was basified with sodium hydroxide solution (10%, 100 mL) and extracted with ethyl acetate (3×200 mL). The combined organic layer was dried over anhydrous magnesium sulfate and concentrated under reduced pressure to afford the crude compound. The crude compound was purified by column chromatography (silica gel: 100-200; eluent: 10% ethyl acetate in hexane) to afford the pure compound (13 g, 81% yield).

Step g: Step-f product (0.5 g, 0.002 mol) was dissolved in dry dimethylformamide (4 mL). 2-chloroethylpropionate (0.36 g, 0.002 mol), NiBr$_2$.bipy (0.06 g, 0.164 mol) and Mn dust (0.226 g, 0.004 mol) were added simaltaneously. It was degasified and trifloroacetic acid (4 µL) was added to the solution. It was heated to 60-65° C. for 7 hours. After starting was consumed water (40 mL) was added and the mixture was passed through celite bed. The filtrate was extracted with ethyl acetate (2×50 mL). The combined organic layer was dried over anhydrous magnesium sulfate and concentrated under reduced pressure to afford the crude compound. The crude compound was purified by column chromatography (silica gel: 100-200, eluent: 15% ethyl acetate in hexane) to afford the pure compound (100 mg, 18% yield).

Step h: Step-g product (0.8 g, 0.002 mol) was dissolved in tetrahydrofuran (6 mL) and aqueous lithium hydroxide solution (1M, 3 mL, 0.003 mol) was added to it. It was stirred at ambient temperature for 10 hours. After starting was consumed, water was added to the reaction mixture and the aqueous part was washed with ethyl acetate (2×30 mL). The water layer was acidified with 2N Hydrochloric acid (3 mL) and extracted with ethyl acetate (2×10 mL). The combined organic layer was dried over anhydrous magnesium sulfate and concentrated under reduced pressure to afford the pure compound (0.3 g, 84% yield).

6.19 Synthesis of 2-(3-methylisoquinolin-5-yl)propanoic acid (Employed for the Synthesis of Example Compound No. 65)

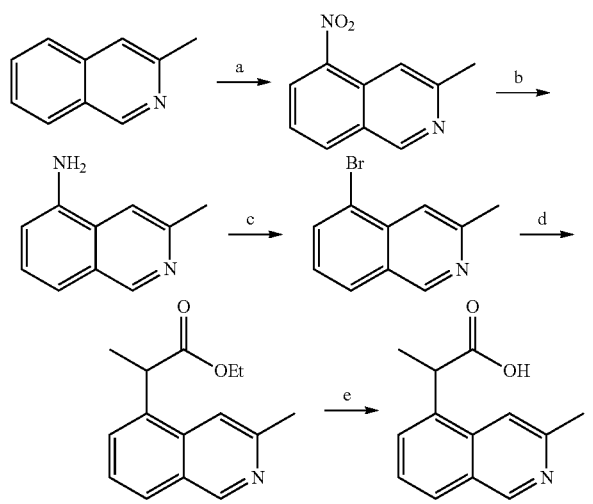

Step a: To a stirred solution of 3-methylisoquinoline (5 g, 0.035 mol) in concentrated sulfuric acid (20 mL) was added potassium nitrate (3.6 g, 0.036 mol) in concentrated sulfuric acid (25 ml) solution slowly at −15° C. in 30 minutes. It was allowed to stir for 12 hours. After complete conversion the reaction mixture was poured into crushed ice. A yellow precipitate came out which was filtered and washed with water (3×50 mL). The solid was dried under vacuum at 80° C. to afford 6 g of the crude product.

Step b: Step-a product (6 g, 0.032 mol) was taken in ethyl acetate (120 mL), Palladium on charcoal (600 mg, 10% Pd) was added to it and it was hydrogenated in Parr apparatus at 50 psi for 2 hours. After checking the TLC (starting was consumed totally) it was filtered through celite bed and the filtrate was concentrated under reduced pressure to afford the crude compound (yield: 4.5 g).

Step c: Step-b product (4.5 g, 0.028 mol) was taken in hydrobromic acid (13.5 mL) and water (13.5 mL) and the solution was cooled to 0 to −5° C. Sodium nitrite (2.15 g) dissolved in water (13.5 mL) was added drop wise for 10 minutes maintaining temperature between 0 to −5° C. It was allowed to stir at 0° C. for another 10 minutes. It was added to copper bromide (5.38 g, 0.004 mol) in hydrobromic acid (45 mL) slowly at 75° C. for 10 minutes and allowed to come at room temperature and stirred for 12 hours. After starting was consumed it was basified with sodium hydroxide solution (10%, 100 mL) and extracted with ethyl acetate (3×50 mL). The combined organic layer was dried over anhydrous magnesium sulfate and concentrated under reduced pressure to afford the crude compound. The crude compound was purified by column chromatography (silica gel: 100-200; eluent: 15% ethyl acetate in hexane) to afford the pure compound (3.5 g, 81% yield).

Step d: Step-c product (1 g, 0.0045 mol) was dissolved in dry dimethylformamide (9 mL). 2-chloroethylpropionate (0.79 g, 0.0058 mol), $NiBr_2$-bipy (0.11 g, 0.0003 mol) and Mn dust (0.49 g, 0.009 mol) were added simultaneously. It was degasified and trifloroacetic acid (9 μL) was added to the solution. It was heated to 60-65° C. and continued for 16 hours. After starting was consumed water (90 mL) was added and the mixture was passed through celite bed. The filtrate was extracted with ethyl acetate (3×100 mL). The combined organic layer was dried over anhydrous magnesium sulfate and concentrated under reduced pressure to afford the crude compound. The crude compound was purified by column chromatography (silica gel: 100-200, eluent: 15% ethyl acetate in hexane) to afford 550 mg of the pure compound.

Step e: Step-d product (1.2 g, 0.0049 mol) was dissolved in tetrahydrofuran (10 mL) and aqueous lithium hydroxide solution (1M, 9.8 mL, 0.0098 mol) was added to it. It was stirred at ambient temperature for 10 hours. After starting was consumed, water was added to the reaction mixture and the aqueous part was washed with ethyl acetate (2×50 mL). The water layer was acidified with 2N hydrochloric acid (10 mL) and extracted with ethyl acetate (2×10 mL). The combined organic layer was dried over anhydrous magnesium sulfate and concentrated under reduced pressure to afford the desired compound (0.9 g).

6.20 Synthesis of 2-(1-methylisoquinolin-5-yl)propanoic acid (Employed for the Synthesis of Example Compound No. 66)

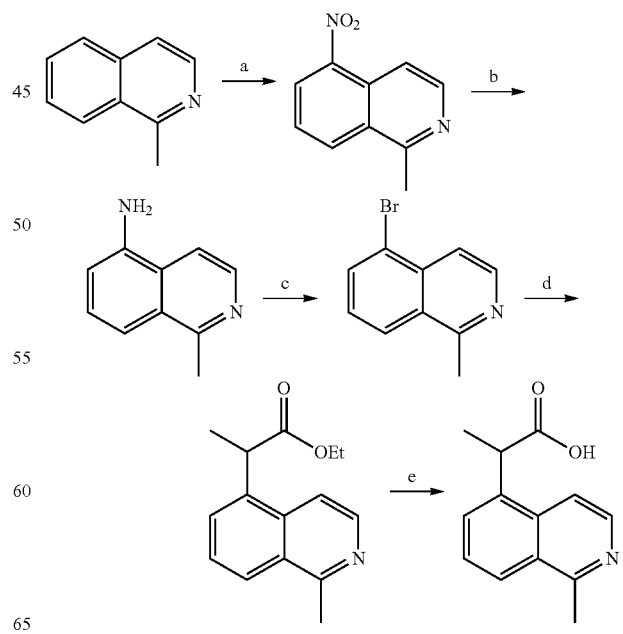

Step a: To a stirred solution of 1-methylisoquinoline (1 g, 0.007 mol) in concentrated sulfuric acid (4 mL), potassium nitrate (733 mg, 0.007 mol) in concentrated sulfuric acid (4.4 mL) was added slowly at −15° C. in 10 minutes. It was allowed to stir for 12 hours at ambient temperature. After complete conversion the reaction mixture was poured into crushed ice. A yellow precipitate came out which was filtered and washed with water (3×20 mL). The solid was dried under vacuum at 80° C. to afford the crude compound (yield: 1.4 g).

Step b: step-a product (1.4 g, 0.007 mol) was taken in ethyl acetate (15 mL), Palladium on charcoal (140 mg, 10% Pd) was added to it and it was hydrogenated in Parr apparatus at 50 psi for 2 hours. After checking the TLC (starting was consumed totally) it was filtered through celite bed and the filtrate was concentrated under reduced pressure to afford the crude compound (1.0 g, 85% yield).

Step c: Step-b product (1.0 g, 0.006 mol) was taken in hydrobromic acid (4 mL) and water (4 mL) and the solution was cooled to 0 to −5° C. Sodium nitrite (480 mg, 0.007 mol) dissolved in water (4 mL) was added drop wise for 10 minutes maintaining temperature between 0 to −5° C. It was allowed to stir at 0° C. for another 10 minutes. It was added to copper bromide (1.2 g, 0.008 mol) in hydrobromic acid (10 mL) slowly at 75° C. for 5 minutes and allowed to come at room temperature and stirred for 12 hours. After complete consumption of the starting material, it was basified with sodium hydroxide solution (10%, 15 mL) and extracted with ethyl acetate (3×20 mL). The combined organic layer was dried over anhydrous magnesium sulfate and concentrated under reduced pressure to afford the crude compound. The crude compound was purified by column chromatography (silica gel: 100-200; eluent: 15% ethyl acetate in hexane) to afford the pure compound (0.9 g, 64% yield).

Step d: Step-c product (0.5 g, 0.002 mol) was dissolved in dry dimethylformamide (4.5 mL). 2-chloroethylpropionate (0.4 g, 0.0029 mol), NiBr$_2$-bipy (0.059 g, 0.00016 mol) and Mn dust (0.25 g, 0.0045 mol) were added simultaneously. It was degasified and trifloroacetic acid (4.5 μL) was added to the solution. It was heated to 60-65° C. and continued for 16 hours. After starting was consumed, water (40 mL) was added and the mixture was passed through celite bed. The filtrate was extracted with ethyl acetate (3×40 mL). The combined organic layer was dried over anhydrous magnesium sulfate and concentrated under reduced pressure to afford the crude compound. The crude compound was purified by column chromatography (silica gel: 100-200, eluent: 15% ethyl acetate in hexane) to afford the pure compound (0.15 g, 27% yield).

Step e: Step-d product (500 mg, 0.00205 mol) was dissolved in tetrahydrofuran (4 mL) and aqueous lithium hydroxide solution (1M, 4.11 mL, 0.0041 mol) was added to it. It was stirred at ambient temperature for 10 hours. After starting was consumed, water was added to the reaction mixture and the aqueous part was washed with ethyl acetate (2×20 mL). The water layer was acidified with 2N hydrochloric acid (2.2 mL) to make the pH=6 and extracted with 5% methanol in ethyl acetate (4×20 mL). The combined organic layer was dried over anhydrous magnesium sulfate and concentrated under reduced pressure to afford the pure compound (yield: 0.3 g).

6.21 Synthesis of 2-(1,3-dimethylisoquinolin-5-yl)propanoic acid (Employed for the Synthesis of Example Compound No. 67)

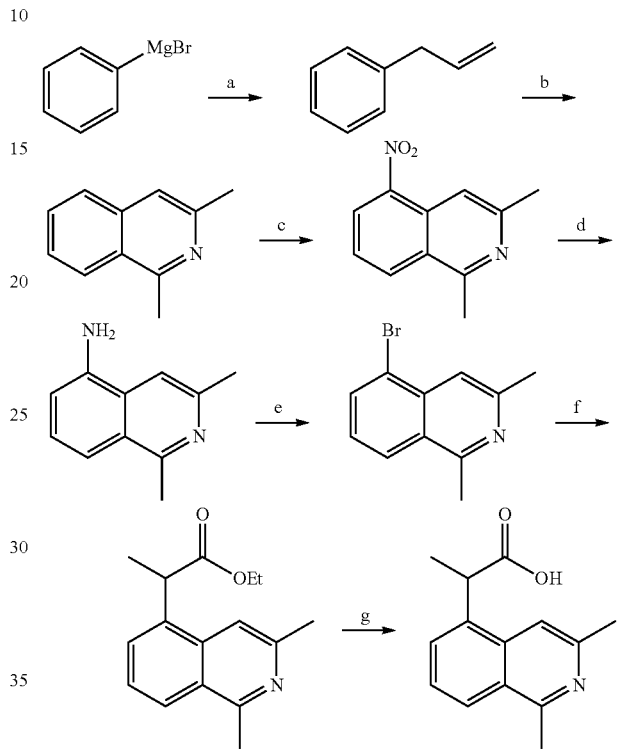

Step a: To a stirred solution of allyl chloride (5 g, 0.065 mol) in tetrahydrofuran (50 mL) phenylmagnesium bromide (1M, 54 mL) was added dropwise at 10-15° C. The resulting reaction mixture was stirred at ambient temperature for 2 hours. TLC (hexane, R$_f$=0.8) showed complete consumption of starting material. The reaction mixture was quenched with saturated solution of ammonium chloride (50 mL) and the aqueous part was extracted with hexane (3×50 mL). The combined organic layer was washed with brine (100 mL) and dried over anhydrous magnesium sulfate. The organic part was concentrated under reduced pressure followed by fractional distillation process to afford pure compound (3.8 g, 48% yield).

Step b: To a solution of silver triflate (8.26 g, 0.032 mol) in acetonitrile (64 mL) step-a product (3.8 g, 0.032 mol) in acetonitrile (64 mL) was added at ambient temperature. A solution of Iodine (4.0 g, 0.032 mol) in acetonitrile (64 mL) was added drop wise to the reaction mixture at 0° C. under stirring over the period of 15 minutes. The resulting mixture was stirred at ambient temperature for overnight. A yellow precipitate of silver iodide was formed. Silver iodide was filtered off and the filtrate was mixed with methanolic potassium hydroxide solution (9 g, in 100 mL MeOH) and heated to 40° C. for 2 hours. TLC showed product formed but starting material was left. Then the solvent was removed under reduced pressure and diluted with water (200 mL). The aqueous phase was extracted with ethyl acetate (3×100 mL) and the combined organic layer was dried over anhydrous magnesium sulfate. The organic part was concentrated under reduced pressure to afford the crude compound, which was purified by column chromatography (silica gel: 100-200 mesh, eluent: 20% ethyl acetate in hexane) to afford the pure compound (1 g, 20% yield).

Step c: To a stirred solution of step-b product (1.6 g, 0.010 mol) in concentrated sulfuric acid (10 mL), potassium nitrate (1.08 g, 0.011 mol) in concentrated sulfuric acid (5 mL) was added slowly at −15° C. in 10 minutes. It was allowed to stir for 12 hours at ambient temperature. After complete conversion the reaction mixture was poured into crushed ice. A yellow precipitate came out which was filtered and washed with water (3×40 mL). The solid was dried under vacuum at 80° C. to afford 2.1 g of the crude product.

Step d: Step-c product (2.0 g, 0.01 mol) was taken in ethyl acetate (50 mL), palladium on charcoal (200 mg, 10% Pd) was added to it and it was hydrogenated in Parr apparatus at 50 psi for 2 hours. After checking the TLC (starting was consumed totally) it was filtered through celite bed and the filtrate was concentrated under reduced pressure to afford 1.4 g of the crude compound (82% yield).

Step e: Step-d product (1.5 g, 0.0087 mol) was taken in hydrobromic acid (8 mL) and water (8 mL) and the solution was cooled to 0 to −5° C. Sodium nitrite (660 mg, 0.0096 mol) dissolved in water (8 mL) was added drop wise for 10 minutes maintaining temperature between 0 to −5° C. It was allowed to stir at 0° C. for another 10 minutes. It was added to copper bromide (1.65 g, 0.011 mol) in hydrobromic acid (20 mL) slowly at 75° C. for 5 minutes and allowed to come at room temperature and stirred for 12 hours. After complete consumption of the starting material, it was basified with sodium hydroxide solution (20%, 100 mL) and extracted with ethyl acetate (5×50 mL). The combined organic layer was dried over anhydrous magnesium sulfate and concentrated under reduced pressure to afford the crude compound. The crude compound was purified by column chromatography (silica gel: 100-200; eluent: 15% ethyl acetate in hexane) to afford the pure compound (1.6 g, 80% yield).

Step f: Step-e product (0.5 g, 0.0021 mol) was dissolved in dry dimethylformamide (4.2 mL). 2-chloroethylpropionate (0.376 g, 0.0027 mol), NiBr$_2$-bipy (0.064 g, 0.00017 mol) and Mn dust (0.23 g, 0.0042 mol) were added simultaneously. It was degasified and trifloroacetic acid (4.2 μL) was added to the solution. It was heated to 60-65° C. and continued for 16 hours. After starting was consumed, water (40 mL) was added and the mixture was passed through celite bed. The filtrate was extracted with ethyl acetate (3×40 mL). The combined organic layer was dried over anhydrous magnesium sulfate and concentrated under reduced pressure to afford the crude compound. The crude compound was purified by column chromatography (silica gel: 100-200, eluent: 15% ethyl acetate in hexane) to afford the pure compound (0.28 g, 51% yield).

Step g: Step-f product (1.1 g, 0.00427 mol) was dissolved in tetrahydrofuran (17 mL) and aqueous lithium hydroxide solution (1M, 17 mL, 0.017 mol) was added to it. It was stirred at ambient temperature for 12 hours. After starting was consumed, water was added to the reaction mixture and the aqueous part was washed with ethyl acetate (2×40 mL). The water layer was acidified with 2N hydrochloric acid (10 mL) to make the pH=3. The aqueous layer was concentrated under reduced pressure and the crude was purified by column chromatography (silica gel; eluent: 5% methanol in chloroform) to afford the pure compound, which was re-purified by trituration with ether to afford the title compound (0.6 g, 60% yield).

7. Preparation of Selected Amines of General Formula (VI)

7.1 Synthesis of 4-amino 2-indanol (Employed for the Synthesis of Example Compound No. 81)

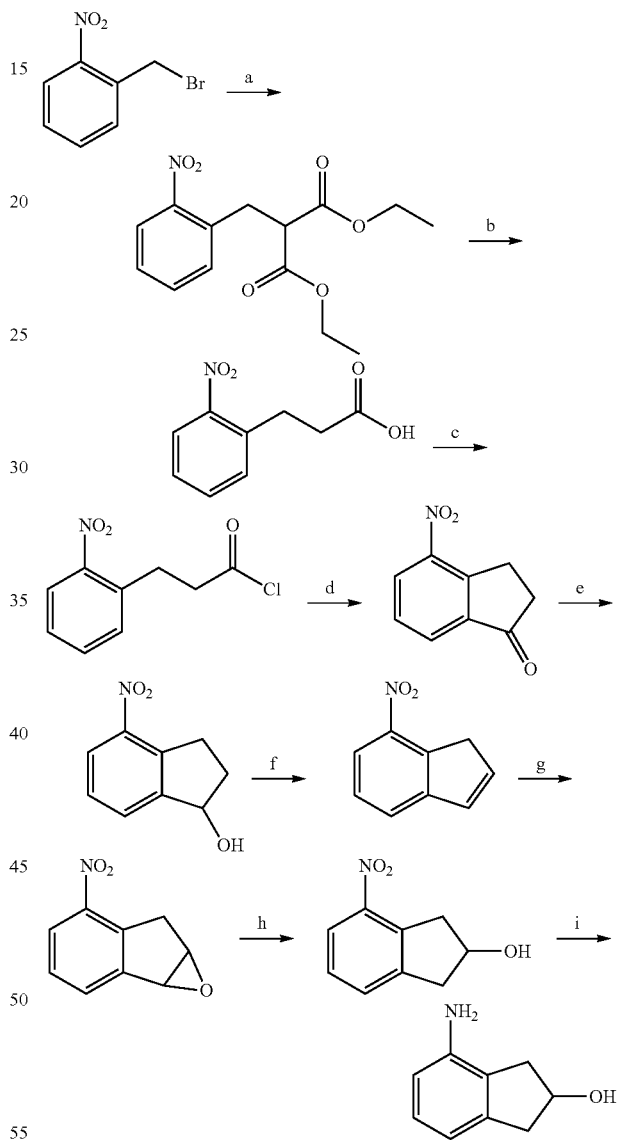

Step a: To a stirred solution of diethylmalonate (8.89 g, 0.055 mol) in dimethylformamide (50 mL), potassium carbonate (9.6 g, 0.069 mol) was added and it was stirred for 15 minutes in an inert atmosphere. 1-(bromomethyl)-2-nitrobenzene (10 g, 0.046 mol) in dimethylformamide (10 mL) was added to the reaction mixture. The reaction mixture was stirred at ambient temperature for 2 hours. TLC showed the total consumption of the starting material. The reaction mixture was diluted with water (600 mL) and the aqueous part was extracted with ethyl acetate (3×250 mL). The organic part was dried over anhydrous magnesium sulfate and concentrated under reduced pressure. The crude product was purified by column chromatography (silica gel: 100-200 mesh, eluent: 5% ethyl acetate in hexane) to afford the pure compound (8.7 g, 63% yield).

Step b: In a single necked round-bottomed flask (2 L), step-a product (8.7 g, 0.029 mol), hydrochloric acid (131 mL, 6N) and acetic acid (131 mL) were charged. The reaction mixture was refluxed for 48 hours. The progress of the reaction was checked by TLC. The reaction mixture was basified with sodium hydroxide (500 mL, 6M) and was extracted with ethyl acetate (3×250 mL). The organic part was dried over anhydrous magnesium sulfate and concentrated under reduced pressure. The crude product was purified by column chromatography (silica gel: 100-200 mesh, eluent: 40% ethyl acetate in hexane) to afford the pure compound (5.4 g, 94% yield).

Step c: In a single necked round-bottomed flask (100 mL), step-b product (5.8 g, 0.029 mol) was taken followed by dichloromethane (33 mL) and catalytic amount of dimethylformamide (0.1 mL). Thionyl chloride (2.2 mL) was added to it slowly. The reaction mixture was refluxed for 3 hours. The reaction mixture was concentrated under reduced pressure and thionyl chloride was removed by benzene (3×50 mL). The crude compound was directly taken for the next step without further purification (5.4 g).

Step d: In a single necked round-bottomed flask (100 mL), step-c product (5.4 g, 0.025 mol) was taken followed by carbon disulfide (30 mL). Anhydrous aluminium chloride (5.14 g, 0.038 mol) was added at 0° C. under stirring in an inert atmosphere. The reaction mixture was refluxed for 16 hours. Progress of the reaction was checked by TLC. The reaction mixture was diluted with cold water and then extracted with ethyl acetate (3×100 mL). The organic part was dried over anhydrous magnesium sulfate and concentrated under reduced pressure. The crude product was purified by column chromatography (silica gel: 100-200 mesh, eluent: 10% ethyl acetate in hexane) to afford the pure compound (2.1 g, 46% yield).

Step e: In a single necked round-bottomed flask step-d product (1.8 g, 0.01 mol) was taken followed by tetrahydrofuran (18 ml). Sodium borohydride (0.15 g, 0.004 mol) was added slowly under stirring followed by methanol (1.8 mL). The reaction mixture was stirred for 30 minutes at ambient temperature. Total consumption of the starting material was checked by TLC. The reaction mixture was concentrated under reduced pressure. The residue was diluted with water and extracted with 50% ethyl acetate in hexane (3×50 mL). The organic part was dried over anhydrous magnesium sulfate and concentrated under reduced pressure. The crude product was purified by column chromatography (silica gel: 100-200 mesh, eluent: 50% ethyl acetate in hexane) to afford the pure compound (1.8 g, 98% yield).

Step f: In a single necked round-bottomed flask, step-e product (1.8 g, 0.01 mol) was taken followed by benzene (40 mL). p-toluenesulfonic acid (0.19 g, 0.001 mol) was added to the reaction mixture under stirring. TLC showed the total consumption of the starting material. The reaction mixture was washed with saturated sodium bicarbonate (50 mL). The aqueous part was washed with 10% ethyl acetate in hexane (2×25 mL). The organic part was dried over anhydrous magnesium sulfate and was concentrated under reduced pressure. The crude product was purified by column chromatography (silica gel: 100-200 mesh, eluent: 5% ethyl acetate in hexane) to afford the pure compound (1.6 g, 99% yield).

Step g: In a single necked round-bottomed flask step-f product (1.6 g, 0.01 mol) was taken followed by dicloromethane (50 mL). m-chloroperoxybenzoic acid (4.23 g, 0.024 mol) was added slowly under stirring at 0° C. The reaction mixture was stirred for 6 hours at 0° C. temperature. Total consumption of the starting material was checked by TLC. The reaction mixture then diluted with 20% sodium carbonate (100 mL). Then the solution was extracted with dichloromethane (3×50 mL). The organic part was dried over anhydrous magnesium sulfate and concentrated under reduced pressure. The crude product was purified by column chromatography (silica gel: 100-200 mesh, eluent: 10% ethyl acetate in hexane) to afford the pure compound (1.7 g, 96% yield).

Step h: In a single necked round-bottomed flask (250 mL) step-g product (1.7 g, 0.0096 mol) was taken followed by dichloroethane (25 mL). Zinc iodide (4.51 g, 0.014 mol) and sodium cyanoborohydride (4.57 g, 0.073 mol) was added slowly under stirring at ambient temperature. The reaction mixture was refluxed for 1 hour. The consumption of the starting material was checked by TLC. The reaction mixture was cooled at 0° C. and then diluted with 2N HCl (200 mL) to quench the excess sodium cyanoborohydride. Then the solution was extracted with dichloromethane (3×50 mL). The organic part was dried over anhydrous magnesium sulfate and concentrated under reduced pressure. The crude product was purified by column chromatography (silica gel: 100-200 mesh, eluent: 20% ethyl acetate in hexane) to afford the pure compound (1.5 g, 87% yield).

Step i: In a Parr hydrogenetion bottle (500 mL) step-h product (1.5 g, 0.0084 mol) was taken followed by methanol (20 mL). Then palladium on charcoal (10% Pd, 150 mg) was added slowly under an inert atmosphere. The reaction mixture was hydrogenated in a Parr shaker apparatus for 2 hours at ambient temperature. Consumption of the starting material was checked by TLC. The catalyst was filtered over a celite bed and the filtrate was concentrated under reduced pressure. The crude product was purified by column chromatography (silica gel: 100-200 mesh, eluent: 20% ethyl acetate in hexane) to afford the title compound (1.0 g, 81% yield).

7.2 Synthesis of
8-amino-1,2,3,4-tetrahydronaphthalen-2-ol
(Employed for the Synthesis of Example Compound
No. 82)

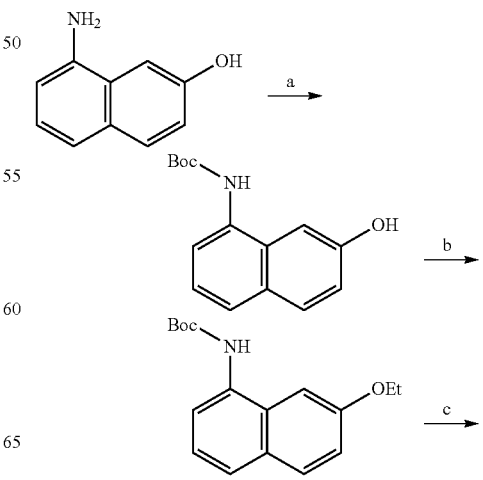

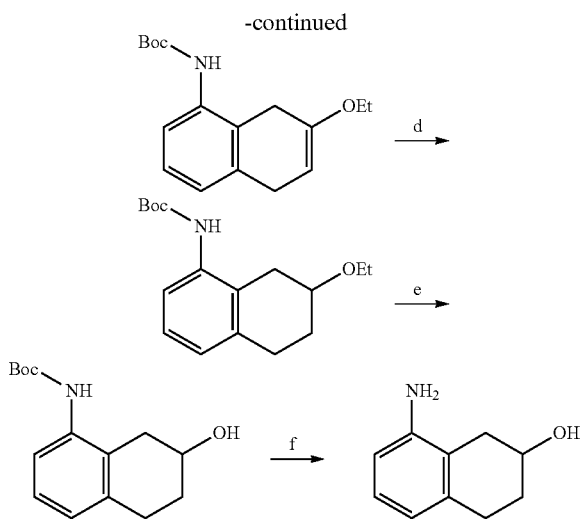

Step a: To a stirred solution of 8-amino-2-naphthol (40 g, 0.25 mol) in THF (800 ml, 20 times), Boc anhydride (54.8 g (57.7 ml), 0.25 mol, 1 eq) was added at rt. The overall reaction mass was heated to 70° C. and maintained for 24 hrs at the same temperature. Progress of the reaction was monitored by TLC (20% ethyl acetate/hexane, $R_f\sim 0.6$). On completion of the reaction, solvent was distilled off completely and the residue obtained was taken in ethyl acetate (200 ml). Organic layer was washed with saturated sodium carbonate solution (2×200 ml) followed by with water (2×200 ml), dried the contents over sodium sulfate and concentrated under reduced pressure. The crude obtained was taken in diisopropyl ether (150 ml), stirred for 15 min and filtered. Solid obtained was washed with diisopropyl ether again and dried to yield the required product as an off white solid (49 g, 75% yield).

Step b: To a solution of step-a product (30 g, 0.118 mol) in acetonitrile (240 ml, 8 times), cesium carbonate (71.7 g, 0.22 mol, 1.9 eq) was added and stirred for some time. Ethyl iodide (19.8 g (10.19 ml), 0.12 mol, 1.1 eq) was added and the overall reaction mixture was stirred for 1 hr at rt. Progress of the reaction was monitored by TLC (10% ethyl acetate/hexane, $R_f\sim 0.6$). On completion of the reaction, filtered the contents, washed with acetonitrile (2×50 ml) and distilled off the solvent. Residue obtained was diluted with ethyl acetate (200 ml) and washed with water 92×100 ml). Dried the contents over sodium sulfate and distilled off the solvent completely. The crude obtained was taken in diisopropyl ether (100 ml), stirred for 10-15 min and filtered. Solid obtained was washed with diisopropyl ether again and dried to yield the required product as an off white solid (23 g, 69% yield).

Step c: To a solution of step-c product (23 g, 0.08 mol) in THF (253 ml, 11 times), tert-butanol (5.93 g (7.54 ml), 0.08 mol, 2.9 eq) was added. Condensed ammonia solution (3.9 ltrs, 170 times) was added (Condensed with the help of ammonia cylinder at −78° C. for 2 hrs). Sodium metal (5.51 g, 0.23 mol, 2.99 eq) was added portion wise (Reaction mixture colour changed during the addition sodium White-Blue—Disappearance of color) at −78° C. The overall reaction mass was stirred for 1.5 hrs at −78° C. and allowed to stir at RT for overnight. Progress of the reaction was monitored by TLC (20% ethyl acetate/hexane, $R_f\sim 0.6$). On completion of the reaction, (Total ammonia disappeared), reaction contents were diluted with water (100 ml) and the extracted with ethyl acetate (2×100 ml). Combined extract was dried over sodium sulfate, concentrated under reduced pressure and the crude obtained was purified by column chromatography (silica gel, 8% ethyl acetate/hexane) to yield the required product as a white solid (12 g, 53% yield).

Step d: To a solution of step-c product (7.4 g, 0.025 mol) in THF (150 ml, 20 times), 2N HCl (37 ml, 5 times) was added at 0° C. and the overall reaction mixture was allowed to stir for 30 min at the same temperature. Progress of the reaction was monitored by TLC (20% ethyl acetate/hexane, $R_f\sim 0.2$). On completion of the reaction, ethyl acetate (300 ml) was added to the reaction mixture and the layers formed were separated out. Organic layer was washed with saturated NaHCO$_3$ solution (2×100 ml) followed by with water (2×100 ml). The contents obtained (6.6 g in THF+EtOAc) were directly used for the next step.

Step e: To a solution of step-d contents (6.6 g in 450 ml of THF+EtOAc mixture) in methanol (30 ml), sodiumboro hydride (0.77 g, 0.02 mol, 0.8 eq) was added at 0° C. The overall reaction mixture was allowed to stir for 30 min at 0° C. and the progress of the reaction was monitored by TLC (30% ethyl acetate/hexane, $R_f\sim 0.2$). On completion of the reaction, solvent was distilled off completely, residue obtained was diluted with ethyl acetate (200 ml) and washed with water (2×100 ml). Dried the contents over sodium sulfate, ethyl acetate distilled off under reduced pressure and the crude obtained was purified by column chromatography (silica gel, 20% ethyl acetate/hexane) to yield the required product as white colored solid (5.4 g, 80% yield over two steps).

Step f: Through a stirred solution of step-e product (7.5 g, 0.028 mol) in DCM (150 ml), HCl gas was passed for 30 min at 0° C. Progress of the reaction was monitored by TLC (50% ethyl acetate/hexane, $R_f\sim 0.1$). On completion of the reaction, DCM was distilled off completely and the residue obtained was dissolved in water (75 ml). Then the contents were neutralized with saturated NaHCO$_3$ solution at 0° C. and the compound extracted with ethyl acetate (5×75 ml). Combined extract was washed with water (2×100 ml), dried over sodium sulfate and concentrated under reduced pressure to yield the titled product as a white solid (4.3 g, 92% yield, mp 88-91° C.).

7.3 Synthesis of (S)-8-amino-1,2,3,4-tetrahydronaphthalen-2-ol (Employed for the Synthesis of Example Compound No. 214)

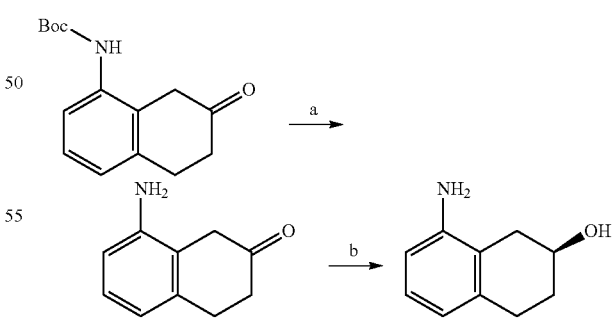

Step a: tert-butyl 7-oxo-5,6,7,8-tetrahydronaphthalen-1-ylcarbamate (5 g, 0019 mol) was dissolved in DCM (75 ml, 15 times) and cooled the contents to 0° C. HCl gas was passed through the reaction mixture for 45 min at 0° C. Progress of the reaction was monitored by TLC (10% ethyl acetate/hexane, $R_f\sim 0.2$). On completion of the reaction, poured the reaction contents into ice water (150 ml). Then the reaction contents were basified with sodium carbonate solution and extracted with ethyl acetate (5×75 ml). Combined extract was washed with water (2×100 ml), dried over sodium sulfate and concentrated under reduced pressure to obtain the crude product as a brown colored solid (2.8 g, crude).

Step b: Benzene ruthenium(II)chloride dimmer (0.17 g, 0.0008 mol, 0.02 eq), (1R,2S)-(+)-cis-1-Amino-2-indanol (0.207 g, 0.0013 mol, 0.08 eq) were taken in nitrogen bubbled IPA (50 ml). This solution was heated at 80° C. for 20 min and cooled back to RT. Step-a product (2.8 g, 0.017 mol) was taken in nitrogen bubbled IPA (78 ml), a solution of KOH (0.19 g, 0.0034 mol, 0.2 eq) in IPA (40 ml) and the earlier prepared ruthenium solution were added drop wise simultaneously at RT. The overall reaction mixture was heated to 50° C. and stirred for 30 min at the same temperature. Progress of the reaction was monitored by TLC (50% ethyl acetate/hexane, $R_f$~0.2). On completion of the reaction, cooled the reaction contents to rt, filtered on a silica gel bed and the bed was washed with ethyl acetate (2×30 ml). Filtrate was concentrated under reduced pressure, residue was taken in DCM (75 ml) and treated with charcoal. Filtered the contents over a silica gel bed and the bed washed with DCM (4×30 ml). DCM was distilled off completely and the crude obtained was purified by column chromatography (silica gel, 20% ethyl acetate/hexane) to yield the titled product as a red colored solid (1.8 g, 63% yield, mp 89-94° C.).

7.4 Synthesis of (R)-8-amino-1,2,3,4-tetrahydronaphthalen-2-ol (Employed for the Synthesis of Example Compound No. 215)

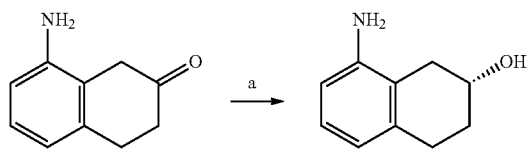

Step a: Benzene ruthenium(II)chloride dimmer (0.2 g, 0.0004 mol, 0.02 eq), (1S,2R)-(−)-cis-1-Amino-2-indanol (0.24 g, 0.0016 mol, 0.08 eq) were taken in nitrogen bubbled IPA (50 ml). This solution was heated at 80° C. for 20 min and cooled back to RT. 8-amino-3,4-dihydronaphthalen-2(1H)-one (3.3 g, 0.02 mol) was taken in nitrogen bubbled IPA (98 ml), a solution of KOH (0.23 g, 0.004 mol, 0.2 eq) in IPA (50 ml) and the earlier prepared ruthenium solution were added drop wise simultaneously at RT. The overall reaction mixture was heated to 45° C. and stirred for 30 min at the same temperature. Progress of the reaction was monitored by TLC (50% ethyl acetate/hexane, $R_f$~0.2). On completion of the reaction, cooled the reaction contents to rt, filtered on a silica gel bed and the bed was washed with ethyl acetate (4×30 ml). Filtrate was concentrated under reduced pressure, residue was taken in DCM (75 ml) and treated with charcoal. Filtered the contents over a silica gel bed and the bed washed with DCM (4×30 ml). DCM was distilled off completely and the crude obtained was purified by column chromatography (silica gel, 20% ethyl acetate/hexane) to yield the titled product as a brown colored solid (2.1 g, 63% yield, mp 58-87° C.).

8. Preparation of Selected Carbamate Phenyl Esters of General Formula (VIa) or (V) and Phenyl Esters of General Formula (IVa)

8.1 Synthesis of methyl 4-(phenoxycarbonylamino)-1H-indazole-1-carboxylate (Employed for the Synthesis of Example Compound No. 88, 122, 130, 147, 151, 152, 155, 167)

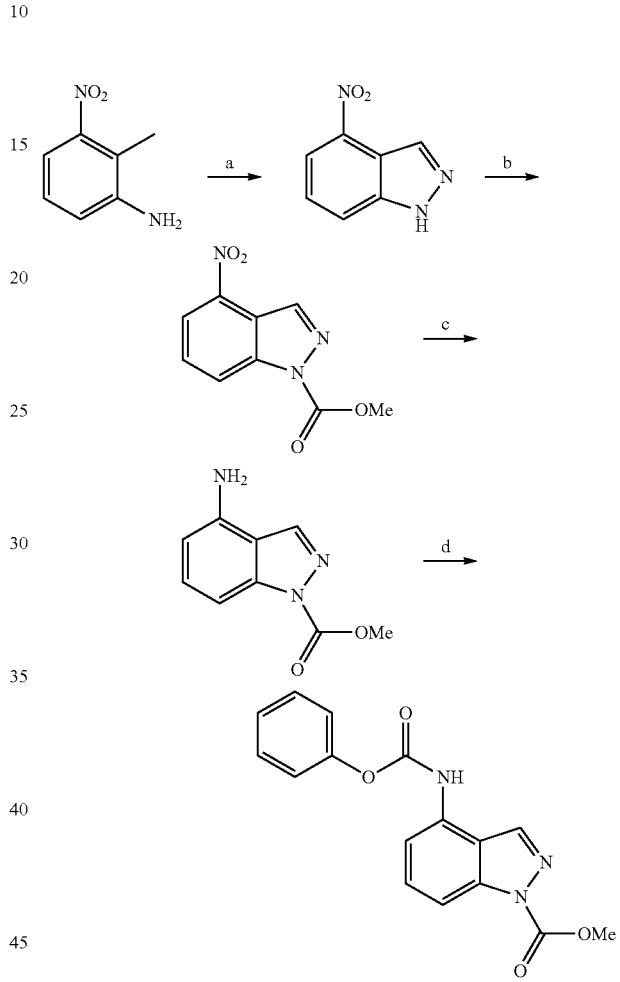

Step a: 2-methyl-3-nitro aniline (10 g, 0.005 mol) was taken in acetic acid (100 ml, 10 times) and cooled to 20° C. A solution of sodium nitrite (10 g, 0.14 mol, 2.25 eq) in water (25 ml) was added drop wise for 15 min at 20° C. The overall reaction mixture was stirred for 30 min at 20° C. and later stirred for 2 hrs at rt. Progress of the reaction was monitored by TLC (15% ethyl acetate/hexane, $R_f$~0.2). On completion of the reaction, acetic acid was distilled off completely and the residue obtained was taken in cold water (200 ml). Solid thrown out was filtered and dried to yield the required product as an yellow colored solid (8.5 g, 68% yield).

Step b: Step-a product (13 g, 0.079 mol) was added portion wise to a mixture of 60% NaH (3 g, 0.09 mol, 1.25 eq) in DMF (52 ml) at 0° C. and stirred the contents for 1 hr at rt. Reaction contents were again cooled to 0° C., methyl chloroformate (11.19 g, 0.115 mol, 1.5 eq) was added drop wise for 30 min and the overall reaction mass was stirred for another 30 min. Progress of the reaction was monitored by TLC (30% ethyl acetate/hexane, $R_f \sim 0.5$). On completion of the reaction, ice cold water (300 ml) was added to the reaction contents. Solid thrown out was filtered and dried to yield the required product as a pale yellow colored solid (13 g, 73% yield).

Step c: To a solution of step-b product (10 g, 0.045 mol) in methanol (150 ml, 15 times), 10% Pd/C (1 g, catalytic) was added. The reaction mixture was hydrogenated for 1.5 hrs at 40 psi. Progress of the reaction was monitored by TLC (30% ethyl acetate/hexane, $R_f \sim 0.1$). On completion of the reaction, filtered the reaction contents and washed with methanol (2×100 ml). Methanol was distilled off completely and the residue obtained was taken in ether. Solid thrown out was filtered and dried to yield the product as a brown colored solid (7.5 g, 86% yield).

Step d: To a stirred solution of stage-c product (5 g, 0.026 mol) in DMF (25 ml, 5 times), potassium carbonate (12.64 g, 0.09 mol, 3.5 eq) was added. Cooled the contents to 0° C., phenyl chloroformate (4.5 g (3.63 ml), 0.023 mol) was added drop wise and stirred the contents for 15-20 min. Progress of the reaction was monitored by TLC (50% ethyl acetate/hexane, $R_f \sim 0.5$). On completion of the reaction, filtered the contents and washed with ethyl acetate (100 ml). Filtrate was taken in cold water (150 ml), organic layer was separated and dried over sodium sulfate. The solvent removed under reduced pressure and the crude obtained was purified by column chromatography (silica gel, 20% ethyl acetate/hexane) to yield the titled product as a pale yellow colored solid (4.3 g, 53% yield, mp 142-144° C.).

8.2 Synthesis of ethyl 6-fluoro-4-(2-oxo-2-phenoxyethyl)-1H-indazole-1-carboxylate (Employed for the Synthesis of Example Compound No. 194 and 217)

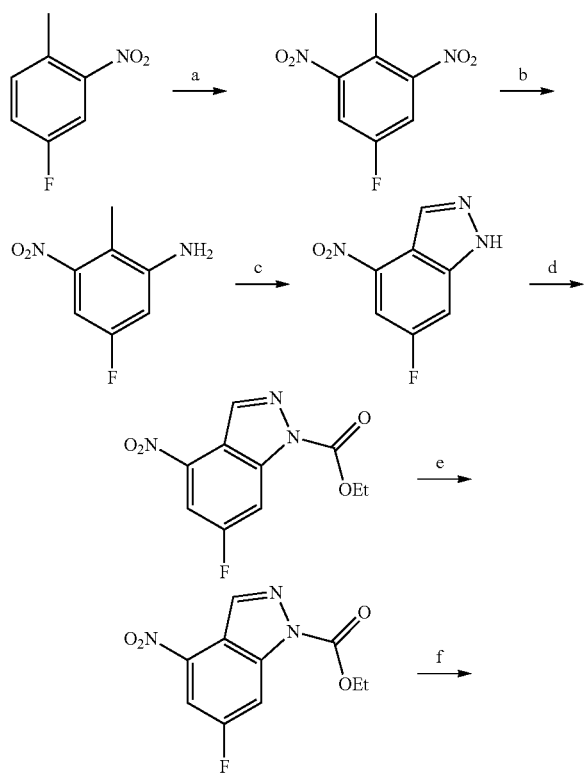

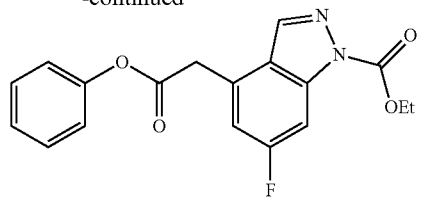

Step a: 4-fluoro-1-methyl-2-nitrobenzene (10 g, 0.64 mol) was dissolved in fuming sulphuric acid (35 mL) at 0° C. and a mixture of fuming sulphuric acid (17.4 mL) and fuming nitric acid (5.8 mL) was added to it drop wise at 0° C. over the period of 45 minutes. After complete addition, the reaction mixture was stirred for 3 hours at ambient temperature. TLC showed complete conversion of starting material to the product. The reaction mass was poured into ice and extracted with dichloromethane (3×100 mL). The combined organic layer was washed with water (200 mL) and brine (100 mL). It was dried over anhydrous magnesium sulfate and concentrated under reduced pressure to get the crude product, which was purified by column chromatography (silica gel: 100-200 mesh; eluent: 5% ethyl acetate in hexane) to afford the pure compound (yield: 4.5 g).

Step b: In a 500 mL single necked round bottom flask step-a product (7 g, 0.034 mol) was dissolved in ethanol (110 mL) and aqueous solution of sodium sulphide nonahydrate (14.16 g, 0.058 mol in 78 mL water) was added to it under 0-5° C. It was stirred for 2 hours at ambient temperature. After total consumption of starting material, ethanol was removed under reduced pressure and residue was diluted with water (300 mL). The aqueous part was extracted with ethyl acetate (3×300 mL). The combined organic layer was dried over anhydrous magnesium sulfate and concentrated under reduced pressure. The crude was purified by column chromatography using 20% ethyl acetate in hexane to afford 3 g pure compound.

Step c: In a 2 L round bottomed flask, step-b product (5 g, 0.029 mol) was dissolved in glacial acetic acid (750 mL). Aqueous sodium nitrite solution (2.27 g, 0.032 mol in 7.5 mL water) was added drop wise to the reaction mixture at ambient temperature. It was stirred for 24 hours. After total consumption of starting material acetic acid was removed under reduced pressure. The crude was dissolved in ethyl acetate and filtered through a plug of silica gel to afford 3.5 g compound.

Step d: Sodium hydride (1.15 g, 0.029 mol) was charged into a 250 mL two necked round bottom flask equipped with inert atmosphere. Dry DMF (20 mL) was added to it and it was cooled to 0° C. step-c product (3.5 g, 0.019 mol) was dissolved in dry DMF (15 mL) and was added to the suspension of sodium hydride in DMF drop wise at 0° C. The reaction mixture was allowed to stir for one hour at ambient temperature. After that ethyl chloroformate (3.14 g, 0.029 mol) was added to it at 0° C. It was stirred for 2 hours at ambient temperature. After total consumption of starting material the reaction mixture was quenched with cold water (150 mL) and extracted with 50% ethyl acetate in hexane. The combined organic layer was dried over anhydrous magnesium sulfate and concentrated under reduced pressure. The crude was purified by column chromatography (silica gel: 100-200; eluent: 10% ethyl acetate in hexane) to afford 4.5 g compound.

Step e: Step-d product (3.5 g, 0.014 mol) was dissolved in acetic acid (35 mL) and water (21 mL) was added to it followed by iron dust (3.09 g, 0.055 mol). The reaction mixture was warmed to 60° C. and stirred for 1-2 hours. After total consumption of starting material the reaction mixture was basified with sodium carbonate solution and it was filtered through a sintered funnel to remove the inorganic waste. After that the filtrate was extracted with ethyl acetate (3×100 mL). The combined organic layer was dried over anhydrous magnesium sulfate and solvent was removed under reduced pressure to afford pure compound (yield: 3.0 g).

Step f: Step-e product (4.0 g, 0.018 mol) was dissolved in tetrahydrofuran (91.5 mL) and calcium carbonate (3.6 g, 0.036 mol) was added to it under argon atmosphere. Phenyl chloroformate (3.37 g, 0.0215 mol) was dissolved in THF (22.8 mL) was added to it drop wise. The reaction mixture was allowed to stir for 3 hours at ambient temperature. After total consumption of starting material reaction mixture was filtered off and filtrate was concentrated under reduced pressure. After that it was diluted with water and extracted with ethyl acetate (3×100 mL). The combined organic layer was dried over anhydrous magnesium sulfate and solvent was removed under reduced pressure. The crude was purified by column chromatography (silica gel: 100-200; eluent: 20% ethyl acetate in hexane) to afford desired compound (yield: 4.5 g).

8.3 Synthesis of phenyl(3-tert-butyl-1-(3-chlorophenyl)-1H-pyrazol-5-yl)methylcarbamate (Employed for the Synthesis of Example Compound No. 78, 79, 80, 85, 98, 99, 100, 103, 104, 105, 106, 107, 108, 109, 111, 112, 113, 185, 187)

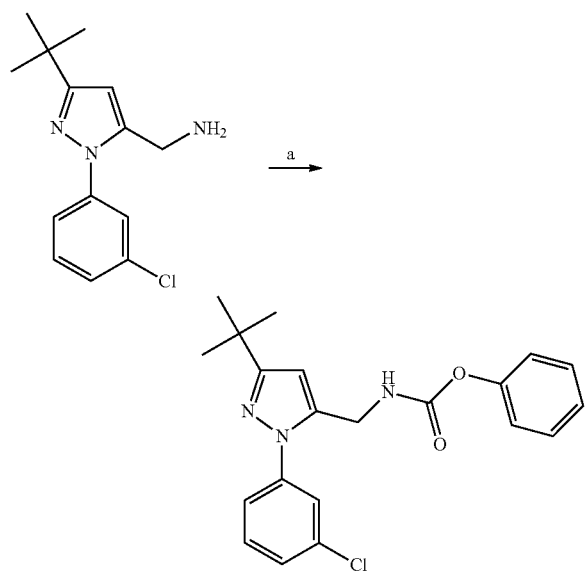

Step a: To a solution of (3-tert-butyl-1-(3-chlorophenyl)-1H-pyrazol-5-yl)methanamine (5 g, 0.018 mol) in DMF (25 ml, 5 times), potassium carbonate (9.16 g, 0.066 mol, 3.5 eq) was added and cooled the contents to 0° C. Then phenyl chloroformate (3.28 g (2.65 ml), 0.02 mol, 1.1 eq) was added drop wise for 15 min and the overall reaction mixture was stirred for another 15 min at 0° C. Progress of the reaction was monitored by TLC (20% ethyl acetate/hexane, $R_f$~0.3). On completion of the reaction, reaction contents were filtered, filtrate was diluted with cold water (100 ml) and the product extracted with ethyl acetate (3×25 ml). Combined organic layer was washed with brine solution (100 ml), dried over sodium sulfate and concentrated under reduced pressure. Crude obtained was purified by column chromatography (silica gel, 10% ethyl acetate/hexane) to yield the required product as a white solid (3.2 g, 45% yield).

9. Preparation of Additional Selected Pyrazol Derivatives According to General Formula (II)

9.1 Synthesis of (1-(3-chlorophenyl)-4-methyl-3-(trifluoromethyl)-1H-pyrazol-5-yl)methanamine (Employed for the Synthesis of Example Compounds No. 122 and 200)

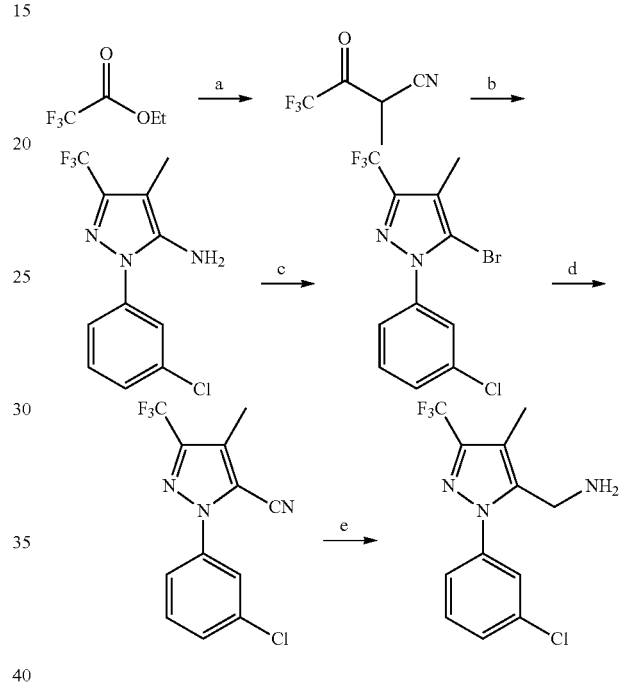

Step a: To a solution of diisopropylamine (40.8 g (57 ml), 0.404 mol, 2.3 eq) in THF (400 ml), n-BuLi (1.6 molar) (24.7 g (258.3 ml, 0.38 mol, 2.2 eq) was added drop wise for 2 hrs at −20° C. and stirred the contents for 30-45 min at 0° C. Cooled the contents to −75° C., a solution of ethyl 2,2,2-trifluoroacetate (25 g, 0.17 mol) in THF (200 ml) was added drop wise for 2 hrs. The reaction mixture was stirred initially for 1 hr at −75° C. and later for another 1 hr at rt. Progress of the reaction was monitored by TLC (50% ethyl acetate/hexane, $R_f$~0.5). On completion of the reaction, quenched the reaction with ice water (700 ml) and the solvents were distilled off completely. Residue washed with DCM (3×300 ml), acidified the contents with 30% HCl solution and the product extracted with ether (3×400 ml). Combined organic layer was dried over sodium sulfate, concentrated under reduced pressure and the crude obtained was distilled under vacuum to yield the product at 35° C./0.1 mm as a colorless liquid (17 g, 64% yield).

Step b: A step-a product (10 g, 0.066 mol) was taken in ethanolic HCl (300 ml, 30 times) and 3-chlorophenyl hydrazine (9.43 g, 0.066 mol, 1 eq) was added. The reaction mixture was heated to reflux for 2 hrs. Progress of the reaction was monitored by TLC (20% ethyl acetate/hexane, $R_f$~0.3). On completion of the reaction, reaction contents were concentrated and the residue taken in water (200 ml). Basified the contents to a pH~12 with 1N NaOH solution and filtered the contents. Solid obtained was taken in ethyl acetate (200 ml), dried the contents over sodium sulfate and concentrated under reduced pressure to yield the required product as a red colored solid (12 g, 65% yield).

Step c: Cupric bromide (11.33 g, 0.0511 mol, 1.2 eq) was taken in acetonitrile (176 ml) and heated to 150° C. Then n-butyl nitrite (6.59 g (7.47 ml), 0.063 mol, 1.5 eq) was added followed by a solution of step-b product (11.75 g, 0.042 mol) in acetonitrile (176 ml) was added drop wise for 30 min at 150° C. and stirred for 15 min. Progress of the reaction was monitored by TLC (5% ethyl acetate/hexane, Rf~0.7). On completion of the reaction, acetonitrile was distilled off, residue was taken in ice cold water (300 ml) and the product extracted with ethyl acetate (5×100 ml). Combined extract was dried over sodium sulfate, concentrated under reduced pressure and the crude obtained was subjected to column chromatography (silica gel, pure hexane). Pure product was not isolated and a mixture was obtained as a red colored liquid (16 g, crude) and the same product used for the next step.

Step d: To a solution of step-c product (13 g, 0.038 mol) in NMP (130 ml, 10 times), copper cyanide (6.8 g, 0.076 mol, 2 eq), sodium iodide (100 mg, catalytic) were added. The reaction mixture was placed in a pre-heated oil bath at 180° C. and allowed to stir for 8 hr. Progress of the reaction was monitored by TLC (5% ethyl acetate/hexane, $R_f$~0.4). On completion of the reaction, diluted the reaction contents with water (200 ml) and the product extracted with ethyl acetate (5×100 ml). Combined extract was washed with cold water (5×50 ml), dried over sodium sulfate and concentrated under reduced pressure. The crude obtained was purified by column chromatography (silica gel, 2% ethyl acetate/hexane) to yield the required product as a pale yellow colored solid (8 g).

Step e: To a solution of step-d product (5 g, 0.017 mol) in dry THF (30 ml, 6 times), Boran-THF in THF (70 ml) was added drop wise for 30 min at 0-5° C. Reaction mixture was slowly heated to 50° C. and allowed to stir for 12 hrs. Progress of the reaction was monitored by TLC (75% ethyl acetate/hexane, $R_f$~0.2). On completion of the reaction, acidified the contents to 0-5° C. with conc.HCl at 0° C. and stirred the contents for 2 hrs at rt. Then basified the contents to a pH~12 with 10% NaOH solution and the product extracted with ethyl acetate (5×50 ml). Combined extract was dried over sodium sulfate and concentrated under reduced pressure. Solid obtained was washed with 10% ether/hexane and dried to yield the required product as a white colored solid (3 g, 59% yield, mp 82-86° C.).

9.2 Synthesis of (1-(3-chlorophenyl)-3-cyclopropyl-1H-pyrazol-5-yl)methanamine (Employed for the Synthesis of Example Compound No. 183)

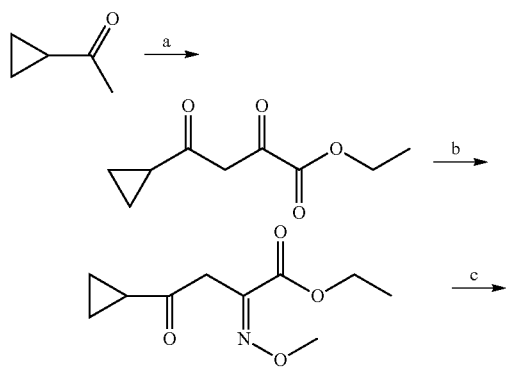

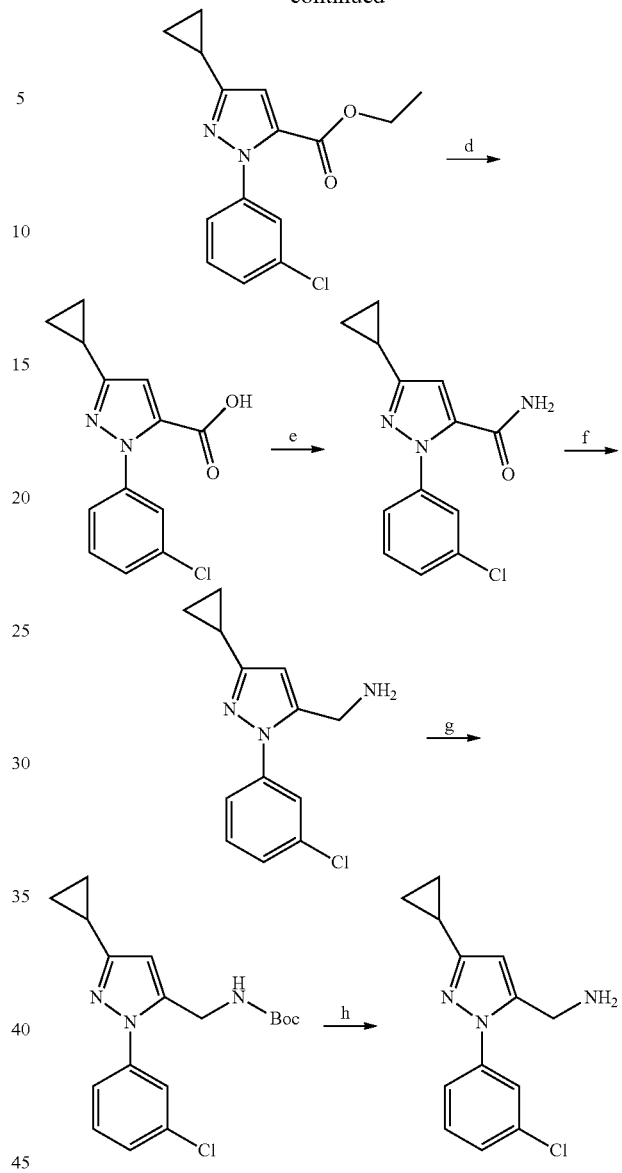

Step a: Sodium metal was dissolved into a solution of EtOH (150 ml) at RT under nitrogen atmosphere to form NaOEt (16.19 gm). This mixture was cooled to 0° C. Diethyl oxalate (34.76 gm) and isopropyl methyl ketone (20 gm) was added drop wise for about 15 min and warmed to RT. Now EtOH (100 ml) was added and stirred at RT for about 1 hour. Heat this reaction mixture to 80° C. for about 45 minuets and cooled to RT and concentrated under reduced pressure. To this resulting solid, add EtOAC. Wash with EtOH and filtered on cloth to get fine smooth powder. This solid is dissolved in water and acidified with dilute Sulphuric acid (pH-2). This compound is extracted with diethyl ether and dried over sodium sulphate and was concentrated under reduced pressure to obtain the brown colored liquid compound (40 g, 93% yield).

Step b: To a solution of step-a product (40 g) taken in ethanol (200 ml, 5 times), molecular sieves (40 g) was added at RT and stirred under nitrogen atmosphere for few minutes. keto ester was added at RT under nitrogen atmosphere and stirred the reaction for 12 hrs at RT. Progress of the reaction was monitored by TLC (10% ethyl acetate/hexane). On completion of the reaction, filtered the reaction contents with EtOH or MeOH and the filtrate was distilled under reduced pressure. Residue obtained was dissolved in water (100 ml) and extracted with ethyl acetate (300 ml). Combined extract was dried over sodium sulfate and distilled under reduced pressure to obtain the crude product as brownish liquid (40 g). The crude obtained was used for the next step directly.

Step c: To a stirred solution of step-b compound (40 g, 0.18 mol) in a 1:1 mixture of acetic acid and ethanol (400 ml, 10 times) was dissolved at RT. To this reaction mixture 3-chlorophenylhydrazine (32.07 g, 1.2 eq) was added and stirred for about 10 minutes. The overall reaction was heated and reflux for 24 hrs. Progress of the reaction was monitored by TLC (10% ethyl acetate/hexane, 30% ethyl acetate/hexane). On completion of the reaction, Acetic acid and ethanol was distilled off under reduced pressure. Obtained crude was added to water (200 ml) and the extract was added to EtOAc (350 ml) to get separate layers. The organic layer obtained was dried over sodium sulfate and concentrated under reduced pressure. The crude compound brown colored liquid was obtained (33 g).

Step d: To a stirred solution of step-c product (16 g, 0.055 mol) in methanol (160 ml, 10 times), a solution of NaOH (6.6 g, 0.165 mol, 3 eq) in water (32 ml, 2 times) was added. The overall reaction was stirred for 5 minutes at RT. Progress of the reaction was monitored by TLC (50% ethyl acetate/hexane). On completion of the reaction, methanol and water were distilled off under reduced pressure. Add water (100 ml) to this compound and neutralize it with dilute with HCl (pH~4). Then the contents were extracted with DCM (250 ml) and the layers were separated. The Combined DCM was dried over sodium sulfate and distilled under reduced pressure. The crude was obtained as white colored solid (13.5 g, 93.36% yield).

Step e: To a stirred solution of step-d product (11.5 g), DCM (115 ml, 10 times) was added. The overall reaction was cooled to 0-5° C. At 0-5° C., $SOCl_2$ (3.8 L, 1.2 eq) was added by dropping funnel for about 10 min. The overall reaction was stirred for 3 hrs at RT. Progress of the reaction was monitored by TLC (50% ethyl acetate/hexane). On completion of the reaction, DCM and $SOCl_2$ were distilled off under reduced pressure. Again add DCM to this compound and stirred at RT. Then this solution was added drop wise to the solution of $NH_3$ in DCM and maintained at 0-5° C. for 15 min and leave the reaction to get RT. This reaction mixture was stirred for overnight and the progress of the reaction was monitored by TLC (50% ethyl acetate/hexane). On completion of the reaction, DCM was distilled off under reduced pressure. Again add DCM (200 ml) and washed with cooled water (200 ml). and the layers were separated. The combined DCM layer was dried over sodium sulfate and distilled under reduced pressure. The crude compound was obtained as white colored solid (11.0 g, 96% yield).

Step f: To a stirred solution of step-e product (11 g), amide and THF (110 ml, 10 times) was added. This reaction mixture was dried at RT and cooled to 0-5° C. $BH_3$.DMS (189.14 ml) and THF (14.37 gm, 4.5 eq) were added carefully drop wise by dropping funnel for about 1 hr. The overall reaction mass was maintained and reflux for about 24 hrs. The progress of the reaction was monitored by TLC (50% ethyl acetate/hexane). On completion of the reaction, mixture was cooled to 0° C. and quenched with diluted HCl (5M) and keep the reaction mixture undisturbed at RT for about 12 hrs. This compound was basidified with NaOH solution to Ph~10. Then the contents were extracted with IPA/$CHCl_3$ and the layers were separated. The organic layer was dried over sodium sulfate and distilled under reduced pressure. The crude obtained is a brownish colored solid (11.4 g).

Step g: To a stirred solution of step-f product (11.4 g), DCM (114 ml, 10 times), was added at RT and stirred for about 10 min. This reaction mixture was cooled to 0-5° C. in ice cold water. BOC-anhydride was added drop wise to the reaction mixture for about 15 min. Progress of the reaction was monitored by TLC (10% ethyl acetate/hexane/50% ethyl acetate/hexane). On completion of the reaction, added water (50 ml) and stirred the layer were separated. The organic layer was washed with water and the layer were separated. The organic layer was dried over sodium sulfate and distilled of under reduced pressure. The compound was obtained white colored solid (6.5 g, 40.6% yield).

Step h: To a stirred solution of Boc-compound (9.0 g), DCM (100 ml) was added at RT and stirred for about 10 min. This reaction mixture was cooled to 0-5° C. and pass the HCl gas for about 20-30 min. Progress of the reaction was monitored by TLC (10% ethyl acetate/hexane/50% ethyl acetate/hexane). On completion of the reaction, distill off DCM. Add water (100 ml) then extract the compound with 20% IPA/$CHCl_3$ and the layer were separated. The organic layer was distilled off under reduced pressure and dried under high vacuum. The crude was obtained by washing with heptane and drying under high vacuum. The compound was obtained light yellow colored viscous liquid (0.5 g, 78% yield).

9.3 Synthesis of (3-tert-butyl-1-(pyridin-2-yl)-1H-pyrazol-5-yl)methanamine (Employed for the Synthesis of Example Compound No. 216)

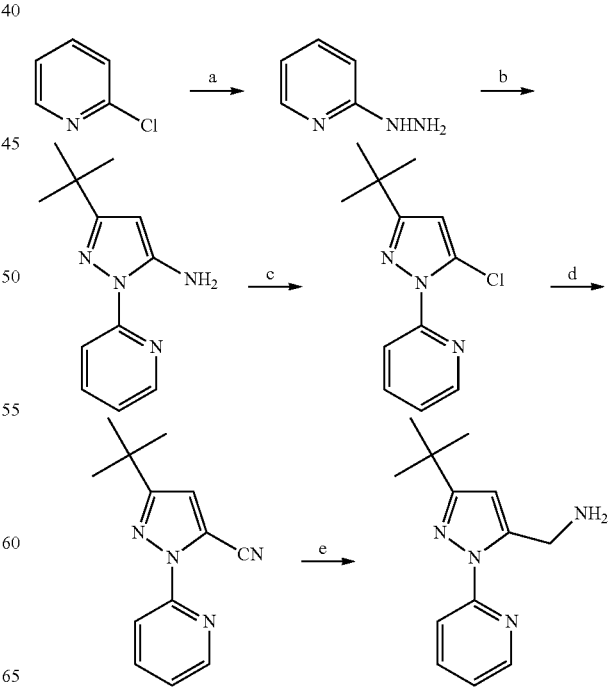

Step a: To a solution of 2-chloropyridine (20 g, 0.17 mol) in ethanol (100 ml, 5 times), hydrazine hydrate (132 ml, 6.6 times) was added and the reaction mixture was heated to reflux for 15 hrs. Progress of the reaction was monitored by TLC (40% ethyl acetate/hexane, Rf~0.1). As the reaction not completed, continued to reflux for another 15 hrs and monitored by TLC. On completion of the reaction, ethanolic hydrazine hydrochloride was distilled off completely at 100° C., residue was taken in DCM (500 ml) and washed the contents with saturated sodium carbonate solution (100 ml). Combined organic layer was dried over sodium sulfate and concentrated under reduced pressure to obtain the crude product as a low melting solid (11 g, crude). The crude obtained was directly used for the next step.

Step b: To a stirred solution of step-a product (11 g, crude) in ethanol (110 ml, 10 times), 4,4-dimethyl-3-oxopentanenitrile (11.3 g, 0.09 mol, 0.9 eq) was added portion wise followed by catalytic amount of HCl. The reaction mixture was heated to 100° C. and refluxed for 6 hrs. Progress of the reaction was monitored by TLC (20% ethyl acetate/hexane, Rf~0.7). On completion of the reaction, ethanol was distilled off, residue was taken in water (200 ml) and the product extracted with ethyl acetate (2×100 ml). Combined extract was dried over sodium sulfate, concentrated under reduced pressure and the crude obtained was purified by column chromatography (silica gel, 10% ethyl acetate/hexane) to yield the required product as an off white solid (18 g).

Step c: To a solution of step-b product (4 g, 0.01 mol) in acetonitrile (80 ml), cupric chloride (12.3 g, 0.09 mol, 5 eq) was added. A solution of tert-butyl nitrite (2.8 (3.3 ml), 0.023 mol, 1.5 eq) in acetonitrile (40 ml (total 120 ml, 30 times)) was added drop wise for 10 min and the overall reaction mass was stirred for 5 hrs at rt. Progress of the reaction was monitored by TLC (10% ethyl acetate/hexane, Rf~0.3). On completion of the reaction, acetonitrile was distilled off, residue was taken in water (100 ml) and the product extracted with ethyl acetate (2×200 ml). Combined extract was dried over sodium sulfate, concentrated under reduced pressure and the crude was purified by column chromatography (silica gel, 4% ethyl acetate/hexane) to yield the required product as a pale yellow colored liquid (2.1 g, 48% yield).

Step d: To a stirred solution of step-c product (2.1 g, 0.008 mol) in NMP (21 ml, 1 time), copper cyanide (1.56 g, 0.017 mol, 2 eq) was added portion wise followed by a catalytic amount of sodium iodide was added. The reaction mixture was heated to 180° C. and maintained at that temperature for 4 hrs. Progress of the reaction was monitored by TLC (10% ethyl acetate/hexane, Rf~0.5). On completion of the reaction, diluted the reaction contents with ethyl acetate, filtered the contents through celite bed and the filtrate washed with cold water (50 ml). Organic layer was dried over sodium sulfate, concentrated under reduced pressure and the crude was purified by column chromatography (silica gel, 6-8% ethyl acetate/hexane) to yield the required product as an off white solid (0.8 g, 40% yield).

Step e: To a solution of step-d product (1.5 g, 0.006 mol) in methanol (20 ml), catalytic amount of raney nickel. The reaction mixture was hydrogenated for 1 hr at 60 psi. Progress of the reaction was monitored by TLC (15% ethyl acetate/hexane, Rf~0.1). On disappearance of the starting material, filtered the contents on celite bed and washed with methanol. To the filtrate was purified by column chromatography (silica gel, 6% ethyl acetate/hexane) to yield the titled product as a cream colored oil (1.4 g, 97% yield).

9.4 Synthesis of 5-(aminomethyl)-3-tert-butyl-N-(2,2,2-trifluoroethyl)-1H-pyrazol-1-amine (Employed for the Synthesis of Example Compound No. 201)

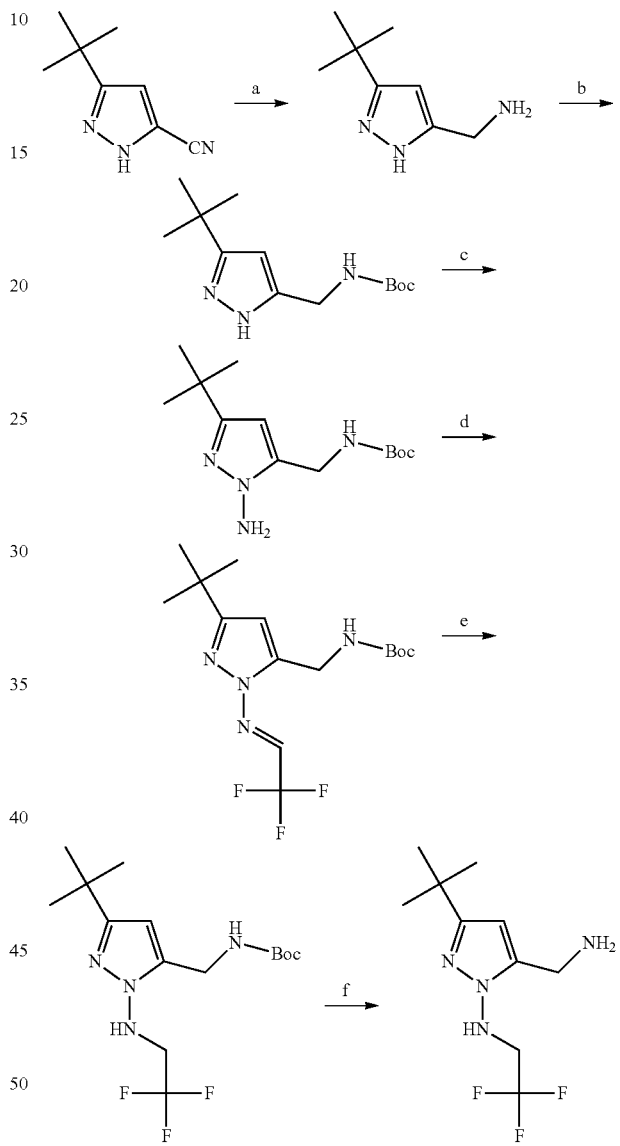

Step a: To a solution of tert-butyl-1H-pyrazole-5-carbonitrile (5 g, 0.033 mol) in methanol (100 ml, 20 times), Raney nickel (5 g, 1 times) was added and the reaction mixture was hydrogenated for 1-2 hrs 70 psi. Progress of the reaction was monitored by TLC (40% ethyl acetate/hexane, R$_f$~0.1). On completion of the reaction, filtered the reaction contents and the bed was washed with methanol (100 ml). Methanol was distilled off completely and the crude obtained as a pale yellow colored liquid (5 g., crude) was directly used for the next step.

Step b: To a stirred solution of step-a product (5 g, crude) in methanol (50 ml, 10 times), sodium carbonate (5.1 g, 0.04 mol, 1.5 eq) was added and stirred for 15 min. Cooled the contents to 0° C., Boc anhydride (6.97 g, 1.1 eq) was added drop wise for 10 min and the overall reaction mixture was stirred for 30 min at 0° C. Progress of the reaction was monitored by TLC (50% ethyl acetate/hexane, Rf~0.3). On completion of the reaction, methanol was distilled off completely, residue was taken in water (100 ml) and the product extracted with ethyl acetate (2×100 ml). Combined extract was dried over sodium sulfate, concentrated under reduced pressure and the crude was recrystalised from hexane to yield the required product as a white solid (4.5 g).

Step c: To a stirred solution of step-b product (5 g, 0.019 mol) in DMF (50 ml, 10 times), sodium hydroxide (7.9 g, 0.19 mol, 10 eq) was added. Cooled the contents to 0° C., Hydroxylamine-o-sulfonic acid (6.4 g, 0.057 mol, 3 eq) was added portion wise for 30 min and the reaction mixture was stirred for 2 hrs at 0° C. Progress of the reaction was monitored by TLC (30% ethyl acetate/hexane, Rf~0.4). On completion of the reaction, poured the reaction contents into crushed ice (200 g) and filtered the contents. Solid obtained was taken in hexane (100 ml), filtered and dried to yield the required product as a white solid (4 g, 75% yield).

Step d: To a stirred solution of step-c product (2 g, 0.001 mol) in ethanol (20 ml, 10 times), ether containing trifluoroacetaldehyde (1.41 g in 50 ml (0.014 mol, 2 eq)) was added. The reaction mixture was stirred for 12 hrs at rt. Progress of the reaction was monitored by TLC (10% ethyl acetate/hexane, R$_f$~0.7). On completion of the reaction, ethanol was distilled off completely and the crude obtained was purified by column chromatography (silica gel, hexane) to yield the required product as a white solid (2 g, 77% yield).

Step e: To a stirred solution of step-d product (1.7 g, 0.0048 mol) in methanol (170 ml), 10% Pd/C (0.5 g, catalytic) was added. The reaction mixture was stirred for 12 hrs under Hydrogen balloon pressure. Progress of the reaction was monitored by TLC (10% ethyl acetate/hexane, R$_f$~0.3). On completion of the reaction, filtered the contents over celite bed and the bed washed with methanol. Methanol distilled off from the filtrate and the crude obtained was purified by column chromatography (basic alumina, hexane) to yield the titled product as a white solid (1.02 g, 50% yield, mp 80-83° C.).

Step f: To a stirred solution of Boc-compound step e product (1.0 g), DCM (20 ml) was added at RT and stirred for about 20 min. This reaction mixture was cooled to 0-5° C. and pass the HCl gas for about 30 min. Progress of the reaction was monitored by TLC (10% ethyl acetate/hexane/50% ethyl acetate/hexane). On completion of the reaction, distill off DCM. Add water (20 ml) then extract the compound with 20% IPA/CHCl$_3$ and the layer were separated. The organic layer was distilled off under reduced pressure and dried under high vacuum. The crude was obtained by washing with heptane and drying under high vacuum. The compound was obtained light yellow colored viscous liquid (0.65 g, 91% yield).

9.5 Synthesis of (1-(4-methoxybenzyl)-3-(trifluoromethyl)-1H-pyrazol-5-yl)methanamine (Employed for the Synthesis of Example Compound No. 202)

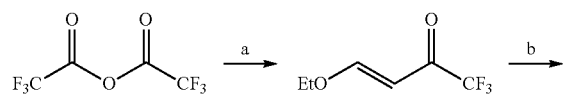

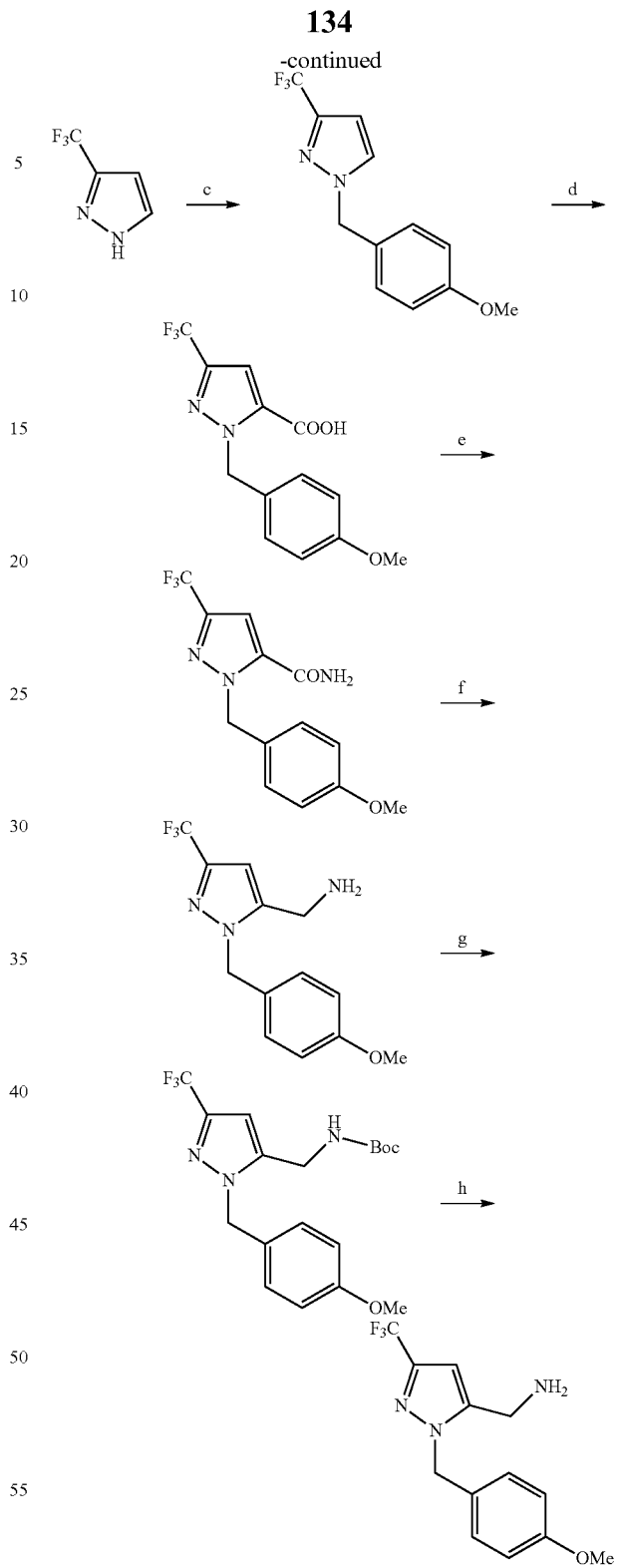

Step a: DMAP (4.25 g, 0.034 mol, 0.01 eq) was added to DCM (3 ltrs) and cooled the contents to −10° C. Trifluoroacetic anhydride (765 g (510 ml), 3.2 mol, 1.05 eq) was added followed by ethyl vinyl ether (250 g, 3.04 mol) was added drop wise for 45 min at −10° C. Then the overall reaction mixture was initially stirred for 8 hrs at 0° C. and later for overnight at RT. Progress of the reaction was monitored by TLC (10% ethyl acetate/hexane, Rf~0.7). On completion of the reaction, reaction contents were quenched with saturated NaHCO₃ solution (600 ml) and organic layer was separated. Aqueous layer was extracted with DCM (2×500 ml). Combined organic layer was washed with water (2×1 ltr), dried over sodium sulfate and concentrated under reduced pressure to obtain the crude product as a brown colored liquid (450 g, crude).

Step b: Hydrazine dihydrochloride (225 g, 2.14 mol, 1.6 eq) was taken in ethanol (1400 ml) and stirred well. TEA (135.4 g (185.4 ml), 1.34 mol, 1 eq) was added drop wise for 45 min at RT. Then step-a product (225 g, crude) was added drop wise at RT and the overall reaction mixture was refluxed for overnight. Progress of the reaction was monitored by TLC (20% ethyl acetate/hexane, R$_f$~0.4). On completion of the reaction, ethanol was distilled off completely, residue was taken in ice water (500 ml) and the product extracted with ethyl acetate (2×400 ml). Combined extract was washed with ice water (300 ml), dried over sodium sulfate and concentrated under reduced pressure to yield the required product as and off white solid (195 g).

Step c: NaH (33.08 g (19.85, 60%), 1.5 eq) was added to small quantity of hexane and stirred well for 10 min. Hexane was decanted, dry DMF (500 ml) was added drop wise under N₂ atmosphere and stirred well. A solution of step-b product (75 g, 0.55 mol) in DMF (125 ml) was added drop wise under N₂ atmosphere. Then a solution of 4-methoxybenzoyl chloride (86.3 g, 0.55 mol, 1 eq) in DMF (125 ml) was added drop wise and the overall reaction mixture was allowed to stir for 12 hrs at RT. Progress of the reaction was monitored by TLC (10% ethyl acetate/hexane, Rf~0.4). On completion of the reaction, reaction contents were poured into ice water (500 ml) and the product extracted with ethyl acetate (2×400 ml). Then the contents were dried over sodium sulfate and concentrated under reduced pressure to yield the required product as a brown colored liquid (125 g, 88% yield).

Step d: Diisopropyl amine (28.4 (39.4 ml), 1.2 eq) was taken in THF (500 ml), stirred well and cooled the contents to 0° C. n-BuLi (234.4 ml, 1.5 eq) was added drop wise at 0° C. and cooled the contents to −78° C. A solution of step-c product (62 g, 0.24 mol) in THF (200 ml) was added drop wise for 30 min and stirred the contents for another 30 min at −78° C. Then dry CO₂ gas was bubbled through the reaction mixture for 1.5 hrs and the progress of the reaction was monitored by TLC (10% ethyl acetate/hexane, R$_f$~0.1). On completion of the reaction, reaction contents were poured into ice water (300 ml) and the aqueous layer was extracted with ethyl acetate (2×200 ml) in basic condition. Aqueous layer was acidified with 20% HCl solution and extracted with ethyl acetate (2×200 ml). Combined organic layer was dried over sodium sulfate and concentrated under reduced pressure to yield the required product as an off white solid (42 g, 58% yield).

Step e: To a solution of step-d product (50 g, 0.16 mol) in DCM (750 ml, 15 times), catalytic amount of DMF was added and cooled to 0° C. Thionyl chloride (99.3 g (61 ml), 0.83 mol, 5 eq) was added drop wise for 30 min at 0° C. Overall reaction mixture was slowly heated to a reflux temperature and allowed to reflux for 2 hrs. Progress of the reaction was monitored by TLC (10% ethyl acetate/hexane, R$_f$~0.4). On disappearance of the starting material, DCM was distilled off completely. Above prepared acid chloride was dissolved in DCM (500 ml) and added drop wise to aqueous ammonia solution (600-700 ml) at 0° C. Overall reaction mixture was allowed to stir for 1 hr and the progress of the reaction was monitored by TLC (10% ethyl acetate/hexane, Rf~0.7). On completion of the reaction, ice cold water (200 ml) was added and the product extracted with ethyl acetate (2×200 ml). Combined organic layer was dried over sodium sulfate and concentrated under reduced pressure to yield the required product as an off white solid (37 g, crude). Crude obtained was directly used for the next step.

Step f: LAH (4.7 g, 0.12 mol, 1 eq) was added to small quantity of hexane and stirred well for 10 min. Hexane was decanted and THF (250 ml) was added to LAH under cold condition. Then a solution of step-e product (37 g, 0.12 mol) in THF (120 ml) was added drop wise for 30 min at 0° C. and reaction mixture was heated to reflux for 5 hrs. Progress of the reaction was monitored by TLC (50% ethyl acetate/hexane, R$_f$~0.2). As the reaction moved completely, LAH (2.3 g) was added and refluxed for another 4 hrs. This time reaction was moved completely. Then the reaction contents were slowly added to saturated solution of sodium sulfate (1 ltr) and the product extracted with ethyl acetate (2×500 ml). Combined extract was dried over sodium sulfate and concentrated under reduced pressure to obtain the crude product as an off white solid (32.5 g). Crude obtained was directly used for the next step.

Step g: To a solution of step-f product ((80 g, 0.28 mol) in DCM (600 ml) cooled at 0° C., TEA (22.7 g (30.2 ml), 0.026 mol, 0.8 eq) was added drop wise for 10 min. Then Boc anhydride (61.2 g (62.5 ml), 0.28 mol, 1 eq) taken in DCM (200 ml) was added drop wise for 20-30 min at 0° C. Overall reaction mixture initially stirred for 30 min at 0° C. and alter for another 30 min at RT. Progress of the reaction was monitored by the TLC (20% ethyl acetate/hexane, R$_f$~0.6). On completion of the reaction, DCM was distilled off completely, residue was taken in ice water (500 ml) and the product extracted with ethyl acetate (2×300 ml). Combined extract was dried over sodium sulfate and concentrated under reduced pressure. Crude obtained was recrystalised from hexane (200 ml) to yield the required product as an off white solid (80 g, 74% yield).

Step h: Step-g (5 g, 0.012 mol) product was taken in DCM (30 ml, 6 times) and cooled to 0° C. HCl gas was bubbled through the reaction mixture for 45 min at 0° C. Progress of the reaction was monitored by TLC (30% ethyl acetate/hexane, R$_f$~0.2). On completion of the reaction, DCM was distilled off completely. Residue was taken in ice water (200 ml) and the product extracted with 20% ethyl acetate/hexane (2×100 ml). Aqueous layer was basified to a pH~10 with 2N NaOH solution and extracted with ethyl acetate (5×100 ml). Combined organic layer was washed with water (2×200 ml), dried over sodium sulfate and concentrated under reduced pressure to yield the required product as an yellow colored liquid (2.4 g, 64% yield).

9.6 Synthesis of N-(5-(aminomethyl)-3-(trifluoromethyl)-1H-pyrazol-1-yl)benzamide (Employed for the Synthesis of Example Compound No. 217)

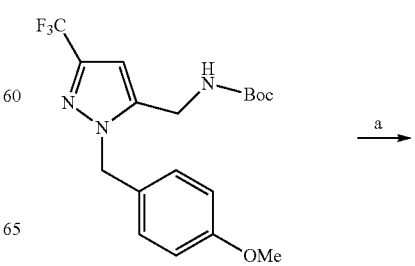

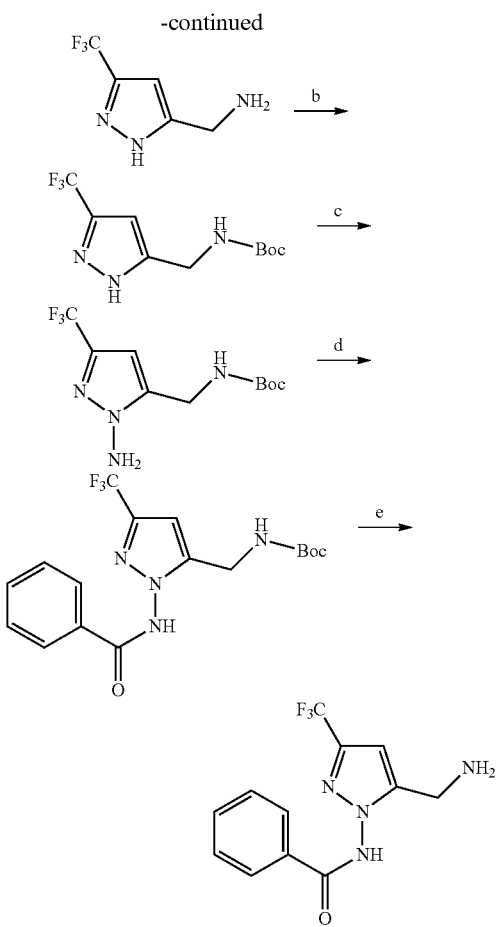

Step a: To a stirred solution of tert-butyl(1-(4-methoxybenzyl)-3-(trifluoromethyl)-1H-pyrazol-5-yl)methylcarbamate (20 g, 0.052 mol) in toluene (300 ml, 15 times) cooled at 0° C., aluminum chloride (17.34 g, 0.129 mol, 2.5 eq) was added portion wise for 30 min. Reaction mixture was slowly heated to 50-60° C. and allowed stir for 2 hrs at the same temperature. Progress of the reaction was monitored by TLC (20% ethyl acetate/hexane, $R_f$~0.1). On completion of the reaction, reaction contents were quenched with dilute HCl, ice cold water (300 ml) was added and extracted with ethyl acetate (2×100 ml). Aqueous layer was basified with sodium hydroxide solution and extracted with ethyl acetate. Combined extract was dried over sodium sulfate and concentrated under reduced pressure to obtain the crude product as a brown colored solid (4.6 g). The crude obtained was directly used for the next step.

Step b: To a stirred solution of step-a product (5.7 g, 0.034 mol) in DCM (37 ml) cooled at 0° C., TEA (1.74 g (2.4 ml), 0.017 mol, 0.5 eq) was added drop wise for 10 min. Then Boc anhydride (3.76 g (3.9 ml), 0.017 mol, 0.5 eq) taken in DCM (20 ml) was added drop wise for 10-15 min at 0° C. Overall reaction mixture initially stirred for 30 min at 0° C. and alter for another 30 min at RT. Progress of the reaction was monitored by the TLC (20% ethyl acetate/hexane, $R_f$~0.6). As the reaction not moved completely, Boc anhydride (0.3 eq) was added and stirred for another 15 min at RT. Progress of the reaction was monitored by TLC and found that the reaction moved completely. DCM was distilled off completely, residue was taken in ice water (300 ml) and the product extracted with ethyl acetate (2×200 ml). Combined extract was dried over sodium sulfate and concentrated under reduced pressure to yield the required product as and off white solid (7 g, 76% yield).

Step c: A solution of step-b product (10 g, 0.037 mol) in DMF (50 ml) was added drop wise to a mixture of NaH (1.85 g, 0.077 mol, 1.2 eq) in DMF (50 ml) for 45 min at RT. Then 0.5M monochloro amine solution (322 ml) was added drop wise for 30 min and the overall reaction mixture was allowed to stir for 20 min at RT. Progress of the reaction was monitored by TLC (30% ethyl acetate/hexane, $R_f$~0.5). On completion of the reaction, reaction contents were quenched with saturate $Na_2S_2O_3$ solution in cold condition and the product was extracted with ethyl acetate (5×100 ml). Combined extract was dried over sodium sulfate, concentrated under reduced pressure and the crude obtained was purified by column chromatography (silica gel, 4% ethyl acetate/hexane) to yield the required product as an off white solid (4 g, 62% yield).

Step d: To a solution of step-c product (1.2 g, 0.0042 mol) in toluene (12 ml, 10 times), potassium carbonate (1.18 g, 2 eq), water (12 ml, 10 times) and TBAB (0.137 g, 0.0004 mol, 0.1 eq) were added. Then the contents were stirred for 15 min and cooled to 0° C. Benzoyl chloride (0.72 g, 0.005 mol, 1.2 eq) taken in toluene (6 ml) was added drop wise at 0° C. and the overall reaction mixture was stirred for 2 hrs at RT. Progress of the reaction was monitored by TLC (30% ethyl acetate/hexane, $R_f$~0.6). On completion of the reaction, ice water (100 ml) was added, organic layer separated and the aqueous layer extracted with ethyl acetate (5×75 ml). Combined organic layer was washed with water (2×100 ml) and dried over sodium sulfate. Then the contents were concentrated under reduced pressure and the crude obtained was purified by column chromatography (silica gel, 3% ethyl acetate/hexane) to yield the required product as a pale yellow colored liquid (1.1 g, 67% yield).

Step e: To a solution of step-d product (1.1 g, 0.0028 mol) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, Rf~0.2). On completion of the reaction, DCM was distilled off completely. Residue was taken in cold water (200 ml), basified with saturated $NaHCO_3$ solution and the product extracted with ethyl acetate (4×50 ml). Combined extract was washed with water (2×50 ml), dried over sodium sulfate and concentrated under reduced pressure. Crude obtained was purified by column chromatography (silica gel, 10% ethyl acetate/hexane) to yield the required product as a white solid (0.24 g, 30% yield).

9.7 Synthesis of 5-(aminomethyl)-N-(pyridin-2-ylmethyl)-3-(trifluoromethyl)-1H-pyrazol-1-amine (Employed for the Synthesis of Example Compound No. 204)

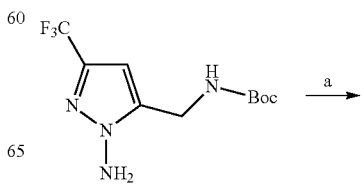

-continued

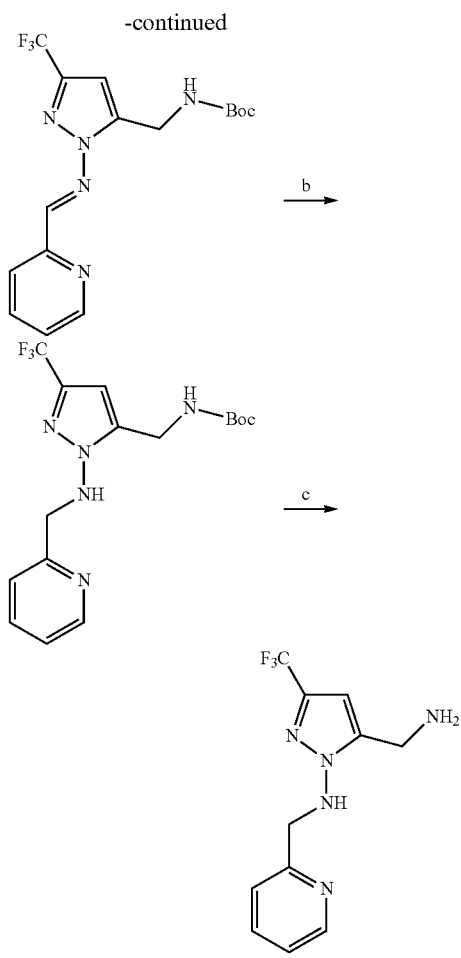

Step a: To a solution of tert-butyl(1-amino-3-(trifluoromethyl)-1H-pyrazol-5-yl)methylcarbamate (2 g, 0.0071 mol) in methanol (15 ml), picolinaldehyde (1.14 g (1 ml), 0.016 mol, 1.5 eq) taken in methanol (5 ml) was added. Then the reaction mixture was acidified with acetic acid (0.2 ml, catalytic) and heated to reflux for 24 hrs. Progress of the reaction was monitored by TLC (10% ethyl acetate/hexane, $R_f$~0.4). On completion of the reaction, methanol was distilled off completely. Residue was taken in ice water (200 ml) and the product extracted with ethyl acetate (4×50 ml). Combined extract was washed with water (2×50 ml), dried over sodium sulfate and the ethyl acetate was distilled off completely. Crude obtained was recrystalised from hexane (10 ml) to yield the required product as liquid (2 g, 76% yield).

Step b: To a solution of step-a product (2 g, 0.0054 mol) in methanol (20 ml, 10 times) cooled to at 0° C., NaBH$_4$ (0.2 g, 0.0054 mol, 1 eq) was added slowly. Overall reaction mixture was allowed to stir for 1 hr at RT. Progress of the reaction was monitored by TLC (20% ethyl acetate/hexane, Rf~0.2). On completion of the reaction, methanol was distilled off completely. Residue was taken in cold water (100 ml) and the product extracted with ethyl acetate (5×50 ml). Combined extract was washed with water (2×50 ml), dried over sodium sulfate and concentrated under reduced pressure. Crude obtained was purified by column chromatography (silica gel, 10% ethyl acetate/hexane) to yield the required product pale yellow colored solid (1.1 g, 57% yield).

Step c: To a solution of the Boc compound step b product (1.1 g) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, $R_f$~0.2). On completion of the reaction, DCM was distilled off completely. Residue was taken in cold water (200 ml), basified with saturated NaHCO$_3$ solution and the product extracted with ethyl acetate (4×50 ml). Combined extract was washed with water (2×50 ml), dried over sodium sulfate and concentrated under reduced pressure. Crude obtained was purified by column chromatography (silica gel, 10% ethyl acetate/hexane) to yield the required product as a white solid (0.425 g, 53% yield).

Synthesis of the Exemplary Compounds:

1. Preparation of Amides (A=CR$^{5b}$)

General directions for reacting amines of general formula (II) with carboxylic acids of general formula (III) or carboxylic acid derivatives of general formula (IV) to form compounds of general formula (I), wherein A=CR$^{5b}$ (amides), as in scheme 1a (step j09).

1.1 Method A:

The acid of general formula (III) (1 equivalent), the amine of general formula (II) (1.2 equivalents) and EDCl (1.2 equivalents) are stirred in DMF (10 mmol of acid/20 ml) for 12 hours at RT and water is subsequently added thereto. The reaction mixture is repeatedly extracted with EE, the aqueous phase is saturated with NaCl and subsequently reextracted with EE. The combined organic phases are washed with 1 N HCl and brine, dried over magnesium sulphate and the solvent is removed under vacuum. The residue is purified by means of flash chromatography (SiO$_2$, EE/hexane in different ratios such as 1:2) and the product (I) is in this way obtained.

1.2 Method B:

The acid of general formula (III) (1 equivalent) and the amine of general formulae (II) (1.1 equivalents) are dissolved in dichloromethane (1 mmol of acid in 6 ml) and mixed with EDCl (1.5 equivalents), HOBt (1.4 equivalents) and triethylamine (3 equivalents) at 0° C. The reaction mixture is stirred for 20 h at room temperature and the crude product is purified by means of column chromatography (SiO$_2$, n-hexane/EE in different ratios such as 2:1) and (I) is in this way obtained.

1.3 Method C:

The acid of general formula (III) (1 equivalent) is first mixed with a chlorinating agent, preferably with thionyl chloride and the mixture obtained in this way is boiled under reflux and the acid (III) is in this way converted into the corresponding acid chloride (IV). The amine of general formulae (II) (1.1 equivalents) is dissolved in dichloromethane (1 mmol of acid in 6 ml) and mixed with triethylamine (3 equivalents) at 0° C. The reaction mixture is stirred for 20 h at room temperature and the crude product is purified by means of column chromatography (SiO$_2$, n-hexane/EE in different ratios such as 2:1) and (I) is in this way obtained.

1.4 Method D:

The phenyl ester (IVa) obtained (1 equivalent) and the corresponding amine (II) (1.1 equivalents) are dissolved in THF (10 mmol of the reaction mixture in 120 ml) and stirred for 16 h at room temperature after addition of DBU (1.5 equivalents). After removal of the solvent under vacuum, the residue obtained is purified by means of flash chromatography (SiO$_2$, EE/hexane in different ratios such as 1:1) and (I) is in this way obtained.

The following exemplary compounds 1-77, 183-184, 186, 188-191, 193, 195, 197-204 and 206-213 were obtained by one of the methods disclosed above.

| | |
|---|---|
| 1 | N-((1-(3-chlorophenyl)-3-(trifluoromethyl)-1H-pyrazol-5-yl)methyl)-2-(2,3-dihydro-1H-inden-4-yl)propanamide |
| 2 | N-((1-(3-chlorophenyl)-3-(trifluoromethyl)-1H-pyrazol-5-yl)methyl)-2-(5,6,7,8-tetrahydronaphthalen-1-yl)propanamide |
| 3 | N-((1-(3-chlorophenyl)-3-(trifluoromethyl)-1H-pyrazol-5-yl)methyl)-2-(3-hydroxy-2,3-dihydro-1H-inden-5-yl)propanamide |
| 4 | N-((1-(3-chlorophenyl)-3-(trifluoromethyl)-1H-pyrazol-5-yl)methyl)-2-(2-hydroxy-2,3-dihydro-1H-inden-5-yl)propanamide |
| 5 | N-((1-(3-chlorophenyl)-3-(trifluoromethyl)-1H-pyrazol-5-yl)methyl)-2-(7-hydroxy-5,6,7,8-tetrahydronaphthalen-1-yl)propanamide |
| 6 | N-((1-(3-chlorophenyl)-3-(trifluoromethyl)-1H-pyrazol-5-yl)methyl)-2-(3-oxo-2,3-dihydro-1H-inden-5-yl)propanamide |
| 7 | (E)-N-((1-(3-chlorophenyl)-3-(trifluoromethyl)-1H-pyrazol-5-yl)methyl)-2-(3-(hydroxyimino)-2,3-dihydro-1H-inden-5-yl)propanamide |
| 8 | N-((1-(3-chlorophenyl)-3-(trifluoromethyl)-1H-pyrazol-5-yl)methyl)-2-(indolin-5-yl)propanamide hydrochloride |
| 9 | N-((1-(3-chlorophenyl)-3-(trifluoromethyl)-1H-pyrazol-5-yl)methyl)-2-(1-methylindolin-5-yl)propanamide |
| 10 | N-((3-tert-butyl-1-(3-chlorophenyl)-1H-pyrazol-5-yl)methyl)-2-(1-(methylsulphonyl)indolin-5-yl)propanamide |
| 11 | 2-(benzo[d][1,3]dioxol-5-yl)-N-((3-tert-butyl-1-(3-chlorophenyl)-1H-pyrazol-5-yl)methyl)propanamide |
| 12 | N-((3-tert-butyl-1-(4-chlorophenyl)-1H-pyrazol-5-yl)methyl)-2-(2,3-dihydrobenzo[b][1,4]dioxin-6-yl)acetamide |
| 13 | N-((3-tert-butyl-1-(3-chlorophenyl)-1H-pyrazol-5-yl)methyl)-2-(2,3-dihydrobenzo[b][1,4]dioxin-6-yl)propanamide |
| 14 | N-((3-tert-butyl-1-(3-chlorophenyl)-1H-pyrazol-5-yl)methyl)-2-(2,3-dihydrobenzo[b][1,4]dioxin-5-yl)propanamide |
| 15 | N-((3-tert-butyl-1-(3-chlorophenyl)-1H-pyrazol-5-yl)methyl)-2-(3,4-dihydro-2H-benzo[b][1,4]dioxepin-7-yl)propanamide |
| 16 | N-((1-(3-chlorophenyl)-3-(trifluoromethyl)-1H-pyrazol-5-yl)methyl)-2-(1,2,3,4-tetrahydroquinolin-6-yl)propanamide hydrochloride |
| 17 | N-((1-(3-chlorophenyl)-3-(trifluoromethyl)-1H-pyrazol-5-yl)methyl)-2-(1-methyl-1,2,3,4-tetrahydroquinolin-6-yl)propanamide |
| 18 | N-((1-(3-chlorophenyl)-3-(trifluoromethy))-1H-pyrazol-5-yl)methyl)-2-(1-(methylsulphonyl)-1,2,3,4-tetrahydroquinolin-6-yl)propanamide |
| 19 | N-((1-(3-chlorophenyl)-3-(trifluoromethyl)-1H-pyrazol-5-yl)methyl)-2-(3,4-dihydro-2H-benzo[b][1,4]oxazin-7-yl)propanamide |
| 20 | N-((1-(3-chlorophenyl)-3-(trifluoromethyl)-1H-pyrazol-5-yl)methyl)-2-(3,4-dihydro-2H-benzo[b][1,4]oxazin-6-yl)propanamide |
| 21 | N-((1-(3-chlorophenyl)-3-(trifluoromethyl)-1H-pyrazol-5-yl)methyl)-2-(2-oxo-2,3-dihydrobenzo[d]oxazol-6-yl)propanamide |
| 22 | N-((1-(3-chlorophenyl)-3-(trifluoromethyl)-1H-pyrazol-5-yl)methyl)-2-(2-oxo-1,2,3,4-tetrahydroquinolin-6-yl)propanamide |
| 23 | N-((1-(3-chlorophenyl)-3-(trifluoromethyl)-1H-pyrazol-5-yl)methyl)-2-(3-oxo-3,4-dihydro-2H-benzo[b][1,4]oxazin-7-yl)propanamide |
| 24 | N-((1-(3-chlorophenyl)-3-(trifluoromethyl)-1H-pyrazol-5-yl)methyl)-2-(1H-inden-7-yl)propanamide |
| 25 | N-((3-tert-butyl-1-(3-chlorophenyl)-1H-pyrazol-5-yl)methyl)-2-(1H-indol-4-yl)propanamide |
| 26 | N-((1-(3-chlorophenyl)-3-(trifluoromethyl)-1H-pyrazol-5-yl)methyl)-2-(1-methyl-1H-indol-4-yl)propanamide |
| 27 | N-((1-(3-chlorophenyl)-3-(trifluoromethyl)-1H-pyrazol-5-yl)methyl)-2-(1H-indazol-4-yl)propanamide |
| 28 | N-((1-(3-chlorophenyl)-3-(trifluoromethyl)-1H-pyrazol-5-yl)methyl)-2-(1-methyl-1H-indazol-4-yl)propanamide |
| 29 | N-((1-(3-chlorophenyl)-3-(trifluoromethyl)-1H-pyrazol-5-yl)methyl)-2-(1-phenyl-1H-indazol-4-yl)propanamide |
| 30 | 2-(1H-benzo[d][1,2,3]triazol-4-yl)-N-((1-(3-chlorophenyl)-3-(trifluoromethyl)-1H-pyrazol-5-yl)methyl)propanamide |
| 31 | N-((1-(3-chlorophenyl)-3-(trifluoromethyl)-1H-pyrazol-5-yl)methyl)-2-(1H-indol-5-yl)propanamide |
| 32 | N-((1-(3-chlorophenyl)-3-(trifluromethyl)-1H-pyrazol-5-yl)methyl)-2-(1-methyl-1H-indol-5-yl)propanamide |
| 33 | 2-(1H-benzo[d]imidazol-5-yl)-N-((1-(3-chlorophenyl)-3-(trifluoromethyl)-1H-pyrazol-5-yl)methyl)propanamide |
| 34 | 2-(2-amino-1H-benzo[d]imidazol-5-yl)-N-((1-(3-chlorophenyl)-3-(trifluromethyl)-1H-pyrazol-5-yl)methyl)propanamide |
| 35 | N-((1-(3-chlorophenyl)-3-(trifluoromethyl)-1H-pyrazol-5-yl)methyl)-2-(1H-indazol-5-yl)propanamide |
| 36 | 2-(benzo[d]oxazol-4-yl)-N-((1-(3-chlorophenyl)-3-(trifluoromethyl)-1H-pyrazol-5-yl)methyl)propanamide |
| 37 | 2-(benzo[d]oxazol-7-yl)-N-((1-(3-chlorophenyl)-3-(trifluoromethyl)-1H-pyrazol-5-yl)methyl)propanamide |
| 38 | 2-(benzo[d]thiazol-4-yl)-N-((1-(3-chlorophenyl)-3-(trifluoromethyl)-1H-pyrazol-5-yl)methyl)propanamide |
| 39 | 2-(benzo[d]thiazol-7-yl)-N-((1-(3-chlorophenyl)-3-(trifluoromethyl)-1H-pyrazol-5-yl)methyl)propanamide |
| 40 | 2-(benzo[d]oxazol-5-yl)-N-((3-tert-butyl-1-(3-chlorophenyl)-1H-pyrazol-5-yl)methyl)propanamide |

| | |
|---|---|
| 41 | 2-(benzo[d]oxazol-6-yl)-N-((3-tert-butyl-1-(3-chlorophenyl)-1H-pyrazol-5-yl)methyl)propanamide |
| 42 | 2-(benzo[d]thiazol-6-yl)-N-((1-(3-chlorophenyl)-3-(trifluoromethyl)-1H-pyrazol-5-yl)methyl)propanamide |
| 43 | 2-(2-aminobenzo[d]thiazol-6-yl)-N-((1-(3-chlorophenyl)-3-(trifluoromethyl)-1H-pyrazol-5-yl)methyl)propanamide |
| 44 | N-((1-(3-chlorophenyl)-3-(trifluoromethyl)-1H-pyrazol-5-yl)methyl)-2-(2-(methylsulphonamido)benzo[d]thiazol-6-yl)propanamide |
| 45 | N-((1-(3-chlorophenyl)-3-(trifluoromethyl)-1H-pyrazol-5-yl)methyl)-2-(2-methylbenzo[d]thiazol-6-yl)propanamide |
| 46 | 2-(benzo[d]thiazol-5-yl)-N-((1-(3-chlorophenyl)-3-(trifluoromethyl)-1H-pyrazol-5-yl)methyl)propanamide |
| 47 | N-((3-tert-butyl-1-(3-chlorophenyl)-1H-pyrazol-5-yl)methyl)-2-(naphthalen-1-yl)propanamide |
| 48 | N-((3-tert-butyl-1-(3-chlorophenyl)-1H-pyrazol-5-yl)methyl)-2-(naphthalen-2-yl)propanamide |
| 49 | N-((3-tert-butyl-1-(3-chlorophenyl)-1H-pyrazol-5-yl)methyl)-2-(6-hydroxynaphthalen-2-yl)propanamide |
| 50 | N-((1-(3-chlorophenyl)-3-(trifluoromethyl)-1H-pyrazol-5-yl)methyl)-2-(6-hydroxynaphthalen-2-yl)propanamide |
| 51 | N-((1-(3-chlorophenyl)-3-(trifluoromethyl)-1H-pyrazol-5-yl)methyl)-2-(6-methoxynaphthalen-2-yl)propanamide |
| 52 | N-((3-tert-butyl-1-methyl-1H-pyrazol-5-yl)methyl)-2-(7-hydroxynaphthalen-1-yl)propanamide |
| 53 | N-((3-tert-butyl-1-hexyl-1H-pyrazol-5-yl)methyl)-2-(7-hydroxynaphthalen-1-yl)propanamide |
| 54 | N-((3-tert-butyl-1-p-tolyl-1H-pyrazol-5-yl)methyl)-2-(7-hydroxynaphthalen-1-yl)propanamide |
| 55 | N-((3-tert-butyl-1-(4-tert-butylphenyl)-1H-pyrazol-5-yl)methyl)-2-(7-hydroxynaphthalen-1-yl)propanamide |
| 56 | N-((3-tert-butyl-1-(4-chlorophenyl)-1H-pyrazol-5-yl)methyl)-2-(7-hydroxynaphthalen-1-yl)propanamide |
| 57 | N-((3-tert-butyl-1-(3-chlorophenyl)-1H-pyrazol-5-yl)methyl)-2-(7-hydroxynaphthalen-1-yl)propanamide |
| 58 | N-((1-(3-chlorophenyl)-3-(trifluoromethyl)-1H-pyrazol-5-yl)methyl)-2-(7-hydroxynaphthalen-1-yl)propanamide |
| 59 | N-((3-tert-butyl-1-(3-chloro-4-fluorophenyl)-1H-pyrazol-5-yl)methyl)-2-(7-hydroxynaphthalen-1-yl)propanamide |
| 60 | N-((3-tert-butyl-1-cyclohexenyl-1H-pyrazol-5-yl)methyl)-2-(7-hydroxynaphthalen-1-yl)propanamide |
| 61 | N-((3-tert-butyl-1-(3-chlorophenyl)-1H-pyrazol-5-yl)methyl)-2-(quinolin-8-yl)propanamide |
| 62 | N-((3-tert-butyl-1-(3-chlorophenyl)-1H-pyrazol-5-yl)methyl)-2-(isoquinolin-8-yl)propanamide |
| 63 | N-((3-tert-butyl-1-(3-chlorophenyl)-1H-pyrazol-5-yl)methyl)-2-(isoquinolin-5-yl)propanamide |
| 64 | N-((1-(3-chlorophenyl)-3-(trifluoromethyl)-1H-pyrazol-5-yl)methyl)-2-(isoquinolin-5-yl)propanamide |
| 65 | N-((1-(3-chlorophenyl)-3-(trifluoromethyl)-1H-pyrazol-5-yl)methyl)-2-(3-methylisoquinolin-5-yl)propanamide |
| 66 | N-((1-(3-chlorophenyl)-3-(trifluoromethyl)-1H-pyrazol-5-yl)methyl)-2-(1-methylisoquinolin-5-yl)propanamide |
| 67 | N-((1-(3-chlorophenyl)-3-(trifluoromethyl)-1H-pyrazol-5-yl)methyl)-2-(1,3-dimethylisoquinolin-5-yl)propanamide |
| 68 | N-((1-(4-chlorophenyl)-3-(trifluoromethyl)-1H-pyrazol-5-yl)methyl)-2-(isoquinolin-5-yl)propanamide |
| 69 | N-((3-tert-butyl-1-(3-chloro-4-fluorophenyl)-1H-pyrazol-5-yl)methyl)-2-(isoquinolin-5-yl)propanamide |
| 70 | N-((3-tert-butyl-1-(3-chlorophenyl)-1H-pyrazol-5-yl)methyl)-2-(quinolin-5-yl)propanamide |
| 71 | N-((3-tert-butyl-1-(3-chlorophenyl)-1H-pyrazol-5-yl)methyl)-2-(quinolin-7-yl)propanamide |
| 72 | N-((1-(3-chlorophenyl)-3-(trifluoromethyl)-1H-pyrazol-5-yl)methyl)-2-(quinolin-7-yl)propanamide |
| 73 | N-((3-tert-butyl-1-(3-chlorophenyl)-1H-pyrazol-5-yl)methyl)-2-(isoquinolin-7-yl)propanamide |
| 74 | N-((3-tert-butyl-1-(3-chlorophenyl)-1H-pyrazol-5-yl)methyl)-2-(isoquinolin-6-yl)propanamide |
| 75 | N-((3-tert-butyl-1-(3-chlorophenyl)-1H-pyrazol-5-yl)methyl)-2-(quinolin-6-yl)propanamide |
| 76 | N-((3-tert-butyl-1-(3-chlorophenyl)-1H-pyrazol-5-yl)methyl)-2-(quinazolin-6-yl)propanamide |
| 77 | N-((3-tert-butyl-1-(3-chlorophenyl)-1H-pyrazol-5-yl)methyl)-2-(quinoxalin-6-yl)propanamide |
| 183 | 2-(benzo[d][1,3]dioxol-5-yl)-N-((1-(3-chlorophenyl)-3-cyclopropyl-1H-pyrazol-5-yl)methyl)propanamide |
| 184 | N-((1-cyclohexyl-3-(trifluoromethyl)-1H-pyrazol-5-yl)methyl)-2-(2,3-dihydrobenzo[b][1,4]dioxin-6-yl)propanamide |
| 186 | N-((3-tert-butyl-1-(3-chlorophenyl)-1H-pyrazol-5-yl)methyl)-2-(2,3-dihydro-1H-inden-5-yl)acetamide |

| | |
|---|---|
| 188 | N-((3-tert-butyl-1-(3-chlorophenyl)-1H-pyrazol-5-yl)methyl)-2-(2,3-dihydrobenzo[b][1,4]dioxin-6-yl)acetamide |
| 189 | N-((1-(3-chlorophenyl)-3-(trifluoromethyl)-1H-pyrazol-5-yl)methyl)-2-(2,2-dimethylchroman-6-yl)propanamide |
| 190 | N-((1-(3-chlorophenyl)-3-(trifluoromethyl)-1H-pyrazol-5-yl)methyl)-2-(2,2-dimethyl-2H-chromen-6-yl)propanamide |
| 191 | N-((1-(3-chlorophenyl)-3-(trifluoromethyl)-1H-pyrazol-5-yl)methyl)-2-(1-(methylsulfonyl)-1H-indazol-5-yl)propanamide |
| 193 | N-((3-tert-butyl-1-(3-chlorophenyl)-1H-pyrazol-5-yl)methyl)-2-(6-fluoro-1H-indazol-4-yl)propanamide |
| 195 | N-((1-(3-chlorophenyl)-3-(trifluoromethyl)-1H-pyrazol-5-yl)methyl)-2-(7-fluoro-1H-indazol-4-yl)propanamide |
| 197 | N-((1-(3-chlorophenyl)-3-(trifluoromethyl)-1H-pyrazol-5-yl)methyl)-2-(5-fluoronaphthalen-1-yl)propanamide |
| 198 | 5-(1-((1-(3-chlorophenyl)-3-(trifluoromethyl)-1H-pyrazol-5-yl)methylamino)-1-oxopropan-2-yl)quinolin 1-oxide |
| 199 | 2-(1H-indazol-4-yl)-N-((1-pentyl-3-(trifluoromethyl)-1H-pyrazol-5-yl)methyl)propanamide |
| 200 | N-((1-(3-chlorophenyl)-4-methyl-3-(trifluoromethyl)-1H-pyrazol-5-yl)methyl)-2-(2,3-dihydrobenzo[b][1,4]dioxin-6-yl)propanamide |
| 201 | N-((3-tert-butyl-1-(2,2,2-trifluoroethylamino)-1H-pyrazol-5-yl)methyl)-2-(2,3-dihydrobenzo[b][1,4]dioxin-6-yl)propanamide |
| 202 | 2-(2,3-dihydrobenzo[b][1,4]dioxin-6-yl)-N-((1-(4-methoxybenzyl)-3-(trifluoromethyl)-1H-pyrazol-5-yl)methyl)propanamide |
| 203 | 2-(1H-indazol-4-yl)-N-((1-(2-methoxyethylamino)-3-(trifluoromethyl)-1H-pyrazol-5-yl)methyl)propanamide |
| 204 | 2-(1H-indazol-4-yl)-N-((1-(pyridin-2-ylmethylamino)-3-(trifluoromethyl)-1H-pyrazol-5-yl)methyl)propanamide |
| 206 | N-((1-(3-chlorophenyl)-3-(trifluoromethyl)-1H-pyrazol-5-yl)methyl)-2-(1-oxo-2,3-dihydro-1H-inden-4-yl)propanamide |
| 207 | N-((1-(3-chlorophenyl)-3-(trifluoromethyl)-1H-pyrazol-5-yl)methyl)-2-(1-hydroxy-2,3-dihydro-1H-inden-4-yl)propanamide |
| 208 | N-((1-(3-chlorophenyl)-3-(trifluoromethyl)-1H-pyrazol-5-yl)methyl)-2-(2-hydroxy-2,3-dihydro-1H-inden-4-yl)propanamide |
| 209 | N-((1-(3-chlorophenyl)-3-(trifluoromethyl)-1H-pyrazol-5-yl)methyl)-2-(1H-indazol-6-yl)propanamide |
| 210 | N-((1-(3-chlorophenyl)-3-(trifluoromethyl)-1H-pyrazol-5-yl)methyl)-2-(1H-indazol-7-yl)propanamide |
| 211 | N-((1-(3-chlorophenyl)-3-(trifluoromethyl)-1H-pyrazol-5-yl)methyl)-2-(6-fluornaphthalen-1-yl)propanamide |
| 212 | N-((1-(3-chlorophenyl)-3-(trifluoromethyl)-1H-pyrazol-5-yl)methyl)-2-(7-methoxynaphthalen-1-yl)propanamide |
| 213 | 2-(3-chloroisoquinolin-5-yl)-N-((1-(3-chlorophenyl)-3-(trifluoromethyl)-1H-pyrazol-5-yl)methyl)propanamide |

2. Preparation of Ureas (A=N)

General directions for reacting amines of general formula (II) or (VI) with phenyl chloroformate to form compounds of formula (V) or (VIa) (step j07 and step j10, respectively) and subsequent reaction of compounds of formula (V) with amines of general formula (VI) or of compounds of formula (VIa) with amines of general formula (II) to form compounds of general formula (I), wherein A=N, as in scheme 1a and 1c (step j08 and step j11, respectively):

Step j07/step j10: The amine of general formula (II) or (VI) (1 equivalent) is placed in dichloromethane (10 mmol of amine in 70 ml) and phenyl chloroformate (1.1 equivalents) is added thereto at room temperature and the mixture is stirred for 30 min. After removal of the solvent under vacuum, the residue is purified by means of flash chromatography (SiO$_2$, diethyl ether/hexane in different ratios such as 1:2) and (V) or (VIa) is in this way obtained.

Step j08/step j11: The carbamic acid phenyl ester (V) or (VIa) obtained (1 equivalent) and the corresponding amine (VI) or (II) (1.1 equivalents) are dissolved in THF (10 mmol of the reaction mixture in 120 ml) and stirred for 16 h at room temperature after addition of DBU (1.5 equivalents). After removal of the solvent under vacuum, the residue obtained is purified by means of flash chromatography (SiO$_2$, EE/hexane in different ratios such as 1:1) and (I) is in this way obtained.

The following exemplary compounds 78-113, 174-182, 185, 187, 192, 194, 196, 205 and 214-217 were obtained according to the methods disclosed above.

| | |
|---|---|
| 78 | 1-((3-tert-butyl-1-(3-chlorophenyl)-1H-pyrazol-5-yl)methyl)-3-(2,3-dihydro-1H-inden-4-yl)urea |
| 79 | 1-((3-tert-butyl-1-(3-chlorophenyl)-1H-pyrazol-5-yl)methyl)-3-(2,3-dihydro-1H-inden-5-yl)urea |
| 80 | 1-((3-tert-butyl-1-(3-chlorophenyl)-1H-pyrazol-5-yl)methyl)-3-(5,6,7,8-tetrahydronaphthalen-1-yl)urea |
| 81 | 1-((1-(3-chlorophenyl)-3-(trifluoromethyl)-1H-pyrazol-5-yl)methyl)-3-(2-hydroxy-2,3-dihydro-1H-inden-4-yl)urea |
| 82 | 1-((1-(3-chlorophenyl)-3-(trifluoromethyl)-1H-pyrazol-5-yl)methyl)-3-(7-hydroxy-5,6,7,8-tetrahydronaphthalen-1-yl)urea |
| 83 | 1-(benzo[d][1,3]dioxol-5-yl)-3-((1-(3-chlorophenyl)-3-(trifluoromethyl)-1H-pyrazol-5-yl)methyl)urea |

-continued

| | |
|---|---|
| 84 | 1-((1-(3-chlorophenyl)-3-(trifluoromethyl)-1H-pyrazol-5-yl)methyl)-3-(2,3-dihydrobenzo[b][1,4]dioxin-6-yl)urea |
| 85 | 1-((3-tert-butyl-1-(3-chlorophenyl)-1H-pyrazol-5-yl)methyl)-3-(2,3-dihydrobenzo[b][1,4]dioxin-5-yl)urea |
| 86 | 1-((1-(3-chlorophenyi)-3-(trifluoromethyl)-1H-pyrazol-5-yl)methyl)-3-(1H-indol-4-yl)urea |
| 87 | 1-((1-(3-chlorophenyl)-3-(trifluoromethyl)-1H-pyrazol-5-yl)methyl)-3-(1-methyl-1H-indol-4-yl)urea |
| 88 | 1-((1-(3-chlorophenyl)-3-(trifluoromethyl)-1H-pyrazol-5-yl)methyl)-3-(1H-indazol-4-yl)urea |
| 89 | 1-((1-(3-chlorophenyl)-3-(trifluoromethyl)-1H-pyrazol-5-yl)methyl)-3-(1-methyl-1H-indazol-4-yl)urea |
| 90 | 1-((1-(3-chlorophenyl)-3-(trifluoromethyl)-1H-pyrazol-5-yl)methyl)-3-(1H-indol-5-yl)urea |
| 91 | 1-((1-(3-chlorophenyl)-3-(trifluoromethyl)-1H-pyrazol-5-yl)methyl)-3-(2-methyl-1H-indol-5-yl)urea |
| 92 | 1-(1H-benzo[d]imidazol-5-yl)-3-((1-(3-chlorophenyl)-3-(trifluoromethyl)-1H-pyrazol-5-yl)methyl)urea |
| 93 | 1-((1-(3-chlorophenyl)-3-(trifluoromethyl)-1H-pyrazol-5-yl)methyl)-3-(1H-indazol-5-yl)urea |
| 94 | 1-(benzo[d]oxazol-6-yl)-3-((1-(3-chlorophenyl)-3-(trifluoromethyl)-1H-pyrazol-5-yl)methyl)urea |
| 95 | 1-(benzo[d]oxazol-5-yl)-3-((1-(3-chlorophenyl)-3-(trifluoromethyl)-1H-pyrazol-5-yl)methyl)urea |
| 96 | 1-(benzo[d]thiazol-6-yl)-3-((1-(3-chlorophenyl)-3-(trifluoromethyl)-1H-pyrazol-5-yl)methyl)urea |
| 97 | 1-(benzo[d]thiazol-5-yl)-3-((1-(3-chlorophenyl)-3-(trifluoromethyl)-1H-pyrazol-5-yl)methyl)urea |
| 98 | 1-((3-tert-butyl-1-(3-chlorophenyl)-1H-pyrazol-5-yl)methyl)-3-(naphthalen-1-yl)urea |
| 99 | 1-((3-tert-butyl-1-(3-chlorophenyl)-1H-pyrazol-5-yl)methyl)-3-(6-hydroxynaphthalen-2-yl)urea |
| 100 | 1-((3-tert-butyl-1-(3-chlorophenyl)-1H-pyrazol-5-yl)methyl)-3-(5-hydroxynaphthalen-2-yl)urea |
| 101 | 1-((3-tert-butyl-1-(3-chlorophenyl)-1H-pyrazol-5-yl)methyl)-3-(7-hydroxynaphthalen-1-yl)urea |
| 102 | 1-((1-(3-chlorophenyl)-3-(trifluoromethyl)-1H-pyrazol-5-yl)methyl)-3-(7-hydroxynaphthalen-1-yl)urea |
| 103 | 1-((3-tert-butyl-1-(3-chlorophenyl)-1H-pyrazol-5-yl)methyl)-3-(7-ethoxynaphthalen-1-yl)urea |
| 104 | 1-((3-tert-butyl-1-(3-chlorophenyl)-1H-pyrazol-5-yl)methyl)-3-(6-hydroxynaphthalen-1-yl)urea |
| 105 | 1-((3-tert-butyl-1-(3-chlorophenyl)-1H-pyrazol-5-yl)methyl)-3-(5-hydroxynaphthalen-1-yl)urea |
| 106 | 1-((3-tert-butyl-1-(3-chlorophenyl)-1H-pyrazol-5-yl)methyl)-3-(4-hydroxynaphthalen-1-yl)urea |
| 107 | 1-((3-tert-butyl-1-(3-chlorophenyl)-1H-pyrazol-5-yl)methyl)-3-(quinolin-8-yl)urea |
| 108 | 1-((3-tert-butyl-1-(3-chlorophenyl)-1H-pyrazol-5-yl)methyl)-3-(isoquinolin-8-yl)urea |
| 109 | 1-((3-tert-butyl-1-(3-chlorophenyl)-1H-pyrazol-5-yl)methyl)-3-(isoquinolin-5-yl)urea |
| 110 | 1-((1-(3-chlorophenyl)-3-(trifluoromethyl)-1H-pyrazol-5-yl)methyl)-3-(isoquinolin-5-yl)urea |
| 111 | 1-((3-tert-butyl-1-(3-chlorophenyl)-1H-pyrazol-5-yl)methyl)-3-(quinolin-5-yl)urea |
| 112 | 1-((3-tert-butyl-1-(3-chlorophenyl)-1H-pyrazol-5-yl)methyl)-3-(isoquinolin-4-yl)urea |
| 113 | 1-((3-tert-butyl-1-(3-chlorophenyl)-1H-pyrazoi-5-yl)methyl)-3-(quinolin-3-yl)urea |
| 174 | 1-((1-(4-chlorophenyl)-3-(trifluoromethyl)-1H-pyrazol-5-yl)methyl)-3-(2,3-dihydro-1H-inden-5-yl)urea |
| 175 | 1-(2,3-dihydro-1H-inden-5-yl)-3-((1-(4-fluorophenyl)-3-(trifluoromethyl)-1H-pyrazol-5-yl)methyl)urea |
| 176 | 1-((3-tert-butyl-1-(3-fluorophenyl)-1H-pyrazol-5-yl)methyl)-3-(2,3-dihydro-1H-inden-5-yl)urea |
| 177 | 1-((3-tert-butyl-1-(3-chloro-4-fluorophenyl)-1H-pyrazol-5-yl)methyl)-3-(2,3-dihydro-1H-inden-5-yl)urea |
| 178 | 1-(2,3-dihydro-1H-inden-5-yl)-3-((1-(4-methoxyphenyl)-3-(trifluoromethyl)-1H-pyrazol-5-yl)methyl)urea |
| 179 | 1-(2,3-dihydro-1H-inden-5-yl)-3-((3-(trifluoromethyl)-1-(4-(trifluoromethyl)phenyl)-1H-pyrazol-5-yl)methyl)urea |
| 180 | 1-(2,3-dihydro-1H-inden-5-yl)-3-((1-(4-(trifluoromethoxy)phenyl)-3-(trifluoromethyl)-1H-pyrazol-5-yl)methyl)urea |
| 181 | 1-(2,3-dihydro-1H-inden-5-yl)-3-((1-(3,4-dimethylphenyl)-3-(trifluoromethyl)-1H-pyrazol-5-yl)methyl)urea |
| 182 | 1-((3-tert-butyl-1-(3,5-dichlorophenyl)-1H-pyrazol-5-yl)methyl)-3-(2,3-dihydro-1H-inden-5-yl)urea |
| 185 | 1-((3-tert-butyl-1-(3-chlorophenyl)-1H-pyrazol-5-yl)methyl)-3-(2,3-dihydrobenzofuran-7-yl)urea |

-continued

| | |
|---|---|
| 187 | 1-((3-tert-butyl-1-(3-chlorophenyl)-1H-pyrazol-5-yl)methyl)-3-(2,2-difluorobenzo[d][1,3]dioxol-5-yl)urea |
| 192 | 1-((1-(3-chlorophenyl)-3-(trifluoromethyl)-1H-pyrazol-5-yl)methyl)-3-(2-methyl-1H-indol-4-yl)urea |
| 194 | 1-((1-(3-chlorophenyl)-3-(trifluoromethyl)-1H-pyrazol-5-yl)methyl)-3-(6-fluoro-1H-indazol-4-yl)urea |
| 196 | 1-((1-(3-chlorophenyl)-3-(trifluoromethyl)-1H-pyrazol-5-yl)methyl)-3-(1-oxo-1,2-dihydroisoquinolin-5-yl)urea |
| 205 | 1-(5-chloro-1H-indazol-4-yl)-3-((1-(3-chlorophenyl)-3-(trifluoromethyl)-1H-pyrazol-5-yl)methyl)urea |
| 214 | (S)-1-((1-(3-chlorophenyl)-3-(trifluoromethyl)-1H-pyrazol-5-yl)methyl)-3-(7-hydroxy-5,6,7,8-tetrahydronaphthalen-1-yl)urea |
| 215 | (R)-1-((1-(3-chlorophenyl)-3-(trifluoromethyl)-1H-pyrazol-5-yl)methyl)-3-(7-hydroxy-5,6,7,8-tetrahydronaphthalen-1-yl)urea |
| 216 | 1-((3-tert-butyl-1-(pyridin-2-yl)-1H-pyrazol-5-yl)methyl)-3-(6-fluoro-1H-indazol-4-yl)urea |
| 217 | N-(5-((3-(6-fluoro-1H-indazol-4-yl)ureido)methyl)-3-(trifluormethyl)-1H-pyrazol-1-yl)benzamide |

The methods illustrated hereinbefore for synthesising the compounds according to the invention enable a person skilled in the art also to synthesise the following exemplary compounds 114-173:

| | |
|---|---|
| 114 | N-[[2-(6-chloro-pyridin-2-yl)-5-(trifluoromethyl)-2H-pyrazol-3-yl]-methyl]-2-(6-hydroxy-naphthalen-2-yl)-propionamide |
| 115 | 1-[[2-(6-chloro-pyridin-2-yl)-5-(trifluoromethyl)-2H-pyrazol-3-yl]-methyl]-3-(7-hydroxy-naphthalen-1-yl)-urea |
| 116 | N-[[2-(6-chloro-pyridin-2-yl)-5-(trifluoromethyl)-2H-pyrazol-3-yl]-methyl]-2-(1H-indol-5-yl)-propionamide |
| 117 | N-[[5-tert-butyl-2-(6-chloro-pyridin-2-yl)-2H-pyrazol-3-yl]-methyl]-2-isoquinolin-5-yl-propionamide |
| 118 | 1-[[5-tert-butyl-2-(6-chloro-pyridin-2-yl)-2H-pyrazol-3-yl]-methyl]-3-(1-methyl-isoquinolin-5-yl)-urea |
| 119 | 2-(1,3-benzodioxol-5-yl)-N-[[5-tert-butyl-2-(6-chloro-pyridin-2-yl)-2H-pyrazol-3-yl]-methyl]-propionamide |
| 120 | 2-(1H-indol-5-yl)-N-[[2-pyridin-2-yl-5-(trifluoromethyl)-2H-pyrazol-3-yl]-methyl]-propionamide |
| 121 | N-[[5-tert-butyl-2-(3,3-difluoro-cyclobutanecarbonyl)-2H-pyrazol-3-yl]-methyl]-2-(1H-indazol-4-yl)-propionamide |
| 122 | 1-[[2-(3-chlorophenyl)-4-methyl-5-(trifluoromethyl)-2H-pyrazol-3-yl]-methyl]-3-(1H-indazol-4-yl)-urea |
| 123 | N-[[2-(dipropyl-amino)-5-(trifluoromethyl)-2H-pyrazol-3-yl]-methyl]-2-(6-hydroxy-naphthalen-2-yl)-propionamide |
| 124 | 1-[[2-(dipropyl-amino)-5-(trifluoromethyl)-2H-pyrazol-3-yl]-methyl]-3-(7-hydroxy-naphthalen-1-yl)-urea |
| 125 | N-[[2-(dipropyl-amino)-5-(trifluoromethyl)-2H-pyrazol-3-yl]-methyl]-2-isoquinolin-5-yl-propionamide |
| 126 | N-[[2-(dipropyl-amino)-5-(trifluoromethyl)-2H-pyrazol-3-yl]-methyl]-2-(1H-indol-5-yl)-propionamide |
| 127 | 2-(1H-benzotriazol-4-yl)-N-[[2-(dipropyl-amino)-5-(trifluoromethyl)-2H-pyrazol-3-yl]-methyl]-propionamide |
| 128 | 1-(benzothiazol-6-yl)-3-[[2-(dipropyl-amino)-5-(trifluoromethyl)-2H-pyrazol-3-yl]-methyl]-urea |
| 129 | 1-(2,3-dihydro-1H-inden-5-yl)-3-[[2-(dipropyl-amino)-5-(trifluoromethyl)-2H-pyrazol-3-yl]-methyl]-urea |
| 130 | 1-[[2-(dipropyl-amino)-5-(trifluoromethyl)-2H-pyrazol-3-yl]-methyl]-3-(1H-indazol-4-yl)-urea |
| 131 | 2-(1,3-benzodioxol-5-yl)-N-[[5-tert-butyl-2-(dipropyl-amino)-2H-pyrazol-3-yl]-methyl]-propionamide |
| 132 | 1-(7-hydroxy-naphthalen-1-yl)-3-[[2-piperidin-1-yl-5-(trifluoromethyl)-2H-pyrazol-3-yl]-methyl]-urea |
| 133 | 2-(2-methyl-quinolin-5-yl)-N-[[2-piperidin-1-yl-5-(trifluoromethyl)-2H-pyrazol-3-yl]-methyl]-propionamide |
| 134 | 2-isoquinolin-5-yl-N-[[2-piperidin-1-yl-5-(trifluoromethyl)-2H-pyrazol-3-yl]-methyl]-propionamide |
| 135 | 1-(3-chloro-isoquinolin-5-yl)-3-[[2-piperidin-1-yl-5-(trifluoromethyl)-2H-pyrazol-3-yl]-methyl]-urea |
| 136 | 1-(1-chloro-isoquinolin-5-yl)-3-[[2-piperidin-1-yl-5-(trifluoromethyl)-2H-pyrazol-3-yl]-methyl]-urea |
| 137 | 1-(1-methyl-isoquinolin-5-yl)-3-[[2-piperidin-1-yl-5-(trifluoromethyl)-2H-pyrazol-3-yl]-methyl]-urea |
| 138 | N-[(5-tert-butyl-2-piperidin-1-yl-2H-pyrazol-3-yl)-methyl]-2-(2-methyl-quinolin-5-yl)-propionamide |

-continued

| | |
|---|---|
| 139 | 2-(1H-indol-5-yl)-N-[[2-piperidin-1-yl-5-(trifluoromethyl)-2H-pyrazol-3-yl]-methyl]-propionamide |
| 140 | 2-(1,3-benzodioxol-5-yl)-N-[[2-piperidin-1-yl-5-(trifluoromethyl)-2H-pyrazol-3-yl]-methyl]-propionamide |
| 141 | N-[[2-[(4-fluorophenyl)-methyl-methyl-amino]-5-(trifluoromethyl)-2H-pyrazol-3-yl]-methyl]-2-(6-hydroxy-naphthalen-2-yl)-propionamide |
| 142 | N-[[2-[(4-fluorophenyl)-methyl-methyl-amino]-5-(trifluoromethyl)-2H-pyrazol-3-yl]-methyl]-2-(1-methyl-1H-indazol-4-yl)-propionamide |
| 143 | N-[[2-[(4-fluorophenyl)-methyl-methyl-amino]-5-(trifluoromethyl)-2H-pyrazol-3-yl]-methyl]-2-(2-methyl-quinolin-5-yl)-propionamide |
| 144 | 2-(1,3-benzodioxol-5-yl)-N-[[2-[(4-fluorophenyl)-methyl-methylsulphonyl-amino]-5-(trifluoromethyl)-2H-pyrazol-3-yl]-methyl]-propionamide |
| 145 | N-[[2-[(4-fluorophenyl)-methyl-methylsulphonyl-amino]-5-(trifluoromethyl)-2H-pyrazol-3-yl]-methyl]-2-(1-methyl-1H-indazol-4-yl)-propionamide |
| 146 | N-[[2-[(4-fluorophenyl)-methyl-methylsulphonyl-amino]-5-(trifluoromethyl)-2H-pyrazol-3-yl]-methyl]-2-(1H-indol-5-yl)-propionamide |
| 147 | 1-[[2-butoxy-5-(trifluoromethyl)-2H-pyrazol-3-yl]-methyl]-3-(1H-indazol-4-yl)-urea |
| 148 | 1-[[2-butoxy-5-(trifluoromethyl)-2H-pyrazol-3-yl]-methyl]-3-(1-methyl-1H-indazol-4-yl)-urea |
| 149 | N-[[2-butoxy-5-(trifluoromethyl)-2H-pyrazol-3-yl]-methyl]-2-(1H-indazol-4-yl)-propionamide |
| 150 | 1-[[2-(cyclopropyl-methoxy)-5-(trifluoromethyl)-2H-pyrazol-3-yl]-methyl]-3-(1H-indazol-4-yl)-urea |
| 151 | 1-[[2-cyclopentyloxy-5-(trifluoromethyl)-2H-pyrazol-3-yl]-methyl]-3-(1H-indazol-4-yl)-urea |
| 152 | 1-(1H-indazol-4-yl)-3-[[2-(thiophen-2-yl-methoxy)-5-(trifluoromethyl)-2H-pyrazol-3-yl]-methyl]-urea |
| 153 | 1-[[2-butoxy-5-(trifluoromethyl)-2H-pyrazol-3-yl]-methyl]-3-(2,3-dihydro-1H-inden-5-yl)-urea |
| 154 | N-[[2-butoxy-5-(trifluoromethyl)-2H-pyrazol-3-yl]-methyl]-2-isoquinolin-5-yl-propionamide |
| 155 | 1-(1H-indazol-4-yl)-3-[[2-[(4-methoxyphenyl)-methyl]-5-(trifluoromethyl)-2H-pyrazol-3-yl]-methyl]-urea |
| 156 | 1-[[2-[(4-methoxyphenyl)-methyl]-5-(trifluoromethyl)-2H-pyrazol-3-yl]-methyl]-3-(1-methyl-1H-indazol-4-yl)-urea |
| 157 | 2-(1H-indol-5-yl)-N-[[2-pyridin-4-yloxy-5-(trifluoromethyl)-2H-pyrazol-3-yl]-methyl]-propionamide |
| 158 | 2-(1H-indol-5-yl)-N-[[2-pyridin-2-yloxy-5-(trifluoromethyl)-2H-pyrazol-3-yl]-methyl]-propionamide |
| 159 | 1-[[2-(3-cyano-5-fluoro-phenoxy)-5-(trifluoromethyl)-2H-pyrazol-3-yl]-methyl]-3-(1-methyl-1H-indazol-4-yl)-urea |
| 160 | N-[[2-(3-cyano-5-fluoro-phenoxy)-5-(trifluoromethyl)-2H-pyrazol-3-yl]-methyl]-2-(1H-indol-5-yl)-propionamide |
| 161 | 2-(1,3-benzodioxol-5-yl)-N-[[2-(3-cyano-5-fluoro-phenoxy)-5-(trifluoromethyl)-2H-pyrazol-3-yl]-methyl]-propionamide |
| 162 | 2-(6-hydroxy-naphthalen-2-yl)-N-[[2-phenylmethoxy-5-(trifluoromethyl)-2H-pyrazol-3-yl]-methyl]-propionamide |
| 163 | N-[[2-(benzenesulphonyl)-5-tert-butyl-2H-pyrazol-3-yl]-methyl]-2-(1,3-benzodioxol-5-yl)-propionamide |
| 164 | N-[[2-(benzenesulphonyl)-5-tert-butyl-2H-pyrazol-3-yl]-methyl]-2-(1H-indol-5-yl)-propionamide |
| 165 | 2-(1,3-benzodioxol-5-yl)-N-[(5-tert-butyl-2-phenylsulphanyl-2H-pyrazol-3-yl)-methyl]-propionamide |
| 166 | 1-[[2-(cyclohexylsulphanyl)-5-(trifluoromethyl)-2H-pyrazol-3-yl]-methyl]-3-(7-hydroxy-naphthalen-1-yl)-urea |
| 167 | 1-[[2-(cyclohexylsulphanyl)-5-(trifluoromethyl)-2H-pyrazol-3-yl]-methyl]-3-(1H-indazol-4-yl)-urea |
| 168 | 1-[[5-tert-butyl-2-(cyclohexylsulphanyl)-2H-pyrazol-3-yl]-methyl]-3-(2-methyl-quinolin-5-yl)-urea |
| 169 | N-[[2-(3-chlorophenyl)-5-(trifluoromethyl)-2H-[1,2,4]triazol-3-yl]-methyl]-2-(6-hydroxy-naphthalen-2-yl)-propionamide |
| 170 | 2-(1,3-benzodioxol-5-yl)-N-[[5-tert-butyl-2-(3-chlorophenyl)-2H-[1,2,4]triazol-3-yl]-methyl]-propionamide |
| 171 | 2-(1,3-benzodioxol-5-yl)-N-[[2-(3-chlorophenyl)-5-cyclopropyl-2H-[1,2,4]triazol-3-yl]-methyl]-propionamide |
| 172 | N-[[2-cyclohexyl-5-(trifluoromethyl)-2H-[1,2,4]triazol-3-yl]-methyl]-2-(2-methyl-quinolin-5-yl)-propionamide |
| 173 | 2-(1,3-benzodioxol-5-yl)-N-[[2-cyclohexyl-5-(trifluoromethyl)-2H-[1,2,4]triazol-3-yl]-methyl]-propionamide |

Mass spectrometric data are cited hereinafter by way of example for the following exemplary compounds:

| Exemplary compound | [M + H] |
| --- | --- |
| 2 | 462.1 |
| 6 | 462.4 |
| 10 | 515.3 |
| 11 | 440.3 |
| 12 | 440.0 |
| 13 | 454.3 |
| 14 | 454.3 |
| 15 | 468.3 |
| 24 | 446.4 |
| 25 | 434.2 |
| 26 | 461.3 |
| 27 | 447.3 |
| 35 | 448.1 |
| 37 | 448.1 |
| 40 | 436.4 |
| 42 | 464.3 |
| 43 | 480.2 |
| 45 | 479.3 |
| 49 | 462.3 |
| 50 | 474.4 |
| 57 | 462.3 |
| 58 | 474.2 |
| 63 | 447.3 |
| 64 | 459.2 |
| 65 | 473.2 |
| 67 | 487.2 |
| 68 | 459.2 |
| 69 | 465.3 |
| 70 | 447.3 |
| 71 | 447.2 |
| 72 | 458.9 |
| 75 | 447.3 |
| 77 | 448.3 |
| 78 | 423.3 |
| 79 | 423.3 |
| 83 | 438.4 |
| 84 | 452.6 |
| 88 | 434.3 |
| 96 | 452.1 |
| 97 | 451.9 |
| 101 | 449.3 |
| 102 | 461.2 |
| 107 | 434.6 |
| 108 | 434.5 |
| 109 | 434.2 |
| 110 | 446.2 |
| 111 | 434.2 |
| 112 | 434.2 |
| 113 | 434.2 |
| 174 | 435.9 |
| 175 | 419.4 |
| 176 | 407.7 |
| 177 | 441.9 |
| 178 | 431.8 |
| 179 | 469.5 |
| 180 | 485.4 |
| 181 | 429.3 |
| 182 | 458.3 |
| 183 | 424.6 |
| 184 | 438.0 |
| 185 | 425.6 |
| 186 | 422.7 |
| 187 | 463.1 |
| 188 | 440.8 |
| 189 | 492.2 |
| 190 | 489.9 |
| 191 | 526.1 |
| 192 | 448.3 |
| 193 | 454.0 |
| 194 | 453.2 |
| 195 | 465.9 |
| 196 | 462.3 |
| 197 | 476.3 |
| 198 | 475.2 |
| 199 | 408.1 |
| 200 | 480.3 |
| 201 | 441.3 |
| 202 | 476.0 |
| 203 | 425.1 |
| 204 | 444.1 |
| 205 | 469.8 |
| 206 | 462.1 |
| 207 | 446.2 |
| 208 | 464.2 |
| 210 | 448.3 |
| 211 | 476.3 |
| 212 | 488.2 |
| 213 | 493.2 |
| 216 | 408.0 |

Pharmacological Data

The affinity of the compounds according to the invention for the vanilloid receptor 1 (VR1/TRPV1 receptor) was determined as described hereinbefore (pharmacological methods I and II respectively).

The compounds according to the invention of the above-indicated formula (1) display outstanding affinity to the VR1/TRPV1 receptor (Table 1).

In Table 1 the abbreviations below have the following meanings:
Cap=capsaicin
AG=agonist
pAG=partial agonist
pH=after pH stimulus
NADA=N-arachidonoyl dopamine
NE=no effect
FTm=formalin test carried out on mice
CClm=Bennet model in mice The value after the "@" symbol indicates the concentration at which the inhibition (as a percentage) was respectively determined.

TABLE 1

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm | CClm |
| --- | --- | --- | --- | --- | --- | --- | --- | --- |
| 2 | | 6.6 | | | | | | |
| 6 | | 12.8 | | | | | | |
| 10 | | pAG (75.4) | 42% @ 10 µM | | pAG | 6% @ 2 µM | | |
| 11 | AG | pAG (3.5) | 36% @ 10 µM | | pAG | pAG | 0.1 iv FTm 61% | 0.1 iv CClm 77% |
| 12 | 135 | 77.9 | NE | 58% @ 2 µM | 18% @ 2 µM | | | |
| 13 | pAG (5.5) | pAG (6.4) | 49% @ 10 µM | pAG (4.3) | pAG | | 1 iv FTm 99% | 0.1 iv CClm 85% |
| 14 | AG | | | | | | | |
| 15 | AG | pAG (25) | pAG (412) | | pAG | | | |

TABLE 1-continued

| Compound according to Example | $K_i$ (rat) [nM] Cap | $K_i$ (human being) [nM] Cap | IC$_{50}$ (human being) hVR1 [nM], pH | $K_i$ (rat) [nM] NADA | $K_i$ (human being) [nM] NADA | IC$_{50}$ (human being) [nM], 45° C. | FTm | CClm |
|---|---|---|---|---|---|---|---|---|
| 24 | | 4 | NE | | | 686 | | |
| 25 | | pAG (5.5) | pAG | | | | | |
| 26 | | 21.5 | | | | | | |
| 27 | 11.2 | 1.1 | 13% @ 10 µM | | 0.008 | 297 | 1 po FTm 38% | |
| 31 | | pAG (2.4) | pAG | | | | | |
| 35 | | pAG (0.3) | pAG | | | pAG | | |
| 37 | | AG | | | | | | |
| 40 | pAG (8.4) | 4.2 | | | 1.1 | | 1 po FTm 45% | |
| 42 | | pAG (4.0) | | | | | | |
| 43 | | pAG (22.9) | | | | | | |
| 45 | pAG (14.7) | 15 | | AG | pAG (11.8) | | 1 po FTm 20% | |
| 49 | | AG | AG | | AG | AG | | |
| 50 | pAG (2.5) | pAG (1.3) | pAG | | | pAG | 0.1 iv FTm 56% | 0.1 iv CClm 83% |
| 57 | 4.2 | 1.6 | 13% @ 10 µM | | 0.10 | 25.6 | | |
| 58 | 7.6 | 0.7 | 4931 | | | 41% @ 2.5 µM | 1 po FTm 43% | |
| 63 | pAG (0.5) | 0.2 | 33% @ 10 µM | | | 9% @ 0.6 µM | | |
| 64 | 1 | 0.2 | NE | | 0.02 | 357 | 1 iv FTm 58% | 1 iv CClm 62% |
| 65 | | 0.3 | 23% @ 10 µM | | | 780 | | |
| 67 | | 5.2 | | | | | | |
| 68 | | 0.3 | 33% @ 10 µM | | 0.04 | 245 | | |
| 69 | pAG (0.9) | 0.2 | 13% @ 10 µM | | 0.004 | 26% @ 10 µM | 1 po FTm 1% | |
| 70 | | AG | AG | | | AG | | |
| 71 | | 18% @ 10 µM | NE | | 68.1 | 2712 | | |
| 72 | | 0.5 | | | | | | |
| 77 | 34.2 | 35.4 | 23% @ 10 µM | | | −17% @ 10 µM | 3 po FTm 78% | |
| 78 | | pAG (2.4) | | | | | | |
| 79 | 15.8 | 10.8 | 21% @ 10 µM | 39.1 | 12.6 | | 1 po FTm 44% | 1 po CClm 70% |
| 83 | | 50.7 | | | | 16% @ 2.5 µM | | |
| 84 | 181 | 51.6 | | | | 235 | | |
| 88 | | 0.9 | | | | | | |
| 96 | | pAG (7.3) | pAG | | | | | |
| 97 | | 4.9 | | | | 396 | | |
| 101 | | 0.5 | | | | 46% @ 2.5 µM | | |
| 102 | | 0.2 | | | | 48% @ 2.5 µM | | |
| 107 | | 22.4 | | | | | | |
| 108 | | 0.5 | | | | 375 | | |
| 109 | | pAG (0.2) | pAG | | pAG | pAG | | |
| 110 | | 0.4 | | | | 110 | | |
| 111 | | AG | AG | | AG | AG | | |
| 112 | 18.2 | 7.3 | | | pAG (6.4) | | | |
| 113 | | 70.7 | NE | | 33.3 | | | |
| 174 | | 75.8 | | | | | | |
| 175 | | 70.2 | | | | | | |
| 176 | | 34.0 | | | | | | |
| 177 | | 10.3 | | | | | | |
| 178 | | 38.4 | | | | | | |
| 179 | | 36.3 | | | | | | |
| 180 | | 41.0 | | | | | | |
| 181 | | 35.9 | | | | | | |
| 182 | | 32.8 | | | | | | |
| 183 | | 28.4 | | | | | | |
| 184 | | 66.2 | | | | | | |
| 185 | | pAG (39.7) | | | | | | |
| 186 | | 2.9 | | | | | | |
| 187 | | AG | | | | | | |
| 188 | | 5.9 | | | | | | |
| 189 | | 41.2 | | | | | | |
| 190 | | 30.4 | | | | | | |
| 191 | | pAG (0.6) | | | | | | |
| 192 | | 10.8 | | | | | | |
| 193 | | 1.6 | | | | | | |
| 194 | | 8.4 | | | | | | |
| 195 | | 6.8 | | | | | | |
| 196 | | AG | | | | | | |
| 197 | | 5.8 | | | | | | |
| 198 | | AG | | | | | | |
| 199 | | 33.5 | | | | | | |
| 200 | | 17.1 | | | | | | |
| 201 | | NE | | | | | | |
| 202 | | 13% @ 5 µM | | | | | | |
| 203 | | NE | | | | | | |
| 204 | | NE | | | | | | |
| 205 | | 0.8 | | | | | | |

TABLE 1-continued

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm | CClm |
|---|---|---|---|---|---|---|---|---|
| 206 | | pAG (0.4) | | | | | | |
| 207 | | pAG (2.4) | | | | 14% @ 10 µM | | |
| 208 | | 62.6 | | | | 298 | | |
| 210 | | 8.1 | | | | | | |
| 211 | | 2.7 | | | | 154 | | |
| 212 | | 8.3 | | | | 626 | | |
| 213 | | 0.07 | | | | 264 | | |
| 216 | | 54.0 | | | | 2123 | | |

The invention claimed is:

1. A compound corresponding to formula (I)

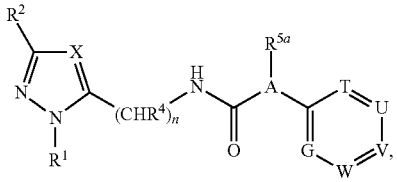

(I)

wherein

X represents $CR^3$, wherein $R^3$ represents H; $C_{1-10}$ alkyl, saturated or unsaturated, branched or unbranched, unsubstituted or mono- or polysubstituted;

A represents N or $CR^{5b}$, n represents 1, 2, 3 or 4;

$R^0$ represents $C_{1-10}$ alkyl, saturated or unsaturated, branched or unbranched, unsubstituted or mono- or polysubstituted; $C_{3-10}$ cycloalkyl or heterocyclyl, respectively saturated or unsaturated, unsubstituted or mono- or polysubstituted; aryl or heteroaryl, respectively unsubstituted or mono- or polysubstituted; $C_{3-10}$ cycloalkyl or heterocyclyl bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted;

$R^1$ represents H; $C_{1-10}$ alkyl, saturated or unsaturated, branched or unbranched, unsubstituted or mono- or polysubstituted; $C_{3-10}$ cycloalkyl$^1$ or heterocyclyl$^1$, respectively saturated or unsaturated, unsubstituted or mono- or polysubstituted; aryl or heteroaryl, respectively unsubstituted or mono- or polysubstituted; $C_{3-10}$ cycloalkyl$^1$ or heterocyclyl$^1$ bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; $C(=O)$—$R^0$; $C(=O)$—OH; $C(=O)$—$OR^0$; $C(=O)$—$NHR^0$; $C(=O)$—$N(R^0)_2$; OH; O—$R^0$; SH; S—$R^0$; $S(=O)_2$—$R^0$; $S(=O)_2$—$OR^0$; $S(=O)_2$—$NHR^0$; $S(=O)_2$—$N(R^0)_2$; $NH_2$; $NHR^0$; $N(R^0)_2$; NH—$S(=O)_2$—$R^0$; $N(R^0)(S(=O)_2$—$R^0)$; or $SCl_3$;

$R^2$ represents H; $R^0$; F; Cl; Br; I; CN; $NO_2$; OH; SH; $CF_3$; $CF_2H$; $CFH_2$; $CF_2Cl$; $CFCl_2$; $CH_2CF_3$; $OCF_3$; $OCF_2H$; $OCFH_2$; $OCF_2Cl$; $OCFCl_2$; $SCF_3$; $SCF_2H$; $SCFH_2$; $SCF_2Cl$; $SCFCl_2$; $S(=O)_2$—$CF_3$; $S(=O)_2$—$CF_2H$; $S(=O)_2$—$CFH_2$; or $SF_5$;

$R^4$ represents H; F; Cl; Br; I; OH; $C_{1-10}$ alkyl, saturated or unsaturated, branched or unbranched, unsubstituted or mono- or polysubstituted;

$R^{5a}$ represents H; OH; $C_{1-10}$ alkyl, saturated or unsaturated, branched or unbranched, unsubstituted or mono- or polysubstituted;

$R^{5b}$ represents H or $R^0$; or $R^{5a}$ and $R^{5b}$ together with the carbon atom connecting them form a $C_{3-10}$ cycloalkyl or a heterocyclyl, respectively saturated or unsaturated, unsubstituted or mono- or polysubstituted;

T represents N or $CR^6$;

U represents N or $CR^7$;

V represents N or $CR^8$;

W represents N or $CR^9$; and

G represents N or $CR^{10}$;

wherein at most three of the residues T, U, V, W and G may represent N simultaneously, $R^6$ and $R^7$ together and/or $R^8$ and $R^9$ together; or $R^7$ and $R^8$ together and/or $R^9$ and $R^{10}$ together; or $R^6$ and $R^7$ together and $R^9$ and $R^{10}$ together;

in pairs, in each case independently of one another, together with the carbon atoms connecting them, form a $C_{3-10}$ cycloalkyl or heterocyclyl, respectively saturated or unsaturated, unsubstituted or mono- or polysubstituted, if appropriate condensed with aryl or heteroaryl, respectively unsubstituted or mono- or polysubstituted; or an aryl or heteroaryl, respectively unsubstituted or mono- or polysubstituted, if appropriate condensed with $C_{3-10}$-cycloalkyl or heterocyclyl, respectively saturated or unsaturated, unsubstituted or mono- or polyunsubstituted; and the respective remaining substituents of $R^6$, $R^7$, $R^8$, $R^9$ and $R^{10}$ each independently of one another represent H; F; Cl; Br; I; $NO_2$; CN; $CF_3$; $CF_2H$; $CFH_2$; $CF_2Cl$; $CFCl_2$; $R^0$; $C(=O)H$; $C(=O)R^0$; $CO_2H$; $C(=O)OR^0$; $CONH_2$; $C(=O)NHR^0$; $C(=O)N(R^0)_2$; OH; $OCF_3$; $OCF_2H$; $OCFH_2$; $OCF_2Cl$; $OCFCl_2$; $OR^0$; O—$C(=O)$—$R^0$; O—$C(=O)$—O—$R^0$; O—$(C=O)$—NH—$R^0$; O—$C(=O)$—$N(R^0)_2$; O—$S(=O)_2$—$R^0$; O—$S(=O)_2OH$; O—$S(=O)_2OR^0$; O—$S(=O)_2NH_2$; O—$S(=O)_2NHR^0$; O—$S(=O)_2N(R^0)_2$; $NH_2$; NH—$R^0$; $N(R^0)_2$; NH—$C(=O)$—$R^0$; NH—$C(=O)$—O—$R^0$; NH—$C(=O)$—$NH_2$; NH—$C(=O)$—NH—$R^0$; NH—$C$ (=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted alkyl", "substituted heterocyclyl" and "substituted cycloalkyl" relate, with respect to the corresponding residues, to the substitution of one or more hydrogen atoms each independently of one another by F; Cl; Br; I; NO₂; CN; =O; =NH; =N(OH); =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; —(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in which "substituted cycloalkyl¹" and "substituted heterocyclyl¹" relate, with respect to the corresponding residues, to the substitution of one or more hydrogen atoms each independently of one another by F; Cl; Br; I; NO₂; CN; =O; =C(NH₂)₂; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂; and in which "aryl substituted" and "heteroaryl substituted" relate, with respect to the corresponding residues, to the substitution of one or more hydrogen atoms each independently of one another by F; Cl; Br; I; NO₂; CN; CF₃; CF₂H; CFH₂; CF₂Cl; CFCl₂; R⁰; C(=O)H; C(=O)R⁰; CO₂H; C(=O)OR⁰; CONH₂; C(=O)NHR⁰; C(=O)N(R⁰)₂; OH; OCF₃; OCF₂H; OCFH₂; OCF₂Cl; OCFCl₂; OR⁰; O—C(=O)—R⁰; O—C(=O)—O—R⁰; O—(C=O)—NH—R⁰; O—C(=O)—N(R⁰)₂; O—S(=O)₂—R⁰; O—S(=O)₂OH; O—S(=O)₂OR⁰; O—S(=O)₂NH₂; O—S(=O)₂NHR⁰; O—S(=O)₂N(R⁰)₂; NH₂; NH—R⁰; N(R⁰)₂; NH—C(=O)—R⁰; NH—C(=O)—O—R⁰; NH—C(=O)—NH₂; NH—C(=O)—NH—R⁰; NH—C(=O)—N(R⁰)₂; NR⁰—C(=O)—R⁰; NR⁰—C(=O)—O—R⁰; NR⁰—C(=O)—NH₂; NR⁰—C(=O)—NH—R⁰; NR⁰—C(=O)—N(R⁰)₂; NH—S(=O)₂OH; NH—S(=O)₂R⁰; NH—S(=O)₂OR⁰; NH—S(=O)₂NH₂; NH—S(=O)₂NHR⁰; NH—S(=O)₂N(R⁰)₂; NR⁰—S(=O)₂OH; NR⁰—S(=O)₂R⁰; NR⁰—S(=O)₂OR⁰; NR⁰—S(=O)₂NH₂; NR⁰—S(=O)₂NHR⁰; NR⁰—S(=O)₂N(R⁰)₂; SH; SCF₃; SCF₂H; SCFH₂; SCF₂Cl; SCFCl₂; SR⁰; S(=O)R⁰; S(=O)₂R⁰; S(=O)₂OH; S(=O)₂OR⁰; S(=O)₂NH₂; S(=O)₂NHR⁰; or S(=O)₂N(R⁰)₂;

in the form of free compounds; tautomers; N-oxides; a racemate; an enantiomer, a diastereomer, a mixture of enantiomers or diastereomers; or in the form of a salt of a physiologically compatible acid or base.

2. A compound according to claim 1, wherein $R^4$ represents H; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

A represents N or $CR^{5b}$;

$R^{5a}$ represents H; OH; $C_{1-10}$ alkyl, saturated or unsaturated, branched or unbranched, unsubstituted or mono- or polysubstituted with one or more substituents each selected independently of one another from the group consisting of F, Cl, Br; I, OH and O—$C_{1-4}$ alkyl;

$R^{5b}$ represents H; $C_{1-10}$ alkyl, saturated or unsaturated, branched or unbranched, unsubstituted or mono- or polysubstituted with one or more substituents each selected independently of one another from the group consisting of F, Cl, Br, I, OH and O—$C_{1-4}$ alkyl; $C_{3-10}$ cycloalkyl or heterocyclyl, respectively saturated or unsaturated, unsubstituted or mono- or polysubstituted with one or more substituents each selected independently of one another from the group consisting of F, Cl, Br, I, OH, =O and O—$C_{1-4}$ alkyl; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br, I, OH, =O and O—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; or aryl, heteroaryl, respectively unsubstituted or mono- or polysubstituted with one or more substituents each selected independently of one another from the group consisting of F, Cl, Br, I, NO₂, CN, OH, O—$C_{1-4}$ alkyl, OCF₃, $C_{1-4}$ alkyl, C(=O)—OH, CF₃, NH₂, NH($C_{1-4}$ alkyl), N($C_{1-4}$ alkyl)₂, SH, S—$C_{1-4}$ alkyl, SCF₃, S(=O)₂OH and NH—S(=O)₂—$C_{1-4}$ alkyl; or aryl or heteroaryl bridged via $C_{1-8}$ alkyl, respectively unsubstituted or mono- or polysubstituted with one or more substituents each selected independently of one another from the group consisting of F, Cl, Br, I, NO₂, CN, OH, O—$C_{1-4}$ alkyl, OCF₃, $C_{1-4}$ alkyl, C(=O)—OH, CF₃, NH₂, NH($C_{1-4}$ alkyl), N($C_{1-4}$ alkyl)₂, SH, S—$C_{1-4}$ alkyl, SCF₃, S(=O)₂OH and NH—S(=O)₂—$C_{1-4}$ alkyl, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; or $R^{5a}$ and $R^{5b}$ together with the carbon atom connecting them form a $C_{3-10}$ cycloalkyl or a heterocyclyl, respectively saturated or unsaturated, unsubstituted or mono- or polysubstituted with one or more substituents each selected independently of one another from the group consisting of F, Cl, Br, I, OH, =O and O—$C_{1-4}$ alkyl.

3. A compound according to claim 1, wherein
$R^4$ represents H; methyl; ethyl; n-propyl; or isopropyl;
A represents N or $CR^{5b}$;
$R^{5a}$ represents H or $CH_3$,
$R^{5b}$ represents H; or $C_{1-4}$ alkyl, saturated or unsaturated, branched or unbranched, unsubstituted; $C_{3-10}$ cycloalkyl, saturated or unsaturated, unsubstituted; or phenyl or benzyl, in each case unsubstituted or mono- or polysubstituted with one or more substituents each selected independently of one another from the group consisting of F, Cl, Br, I, $CF_3$, O—$C_{1-4}$ alkyl, $OCF_3$ and $C_{1-4}$ alkyl, or
$R^{5a}$ and $R^{5b}$ together with the carbon atom connecting them form a $C_{3-10}$ cycloalkyl, saturated or unsaturated, unsubstituted or mono- or polysubstituted with one or more substituents each selected independently of one another from the group consisting of F, Cl, Br, I, OH, =O and O—$C_{1-4}$ alkyl.

4. A compound according to claim 1, wherein
$R^1$ represents substructure (T1)

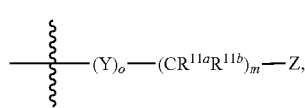

(T1)

in which
Y represents C(=O), O, S, $S(=O)_2$, NH—C(=O) or $NR^{12}$, wherein
$R^{12}$ represents H; $C_{1-8}$ alkyl or $S(=O)_2$—$C_{1-8}$ alkyl, in which $C_{1-8}$ alkyl can be respectively saturated or unsaturated, branched or unbranched, unsubstituted or mono- or polysubstituted with one or more substituents each selected independently of one another from the group consisting of F, Cl, Br, I, OH, O—$C_{1-4}$ alkyl, $OCF_3$, $NH_2$, NH—$C_{1-4}$ alkyl and $N(C_{1-4}$ alkyl$)_2$;
o represents 0 or 1,
$R^{11a}$ and $R^{11b}$ each independently of one another represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, $N(C_{1-4}$ alkyl$)_2$, in which $C_{1-4}$ alkyl can be respectively saturated or unsaturated, branched or unbranched, unsubstituted or mono- or polysubstituted with one or more substituents each selected independently of one another from the group consisting of F, Cl, Br, I, O—$C_{1-4}$ alkyl, OH and $OCF_3$;
on the condition that if $R^{11a}$ and $R^{11b}$ are bound to the same carbon atom, only one of $R^{11a}$ and $R^{11b}$ can represent OH; $OCF_3$; $NH_2$; O—$C_{1-4}$ alkyl, NH—$C_{1-4}$ alkyl or $N(C_{1-4}$ alkyl$)_2$;
m represents 0, 1, 2, 3 or 4; and
Z represents $C_{1-4}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, NH($C_{1-4}$ alkyl), $N(C_{1-4}$ alkyl$)_2$, SH, S—$C_{1-4}$ alkyl, $SCF_3$ and $S(=O)_2OH$; $C_{3-10}$ cycloalkyl[1] or heterocyclyl[1], respectively saturated or unsaturated, unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, SH, S—$C_{1-4}$ alkyl, $SCF_3$, $S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), $N(C_{1-4}$ alkyl$)_2$, SH, S—$C_{1-4}$ alkyl, $SCF_3$ and $S(=O)_2OH$; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), $N(C_{1-4}$ alkyl$)_2$, SH, S—$C_{1-4}$ alkyl, $SCF_3$, $S(=O)_2OH$, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), $N(C_{1-4}$ alkyl$)_2$, SH, S—$C_{1-4}$ alkyl, $SCF_3$ and $S(=O)_2OH$.

5. A compound according to claim 4, wherein
Y represents C(=O), O, S, $S(=O)_2$, NH—C(=O) or $NR^{12}$, wherein
$R^{12}$ represents H; methyl; ethyl; n-propyl; isopropyl; n-butyl; sec.-butyl; tert.-butyl; $S(=O)_2$-methyl; $S(=O)_2$-ethyl;
o represents 0 or 1;
$R^{11a}$ and $R^{11b}$ each independently of one another represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; N(methyl)$_2$; NH-ethyl; N(ethyl)$_2$; or N(methyl)(ethyl);
on the condition that if $R^{11a}$ and $R^{11b}$ are bound to the same carbon atom, only one of $R^{11a}$ and $R^{11b}$ can represent OH; $OCF_3$; O-methyl; O-ethyl; O—$(CH_2)_2$—O—$CH_3$; O—$(CH_2)_2$—OH; $NH_2$; NH-methyl; N(methyl)$_2$; NH-ethyl; N(ethyl)$_2$; or N(methyl)(ethyl);
m represents 0, 1 or 2; and
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, =O, O—$C_{1-4}$ alkyl, $OCF_3$, C(=O)—OH and $CF_3$; phenyl, naphthyl, furyl, pyridyl or thienyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), $N(C_{1-4}$ alkyl$)_2$, SH, S—$C_{1-8}$ alkyl, $SCF_3$, benzyl and phenyl, wherein benzyl and phenyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), $N(C_{1-4}$ alkyl$)_2$, SH, S—$C_{1-4}$ alkyl and $SCF_3$; $C_{3-10}$ cycloalkyl[1] or heterocyclyl[1], respectively saturated or unsaturated, unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, benzyl, phenyl and pyridyl, wherein benzyl, phenyl and pyridyl can be respectively unsubstituted or mono- or polysubstituted with one or more substituents selected independently of one another from the group consisting of F, Cl, Br, I, CN, OH, O—$C_{1-4}$ alkyl, $OCF_3$, $C_{1-4}$ alkyl, $CF_3$, $NH_2$, $NH(C_{1-4}$ alkyl), $N(C_{1-4}$ alkyl)$_2$, SH, S—$C_{1-4}$ alkyl and $SCF_3$.

6. A compound according to claim 1, wherein
$R^2$ represents H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently of one another from the group consisting of F, Cl, Br, I, $NO_2$, CN, OH, =O, O—$C_{1-4}$ alkyl, $OCF_3$, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and S(=O)$_2$OH; $C_{3-10}$ cycloalkyl or heterocyclyl, respectively saturated or unsaturated, unsubstituted or mono- or polysubstituted with one or more substituents selected independently of one another from the group consisting of F, Cl, Br, I, OH, =O, $C_{1-4}$ alkyl, O—$C_{1-4}$ alkyl, $OCF_3$, C(=O)—OH and $CF_3$; or $C_{3-10}$ cycloalkyl or heterocyclyl bridged via $C_{1-8}$ alkyl, respectively saturated or unsaturated, unsubstituted or mono- or polysubstituted with one or more substituents each selected independently of one another from the group consisting of F, Cl, Br, I, OH, =O, $C_{1-4}$ alkyl, O—$C_{1-4}$ alkyl, $OCF_3$, C(=O)—OH and $CF_3$, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl; aryl or heteroaryl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and S(=O)$_2$OH; or aryl or heteroaryl bridged via $C_{1-8}$ alkyl, respectively unsubstituted or mono- or polysubstituted with one or more substituents each selected independently of one another from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently of one another from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, $NH(C_{1-4}$ alkyl), $N(C_{1-4}$ alkyl)$_2$, SH, S—$C_{1-4}$ alkyl, $SCF_3$ and S(=O)$_2$OH, wherein the alkyl chain can be respectively branched or unbranched, saturated or unsaturated, unsubstituted, mono- or polysubstituted with one or more substituents each selected independently of one another from the group consisting of F, Cl, Br, I, OH, =O and O—$C_{1-4}$ alkyl.

7. A compound according to claim 1, wherein in formula (I), the substructure (T2)

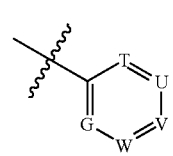

(T2)

represents one of the substructures (T2a), (T2b), (T2c) or (T2d)

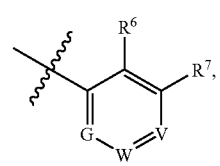

(T2a)

(T2b)

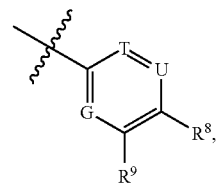

(T2c)

(T2d)

in which
in the substructure (T2a) $R^6$ and $R^7$ together;
in the substructure (T2b) $R^7$ and $R^8$ together;
in the substructure (T2c) $R^8$ and $R^9$ together;
in the substructure (T2d) $R^9$ and $R^{10}$ together;
in pairs, in each case independently of one another, together with the carbon atoms connecting them, form a $C_{3-10}$-cycloalkyl or heterocyclyl, respectively saturated or unsaturated, unsubstituted or mono- or polysubstituted with one or more substituents each selected independently of one another from the group consisting of =O, =N(OH), =NH, F, Cl, Br, I, $C_{1-4}$ alkyl, O—$C_{1-4}$ alkyl, $CF_3$, $OCF_3$, OH, SH, $NH_2$, NH—$C_{1-4}$ alkyl, $N(C_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$, wherein C$_{3-10}$-cycloalkyl or heterocyclyl optionally may be condensed in each case with aryl or heteroaryl, respectively unsubstituted or mono- or polysubstituted with one or more substituents each selected independently of one another from the group consisting of F, Cl, Br, I, C$_{1-4}$ alkyl, O—C$_{1-4}$ alkyl, CF$_3$, OCF$_3$, OH, SH, NH$_2$, NH—C$_{1-4}$ alkyl, N(C$_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$; or form aryl or heteroaryl, respectively unsubstituted or mono- or polysubstituted with one or more substituents each selected independently of one another from the group consisting of C$_{1-4}$ alkyl, O—C$_{1-4}$ alkyl, F, Cl, Br, I, CF$_3$, OCF$_3$, OH, SH, NH$_2$, NH—C$_{1-4}$ alkyl, N(C$_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$, wherein aryl or heteroaryl optionally may be condensed in each case with C$_{3-10}$ cycloalkyl or heterocyclyl, respectively saturated or unsaturated, unsubstituted or mono- or poly-substituted with one or more substituents each selected independently of one another from the group consisting of =O, =N(OH), =NH, F, Cl, Br, I, C$_{1-4}$ alkyl, O—C$_{1-4}$ alkyl, CF$_3$, OCF$_3$, OH, SH, NH$_2$, NH—C$_{1-4}$ alkyl, N(C$_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$; and wherein up to three of the remaining residues T, U, V, W or G optionally may represent N simultaneously and the remaining substituents R$^6$, R$^7$, R$^8$, R$^9$ and R$^{10}$ are each selected independently of one another from the group consisting of H, C$_{1-4}$ alkyl, O—C$_{1-4}$ alkyl, F, Cl, Br, I, CF$_3$, OCF$_3$, OH, SH, NH$_2$, NH—C$_{1-4}$ alkyl, N(C$_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$.

8. A compound according to claim 1, wherein in formula (I), the substructure (T2)

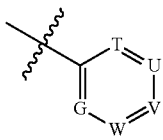

(T2)

(a1) represents one of the substructures (T3a) or (T3b)

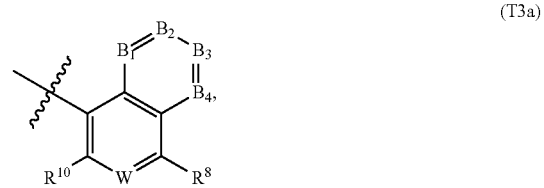

(T3a)

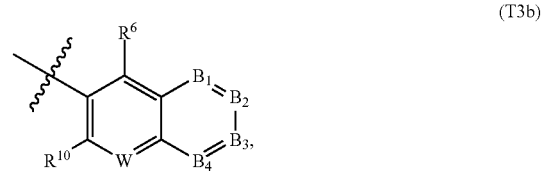

(T3b)

in which
W represents N or CR$^9$;
B$_1$ in each case represents N or CR$^{100a}$;
B$_2$ in each case represents N or CR$^{100b}$;
B$_3$ in each case represents N or CR$^{100c}$;
B$_4$ in each case represents N or CR$^{100d}$;
wherein in each case at most two of the residues B$_1$, B$_2$, B$_3$ and B$_4$ are able to represent N simultaneously;
R$^{100a}$, R$^{100b}$, R$^{100c}$ and R$^{100d}$ are each selected independently of one another from the group consisting of H, C$_{1-4}$ alkyl, O—C$_{1-4}$ alkyl, —O—C$_{1-4}$ alkyl-O—, F, Cl, Br, I, CF$_3$, OCF$_3$, OH, SH, NH$_2$, NH—C$_{1-4}$ alkyl, N(C$_{1-4}$ alkyl)$_2$, NH—SO$_2$—C$_{1-4}$ alkyl, SCF$_3$ and phenyl, unsubstituted or mono- or polysubstituted with one or more substituents each selected independently of one another from the group consisting of F, Cl, Br, I, C$_{1-4}$ alkyl, O—C$_{1-4}$ alkyl, CF$_3$ and OCF$_3$; and
the remaining substituents R$^6$, R$^8$, R$^9$ and R$^{10}$ each independently of one another represent H, OH, C$_{1-4}$ alkyl, O—C$_{1-4}$ alkyl, F, Cl, Br, I, CF$_3$, OCF$_3$, OH, SH, NH$_2$ or SCF$_3$; or
(a2) represents one of the substructures (T3c) or (T3d)

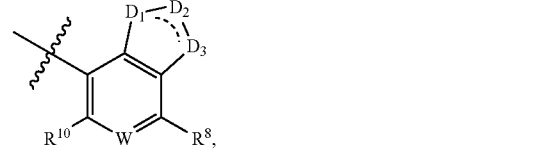

(T3c)

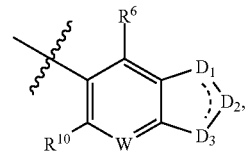

(T3d)

in which
W represents N or CR$^9$;
D$_1$ in each case represents N, N—R$^{101d}$, O, S or CR$^{101a}$ or CH—R$^{101a}$;
D$_2$ in each case represents N, N—R$^{101e}$, O, S or CR$^{101b}$ or CH—R$^{101b}$;
D$_3$ in each case represents N, N—R$^{101f}$, O, S or CR$^{101c}$ or CH—R$^{101c}$;
in each case represents the presence of precisely one double bond between D$_1$ and D$_2$ or between D$_2$ and D$_3$, wherein at most one of the residues $D_1$, $D_2$ and $D_3$ optionally may represent O, S, or N—$R^{101d\text{-}f}$ and in each case at most two of the residues $D_1$, $D_2$ and $D_3$ optionally may simultaneously represent N and at least one of the residues $D_1$, $D_2$ and $D_3$ must represent $CR^{101a}$, $CR^{101b}$ or $CR^{101c}$ if one of the remaining residues $D_1$, $D_2$ or $D_3$ represents O or S;

$R^{101a}$, $R^{101b}$ and $R^{101c}$ are each selected independently of one another from the group consisting of H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, $N(C_{1-4}$ alkyl$)_2$, NH—$SO_2$—$C_{1-4}$ alkyl, $SCF_3$, and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and may also represent =O, =NH or =N(OH) in the groups $CR^{101a}$, $CR^{101b}$ and $CR^{101c}$;

$R^{101d}$, $R^{101e}$, $R^{101f}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and the remaining substituents $R^6$, $R^8$, $R^9$ and $R^{10}$ each independently of one another represent H, OH, $C_{1-4}$ alkyl, O—$C_{1-4}$ alkyl, F, Cl, Br, I, $CF_3$, $OCF_3$, OH, SH, $NH_2$ or $SCF_3$; or (a3) represents one of the substructures (T3e) or (T3f)

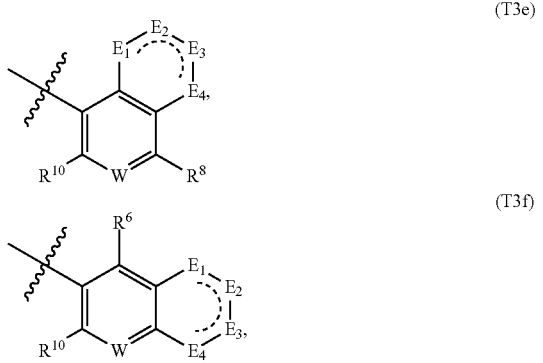

(T3e)

(T3f)

in which

W represents N or $CR^9$;

$E_1$ in each case represents N, N—$R^{102e}$, O, S, $CR^{102a}$, or CH—$R^{102a}$;

$E_2$ in each case represents N, N—$R^{102f}$, O, S, $CR^{102b}$, or CH—$R^{102b}$;

$E_3$ in each case represents N, N—$R^{102g}$, O, S, $CR^{102c}$, or CH—$R^{102c}$;

$E_4$ in each case represents N, N—$R^{102h}$, O, S, $CR^{102d}$, or CH—$R^{102d}$;

in each case represents the presence of precisely one double bond between $E_1$ and $E_2$ or between $E_2$ and $E_3$ or between $E_3$ and $E_4$; or represents the absence of a double bond, i.e. represents a single bond between $E_1$ and $E_2$ and between $E_2$ and $E_3$ and between $E_3$ and $E_4$; wherein it is only possible in each case for two of the residues $E_1$, $E_2$, $E_3$ and $E_4$ simultaneously each independently of one another to represent N, N—$R^{102e\text{-}h}$, O or S, on the condition that that if two of the residues $E_1$, $E_2$, $E_3$ and $E_4$ represent O or S, these are not mutually adjacent;

$R^{102a}$, $R^{102b}$, $R^{102c}$ and $R^{102d}$ are each selected independently of one another from the group consisting of H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, $N(C_{1-4}$ alkyl$)_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and may also represent =O, =NH or =N(OH) in the groups $CR^{103a}$, $CR^{102b}$, $CR^{102c}$ and $CR^{101d}$;

$R^{102e}$, $R^{102f}$, $R^{102g}$, $R^{102h}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and the remaining substituents $R^6$, $R^8$, $R^9$ and $R^{10}$ each independently of one another represent H, OH, $C_{1-4}$ alkyl, O—$C_{1-4}$ alkyl, F, Cl, Br, I, $CF_3$, $OCF_3$, OH, SH, $NH_2$ or $SCF_3$; or (a4) represents one of the substructures (T3g) or (T3h)

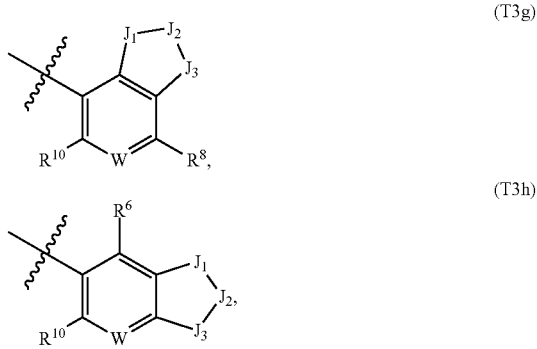

(T3g)

(T3h)

in which

W represents N or $CR^9$;

$J_1$ in each case represents N—$R^{103d}$, O, S, or $C(R^{103a})_2$, $J_2$ in each case represents N—$R^{103e}$, O, S, or $C(R^{103b})_2$, $J_3$ in each case represents N—$R^{103f}$, O, S, or $C(R^{103c})_2$;

wherein it is only possible in each case for two of the residues $J_1$, $J_2$ and $J_3$ simultaneously each independently of one another to represent N—$R^{103d\text{-}f}$, O or S, on the condition that that if two of the residues $J_1$, $J_2$ and $J_3$ represent O or S, these are not mutually adjacent;

$R^{103a}$, $R^{103b}$ and $R^{103c}$ are each selected independently of one another from the group consisting of H, $C_{1-4}$ alkyl, =O; =NH; =N(OH); O—$C_{1-4}$ alkyl, F, Cl, Br, I, $CF_3$, $OCF_3$, OH, SH, $NH_2$, NH—$C_{1-4}$ alkyl, $N(C_{1-4}$ alkyl$)_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;

$R^{103d}$, $R^{103e}$ and $R^{103f}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$;

the remaining substituents $R^6$, $R^8$, $R^9$ and $R^{10}$ each independently of one another represent H, OH, $C_{1-4}$ alkyl, O—$C_{1-4}$ alkyl, F, Cl, Br, I, $CF_3$, $OCF_3$, OH, SH, $NH_2$ or $SCF_3$; or (a5) represents one of the substructures (T3i) or (T3j)

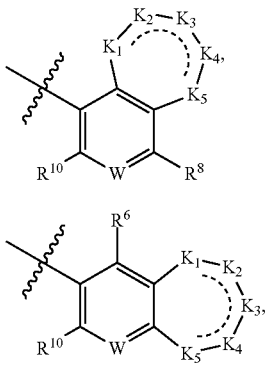

in which
W represents N or $CR^9$;
$K_1$ in each case represents N, N—$R^{104f}$, O, S, $CR^{104a}$, or CH—$R^{104a}$;
$K_2$ in each case represents N, N—$R^{104g}$, O, S, $CR^{104b}$ or CH—$R^{104b}$;
$K_3$ in each case represents N, N—$R^{104h}$, O, S, $CR^{104c}$ or CH—$R^{104c}$;
$K_4$ in each case represents N, N—$R^{104i}$, O, S, $CR^{104d}$ or CH—$R^{104d}$;
$K_5$ in each case represents N, N—$R^{104j}$, O, S, $CR^{104e}$ or CH—$R^{104e}$;
  in each case represents the presence of precisely one double bond between $K_1$ and $K_2$ or between $K_2$ and $K_3$ or between $K_3$ and $K_4$ or between $K_4$ and $K_5$; or represents the absence of a double bond, i.e. represents a single bond between $K_1$ and $K_2$ and between $K_2$ and $K_3$ and between $K_3$ and $K_4$ and between $K_4$ and $K_5$; wherein it is only possible in each case for two of the residues $K_1$, $K_2$, $K_3$, $K_4$ and $K_5$ simultaneously each independently of one another to represent N, N—$R^{104f}$, O or S; on the condition that that if two of the residues $K_1$, $K_2$, $K_3$, $K_4$ and $K_5$ represent O or S, these are not mutually adjacent;
$R^{104a}$, $R^{104b}$, $R^{104c}$, $R^{104d}$ and $R^{104e}$ are each selected independently of one another from the group consisting of H, $C_{1-4}$ alkyl, O—$C_{1-4}$ alkyl, F, Cl, Br, I, $CF_3$, $OCF_3$, OH, SH, $NH_2$, NH—$C_{1-4}$ alkyl, $N(C_{1-4}$ alkyl$)_2$, NH—$SO_2$—$C_{1-4}$ alkyl, $SCF_3$ and phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and may also represent =O, =NH or =N(OH) in the groups $CR^{104a}$, $CR^{104b}$, $CR^{104c}$, $CR^{104d}$ and $CR^{101e}$;
$R^{104f}$, $R^{104g}$, $R^{104h}$, $R^{104i}$ and $R^{104j}$ each independently of one another represent H, $C_{1-4}$ alkyl, $SO_2$—$C_{1-4}$ alkyl or phenyl, unsubstituted or mono- or polysubstituted with one or more substituents each selected independently of one another from the group consisting of F, Cl, Br, I, $C_{1-4}$ alkyl, O—$C_{1-4}$ alkyl, $CF_3$ and $OCF_3$; and
the remaining substituents $R^6$, $R^8$, $R^9$ and $R^{10}$ each independently of one another represent H, OH, $C_{1-4}$ alkyl, O—$C_{1-4}$ alkyl, F, Cl, Br, I, $CF_3$, $OCF_3$, OH, SH, $NH_2$ or $SCF_3$.

9. A compound according to claim 1, corresponding to formula (If),

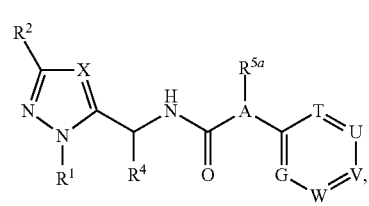

in which
X represents $CR^3$, wherein
  $R^3$ represents H; methyl; ethyl; n-propyl; isopropyl; n-butyl; sec.-butyl; tert.-butyl; or $CF_3$;
A represents N or $CR^{5b}$; wherein
  $R^{5b}$ represents H; methyl; ethyl; n-propyl; isopropyl; cyclopentyl; cyclohexyl; or phenyl or benzyl, in each case unsubstituted or mono-, di- or trisubstituted with one, two or three substituents each selected independently of one another from the group consisting of $C_{1-4}$ alkyl, O—$C_{1-4}$ alkyl, F, Cl, Br, I, $CF_3$ and $OCF_3$;
$R^1$ represents substructure (T1)

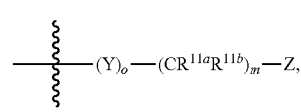

in which
Y represents C(=O), O, S, S(=O)$_2$, NH—C(=O) or $NR^{12}$, wherein
  $R^{12}$ represents H; methyl; ethyl; n-propyl; isopropyl; n-butyl; sec.-butyl; tert.-butyl; or S(=O)$_2$-methyl;
o represents 0 or 1;
$R^{11a}$ and $R^{11b}$ each independently of one another represent H; methyl; ethyl; n-propyl; isopropyl; n-butyl; sec.-butyl; or tert.-butyl;
m represents 0, 1 or 2; and
Z represents $C_{1-4}$ alkyl, saturated or unsaturated, branched or unbranched, unsubstituted or mono- or polysubstituted with one or more substituents each selected independently of one another from the group consisting of F, Cl, Br, I, OH, O—$C_{1-4}$ alkyl; $C_{3-10}$ cycloalkyl$^1$, saturated or unsaturated, morpholinyl, piperidinyl, 4-methylpiperazinyl, piperazinyl, respectively unsubstituted or mono- or polysubstituted with one or more substituents each selected independently of one another from the group consisting of F, Cl, Br, I, OH, O—$C_{1-4}$ alkyl and $C_{1-4}$ alkyl; phenyl or pyridyl, respectively unsubstituted or mono- or polysubstituted with one or more substituents each selected independently of one another from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$;
$R^2$ represents H; F; Cl; Br; I; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently of one another from the group consisting of $C_{1-4}$ alkyl, O—$C_{1-4}$ alkyl, F, Cl, Br, I, $CF_3$ and $OCF_3$;

R⁴ represents H; methyl; ethyl; n-propyl; or isopropyl;
R⁵ᵃ represents H if A represents N; or
represents H; methyl; ethyl; n-propyl; isopropyl if A represents CR⁵ᵇ; or
R⁵ᵃ and R⁵ᵇ together with the carbon atom connecting them form a C₃₋₁₀ cycloalkyl, saturated or unsaturated, unsubstituted,
T represents CR⁶;
U represents CR⁷;
V represents CR⁸;
W represents N or CR⁹;
G represents CR¹⁰;
R⁶ and R⁷ together with the carbon atoms connecting them form a C₃₋₁₀-cycloalkyl, saturated or unsaturated, unsubstituted or mono- or disubstituted with OH, =O, =N(OH); or a phenyl, pyrrolidinyl, piperidinyl, morpholinyl, oxazolyl, oxazolidinyl, pyrrolyl, pyrazolyl, pyridyl, pyrimidinyl, pyrazinyl, imidazolyl, thiazolyl, triazolyl, dioxolanyl, dioxanyl, dioxepanyl, respectively unsubstituted or mono- or disubstituted with F, Cl, Br, I, CF₃, C₁₋₄ alkyl, O—C₁₋₄ alkyl, SO₂—C₁₋₄ alkyl, phenyl, NH₂, =O, NH—SO₂—C₁₋₄ alkyl; and
R⁸, R⁹ and R¹⁰ each independently of one another represent H, F. Cl, Br or OH; or
R⁷ and R⁸ together with the carbon atoms connecting them form a C₃₋₁₀-cycloalkyl, saturated or unsaturated, unsubstituted or mono- or disubstituted with OH, =O, =N(OH); or a phenyl, pyrrolidinyl, piperidinyl, morpholinyl, oxazolyl, oxazolidinyl, pyrrolyl, pyrazolyl, pyridyl, pyrimidinyl, pyrazinyl, imidazolyl, thiazolyl, triazolyl, dioxolanyl, dioxanyl, dioxepanyl, respectively unsubstituted or mono- or disubstituted with F, Cl, Br, I, CF₃, C₁₋₄ alkyl, O—C₁₋₄ alkyl, SO₂—C₁₋₄ alkyl, phenyl, NH₂, =O, NH—SO₂—C₁₋₄ alkyl; and
R⁶, R⁹ and R¹⁰ each independently of one another represent H, F, Cl, Br or OH.

10. A compound according to claim 1, selected from the group consisting of

1  N-((1-(3-chlorophenyl)-3-(trifluoromethyl)-1H-pyrazol-5-yl)methyl)-2-(2,3-dihydro-1H-inden-4-yl)propanamide;
2  N-((1-(3-chlorophenyl)-3-(trifluoromethyl)-1H-pyrazol-5-yl)methyl)-2-(5,6,7,8-tetrahydronaphthalen-1-yl)propanamide;
3  N-((1-(3-chlorophenyl)-3-(trifluoromethyl)-1H-pyrazol-5-yl)methyl)-2-(3-hydroxy-2,3-dihydro-1H-inden-5-yl)propanamide;
4  N-((1-(3-chlorophenyl)-3-(trifluoromethyl)-1H-pyrazol-5-yl)methyl)-2-(2-hydroxy-2,3-dihydro-1H-inden-5-yl)propanamide;
5  N-((1-(3-chlorophenyl)-3-(trifluoromethyl)-1H-pyrazol-5-yl)methyl)-2-(7-hydroxy-5,6,7,8-tetrahydronaphthalen-1-yl)propanamide;
6  N-((1-(3-chlorophenyl)-3-(trifluoromethyl)-1H-pyrazol-5-yl)methyl)-2-(3-oxo-2,3-dihydro-1H-inden-5-yl)propanamide;
7  (E)-N-((1-(3-chlorophenyl)-3-(trifluoromethyl)-1H-pyrazol-5-yl)methyl)-2-(3-(hydroxyimino)-2,3-dihydro-1H-inden-5-yl)propanamide;
8  N-((1-(3-chlorophenyl)-3-(trifluoromethyl)-1H-pyrazol-5-yl)methyl)-2-(indolin-5-yl)propanamide hydrochloride;
9  N-((1-(3-chlorophenyl)-3-(trifluoromethyl)-1H-pyrazol-5-yl)methyl)-2-(1-methylindolin-5-yl)propanamide;
10  N-((3-tert-butyl-1-(3-chlorophenyl)-1H-pyrazol-5-yl)methyl)-2-(1-(methylsulphonyl)indolin-5-yl)propanamide;
11  2-(Benzo[d][1,3]dioxol-5-yl)-N-((3-tert-butyl-1-(3-chlorophenyl)-1H-pyrazol-5-yl)methyl)propanamide;
12  N-((3-tert-butyl-1-(4-chlorophenyl)-1H-pyrazol-5-yl)methyl)-2-(2,3-dihydrobenzo[b][1,4]dioxin-6-yl)acetamide;
13  N-((3-tert-butyl-1-(3-chlorophenyl)-1H-pyrazol-5-yl)methyl)-2-(2,3-dihydrobenzo[b][1,4]dioxin-6-yl)propanamide;
14  N-((3-tert-butyl-1-(3-chlorophenyl)-1H-pyrazol-5-yl)methyl)-2-(2,3-dihydrobenzo[b][1,4]dioxin-5-yl)propanamide;
15  N-((3-tert-butyl-1-(3-chlorophenyl)-1H-pyrazol-5-yl)methyl)-2-(3,4-dihydro-2H-benzo[b][1,4]dioxepin-7-yl)propanamide;
16  N-((1-(3-chlorophenyl)-3-(trifluoromethyl)-1H-pyrazol-5-yl)methyl)-2-(1,2,3,4-tetrahydroquinolin-6-yl)propanamide hydrochloride;
17  N-((1-(3-chlorophenyl)-3-(trifluoromethyl)-1H-pyrazol-5-yl)methyl)-2-(1-methyl-1,2,3,4-tetrahydroquinolin-6-yl)propanamide;
18  N-((1-(3-chlorophenyl)-3-(trifluoromethyl)-1H-pyrazol-5-yl)methyl)-2-(1-(methylsulphonyl)-1,2,3,4-tetrahydroquinolin-6-yl)propanamide;
19  N-((1-(3-chlorophenyl)-3-(trifluoromethyl)-1H-pyrazol-5-yl)methyl)-2-(3,4-dihydro-2H-benzo[b][1,4]oxazin-7-yl)propanamide;
20  N-((1-(3-chlorophenyl)-3-(trifluoromethyl)-1H-pyrazol-5-yl)methyl)-2-(3,4-dihydro-2H-benzo[b][1,4]oxazin-6-yl)propanamide;
21  N-((1-(3-chlorophenyl)-3-(trifluoromethyl)-1H-pyrazol-5-yl)methyl)-2-(2-oxo-2,3-dihydrobenzo[d]oxazol-6-yl)propanamide;
22  N-((1-(3-chlorophenyl)-3-(trifluoromethyl)-1H-pyrazol-5-yl)methyl)-2-(2-oxo-1,2,3,4-tetrahydroquinolin-6-yl)propanamide;
23  N-((1-(3-chlorophenyl)-3-(trifluoromethyl)-1H-pyrazol-5-yl)methyl)-2-(3-oxo-3,4-dihydro-2H-benzo[b][1,4]oxazin-7-yl)propanamide;
24  N-((1-(3-chlorophenyl)-3-(trifluoromethyl)-1H-pyrazol-5-yl)methyl)-2-(1H-inden-7-yl)propanamide;
25  N-((3-tert-butyl-1-(3-chlorophenyl)-1H-pyrazol-5-yl)methyl)-2-(1H-indol-4-yl)propanamide;
26  N-((1-(3-chlorophenyl)-3-(trifluoromethyl)-1H-pyrazol-5-yl)methyl)-2-(1-methyl-1H-indol-4-yl)propanamide;
27  N-((1-(3-chlorophenyl)-3-(trifluoromethyl)-1H-pyrazol-5-yl)methyl)-2-(1H-indazol-4-yl)propanamide;
28  N-((1-(3-chlorophenyl)-3-(trifluoromethyl)-1H-pyrazol-5-yl)methyl)-2-(1-methyl-1H-indazol-4-yl)propanamide;
29  N-((1-(3-chlorophenyl)-3-(trifluoromethyl)-1H-pyrazol-5-yl)methyl)-2-(1-phenyl-1H-indazol-4-yl)propanamide;
30  2-(1H-benzo[d][1,2,3]triazol-4-yl)-N-((1-(3-chlorophenyl)-3-(trifluoromethyl)-1H-pyrazol-5-yl)methyl)propanamide;
31  N-((1-(3-chlorophenyl)-3-(trifluoromethyl)-1H-pyrazol-5-yl)methyl)-2-(1H-indol-5-yl)propanamide;
32  N-((1-(3-chlorophenyl)-3-(trifluoromethyl)-1H-pyrazol-5-yl)methyl)-2-(1-methyl-1H-indol-5-yl)propanamide;
33  2-(1H-benzo[d]imidazol-5-yl)-N-((1-(3-chlorophenyl)-3-(trifluoromethyl)-1H-pyrazol-5-yl)methyl)propanamide;

34 2-(2-amino-1H-benzo[d]imidazol-5-yl)-N-((1-(3-chlorophenyl)-3-(trifluoromethyl)-1H-pyrazol-5-yl)methyl)propanamide;
35 N-((1-(3-chlorophenyl)-3-(trifluoromethyl)-1H-pyrazol-5-yl)methyl)-2-(1H-indazol-5-yl)propanamide;
36 2-(benzo[d]oxazol-4-yl)-N-((1-(3-chlorophenyl)-3-(trifluoromethyl)-1H-pyrazol-5-yl)methyl)propanamide;
37 2-(benzo[d]oxazol-7-yl)-N-((1-(3-chlorophenyl)-3-(trifluoromethyl)-1H-pyrazol-5-yl)methyl)propanamide;
38 2-(benzo[d]thiazol-4-yl)-N-((1-(3-chlorophenyl)-3-(trifluoromethyl)-1H-pyrazol-5-yl)methyl)propanamide;
39 2-(benzo[d]thiazol-7-yl)-N-((1-(3-chlorophenyl)-3-(trifluoromethyl)-1H-pyrazol-5-yl)methyl)propanamide;
40 2-(benzo[d]oxazol-5-yl)-N-((3-tert-butyl-1-(3-chlorophenyl)-1H-pyrazol-5-yl)methyl)propanamide;
41 2-(benzo[d]oxazol-6-yl)-N-((3-tert-butyl-1-(3-chlorophenyl)-1H-pyrazol-5-yl)methyl)propanamide;
42 2-(benzo[d]thiazol-6-yl)-N-((1-(3-chlorophenyl)-3-(trifluoromethyl)-1H-pyrazol-5-yl)methyl)propanamide;
43 2-(2-aminobenzo[d]thiazol-6-yl)-N-((1-(3-chlorophenyl)-3-(trifluoromethyl)-1H-pyrazol-5-yl)methyl)propanamide;
44 N-((1-(3-chlorophenyl)-3-(trifluoromethyl)-1H-pyrazol-5-yl)methyl)-2-(2-(methylsulphonamido)benzo[d]thiazol-6-yl)propanamide;
45 N-((1-(3-chlorophenyl)-3-(trifluoromethyl)-1H-pyrazol-5-yl)methyl)-2-(2-methylbenzo[d]thiazol-6-yl)propanamide;
46 2-(benzo[d]thiazol-5-yl)-N-((1-(3-chlorophenyl)-3-(trifluoromethyl)-1H-pyrazol-5-yl)methyl)propanamide;
47 N-((3-tert-butyl-1-(3-chlorophenyl)-1H-pyrazol-5-yl)methyl)-2-(naphthalen-1-yl)propanamide;
48 N-((3-tert-butyl-1-(3-chlorophenyl)-1H-pyrazol-5-yl)methyl)-2-(naphthalen-2-yl)propanamide;
49 N-((3-tert-butyl-1-(3-chlorophenyl)-1H-pyrazol-5-yl)methyl)-2-(6-hydroxynaphthalen-2-yl)propanamide;
50 N-((1-(3-chlorophenyl)-3-(trifluoromethyl)-1H-pyrazol-5-yl)methyl)-2-(6-hydroxynaphthalen-2-yl)propanamide;
51 N-((1-(3-chlorophenyl)-3-(trifluoromethyl)-1H-pyrazol-5-yl)methyl)-2-(6-methoxynaphthalen-2-yl)propanamide,
52 N-((3-tert-butyl-1-methyl-1H-pyrazol-5-yl)methyl)-2-(7-hydroxynaphthalen-1-yl)propanamide;
53 N-((3-tert-butyl-1-hexyl-1H-pyrazol-5-yl)methyl)-2-(7-hydroxynaphthalen-1-yl)propanamide;
54 N-((3-tert-butyl-1-p-tolyl-1H-pyrazol-5-yl)methyl)-2-(7-hydroxynaphthalen-1-yl)propanamide;
55 N-((3-tert-butyl-1-(4-tert-butylphenyl)-1H-pyrazol-5-yl)methyl)-2-(7-hydroxynaphthalen-1-yl)propanamide;
56 N-((3-tert-butyl-1-(4-chlorophenyl)-1H-pyrazol-5-yl)methyl)-2-(7-hydroxynaphthalen-1-yl)propanamide;
57 N-((3-tert-butyl-1-(3-chlorophenyl)-1H-pyrazol-5-yl)methyl)-2-(7-hydroxynaphthalen-1-yl)propanamide;
58 N-((1-(3-chlorophenyl)-3-(trifluoromethyl)-1H-pyrazol-5-yl)methyl)-2-(7-hydroxynaphthalen-1-yl)propanamide;
59 N-((3-tert-butyl-1-(3-chloro-4-fluorophenyl)-1H-pyrazol-5-yl)methyl)-2-(7-hydroxynaphthalen-1-yl)propanamide;
60 N-((3-tert-butyl-1-cyclohexenyl-1H-pyrazol-5-yl)methyl)-2-(7-hydroxynaphthalen-1-yl)propanamide;
61 N-((3-tert-butyl-1-(3-chlorophenyl)-1H-pyrazol-5-yl)methyl)-2-(quinolin-8-yl)propanamide;
62 N-((3-tert-butyl-1-(3-chlorophenyl)-1H-pyrazol-5-yl)methyl)-2-(isoquinolin-8-yl)propanamide;
63 N-((3-tert-butyl-1-(3-chlorophenyl)-1H-pyrazol-5-yl)methyl)-2-(isoquinolin-5-yl)propanamide;
64 N-((1-(3-chlorophenyl)-3-(trifluoromethyl)-1H-pyrazol-5-yl)methyl)-2-(isoquinolin-5-yl)propanamide;
65 N-((1-(3-chlorophenyl)-3-(trifluoromethyl)-1H-pyrazol-5-yl)methyl)-2-(3-methylisoquinolin-5-yl)propanamide;
66 N-((1-(3-chlorophenyl)-3-(trifluoromethyl)-1H-pyrazol-5-yl)methyl)-2-(1-methylisoquinolin-5-yl)propanamide;
67 N-((1-(3-chlorophenyl)-3-(trifluoromethyl)-1H-pyrazol-5-yl)methyl)-2-(1,3-dimethylisoquinolin-5-yl)propanamide;
68 N-((1-(4-chlorophenyl)-3-(trifluoromethyl)-1H-pyrazol-5-yl)methyl)-2-(isoquinolin-5-yl)propanamide;
69 N-((3-tert-butyl-1-(3-chloro-4-fluorophenyl)-1H-pyrazol-5-yl)methyl)-2-(isoquinolin-5-yl)propanamide;
70 N-((3-tert-butyl-1-(3-chlorophenyl)-1H-pyrazol-5-yl)methyl)-2-(quinolin-5-yl)propanamide;
71 N-((3-tert-butyl-1-(3-chlorophenyl)-1H-pyrazol-5-yl)methyl)-2-(quinolin-7-yl)propanamide;
72 N-((1-(3-chlorophenyl)-3-(trifluoromethyl)-1H-pyrazol-5-yl)methyl)-2-(quinolin-7-yl)propanamide;
73 N-((3-tert-butyl-1-(3-chlorophenyl)-1H-pyrazol-5-yl)methyl)-2-(isoquinolin-7-yl)propanamide;
74 N-((3-tert-butyl-1-(3-chlorophenyl)-1H-pyrazol-5-yl)methyl)-2-(isoquinolin-6-yl)propanamide;
75 N-((3-tert-butyl-1-(3-chlorophenyl)-1H-pyrazol-5-yl)methyl)-2-(quinolin-6-yl)propanamide;
76 N-((3-tert-butyl-1-(3-chlorophenyl)-1H-pyrazol-5-yl)methyl)-2-(quinazolin-6-yl)propanamide;
77 N-((3-tert-butyl-1-(3-chlorophenyl)-1H-pyrazol-5-yl)methyl)-2-(quinoxalin-6-yl)propanamide;
78 1-((3-tert-butyl-1-(3-chlorophenyl)-1H-pyrazol-5-yl)methyl)-3-(2,3-dihydro-1H-inden-4-yl)urea;
79 1-((3-tert-butyl-1-(3-chlorophenyl)-1H-pyrazol-5-yl)methyl)-3-(2,3-dihydro-1H-inden-5-yl)urea;
80 1-((3-tert-butyl-1-(3-chlorophenyl)-1H-pyrazol-5-yl)methyl)-3-(5,6,7,8-tetrahydronaphthalen-1-yl)urea;
81 1-((1-(3-chlorophenyl)-3-(trifluoromethyl)-1H-pyrazol-5-yl)methyl)-3-(2-hydroxy-2,3-dihydro-1H-inden-4-yl)urea;
82 1-((1-(3-chlorophenyl)-3-(trifluoromethyl)-1H-pyrazol-5-yl)methyl)-3-(7-hydroxy-5,6,7,8-tetrahydronaphthalen-1-yl)urea;
83 1-(benzo[d][1,3]dioxol-5-yl)-3-((1-(3-chlorophenyl)-3-(trifluoromethyl)-1H-pyrazol-5-yl)methyl)urea;
84 1-((1-(3-chlorophenyl)-3-(trifluoromethyl)-1H-pyrazol-5-yl)methyl)-3-(2,3-dihydrobenzo[b][1,4]dioxin-6-yl)urea;
85 1-((3-tert-butyl-1-(3-chlorophenyl)-1H-pyrazol-5-yl)methyl)-3-(2,3-dihydrobenzo[b][1,4]dioxin-5-yl)urea;
86 1-((1-(3-chlorophenyl)-3-(trifluoromethyl)-1H-pyrazol-5-yl)methyl)-3-(1H-indol-4-yl)urea;
87 1-((1-(3-chlorophenyl)-3-(trifluoromethyl)-1H-pyrazol-5-yl)methyl)-3-(1-methyl-1H-indol-4-yl)urea;
88 1-((1-(3-chlorophenyl)-3-(trifluoromethyl)-1H-pyrazol-5-yl)methyl)-3-(1H-indazol-4-yl)urea;
89 1-((1-(3-chlorophenyl)-3-(trifluoromethyl)-1H-pyrazol-5-yl)methyl)-3-(1-methyl-1H-indazol-4-yl)urea;

90 1-((1-(3-chlorophenyl)-3-(trifluoromethyl)-1H-pyrazol-5-yl)methyl)-3-(1-indol-5-yl)urea;
91 1-((1-(3-chlorophenyl)-3-(trifluoromethyl)-1H-pyrazol-5-yl)methyl)-3-(2-methyl-1H-indol-5-yl)urea;
92 1-(1H-benzo[d]imidazol-5-yl)-3-((1-(3-chlorophenyl)-3-(trifluoromethyl)-1H-pyrazol-5-yl)methyl)urea;
93 1-((1-(3-chlorophenyl)-3-(trifluoromethyl)-1H-pyrazol-5-yl)methyl)-3-(1H-indazol-5-yl)urea;
94 1-(benzo[d]oxazol-6-yl)-3-((1-(3-chlorophenyl)-3-(trifluoromethyl)-1H-pyrazol-5-yl)methyl)urea;
95 1-(benzo[d]oxazol-5-yl)-3-((1-(3-chlorophenyl)-3-(trifluoromethyl)-1H-pyrazol-5-yl)methyl)urea;
96 1-(benzo[d]thiazol-6-yl)-3-((1-(3-chlorophenyl)-3-(trifluoromethyl)-1H-pyrazol-5-yl)methyl)urea;
97 1-(benzo[d]thiazol-5-yl)-3-((1-(3-chlorophenyl)-3-(trifluoromethyl)-1H-pyrazol-5-yl)methyl)urea;
98 1-((3-tert-butyl-1-(3-chlorophenyl)-1H-pyrazol-5-yl)methyl)-3-(naphthalen-1-yl)urea;
99 1-((3-tert-butyl-1-(3-chlorophenyl)-1H-pyrazol-5-yl)methyl)-3-(6-hydroxynaphthalen-2-yl)urea;
100 1-((3-tert-butyl-1-(3-chlorophenyl)-1H-pyrazol-5-yl)methyl)-3-(5-hydroxynaphthalen-2-yl)urea;
101 1-((3-tert-butyl-1-(3-chlorophenyl)-1H-pyrazol-5-yl)methyl)-3-(7-hydroxynaphthalen-1-yl)urea;
102 1-((1-(3-chlorophenyl)-3-(trifluoromethyl)-1H-pyrazol-5-yl)methyl)-3-(7-hydroxynaphthalen-1-yl)urea;
103 1-((3-tert-butyl-1-(3-chlorophenyl)-1H-pyrazol-5-yl)methyl)-3-(7-ethoxynaphthalen-1-yl)urea;
104 1-((3-tert-butyl-1-(3-chlorophenyl)-1H-pyrazol-5-yl)methyl)-3-(6-hydroxynaphthalen-1-yl)urea;
105 1-((3-tert-butyl-1-(3-chlorophenyl)-1H-pyrazol-5-yl)methyl)-3-(5-hydroxynaphthalin-1-yl)urea;
106 1-((3-tert-butyl-1-(3-chlorophenyl)-1H-pyrazol-5-yl)methyl)-3-(4-hydroxynaphthalin-1-yl)urea;
107 1-((3-tert-butyl-1-(3-chlorophenyl)-1H-pyrazol-5-yl)methyl)-3-(quinolin-8-yl)urea;
108 1-((3-tert-butyl-1-(3-chlorophenyl)-1H-pyrazol-5-yl)methyl)-3-(isoquinolin-8-yl)urea;
109 1-((3-tert-butyl-1-(3-chlorophenyl)-1H-pyrazol-5-yl)methyl)-3-(isoquinolin-5-yl)urea;
110 1-((1-(3-chlorophenyl)-3-(trifluoromethyl)-1H-pyrazol-5-yl)methyl)-3-(isoquinolin-5-yl)urea;
111 1-((3-tert-butyl-1-(3-chlorophenyl)-1H-pyrazol-5-yl)methyl)-3-(quinolin-5-yl)urea;
112 1-((3-tert-butyl-1-(3-chlorophenyl)-1H-pyrazol-5-yl)methyl)-3-(isoquinolin-4-yl)urea;
113 1-((3-tert-butyl-1-(3-chlorophenyl)-1H-pyrazol-5-yl)methyl)-3-(quinolin-3-yl)urea;
114 N-[[2-(6-chloro-pyridin-2-yl)-5-(trifluoromethyl)-2H-pyrazol-3-yl]-methyl]-2-(6-hydroxy-naphthalen-2-yl)-propionamide;
115 1-[[2-(6-chloro-pyridin-2-yl)-5-(trifluoromethyl)-2H-pyrazol-3-yl]-methyl]-3-(7-hydroxy-naphthalen-1-yl)-urea;
116 N-[[2-(6-chloro-pyridin-2-yl)-5-(trifluoromethyl)-2H-pyrazol-3-yl]-methyl]-2-(1H-indol-5-yl)-propionamide;
117 N-[[5-tert-butyl-2-(6-chloro-pyridin-2-yl)-2H-pyrazol-3-yl]-methyl]-2-isoquinolin-5-yl-propionamide;
118 1-[[5-tert-butyl-2-(6-chloro-pyridin-2-yl)-2H-pyrazol-3-yl]-methyl]-3-(1-methyl-isoquinolin-5-yl)-urea;
119 2-(1,3-benzodioxol-5-yl)-N-[[5-tert-butyl-2-(6-chloro-pyridin-2-yl)-2H-pyrazol-3-yl]-methyl]-propionamide;
120 2-(1H-Indol-5-yl)-N-[[2-pyridin-2-yl-5-(trifluoromethyl)-2H-pyrazol-3-yl]-methyl]-propionamide;
121 N-[[5-tert-butyl-2-(3,3-difluoro-cyclobutanecarbonyl)-2H-pyrazol-3-yl]-methyl]-2-(1H-indazol-4-yl)-propionamide;
122 1-[[2-(3-chlorophenyl)-4-methyl-5-(trifluoromethyl)-2H-pyrazol-3-yl]-methyl]-3-(1H-indazol-4-yl)-urea;
123 N-[[2-(dipropyl-amino)-5-(trifluoromethyl)-2H-pyrazol-3-yl]-methyl]-2-(6-hydroxy-naphthalen-2-yl)-propionamide;
124 1-[[2-(dipropyl-amino)-5-(trifluoromethyl)-2H-pyrazol-3-yl]-methyl]-3-(7-hydroxy-naphthalen-1-yl)-urea;
125 N-[[2-(dipropyl-amino)-5-(trifluoromethyl)-2H-pyrazol-3-yl]-methyl]-2-isoquinolin-5-yl-propionamide;
126 N-[[2-(dipropyl-amino)-5-(trifluoromethyl)-2H-pyrazol-3-yl]-methyl]-2-(1H-indol-5-yl)-propionamide;
127 2-(1H-benzotriazol-4-yl)-N-[[2-(dipropyl-amino)-5-(trifluoromethyl)-2H-pyrazol-3-yl]-methyl]-propionamide;
128 1-(benzothiazol-6-yl)-3-[[2-(dipropyl-amino)-5-(trifluoromethyl)-2H-pyrazol-3-yl]-methyl]-urea;
129 1-(2,3-dihydro-1H-inden-5-yl)-3-[[2-(dipropyl-amino)-5-(trifluoromethyl)-2H-pyrazol-3-yl]-methyl]-urea;
130 1-[[2-(dipropyl-amino)-5-(trifluoromethyl)-2H-pyrazol-3-yl]-methyl]-3-(1H-indazol-4-yl)-urea;
131 2-(1,3-benzodioxol-5-yl)-N-[[5-tert-butyl-2-(dipropyl-amino)-2H-pyrazol-3-yl]-methyl]-propionamide;
132 1-(7-hydroxy-naphthalen-1-yl)-3-[[2-piperidin-1-yl-5-(trifluoromethyl)-2H-pyrazol-3-yl]-methyl]-urea;
133 2-(2-methyl-quinolin-5-yl)-N-[[2-piperidin-1-yl-5-(trifluoromethyl)-2H-pyrazol-3-yl]-methyl]-propionamide;
134 2-isoquinolin-5-yl-N-[[2-piperidin-1-yl-5-(trifluoromethyl)-2H-pyrazol-3-yl]-methyl]-propionamide;
135 1-(3-chloro-isoquinolin-5-yl)-3-[[2-piperidin-1-yl-5-(trifluoromethyl)-2H-pyrazol-3-yl]-methyl]-urea;
136 1-(1-chloro-isoquinolin-5-yl)-3-[[2-piperidin-1-yl-5-(trifluoromethyl)-2H-pyrazol-3-yl]-methyl]-urea;
137 1-(1-methyl-isoquinolin-5-yl)-3-[[2-piperidin-1-yl-5-(trifluoromethyl)-2H-pyrazol-3-yl]-methyl]-urea;
138 N-[(5-tert-butyl-2-piperidin-1-yl-2H-pyrazol-3-yl)-methyl]-2-(2-methyl-quinolin-5-yl)-propionamide;
139 2-(1H-indol-5-yl)-N-[[2-piperidin-1-yl-5-(trifluoromethyl)-2H-pyrazol-3-yl]-methyl]-propionamide;
140 2-(1,3-benzodioxol-5-yl)-N-[[2-piperidin-1-yl-5-(trifluoromethyl)-2H-pyrazol-3-yl]-methyl]-propionamide;
141 N-[[2-[(4-fluorophenyl)-methyl-methyl-amino]-5-(trifluoromethyl)-2H-pyrazol-3-y]-methyl]-2-(6-hydroxy-naphthalen-2-yl)-propionamide;
142 N-[[2-[(4-fluorophenyl)-methyl-methyl-amino]-5-(trifluoromethyl)-2H-pyrazol-3-yl]-methyl]-2-(1-methyl-1H-indazol-4-yl)-propionamide;
143 N-[[2-[(4-fluorophenyl)-methyl-methyl-amino]-5-(trifluoromethyl)-2H-pyrazol-3-yl]-methyl]-2-(2-methyl-quinolin-5-yl)-propionamide;
144 2-(1,3-benzodioxol-5-yl)-N-[[2-[(4-fluorophenyl)-methyl-methylsulphonyl-amino]-5-(trifluoromethyl)-2H-pyrazol-3-yl]-methyl]-propionamide;
145 N-[[2-[(4-fluorophenyl)-methyl-methylsulphonyl-amino]-5-(trifluoromethyl)-2H-pyrazol-3-yl]-methyl]-2-(1-methyl-1H-indazol-4-yl)-propionamide;
146 N-[[2-[(4-fluorophenyl)-methyl-methylsulphonyl-amino]-5-(trifluoromethyl)-2H-pyrazol-3-yl]-methyl]-2-(1H-indol-5-yl)-propionamide;
147 1-[[2-butoxy-5-(trifluoromethyl)-2H-pyrazol-3-yl]-methyl]-3-(1H-indazol-4-yl)-urea;

148 1-[[2-butoxy-5-(trifluoromethyl)-2H-pyrazol-3-yl]-methyl]-3-(1-methyl-1H-indazol-4-yl)-urea;
149 N-[[2-butoxy-5-(trifluoromethyl)-2H-pyrazol-3-yl]-methyl]-2-(1H-indazol-4-yl)-propionamide;
150 1-[[2-(cyclopropyl-methoxy)-5-(trifluoromethyl)-2H-pyrazol-3-yl]-methyl]-3-(1H-indazol-4-yl)-urea;
151 1-[[2-cyclopentyloxy-5-(trifluoromethyl)-2H-pyrazol-3-yl]-methyl]-3-(1H-indazol-4-yl)-urea;
152 1-(1H-indazol-4-yl)-3-[[2-(thiophen-2-yl-methoxy)-5-(trifluoromethyl)-2H-pyrazol-3-yl]-methyl]-urea;
153 1-[[2-butoxy-5-(trifluoromethyl)-2H-pyrazol-3-yl]-methyl]-3-(2,3-dihydro-1H-inden-5-yl)-urea;
154 N-[[2-butoxy-5-(trifluoromethyl)-2H-pyrazol-3-yl]-methyl]-2-isoquinolin-5-yl-propionamide;
155 1-(1H-indazol-4-yl)-3-[[2-[(4-methoxyphenyl)-methyl]-5-(trifluoromethyl)-2H-pyrazol-3-yl]-methyl]-urea;
156 1-[[2-[(4-methoxyphenyl)-methyl]-5-(trifluoromethyl)-2H-pyrazol-3-yl]-methyl]-3-(1-methyl-1H-indazol-4-yl)-urea;
157 2-(1H-indol-5-yl)-N-[[2-pyridin-4-yloxy-5-(trifluoromethyl)-2H-pyrazol-3-yl]-methyl]-propionamide;
158 2-(1H-indol-5-yl)-N-[[2-pyridin-2-yloxy-5-(trifluoromethyl)-2H-pyrazol-3-yl]-methyl]-propionamide;
159 1-[[2-(3-cyano-5-fluoro-phenoxy)-5-(trifluoromethyl)-2H-pyrazol-3-yl]-methyl]-3-(1-methyl-1H-indazol-4-yl)-urea;
160 N-[[2-(3-cyano-5-fluoro-phenoxy)-5-(trifluoromethyl)-2H-pyrazol-3-yl]-methyl]-2-(1H-indol-5-yl)-propionamide;
161 2-(1,3-benzodioxol-5-yl)-N-[[2-(3-cyano-5-fluorophenoxy)-5-(trifluoromethyl)-2H-pyrazol-3-yl]-methyl]-propionamide;
162 2-(6-hydroxy-naphthalen-2-yl)-N-[[2-phenylmethoxy-5-(trifluoromethyl)-2H-pyrazol-3-yl]-methyl]-propionamide;
163 N-[[2-(benzenesulphonyl)-5-tert-butyl-2H-pyrazol-3-yl]-methyl]-2-(1,3-benzodioxol-5-yl)-propionamide;
164 N-[[2-(benzenesulphonyl)-5-tert-butyl-2H-pyrazol-3-yl]-methyl]-2-(1H-indol-5-yl)-propionamide;
165 2-(1,3-benzodioxol-5-yl)-N-[(5-tert-butyl-2-phenyl-sulphanyl-2H-pyrazol-3-yl)-methyl]-propionamide;
166 1-[[2-(cyclohexylsulphanyl)-5-(trifluoromethyl)-2H-pyrazol-3-yl]-methyl]-3-(7-hydroxy-naphthalen-1-yl)-urea;
167 1-[[2-(cyclohexylsulphanyl)-5-(trifluoromethyl)-2H-pyrazol-3-yl]-methyl]-3-(1H-indazol-4-yl)-urea;
168 1-[[5-tert-butyl-2-(cyclohexylsulphanyl)-2H-pyrazol-3-yl]-methyl]-3-(2-methyl-quinolin-5-yl)-urea;
174 1-((1-(4-chlorophenyl)-3-(trifluoromethyl)-1H-pyrazol-5-yl)methyl)-3-(2,3-dihydro-1H-inden-5-yl)urea;
175 1-(2,3-dihydro-1H-inden-5-yl)-3-((1-(4-fluorophenyl)-3-(trifluoromethyl)-1H-pyrazol-5-yl)methyl)urea;
176 1-((3-tert-butyl-1-(3-fluorophenyl)-1H-pyrazol-5-yl)methyl)-3-(2,3-dihydro-1H-inden-5-yl)urea;
177 1-((3-tert-butyl-1-(3-chloro-4-fluorophenyl)-1H-pyrazol-5-yl)methyl)-3-(2,3-dihydro-1H-inden-5-yl)urea;
178 1-(2,3-dihydro-1H-inden-5-yl)-3-((1-(4-methoxyphenyl)-3-(trifluoromethyl)-1H-pyrazol-5-yl)methyl)urea;
179 1-(2,3-dihydro-1H-inden-5-yl)-3-((3-(trifluoromethyl)-1-(4-(trifluoromethyl)phenyl)-1H-pyrazol-5-yl)methyl)urea;
180 1-(2,3-dihydro-1H-inden-5-yl)-3-((1-(4-(trifluoromethoxy)phenyl)-3-(trifluoromethyl)-1H-pyrazol-5-yl)methyl)urea;
181 1-(2,3-dihydro-1H-inden-5-yl)-3-((1-(3,4-dimethylphenyl)-3-(trifluoromethyl)-1H-pyrazol-5-yl)methyl)urea;
182 1-((3-tert-butyl-1-(3,5-dichlorophenyl)-1H-pyrazol-5-yl)methyl)-3-(2,3-dihydro-1H-inden-5-yl)urea;
183 2-(benzo[d][1,3]dioxol-5-yl)-N-((1-(3-chlorophenyl)-3-cyclopropyl-1H-pyrazol-5-yl)methyl)propanamide;
184 N-((1-cyclohexyl-3-(trifluoromethyl)-1H-pyrazol-5-yl)methyl)-2-(2,3-dihydrobenzo[b][1,4]dioxin-6-yl)propanamide;
185 1-((3-tert-butyl-1-(3-chlorophenyl)-1H-pyrazol-5-yl)methyl)-3-(2,3-dihydrobenzofuran-7-yl)urea;
186 N-((3-tert-butyl-1-(3-chlorophenyl)-1H-pyrazol-5-yl)methyl)-2-(2,3-dihydro-1H-inden-5-yl)acetamide;
187 1-((3-tert-butyl-1-(3-chlorophenyl)-1H-pyrazol-5-yl)methyl)-3-(2,2-difluorobenzo[d][1,3]dioxol-5-yl)urea;
188 N-((3-tert-butyl-1-(3-chlorophenyl)-1H-pyrazol-5-yl)methyl)-2-(2,3-dihydrobenzo[b][1,4]dioxin-6-yl)acetamide;
189 N-((1-(3-chlorophenyl)-3-(trifluoromethyl)-1H-pyrazol-5-yl)methyl)-2-(2,2-dimethylchroman-6-yl)propanamide;
190 N-((1-(3-chlorophenyl)-3-(trifluoromethyl)-1H-pyrazol-5-yl)methyl)-2-(2,2-dimethyl-2H-chromen-6-yl)propanamide;
191 N-((1-(3-chlorophenyl)-3-(trifluoromethyl)-1H-pyrazol-5-yl)methyl)-2-(1-(methylsulfonyl)-1H-indazol-5-yl)propanamide;
192 1-((1-(3-chlorophenyl)-3-(trifluoromethyl)-1H-pyrazol-5-yl)methyl)-3-(2-methyl-1H-indol-4-yl)urea;
193 N-((3-tert-butyl-1-(3-chlorophenyl)-1H-pyrazol-5-yl)methyl)-2-(6-fluoro-1H-indazol-4-yl)propanamide;
194 1-((1-(3-chlorophenyl)-3-(trifluoromethyl)-1H-pyrazol-5-yl)methyl)-3-(6-fluoro-1H-indazol-4-yl)urea;
195 N-((1-(3-chlorophenyl)-3-(trifluoromethyl)-1H-pyrazol-5-yl)methyl)-2-(7-fluoro-1H-indazol-4-yl)propanamide;
196 1-((1-(3-chlorophenyl)-3-(trifluoromethyl)-1H-pyrazol-5-yl)methyl)-3-(1-oxo-1,2-dihydroisoquinolin-5-yl)urea;
197 N-((1-(3-chlorophenyl)-3-(trifluoromethyl)-1H-pyrazol-5-yl)methyl)-2-(5-fluoronaphthalen-1-yl)propanamide;
198 5-(1-((1-(3-chlorophenyl)-3-(trifluoromethyl)-1H-pyrazol-5-yl)methylamino)-1-oxopropan-2-yl)quinolin 1-oxide;
199 2-(1H-indazol-4-yl)-N-((1-pentyl-3-(trifluoromethyl)-1H-pyrazol-5-yl)methyl)propanamide;
200 N-((1-(3-chlorophenyl)-4-methyl-3-(trifluoromethyl)-1H-pyrazol-5-yl)methyl)-2-(2,3-dihydrobenzo[b][1,4]dioxin-6-yl)propanamide;
201 N-((3-tert-butyl-1-(2,2,2-trifluoroethylamino)-1H-pyrazol-5-yl)methyl)-2-(2,3-dihydrobenzo[b][1,4]dioxin-6-yl)propanamide;
202 2-(2,3-dihydrobenzo[b][1,4]dioxin-6-yl)-N-((1-(4-methoxybenzyl)-3-(trifluoromethyl)-1H-pyrazol-5-yl)methyl)propanamide;
203 2-(1H-indazol-4-yl)-N-((1-(2-methoxyethylamino)-3-(trifluoromethyl)-1H-pyrazol-5-yl)methyl)propanamide;
204 2-(1H-indazol-4-yl)-N-((1-(pyridin-2-ylmethylamino)-3-(trifluoromethyl)-1H-pyrazol-5-yl)methyl)propanamide;
205 1-(5-chloro-1H-indazol-4-yl)-3-((1-(3-chlorophenyl)-3-(trifluoromethyl)-1H-pyrazol-5-yl)methyl)urea;

206 N-((1-(3-chlorophenyl)-3-(trifluoromethyl)-1H-pyrazol-5-yl)methyl)-2-(1-oxo-2,3-dihydro-1H-inden-4-yl)propanamide;
207 N-((1-(3-chlorophenyl)-3-(trifluoromethyl)-1H-pyrazol-5-yl)methyl)-2-(1-hydroxy-2,3-dihydro-1H-inden-4-yl)propanamide;
208 N-((1-(3-chlorophenyl)-3-(trifluoromethyl)-1H-pyrazol-5-yl)methyl)-2-(2-hydroxy-2,3-dihydro-1H-inden-4-yl)propanamide;
209 N-((1-(3-chlorophenyl)-3-(trifluoromethyl)-1H-pyrazol-5-yl)methyl)-2-(1H-indazol-6-yl)propanamide;
210 N-((1-(3-chlorophenyl)-3-(trifluoromethyl)-1H-pyrazol-5-yl)methyl)-2-(1H-indazol-7-yl)propanamide;
211 N-((1-(3-chlorophenyl)-3-(trifluoromethyl)-1H-pyrazol-5-yl)methyl)-2-(6-fluornaphthalen-1-yl)propanamide;
212 N-((1-(3-chlorophenyl)-3-(trifluoromethyl)-1H-pyrazol-5-yl)methyl)-2-(7-methoxynaphthalen-1-yl)propanamide;
213 2-(3-chloroisoquinolin-5-yl)-N-((1-(3-chlorophenyl)-3-(trifluoromethyl)-1H-pyrazol-5-yl)methyl)propanamide;
214 (S)-1-((1-(3-chlorophenyl)-3-(trifluoromethyl)-1H-pyrazol-5-yl)methyl)-3-(7-hydroxy-5,6,7,8-tetrahydronaphthalen-1-yl)urea;
(R)-1-((1-(3-chlorophenyl)-3-(trifluoromethyl)-1H-pyrazol-5-yl)methyl)-3-(7-hydroxy-5,6,7,8-tetrahydronaphthalen-1-yl)urea;
216 1-((3-tert-butyl-1-(pyridin-2-yl)-1H-pyrazol-5-yl)methyl)-3-(6-fluoro-1H-indazol-4-yl)urea; and
217 N-(5-((3-(6-fluoro-1H-indazol-4-yl)ureido)methyl)-3-(trifluormethyl)-1H-pyrazol-1-yl)benzamide;
respectively in the form of a free compound; a racemate; an entiomer, a diastereomer, a mixture of enantiomers or diastereomers; or in the form of a salt of a physiologically compatible acid or base.

11. A pharmaceutical composition comprising a compound according to claim 1 and at least one pharmaceutically acceptable carrier or auxiliary substance.

12. A method of treating a disorder selected from the group consisting of pain; hyperalgesia; allodynia; causalgia; migraine; depression; nervous affection; axonal injuries; neurodegenerative diseases; cognitive dysfunctions; epilepsy; respiratory diseases; coughs; urinary incontinence; overactive bladder; disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations; diarrhoea; pruritus; osteoporosis; arthritis; osteoarthritis; rheumatic diseases; eating disorders; medication dependency; misuse of medication; withdrawal symptoms in medication dependency; development of tolerance to medication; drug dependency; misuse of drugs; withdrawal symptoms in drug dependency; alcohol dependency; misuse of alcohol and withdrawal symptoms in alcohol dependency; or for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects selected from the group consisting of hyperthermia, hypertension and bronchoconstriction triggered by the administration of vanilloid receptor 1 agonists in a subject in need thereof, said method comprising administering to said subject a pharmaceutically effective amount of a compound according to claim 1.

13. Process for preparing a compound according to claim 1,
wherein a compound of formula (II),

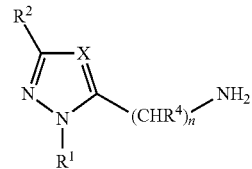

(II)

in which X, $R^1$, $R^2$, $R^4$ and n have the respective meanings given in claim 1, is reacted in a reaction medium, optionally in the presence of at least one suitable coupling reagent, and optionally in the presence of at least one base, with a compound of formula (III) or (IV),

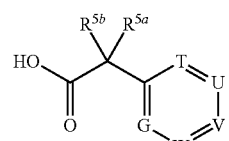

(III)

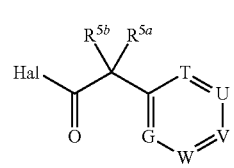

(IV)

in which Hal represents a halogen, and $R^{5a}$, $R^{5b}$, T, U, V, W and G each have the respective meanings given in claim 1, in a reaction medium, optionally in the presence of at least one suitable coupling reagent, and optionally in the presence of at least one base, to form a compound of formula (I),

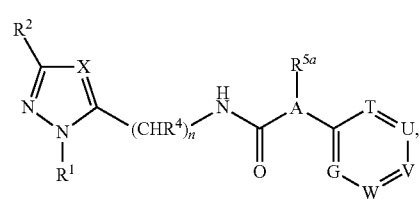

(I)

in which A represents $CR^{5b}$ and X, $R^1$, $R^2$, $R^{5a}$, $R^{5b}$, U, V, W and G and n have the respective meanings given in claim 1; or
wherein a compound of formula (II),

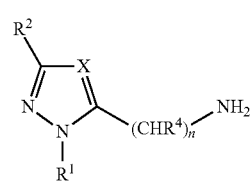

(II)

in which X, $R^1$, $R^2$, $R^4$ and n have the respective meanings given in claim 1, is reacted to form a compound of formula (V)

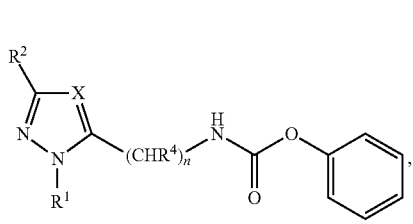
(V)

in which X, $R^1$, $R^2$, $R^4$ and n have the respective meanings given in claim 1, in a reaction medium, in the presence of phenyl chloroformate, optionally in the presence of at least one base and/or at least one coupling reagent, and said compound is optionally purified and/or isolated, and the compound of general formula (V) is reacted with a compound of formula (VI),

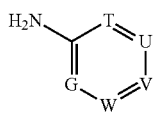
(VI)

in which T, U, V, W and G have the respective meanings given in claim 1, in a reaction medium, optionally in the presence of at least one suitable coupling reagent, and optionally in the presence of at least one base, to form a compound of formula (I),

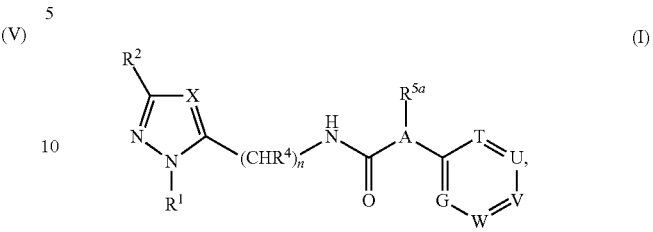
(I)

in which A represents N and X, $R^1$, $R^2$, $R^4$, $R^{5a}$, U, V, W and G and n have a the respective meanings given in claim 1.

14. A method according to claim 12, wherein said disorder is pain selected from the group consisting of acute pain, chronic pain, neuropathic pain, visceral pain and joint pain; or a neurodegenerative disease selected from the group consisting of multiple sclerosis, Alzheimer's disease, Parkinson's disease and Huntington's disease; or a memory disorder; or a respiratory disease selected from the group consisting of asthma, bronchitis and pulmonary inflammation; or an inflammation of the intestine, the eyes, the bladder, the skin or the nasal mucous membrane; or an eating disorder selected from the group consisting of bulimia, cachexia, anorexia and obesity; or development of tolerance to natural or synthetic opioids.

\* \* \* \* \*